United States Patent
Orengo et al.

(10) Patent No.: US 11,629,195 B2
(45) Date of Patent: Apr. 18, 2023

(54) ANTI-IL2 RECEPTOR GAMMA ANTIGEN-BINDING PROTEINS

(71) Applicant: Regeneron Pharmaceuticals, Inc., Tarrytown, NY (US)

(72) Inventors: Jamie M. Orengo, Cortlandt Manor, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 251 days.

(21) Appl. No.: 16/776,928

(22) Filed: Jan. 30, 2020

(65) Prior Publication Data

US 2020/0247894 A1    Aug. 6, 2020

Related U.S. Application Data

(60) Provisional application No. 62/799,851, filed on Feb. 1, 2019.

(51) Int. Cl.
| | | |
|---|---|---|
| C07K 16/28 | (2006.01) | |
| A61K 39/395 | (2006.01) | |
| C12N 15/63 | (2006.01) | |
| A61P 37/06 | (2006.01) | |
| A61K 9/00 | (2006.01) | |

(52) U.S. Cl.
CPC ........ *C07K 16/2866* (2013.01); *A61K 9/0019* (2013.01); *A61K 39/3955* (2013.01); *A61P 37/06* (2018.01); *C12N 15/63* (2013.01); *C07K 2317/31* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,740,461 | A | 4/1988 | Kaufman |
| 4,816,567 | A | 3/1989 | Cabilly et al. |
| 4,912,040 | A | 3/1990 | Kaufman et al. |
| 4,952,496 | A | 8/1990 | Studier et al. |
| 4,959,455 | A | 9/1990 | Clark et al. |
| 5,168,062 | A | 12/1992 | Stinski |
| 5,385,839 | A | 1/1995 | Stinski |
| 5,510,259 | A | 4/1996 | Sugamura et al. |
| 5,693,489 | A | 12/1997 | Studier et al. |
| 6,323,027 | B1 | 11/2001 | Burkly et al. |
| 6,576,236 | B1 | 6/2003 | Boussiotis et al. |
| 6,596,541 | B2 | 7/2003 | Murphy et al. |
| 6,770,745 | B2 | 8/2004 | Burkly et al. |
| 7,816,091 | B2 | 10/2010 | Ruben et al. |
| 8,697,396 | B2 | 4/2014 | Dall'Acqua et al. |
| 2002/0028202 | A1 | 3/2002 | Burkly et al. |
| 2011/0250213 | A1 | 10/2011 | Tso et al. |
| 2014/0134162 | A1 | 5/2014 | Stavenhagen et al. |
| 2014/0171623 | A1 | 6/2014 | Dall'Acqua et al. |
| 2014/0243504 | A1 | 8/2014 | Davis et al. |

FOREIGN PATENT DOCUMENTS

| | | |
|---|---|---|
| EP | 3172227 B1 | 9/2019 |
| WO | 1996001122 A1 | 1/1996 |
| WO | 1997017360 A2 | 5/1997 |
| WO | 1997043416 A1 | 11/1997 |
| WO | 2001077288 A2 | 10/2001 |
| WO | 2012096994 A2 | 7/2012 |
| WO | 2014043361 A1 | 3/2014 |
| WO | 2017021540 A1 | 2/2017 |
| WO | 2018156649 A1 | 8/2018 |

OTHER PUBLICATIONS

Goldsby, Immunology, 5th edition, 2003, pp. 82-84.*
Rudikoff, et al. (Proc. Natl. Acad. Sci. USA, 79(6):1979-1983, 1982.*
Brummell et al. (Biochemistry 32:1180-1187 (1993).*
Kobayashi et al. (Protein Engineering 12:879-844 (1999)).*
Brorson et al. (J. Immunol. 163:6694-6701 (1999)).*
Coleman (Research in Immunol. 145:33-36 (1994)).*
Casset et al; Biochemical and Biophysical Research Communications, 2003; 307:198-205.*
Paul, Fundamental Immunology, 3rd Edition, 1993, pp. 292-295.*
Altschul et al., "Protein Databse Searches Using Compositionally Adjusted Substitution Matrices", (2005) FEBS J. 272(20): 5101-5109.
Altschul, "Amino acid substitution matrices from an information theoretic perspective", J. Mol. Biol. 219:555-565 (1991).
Altschul et al., "Basic Local Alignment Search Tool", (1990) J. Mol. Biol. 215:403-410.
Altschul et al.,, "A Protein Alignment Scoring System Sensitve at All Evolutionary Distances", (1993) J. Mol. Evol. 36:290-300.
Altschul et al., "Gapped BLAST and PSI-BLAST: a new generation of protein database search programs", (1997) Nucleic Acids Res. 25:3389-3402.
Avis et al. (eds.) (1993) "Pharmaceutical Dosage Forms: Parenteral Medications", Marcel Dekker, NY (Synopsis only).
Baldassari & Rose, "Daclizumab: Development, Clinical Trials, and Practical Aspects of Use in Multiple Sclerosis", Neurotherapeutics 14(4):842-858 (2017).
Benoist et al., "In vivo sequence requirements of the SV40 early promoter region", Nature 290:304-310 (1981) (Abstract).
Brinster et al., "Regulation of metallothionein-thymidine kinase fusion plasmids injected into mouse eggs", Nature 296:39-42 (1992) (Abstract).

(Continued)

*Primary Examiner* — Bridget E Bunner
*Assistant Examiner* — Fozia M Hamud
(74) *Attorney, Agent, or Firm* — Fox Rothschild LLP; Lisa D. Flanagan

(57) ABSTRACT

The present invention provides antibodies and antigen-binding fragments (e.g., human antibodies) that bind specifically to human IL2 receptor gamma (IL2Rγ). Methods for treating or preventing diseases mediated by IL2Rγ (e.g., graft vs host disease) using the antibodies and fragments are also provided along with methods of making the antibodies and fragments.

23 Claims, 22 Drawing Sheets

Specification includes a Sequence Listing.

(56) References Cited

OTHER PUBLICATIONS

Buzney et al., "Asthma and Atopic Dermatitis: A Review of Targeted Inhibition of Interleukin-4 and Interleukin-13 As Therapy for Atopic Disease", J Drugs Dermatol. 15(2):165-71 (2016).
Dantas et al., "Increased Serum Interleukin-9 Levels in Rheumatoid Arthritis and Systemic Lupus Erythematosus: Pathogenic Role or Just an Epiphenomenon?", Dis Markers. 2015:2015:519638 (2015).
Dayhoff et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.
DeBoer et al., "The tac promoter: a functional hybrid derived from the trp and lac promoters" Proc. Natl. Acad. Sci. USA 80:21-25 (1983).
Dembo et al., "Limit Distribution of Maximal Non-Aligned Two-Sequence Segmental Score", (1994) Ann. Prob. 22:2022-2039.
Dinesh & Rasool, "Multifaceted role of IL-21 in rheumatoid arthritis: Current understanding and future perspectives", J Cell Physiol. 233(5):3918-3928 (2018).
Ehring, "Hydrogen Enchange/Electrospray Ionization Mass Spectrometry Studies of Structural Features of Proteins and Protein/Protein Interactions", Analytical Biochemistry 267: 252-259 (1999).
Engen and Smith, "Investigating protein structure and dynamics by hydrogen exchange MS", Anal. Chem. 73:256A-265A (2001).
Generoso et al., "Prospects for Monoclonal Antibody Therapy in Pediatric Asthma", Curr Allergy Asthma Rep. 18(9):45 (2018).
Gennaro "Remington: The Science and Practice of Pharmacy", (2000) Lippincott, Williams, and Wilkins, New York, N.Y. (Abstract).
Gish et al., "Identification of protein coding regions by database similarity search", Nature Genet. 3:266-272 (1993) (Abstract).
Gonnet et al., "Exhaustive Matching of the Entire Protein Sequence Database", Science 256: 1443-45 (1992).
Hancock et al., "SIMPLE34: an improved and enhanced implementation for VAX and Sun computers of the SIMPLE algorithm for analysis of clustered repetitive motifs in nucleotide sequences", Comput. Appl. Biosci. 10:67-70 (1994) (Abstract).
Hardman et al., (2001) "Goodman & Gilman's The Pharmacological Basis of Therapeutics", 10th Edition, McGraw-Hill, NY (Abstract).
Henikoff et al., "Amino Acid Substitution Matrices From Protein Blocks", Proc. Natl. Acad. Sci. USA 89:10915-10919 (1992).
Holm et al., "Evaluating IL-21 as a Potential Therapeutic Target in Crohn's Disease", Gastroenterol Res Pract. 2018:5962624 (2018).
Hughes-Austin et al., "Multiple cytokines and chemokines are associated with rheumatoid arthritis-related autoimmunity in first-degree relatives without rheumatoid arthritis: Studies of the Aetiology of Rheumatoid Arthritis (SERA)", Ann Rheum Dis.;72(6):901-7 (2013).
Karlin et al., "Methods for Assessing the Statistical Significance of Molecular Sequence Features by Using General Scoring Schemes", Proc. Natl. Acad. Sci. USA 87:2264-2268 (1990).
Karlin et al., "Applications and Statistics for Multiple High-Scoring Segments in Molecular Sequences", Proc. Natl. Acad. Sci. USA 90:5873-5877 (1993).
Lesiak et al., "Are interleukin-15 and -22 a new pathogenic factor in pustular palmoplantar psoriasis?", Postepy Dermatol Alergol. 33(5):336-339 (2016).
Lieberman et al. (eds.) "Pharmaceutical Dosage Forms: Tablets", (1990) Marcel Dekker, NY (Abstract).
Lloyd & Harker, "Epigenetic Control of Interleukin-9 in Asthma", N Engl J Med. 379(1):87-89 (2018).
Neurath & Finotto, "IL-9 signaling as key driver of chronic inflammation in mucosal immunity", Cytokine Growth Factor Rev. 29:93-9 (2016).
Olosz & Malek, "Structural basis for binding multiple ligands by the common cytokine receptor gamma-chain", J Biol Chem. 277(14):12047-52 (2002).
Pathak, "The expanding role of IL-7 and thymic stromal lymphopoietin as therapeutic target for rheumatoid arthritis" Expert Opin Ther Targets, 18(5):581-94 (2014).
Raeber et al., "The role of cytokines in T-cell memory in health and disease", Immunol Rev. 283(1):176-193 (2018).
Reineke, "Antibody Epitope Mapping Using Arrays of Synthetic Peptides", Methods Mol. Biol. 248: 443-63 (2004).
Rochman et al., "New insights into the regulation of T cells by gamma(c) family cytokines". Nat Rev Immunol. Jul. 2009;9(7):480-90.
States, et al., "Improved Sensitivity of Nucleic Acid Database Searches Using Application-Specific Scoring Matrices", Methods 3:66-70 (1991).
Takeshita et al., "Cloning of the Gamma Chain of the Human IL-2 Receptor", Science 257 (5068): 379-382 (1992).
Tashkin & Wechsler, "Role of eosinophils in airway inflammation of chronic obstructive pulmonary disease", Int J Chron Obstruct Pulmon Dis. 13:335-349 (2018).
Tomer et al., "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Prot. Sci. 9: 487-496 (2000).
Vllla-Komaroff, et al., "A bacterial clone synthesizing proinsulin", Proc. Natl. Acad. Sci. USA 75:3727-3731 (1978) (Abstract).
Wagner, et al., "Nucleotide sequence of the thymidine kinase gene of herpes simplex virus type 1", Proc. Natl. Acad. Sci. USA 78:1441-1445 (1981).
Weiner and Kotkoskie, "Excipient Toxicity and Safety", Marcel Dekker, Inc., (2000) New York, N.Y.
Wootton, et al., "Statistics of Local Complexity in Amino Acid Sequences and Sequence Databases", Comput. Chem. 17:149-163 (1993).
Yamamoto, et al., "Identification of a functional promoter in the long terminal repeat of Rous sarcoma virus", Cell 22:787-797 (1980) (Abstract).
Yang et al., "Therapeutic potential of IL-15 in rheumatoid arthritis", Hum Immunol. Nov. 2015;76(11):812-8.
Zhang, et al., "PowerBLAST: A New Network BLAST Application of INteractive or Automated Sequence Analysis and Annotation" Genome Res. 7:649-656 (1997).
International Search Report and Written Opinion dated Jul. 20, 2020, issued in Application No. PCT/US2020/015841.
Hechinger et al., "Therapeutic Activity of Multiple Common g-Chain Cytokine Inhibition in Acute and Chronic GVHD," Blood, 125(3):1570-580 (Jan. 2015).
He et al., "Expression and Function of the Gamma Subunit of the IL-2, IL-4, and IL-7 Receptors," J. of Immunology, American Assoc of Immunologists, US, 154(4):1596-1605 (Feb. 1995).

\* cited by examiner

* mouse found dead
+ mouse with more than 20% weight loss was euthanized
Day21= start of antibody treatment
Day59= last antibody injection

- - - huPBMCs - isotype control antibody
- - huPBMCs - COMP1499
----- huPBMCs - H4H12889P
—— huPBMCs - H4H12922P2

Day21=start of antibody treatment
Day59=last antibody injection

Day 21 = start of antibody treatment
Day 59 = last antiboby injection

- - - huPBMCs - isotype control antibody
— — huPBMCs - COMP1499
······ huPBMCs - H4H12889P
——— huPBMCs - H4H12922P2

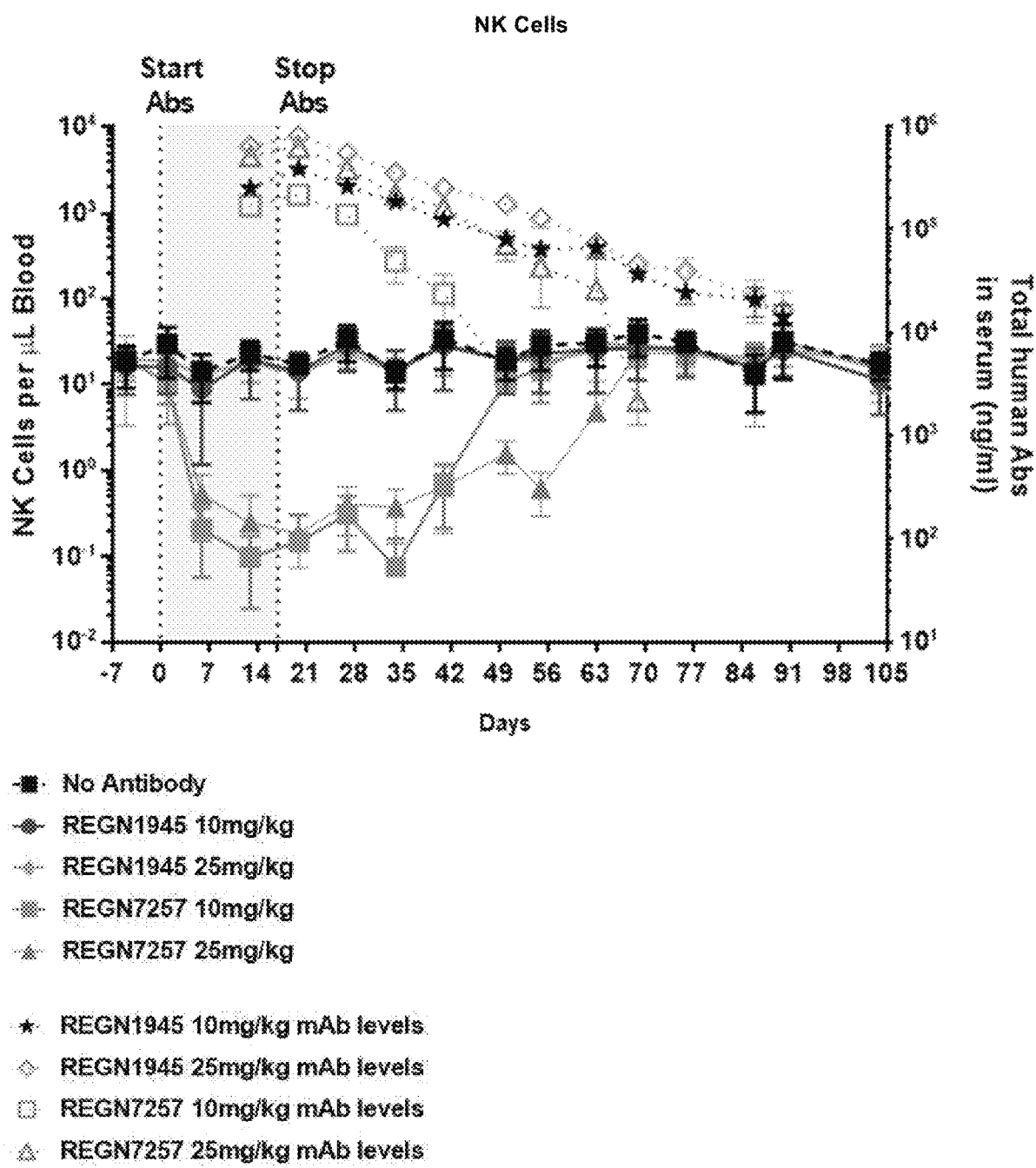

SEQUENCE LISTING

```
<160> NUMBER OF SEQ ID NOS: 386

<210> SEQ ID NO 1
<211> LENGTH: 369
<212> TYPE: DNA
<213> ORGANISM: Homo sapiens

<400> SEQUENCE: 1
caggtgcagc tggtgcagtc tggggctgag gtgaagaagc ctggggcctc agtgcgggtc      60
tcctgcaagg cttctggata caccttcacc gactacgata ttcactgggt gcgacaggcc     120
cctggacatg ggcttgagtg gatggggtgg atcaacccta cagtggtgg cacaaactat      180 gcacagaagt tcagggcag gtcaccatg accaggaca cgtccatcag tacagtctac        240
atggacctga gcaggctgag atctgacgac acggccgtgt attactgtgc gagagctgat     300
tatagtagtt cgtattatta ttacggtatg gacgtctggg gccaagggac cacggtcacc     360
gtctcctca                                                             369

<210> SEQ ID NO 2
<211> LENGTH: 123
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Asp Tyr
            20                  25                  30

Asp Ile His Trp Val Arg Gln Ala Pro Gly His Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Val Tyr
65                  70                  75                  80

Met Asp Leu Ser Arg Leu Arg Ser Asp Asp Thr Ala Val Tyr Tyr Cys
                85                  90                  95

Ala Arg Ala Asp Tyr Ser Ser Ser Tyr Tyr Tyr Gly Met Asp Val
            100                 105                 110

Trp Gly Gln Gly Thr Thr Val Thr Val Ser Ser
        115                 120

<210> SEQ ID NO 3
<211> LENGTH: 24
<212> TYPE: DNA
```

<213> ORGANISM: Homo sapiens

<400> SEQUENCE: 3
ggatacacct tcaccgacta cgat                              24

<210> SEQ ID NO 4
<211> LENGTH: 8
<212> TYPE: PRT
<213> ORGANISM: Homo sapiens

<400> SEQUENCE: 4

Gly Tyr Thr Phe Thr Asp Tyr Asp
1               5

<210> SEQ ID NO 5
<211> LENGTH: 24
<212> TYPE: DNA
<213> ORGANISM: Homo sapiens

<400> SEQUENCE: 5 atcaaccta acagtggtgg caca                               24

<210> SEQ ID NO 6
<211> LENGTH: 8
<212> TYPE: PRT
<213> ORGANISM: Homo sapiens

<400> SEQUENCE: 6

Ile Asn Pro Asn Ser Gly Gly Thr
1               5

<210> SEQ ID NO 7
<211> LENGTH: 48
<212> TYPE: DNA
<213> ORGANISM: Homo sapiens

<400> SEQUENCE: 7
gcgagagctg attatagtag ttcgtattat tattacggta tggacgtc    48

<210> SEQ ID NO 8
<211> LENGTH: 16
<212> TYPE: PRT
<213> ORGANISM: Homo sapiens

<400> SEQUENCE: 8

Ala Arg Ala Asp Tyr Ser Ser Ser Tyr Tyr Tyr Tyr Gly Met Asp Val
1               5                   10                  15

<210> SEQ ID NO 9
<211> LENGTH: 339
<212> TYPE: DNA
<213> ORGANISM: Homo sapiens

<400> SEQUENCE: 9
gacatcgtga tgacccagtc tccagactcc ctggctgtgt ctctgggcga gagggccacc    60
atcaactgca agtccagcca gagtgtttta tacagctcca gaataagaa ctacttatct   120 tggtaccagc agaaaccagg acagcctcct aagttgctca tttactgggc atctacccgg   180
gaattcgggg tccctgaccg attcagtggc cgcgggtctg ggacagattt cactctcacc   240
atcagcagcc tgcaggctga agatgtggca gtttattact gtcaacaata ttatactact   300
ccgtacactt ttggccaggg gaccaagctg gagatcaaa                         339

<210> SEQ ID NO 10
<211> LENGTH: 113
<212> TYPE: PRT
<213> ORGANISM: Homo sapiens

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Lys Asn Lys Asn Tyr Leu Ser Trp Tyr Gln Gln Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Arg Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 11
<211> LENGTH: 36
<212> TYPE: DNA
<213> ORGANISM: Homo sapiens

<400> SEQUENCE: 11
cagagtgttt tatacagctc caagaataag aactac                              36

<210> SEQ ID NO 12
<211> LENGTH: 12
<212> TYPE: PRT
<213> ORGANISM: Homo sapiens

<400> SEQUENCE: 12

Gln Ser Val Leu Tyr Ser Ser Lys Asn Lys Asn Tyr
1               5                   10

<210> SEQ ID NO 13
<211> LENGTH: 9
<212> TYPE: DNA
<213> ORGANISM: Homo sapiens

<400> SEQUENCE: 13 tgggcatct                                                            9

<210> SEQ ID NO 14
<211> LENGTH: 3
<212> TYPE: PRT
<213> ORGANISM: Homo sapiens

<400> SEQUENCE: 14

Trp Ala Ser
1

<210> SEQ ID NO 15
<211> LENGTH: 27
<212> TYPE: DNA
<213> ORGANISM: Homo sapiens -continued

```
<400> SEQUENCE: 15
caacaatatt atactactcc gtacact                                              27

<210> SEQ ID NO 16
<211> LENGTH: 9
<212> TYPE: PRT
<213> ORGANISM: Homo sapiens

<400> SEQUENCE: 16

Gln Gln Tyr Tyr Thr Thr Pro Tyr Thr
1               5

<210> SEQ ID NO 17
<211> LENGTH: 1353
<212> TYPE: DNA
<213> ORGANISM: Homo sapiens

<400> SEQUENCE: 17
caggtgcagc tggtgcagtc tggggctgag gtgaagaagc ctggggcctc agtgcgggtc           60
tcctgcaagg cttctggata caccttcacc gactacgata ttcactgggt gcgacaggcc          120
cctggacatg gcttgagtg gatggggtgg atcaaccta acagtggtgg cacaaactat            180
gcacagaagt ttcagggcag ggtcaccatg accagggaca cgtccatcag tacagtctac          240
atggacctga gcaggctgag atctgacgac acggccgtgt attactgtgc gagagctgat          300
tatagtagtt cgtattatta ttacggtatg gacgtctggg gccaagggac cacggtcacc          360
gtctcctcag cctccaccaa gggcccatcg gtcttccccc tggcgccctg ctccaggagc          420
acctccgaga gcacagccgc cctgggctgc ctggtcaagg actacttccc cgaaccggtg          480
acggtgtcgt ggaactcagg cgccctgacc agcggcgtgc acaccttccc ggctgtccta          540
cagtcctcag gactctactc cctcagcagc gtggtgaccg tgccctccag cagcttgggc          600
acgaagacct acacctgcaa cgtagatcac aagcccagca acaccaaggt ggacaagaga          660
gttgagtcca aatatggtcc cccatgccca ccctgcccag cacctgagtt cctggggga          720 ccatcagtct tcctgttccc cccaaaaccc aaggacactc tcatgatctc ccggacccct          780
gaggtcacgt gcgtggtggt ggacgtgagc caggaagacc ccgaggtcca gttcaactgg          840
tacgtggatg gcgtggaggt gcataatgcc aagacaaagc cgcggggagga gcagttcaac         900 agcacgtacc gtgtggtcag cgtcctcacc gtcctgcacc aggactggct gaacggcaag          960
gagtacaagt gcaaggtctc caacaaaggc ctcccgtcct ccatcgagaa aaccatctcc         1020
aaagccaaag gcagccccg agagccacag gtgtacaccc tgcccccatc ccaggaggag          1080
atgaccaaga accaggtcag cctgacctgc ctggtcaaag gcttctaccc cagcgacatc         1140
gccgtggagt gggagagcaa tgggcagccg gagaacaact acaagaccac gcctcccgtg         1200
ctggactccg acggctcctt cttcctctac agcaggctca ccgtggacaa gagcaggtgg         1260
caggagggga atgtcttctc atgctccgtg atgcatgagg ctctgcacaa ccactacaca         1320
cagaagtccc tctccctgtc tctgggtaaa tga                                     1353

<210> SEQ ID NO 18
<211> LENGTH: 450
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15
```

```
Ser Val Arg Val Ser Cys Lys Ala Ser Gly Tyr Thr Phe Thr Asp Tyr
            20                  25                  30

Asp Ile His Trp Val Arg Gln Ala Pro Gly His Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Val Tyr
65                  70                  75                  80

Met Asp Leu Ser Arg Leu Arg Ser Asp Asp Thr Ala Val Tyr Tyr Cys
            85                  90                  95

Ala Arg Ala Asp Tyr Ser Ser Tyr Tyr Tyr Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430
```

Glu Ala Leu His Asn His Tyr Thr Gln Lys Ser Leu Ser Leu
            435                 440                 445

Gly Lys
    450

<210> SEQ ID NO 19
<211> LENGTH: 663
<212> TYPE: DNA
<213> ORGANISM: Homo sapiens

<400> SEQUENCE: 19
gacatcgtga tgacccagtc tccagactcc ctggctgtgt ctctgggcga gagggccacc    60
atcaactgca agtccagcca gagtgtttta tacagctcca agaataagaa ctacttatct   120
tggtaccagc agaaaccagg acagcctcct aagttgctca tttactgggc atctacccgg   180
gaattcgggg tccctgaccg attcagtggc cgcgggtctg ggacagattt cactctcacc   240
atcagcagcc tgcaggctga agatgtggca gtttattact gtcaacaata ttatactact   300
ccgtacactt ttggccaggg gaccaagctg gagatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tag                                                                 663

<210> SEQ ID NO 20
<211> LENGTH: 220
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Lys Asn Lys Asn Tyr Leu Ser Trp Tyr Gln Gln Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Arg Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
<211> LENGTH: 363
<212> TYPE: DNA
<213> ORGANISM: Homo sapiens

<400> SEQUENCE: 21
caggtgcagc tggtggagtc tgggggaggc gtggtccagc ctgggaggtc cctgagactc     60
tcctgtacag cctctggatt caccttcaga agttatgaca tgtactgggt ccgccaggct    120
ccaggcaagg ggctggagtg ggtgtcagtt ataacatatg atggaaataa taaatactat    180
gcagactccg tgaagggccg attcaccatc tccagagaca attccaagaa cacgctattt    240
ctgcaaatga gcagcctgag acctgaggac acggctgttt attactgtgc gaaaaggggc    300
ttaatatggg tcggggagtc ctttgactac tggggccagg gaaccctggt caccgtctcc    360
tca                                                                 363

<210> SEQ ID NO 22
<211> LENGTH: 121
<212> TYPE: PRT
<213> ORGANISM: Homo sapiens

<400> SEQUENCE: 22

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Arg Ser Tyr
            20                  25                  30

Asp Met Tyr Trp Val Arg Gln Ala Pro Gly Lys Gly Leu Glu Trp Val
        35                  40                  45

Ser Val Ile Thr Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Ser Ser Leu Arg Pro Glu Asp Thr Ala Val Tyr Tyr Cys
                85                  90                  95

Ala Lys Arg Gly Leu Ile Trp Val Gly Glu Ser Phe Asp Tyr Trp Gly
            100                 105                 110

Gln Gly Thr Leu Val Thr Val Ser Ser
        115                 120

<210> SEQ ID NO 23
<211> LENGTH: 24
<212> TYPE: DNA
<213> ORGANISM: Homo sapiens

<400> SEQUENCE: 23
ggattcacct tcagaagtta tgac                                           24

<210> SEQ ID NO 24
<211> LENGTH: 8
<212> TYPE: PRT
<213> ORGANISM: Homo sapiens
```

```
<400> SEQUENCE: 24

Gly Phe Thr Phe Arg Ser Tyr Asp
1               5

<210> SEQ ID NO 25
<211> LENGTH: 24
<212> TYPE: DNA
<213> ORGANISM: Homo sapiens

<400> SEQUENCE: 25
ataacatatg atggaaataa taaa                                            24

<210> SEQ ID NO 26
<211> LENGTH: 8
<212> TYPE: PRT
<213> ORGANISM: Homo sapiens

<400> SEQUENCE: 26

Ile Thr Tyr Asp Gly Asn Asn Lys
1               5

<210> SEQ ID NO 27
<211> LENGTH: 42
<212> TYPE: DNA
<213> ORGANISM: Homo sapiens

<400> SEQUENCE: 27
gcgaaaaggg gcttaatatg ggtcggggag tcctttgact ac                        42

<210> SEQ ID NO 28
<211> LENGTH: 14
<212> TYPE: PRT
<213> ORGANISM: Homo sapiens

<400> SEQUENCE: 28

Ala Lys Arg Gly Leu Ile Trp Val Gly Glu Ser Phe Asp Tyr
1               5                   10

<210> SEQ ID NO 29
<211> LENGTH: 321
<212> TYPE: DNA
<213> ORGANISM: Homo sapiens

<400> SEQUENCE: 29
gacatccaga tgacccagtc tccttccacc ctgtctgcat ctgtaggaga cagagtcacc      60
atcacttgcc gggccagtca gagtattaat agctggttgg cctggtatca gcagaaacca     120
gggaaagccc ctaacctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataagagtt attcgtggac gttcggccaa     300
gggaccaagg tggaaatcaa a                                               321

<210> SEQ ID NO 30
<211> LENGTH: 107
<212> TYPE: PRT
<213> ORGANISM: Homo sapiens

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
```

```
                20                  25                  30
Leu Ala Trp Tyr Gln Gln Lys Pro Gly Lys Ala Pro Asn Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ser Trp
                85                  90                  95

Thr Phe Gly Gln Gly Thr Lys Val Glu Ile Lys
                100                 105
```

<210> SEQ ID NO 31
<211> LENGTH: 18
<212> TYPE: DNA
<213> ORGANISM: Homo sapiens

<400> SEQUENCE: 31
cagagtatta atagctgg                                            18

<210> SEQ ID NO 32
<211> LENGTH: 6
<212> TYPE: PRT
<213> ORGANISM: Homo sapiens

<400> SEQUENCE: 32

Gln Ser Ile Asn Ser Trp
1               5

<210> SEQ ID NO 33
<211> LENGTH: 9
<212> TYPE: DNA
<213> ORGANISM: Homo sapiens

<400> SEQUENCE: 33 aaggcgtct                                                       9

<210> SEQ ID NO 34
<211> LENGTH: 3
<212> TYPE: PRT
<213> ORGANISM: Homo sapiens

<400> SEQUENCE: 34

Lys Ala Ser
1

<210> SEQ ID NO 35
<211> LENGTH: 27
<212> TYPE: DNA
<213> ORGANISM: Homo sapiens

<400> SEQUENCE: 35
caacagtata agagttattc gtggacg                                  27

<210> SEQ ID NO 36
<211> LENGTH: 9
<212> TYPE: PRT
<213> ORGANISM: Homo sapiens

<400> SEQUENCE: 36

Gln Gln Tyr Lys Ser Tyr Ser Trp Thr
1               5

<210> SEQ ID NO 37
<211> LENGTH: 1347
<212> TYPE: DNA
<213> ORGANISM: Homo sapiens

<400> SEQUENCE: 37

```
caggtgcagc tggtggagtc tgggggaggc gtggtccagc ctggagggtc cctgagactc        60
tcctgtacag cctctggatt caccttcaga agttatgaca tgtactgggt ccgccaggct       120
ccaggcaagg ggctggagtg ggtgtcagtt ataacatatg atggaaataa taaatactat       180
gcagactccg tgaagggccg attcaccatc tccagagaca attccaagaa cacgctattt       240
ctgcaaatga gcagcctgag acctgaggac acggctgttt attactgtgc gaaagggggc       300
ttaatatggg tcggggagtc ctttgactac tggggccagg gaaccctggt caccgtctcc       360
tcagcctcca ccaagggccc atcggtcttc cccctggcgc cctgctccag gagcacctcc       420
gagagcacag ccgccctggg ctgcctggtc aaggactact cccccgaacc ggtgacggtg       480
tcgtggaact caggcgccct gaccagcggc gtgcacacct tcccggctgt cctacagtcc       540
tcaggactct actccctcag cagcgtggtg accgtgccct ccagcagctt gggcacgaag       600
acctacacct gcaacgtaga tcacaagccc agcaacacca aggtggacaa gagagttgag       660
tccaaatatg gtcccccatg cccacccctgc ccagcacctg agttcctggg gggaccatca       720
gtcttcctgt tccccccaaa acccaaggac actctcatga tctcccggac ccctgaggtc       780
acgtgcgtgg tggtggacgt gagccaggaa gaccccgagg tccagttcaa ctggtacgtg       840
gatggcgtgg aggtgcataa tgccaagaca aagccgcggg aggagcagtt caacagcacg       900
taccgtgtgg tcagcgtcct caccgtcctg caccaggact ggctgaacgg caaggagtac       960
aagtgcaagg tctccaacaa aggcctcccg tcctccatcg agaaaaccat ctccaaagcc      1020
aaagggcagc cccgagagcc acaggtgtac accctgcccc catcccagga ggagatgacc      1080
aagaaccagg tcagcctgac ctgcctggtc aaaggcttct accccagcga catcgccgtg      1140
gagtgggaga gcaatgggca gccggagaac aactacaaga ccacgcctcc cgtgctggac      1200
tccgacggct ccttcttcct ctacagcagg ctcaccgtgg acaagagcag gtggcaggag      1260
gggaatgtct tctcatgctc cgtgatgcat gaggctctgc acaaccacta cacacagaag      1320
tccctctccc tgtctctggg taaatga                                          1347
```

<210> SEQ ID NO 38
<211> LENGTH: 448
<212> TYPE: PRT
<213> ORGANISM: Homo sapiens

<400> SEQUENCE: 38

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Arg Ser Tyr
            20                  25                  30

Asp Met Tyr Trp Val Arg Gln Ala Pro Gly Lys Gly Leu Glu Trp Val
        35                  40                  45

Ser Val Ile Thr Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Ser Ser Leu Arg Pro Glu Asp Thr Ala Val Tyr Tyr Cys
```

```
                    85                  90                  95
Ala Lys Arg Gly Leu Ile Trp Val Gly Glu Ser Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 39
<211> LENGTH: 645
<212> TYPE: DNA
<213> ORGANISM: Homo sapiens

<400> SEQUENCE: 39
gacatccaga tgacccagtc tccttccacc ctgtctgcat ctgtaggaga cagagtcacc        60
atcacttgcc gggccagtca gagtattaat agctggttgg cctggtatca gcagaaacca       120
```

```
gggaaagccc ctaacctcct gatctataag gcgtctagtt tagaaagtgg ggtcccatca        180
aggttcagcg gcagtggatc tgggacagaa ttcactctca ccatcagcag cctgcagcct        240
gatgattttg caacttatta ctgccaacag tataagagtt attcgtggac gttcggccaa        300
gggaccaagg tggaaatcaa acgaactgtg gctgcaccat ctgtcttcat cttcccgcca        360
tctgatgagc agttgaaatc tggaactgcc tctgttgtgt gcctgctgaa taacttctat        420
cccagagagg ccaaagtaca gtggaaggtg gataacgccc tccaatcggg taactcccag        480
gagagtgtca cagagcagga cagcaaggac agcacctaca gcctcagcag caccctgacg        540
ctgagcaaag cagactacga aaacacaaa gtctacgcct gcgaagtcac ccatcagggc        600
ctgagctcgc ccgtcacaaa gagcttcaac aggggagagt gttag                       645
```

<210> SEQ ID NO 40
<211> LENGTH: 214
<212> TYPE: PRT
<213> ORGANISM: Homo sapiens

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ser Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 360
<212> TYPE: DNA
<213> ORGANISM: Homo sapiens

<400> SEQUENCE: 41

```
caggtgcagc tggtggagtc tgggggaggc gtggtccagc ctggggggtc cctgagactc        60
```

```
tcctgtgcag cctctggatt caacttcaga aactttggca tgcactgggt ccgccaggct    120
ccaggcaagg ggctggaatg ggtggcaggt atattatatg atggaagtag taaatactat    180
gcagactccg tgaaggaccg attcaccatc tccagagaca attccaagaa cacgctgttt    240
ctgcaaatga acagcctgag agctgaggac acggctatgt attactgtgc gaaagaggag    300
gacacagcca tggttccttt tgattcctgg ggcccgggaa ccctggtcac cgtctcctca    360
```

<210> SEQ ID NO 42
<211> LENGTH: 120
<212> TYPE: PRT
<213> ORGANISM: Homo sapiens

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Arg Asn Phe
            20                  25                  30

Gly Met His Trp Val Arg Gln Ala Pro Gly Lys Gly Leu Glu Trp Val
        35                  40                  45

Ala Gly Ile Leu Tyr Asp Gly Ser Ser Lys Tyr Tyr Ala Asp Ser Val
    50                  55                  60

Lys Asp Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Met Tyr Tyr Cys
                85                  90                  95

Ala Lys Glu Glu Asp Thr Ala Met Val Pro Phe Asp Ser Trp Gly Pro
            100                 105                 110

Gly Thr Leu Val Thr Val Ser Ser
        115                 120

<210> SEQ ID NO 43
<211> LENGTH: 24
<212> TYPE: DNA
<213> ORGANISM: Homo sapiens

<400> SEQUENCE: 43
ggattcaact tcagaaactt tggc                                            24

<210> SEQ ID NO 44
<211> LENGTH: 8
<212> TYPE: PRT
<213> ORGANISM: Homo sapiens

<400> SEQUENCE: 44

Gly Phe Asn Phe Arg Asn Phe Gly
1               5

<210> SEQ ID NO 45
<211> LENGTH: 24
<212> TYPE: DNA
<213> ORGANISM: Homo sapiens

<400> SEQUENCE: 45
atattatatg atggaagtag taaa                                            24

<210> SEQ ID NO 46
<211> LENGTH: 8
<212> TYPE: PRT
<213> ORGANISM: Homo sapiens

```
<400> SEQUENCE: 46

Ile Leu Tyr Asp Gly Ser Ser Lys
1               5

<210> SEQ ID NO 47
<211> LENGTH: 39
<212> TYPE: DNA
<213> ORGANISM: Homo sapiens

<400> SEQUENCE: 47
gcgaaagagg aggacacagc catggttcct tttgattcc                              39

<210> SEQ ID NO 48
<211> LENGTH: 13
<212> TYPE: PRT
<213> ORGANISM: Homo sapiens

<400> SEQUENCE: 48

Ala Lys Glu Glu Asp Thr Ala Met Val Pro Phe Asp Ser
1               5                   10

<210> SEQ ID NO 49
<211> LENGTH: 321
<212> TYPE: DNA
<213> ORGANISM: Homo sapiens

<400> SEQUENCE: 49
gacatccagt tgacccagtc tccatccttc ctgtctgctt ctgtaggaga cagagtcacc       60
atcacttgct gggccagtca gggcattagt agttatttag cctggtatca gcaaaaacca     120
gggaaagccc ctaccctcct gatctatgct gcgtccactt tgcaaagtgg ggtcccatca     180
aggttcagcg gcagtggatc tgggacagaa ttcactctca caatcagcag cctgcagcct     240
gaagattttg caagttatta ctgtcaacag cttaagagtt acccgctcac tttcggcgga     300
gggaccaagg tggagatcaa a                                               321

<210> SEQ ID NO 50
<211> LENGTH: 107
<212> TYPE: PRT
<213> ORGANISM: Homo sapiens

<400> SEQUENCE: 50

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Thr Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Tyr Cys Gln Gln Leu Lys Ser Tyr Pro Leu
                85                  90                  95

Thr Phe Gly Gly Gly Thr Lys Val Glu Ile Lys
            100                 105

<210> SEQ ID NO 51
<211> LENGTH: 18
<212> TYPE: DNA
```

<213> ORGANISM: Homo sapiens

<400> SEQUENCE: 51
cagggcatta gtagttat                                                 18

<210> SEQ ID NO 52
<211> LENGTH: 6
<212> TYPE: PRT
<213> ORGANISM: Homo sapiens

<400> SEQUENCE: 52

Gln Gly Ile Ser Ser Tyr
1               5

<210> SEQ ID NO 53
<211> LENGTH: 9
<212> TYPE: DNA
<213> ORGANISM: Homo sapiens

<400> SEQUENCE: 53 gctgcgtcc                                                            9

<210> SEQ ID NO 54
<211> LENGTH: 3
<212> TYPE: PRT
<213> ORGANISM: Homo sapiens

<400> SEQUENCE: 54

Ala Ala Ser
1

<210> SEQ ID NO 55
<211> LENGTH: 27
<212> TYPE: DNA
<213> ORGANISM: Homo sapiens

<400> SEQUENCE: 55
caacagctta agagttaccc gctcact                                       27

<210> SEQ ID NO 56
<211> LENGTH: 9
<212> TYPE: PRT
<213> ORGANISM: Homo sapiens

<400> SEQUENCE: 56

Gln Gln Leu Lys Ser Tyr Pro Leu Thr
1               5

<210> SEQ ID NO 57
<211> LENGTH: 1344
<212> TYPE: DNA
<213> ORGANISM: Homo sapiens

<400> SEQUENCE: 57
caggtgcagc tggtggagtc tgggggaggc gtggtccagc ctggggaggtc cctgagactc     60 tcctgtgcag cctctggatt caacttcaga aactttggca tgcactgggt ccgccaggct    120
ccaggcaagg ggctggaatg ggtggcaggt atattatatg atggaagtag taaatactat    180
gcagactccg tgaaggaccg attcaccatc tccagagaca attccaagaa cacgctgttt    240
ctgcaaatga acagcctgag agctgaggac acggctatgt attactgtgc gaaagaggag    300
gacacagcca tggttccttt tgattcctgg ggccgggaa ccctggtcac cgtctcctca    360

```
gcctccacca agggcccatc ggtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accctgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggctc accgtggaca gagcaggtg gcaggagggg    1260 aatgtcttct catgctccgt gatgcatgag gctctgcaca accactacac acagaagtcc    1320 ctctcccctgt ctctgggtaa atga                                          1344

<210> SEQ ID NO 58
<211> LENGTH: 447
<212> TYPE: PRT
<213> ORGANISM: Homo sapiens

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Arg Asn Phe
            20                  25                  30

Gly Met His Trp Val Arg Gln Ala Pro Gly Lys Gly Leu Glu Trp Val
        35                  40                  45

Ala Gly Ile Leu Tyr Asp Gly Ser Ser Lys Tyr Tyr Ala Asp Ser Val
    50                  55                  60

Lys Asp Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Met Tyr Tyr Cys
                85                  90                  95

Ala Lys Glu Glu Asp Thr Ala Met Val Pro Phe Asp Ser Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
```

```
             195                 200                 205
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 59
<211> LENGTH: 645
<212> TYPE: DNA
<213> ORGANISM: Homo sapiens

<400> SEQUENCE: 59
gacatccagt tgacccagtc tccatccttc ctgtctgctt ctgtaggaga cagagtcacc      60
atcacttgct gggccagtca gggcattagt agttatttag cctggtatca gcaaaaacca    120
gggaaagccc ctaccctcct gatctatgct gcgtccactt tgcaaagtgg ggtcccatca    180
aggttcagcg gcagtggatc tgggacagaa ttcactctca caatcagcag cctgcagcct    240
gaagattttg caagttatta ctgtcaacag cttaagagtt acccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacactgacg    540
ctgagcaaag cagactacga gaaacacaaa gtctacgcct gcgaagtcac ccatcagggc    600
ctgagctcgc ccgtcacaaa gagcttcaac aggggagagt gttag                     645

<210> SEQ ID NO 60
```

```
<211> LENGTH: 214
<212> TYPE: PRT
<213> ORGANISM: Homo sapiens

<400> SEQUENCE: 60
```

| | | | | | | | | | | | | | | | |
|---|---|---|---|---|---|---|---|---|---|---|---|---|---|---|---|
| Asp | Ile | Gln | Leu | Thr | Gln | Ser | Pro | Ser | Phe | Leu | Ser | Ala | Ser | Val | Gly |
| 1 | | | | 5 | | | | | 10 | | | | | 15 | |
| Asp | Arg | Val | Thr | Ile | Thr | Cys | Trp | Ala | Ser | Gln | Gly | Ile | Ser | Ser | Tyr |
| | | | 20 | | | | | 25 | | | | | 30 | | |
| Leu | Ala | Trp | Tyr | Gln | Gln | Lys | Pro | Gly | Lys | Ala | Pro | Thr | Leu | Leu | Ile |
| | | | | 35 | | | | | 40 | | | | | 45 | |
| Tyr | Ala | Ala | Ser | Thr | Leu | Gln | Ser | Gly | Val | Pro | Ser | Arg | Phe | Ser | Gly |
| | 50 | | | | | 55 | | | | | 60 | | | | |
| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Ser | Tyr | Tyr | Cys | Gln | Gln | Leu | Lys | Ser | Tyr | Pro | Leu |
| | | | | 85 | | | | | 90 | | | | | 95 | |
| Thr | Phe | Gly | Gly | Gly | Thr | Lys | Val | Glu | Ile | Lys | Arg | Thr | Val | Ala | Ala |
| | | | | 100 | | | | | 105 | | | | | 110 | |
| Pro | Ser | Val | Phe | Ile | Phe | Pro | Pro | Ser | Asp | Glu | Gln | Leu | Lys | Ser | Gly |
| | | | | 115 | | | | | 120 | | | | | 125 | |
| Thr | Ala | Ser | Val | Val | Cys | Leu | Leu | Asn | Asn | Phe | Tyr | Pro | Arg | Glu | Ala |
| | 130 | | | | | 135 | | | | | 140 | | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | | 180 | | | | | 185 | | | | | 190 | |
| Ala | Cys | Glu | Val | Thr | His | Gln | Gly | Leu | Ser | Ser | Pro | Val | Thr | Lys | Ser |
| | | | | 195 | | | | | 200 | | | | | 205 | |
| Phe | Asn | Arg | Gly | Glu | Cys | | | | | | | | | | |
| | | | | 210 | | | | | | | | | | | |

```
<210> SEQ ID NO 61
<211> LENGTH: 366
<212> TYPE: DNA
<213> ORGANISM: Homo sapiens

<400> SEQUENCE: 61
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt ggtttcatct attacagtgg gaagacctac     180
tacaacccgt ccctcaagag tcgacttacc atctcagtag acacgtctaa gagccagttc     240
tccctgaagc tgaggtctgt gactgccgcg gacacggccg tgtattactg tgcgagactg     300
gggtataccc actcggccgg gtggttcgac ccctggggcc agggaaccct ggtcaccgtc     360
tcctca                                                                366

<210> SEQ ID NO 62
<211> LENGTH: 122
<212> TYPE: PRT
<213> ORGANISM: Homo sapiens

<400> SEQUENCE: 62
```

| | | | | | | | | | | | | | | | |
|---|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gln |

```
              1               5              10              15
            Thr Leu Ser Leu Thr Cys Thr Val Ser Gly Gly Ser Ile Ser Ser Gly
                             20                  25                  30

Gly Tyr Tyr Trp Ser Trp Ile Arg Gln His Pro Gly Lys Gly Leu Glu
                         35                  40                  45

Trp Ile Gly Phe Ile Tyr Tyr Ser Gly Lys Thr Tyr Tyr Asn Pro Ser
                50                  55                  60

Leu Lys Ser Arg Leu Thr Ile Ser Val Asp Thr Ser Lys Ser Gln Phe
             65                  70                  75                  80

Ser Leu Lys Leu Arg Ser Val Thr Ala Ala Asp Thr Ala Val Tyr Tyr
                             85                  90                  95

Cys Ala Arg Leu Gly Tyr Thr Asn Ser Ala Gly Trp Phe Asp Pro Trp
                        100                 105                 110

Gly Gln Gly Thr Leu Val Thr Val Ser Ser
                        115                 120
```

<210> SEQ ID NO 63
<211> LENGTH: 30
<212> TYPE: DNA
<213> ORGANISM: Homo sapiens

<400> SEQUENCE: 63
ggtggctcca tcagcagtgg tggttactac                              30

<210> SEQ ID NO 64
<211> LENGTH: 10
<212> TYPE: PRT
<213> ORGANISM: Homo sapiens

<400> SEQUENCE: 64

Gly Gly Ser Ile Ser Ser Gly Gly Tyr Tyr
 1               5                  10

<210> SEQ ID NO 65
<211> LENGTH: 21
<212> TYPE: DNA
<213> ORGANISM: Homo sapiens

<400> SEQUENCE: 65
atctattaca gtgggaagac c                                       21

<210> SEQ ID NO 66
<211> LENGTH: 7
<212> TYPE: PRT
<213> ORGANISM: Homo sapiens

<400> SEQUENCE: 66

Ile Tyr Tyr Ser Gly Lys Thr
 1               5

<210> SEQ ID NO 67
<211> LENGTH: 42
<212> TYPE: DNA
<213> ORGANISM: Homo sapiens

<400> SEQUENCE: 67
gcgagactgg ggtataccaa ctcggccggg tggttcgacc cc                 42

<210> SEQ ID NO 68
<211> LENGTH: 14
<212> TYPE: PRT

```
<213> ORGANISM: Homo sapiens

<400> SEQUENCE: 68

Ala Arg Leu Gly Tyr Thr Asn Ser Ala Gly Trp Phe Asp Pro
1               5                   10

<210> SEQ ID NO 69
<211> LENGTH: 321
<212> TYPE: DNA
<213> ORGANISM: Homo sapiens

<400> SEQUENCE: 69
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaacctcct gatctatgct gcatccagtt tgcaaagtgg ggtcccatca     180
aggttcagtg gcagtggatc tgggacagat ttcactctca ccatcagcag tctgcaacct     240
gaagatcttg caacttacta ctgtcaacag agttacacaa ccccattcac tttcggccct     300
gggaccaaag tggatatcaa a                                               321

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Thr Thr Pro Phe
                85                  90                  95

Thr Phe Gly Pro Gly Thr Lys Val Asp Ile Lys
            100                 105

<210> SEQ ID NO 71
<211> LENGTH: 18
<212> TYPE: DNA
<213> ORGANISM: Homo sapiens

<400> SEQUENCE: 71
cagagcatta gcagctat                                                    18

<210> SEQ ID NO 72
<211> LENGTH: 6
<212> TYPE: PRT
<213> ORGANISM: Homo sapiens

<400> SEQUENCE: 72

Gln Ser Ile Ser Ser Tyr
1               5

<210> SEQ ID NO 73
```

-continued

```
<211> LENGTH: 9
<212> TYPE: DNA
<213> ORGANISM: Homo sapiens

<400> SEQUENCE: 73 gctgcatcc                                                                 9

<210> SEQ ID NO 74
<211> LENGTH: 27
<212> TYPE: DNA
<213> ORGANISM: Homo sapiens

<400> SEQUENCE: 74
caacagagtt acacaacccc attcact                                            27

<210> SEQ ID NO 75
<211> LENGTH: 9
<212> TYPE: PRT
<213> ORGANISM: Homo sapiens

<400> SEQUENCE: 75

Gln Gln Ser Tyr Thr Thr Pro Phe Thr
1               5

<210> SEQ ID NO 76
<211> LENGTH: 1350
<212> TYPE: DNA
<213> ORGANISM: Homo sapiens

<400> SEQUENCE: 76
caggtgcagc tgcaggagtc gggcccagga ctggtgaagc cttcacagac cctgtccctc        60
acctgcactg tctctggtgg ctccatcagc agtggtggtt actactggag ctggatccgc       120
cagcacccag ggaagggcct ggagtggatt ggtttcatct attacagtgg gaagacctac       180
tacaacccgt ccctcaagag tcgacttacc atctcagtag acacgtctaa gagccagttc       240
tccctgaagc tgaggtctgt gactgccgcg gacacggccg tgtattactg tgcgagactg       300
gggtatacca actcggccgg gtggttcgac cctgggggcc agggaaccct ggtcaccgtc       360
tcctcagcct ccaccaaggg cccatcggtc ttccccctgg cgccctgctc caggagcacc       420
tccgagagca cagccgccct gggctgcctg gtcaaggact acttccccga accggtgacg       480
gtgtcgtgga actcaggcgc cctgaccagc ggcgtgcaca ccttcccggc tgtcctacag       540
tcctcaggac tctactccct cagcagcgtg gtgaccgtgc cctccagcag cttgggcacg       600
aagacctaca cctgcaacgt agatcacaag cccagcaaca ccaaggtgga caagagagtt       660
gagtccaaat atggtccccc atgcccaccc tgcccagcac ctgagttcct ggggggacca       720
tcagtcttcc tgttccccc aaaacccaag gacactctca tgatctcccg gacccctgag       780
gtcacgtgcg tggtggtgga cgtgagccag gaagacccc g aggtccagtt caactggtac       840
gtggatggcg tggaggtgca taatgccaag acaaagccgc gggaggagca gttcaacagc       900
acgtaccgtg tggtcagcgt cctcaccgtc ctgcaccagg actggctgaa cggcaaggag       960
tacaagtgca aggtctccaa caaaggcctc ccgtcctcca tcgagaaaac catctccaaa      1020
gccaaagggc agccccgaga gccacaggtg tacaccctgc ccccatccca ggaggagatg      1080
accaagaacc aggtcagcct gacctgcctg gtcaaaggct tctacccag c gacatcgcc      1140 gtggagtggg agagcaatgg gcagccggag aacaactaca agaccacgcc tcccgtgctg      1200
gactccgacg gctccttctt cctctacagc aggctcaccg tggacaagag caggtggcag      1260
```
gaggggaatg tcttctcatg ctccgtgatg catgaggctc tgcacaacca ctacacacag    1320
aagtccctct ccctgtctct gggtaaatga                                     1350

<210> SEQ ID NO 77
<211> LENGTH: 449
<212> TYPE: PRT
<213> ORGANISM: Homo sapiens

<400> SEQUENCE: 77

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Phe Ile Tyr Tyr Ser Gly Lys Thr Tyr Tyr Asn Pro Ser
    50                  55                  60

Leu Lys Ser Arg Leu Thr Ile Ser Val Asp Thr Ser Lys Ser Gln Phe
65                  70                  75                  80

Ser Leu Lys Leu Arg Ser Val Thr Ala Ala Asp Thr Ala Val Tyr Tyr
                85                  90                  95

Cys Ala Arg Leu Gly Tyr Thr Asn Ser Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
```

```
            355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 78
<211> LENGTH: 645
<212> TYPE: DNA
<213> ORGANISM: Homo sapiens

<400> SEQUENCE: 78
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaacctcct gatctatgct gcatccagtt tgcaaagtgg ggtcccatca     180
aggttcagtg gcagtggatc tgggacagat ttcactctca ccatcagcag tctgcaacct     240
gaagatcttg caacttacta ctgtcaacag agttacacaa ccccattcac tttcggccct     300
gggaccaaag tggatatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645

<210> SEQ ID NO 79
<211> LENGTH: 214
<212> TYPE: PRT
<213> ORGANISM: Homo sapiens

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Thr Thr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
```

|     |     |     |     | 115 |     |     |     | 120 |     |     |     | 125 |     |

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 80
<211> LENGTH: 375
<212> TYPE: DNA
<213> ORGANISM: Homo sapiens

<400> SEQUENCE: 80
gaggtgcagc tggtggagtc ggggggaggt tggtaaagc ctgggggtc ccttagactc        60 tcctgtgcag cctctggatt cactttcagt accgcctgga tgagctgggt ccgccagtct      120
ccagggaggg gctggagtg ggttggccgt atgaaaagca agactgatgg tgggacaaca       180
ttctacgctg cacccgtgaa aggcagattc accatctcaa gagatgattc aaaaaacaca     240
ctgtatctgc aaatgaacag cctgaaaacc gaggacacac ccgtttatta ctgtaccaca     300
ggattagtcc cggccttcta taagtactac ggcgtggacg tctggggcca agggaccacg     360
gtcaccgtct cctca                                                      375

<210> SEQ ID NO 81
<211> LENGTH: 125
<212> TYPE: PRT
<213> ORGANISM: Homo sapiens

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Ala
            20                  25                  30

Trp Met Ser Trp Val Arg Gln Ser Pro Gly Arg Gly Leu Glu Trp Val
        35                  40                  45

Gly Arg Met Lys Ser Lys Thr Asp Gly Gly Thr Thr Phe Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Leu Val Pro Ala Phe Tyr Lys Tyr Tyr Gly Val
            100                 105                 110

Asp Val Trp Gly Gln Gly Thr Thr Val Thr Val Ser Ser
            115                 120                 125

<210> SEQ ID NO 82
<211> LENGTH: 24
<212> TYPE: DNA
<213> ORGANISM: Homo sapiens

<400> SEQUENCE: 82
ggattcactt tcagtaccgc ctgg                                     24

<210> SEQ ID NO 83
<211> LENGTH: 8
<212> TYPE: PRT
<213> ORGANISM: Homo sapiens

<400> SEQUENCE: 83

Gly Phe Thr Phe Ser Thr Ala Trp
1               5

<210> SEQ ID NO 84
<211> LENGTH: 30
<212> TYPE: DNA
<213> ORGANISM: Homo sapiens

<400> SEQUENCE: 84
atgaaaagca agactgatgg tgggacaaca                               30

<210> SEQ ID NO 85
<211> LENGTH: 10
<212> TYPE: PRT
<213> ORGANISM: Homo sapiens

<400> SEQUENCE: 85

Met Lys Ser Lys Thr Asp Gly Gly Thr Thr
1               5                   10

<210> SEQ ID NO 86
<211> LENGTH: 48
<212> TYPE: DNA
<213> ORGANISM: Homo sapiens

<400> SEQUENCE: 86
accacaggat tagtcccggc cttctataag tactacggcg tggacgtc           48

<210> SEQ ID NO 87
<211> LENGTH: 16
<212> TYPE: PRT
<213> ORGANISM: Homo sapiens

<400> SEQUENCE: 87

Thr Thr Gly Leu Val Pro Ala Phe Tyr Lys Tyr Tyr Gly Val Asp Val
1               5                   10                  15

<210> SEQ ID NO 88
<211> LENGTH: 318
<212> TYPE: DNA
<213> ORGANISM: Homo sapiens

<400> SEQUENCE: 88
gacatccaga tgacccagtc tccatcctcc ctgtctgcat ctgtaggaga cagaatcacc    60
atcacttgcc aggcgagtca ggacattacc aactatttaa attggtatca gcagaagcca   120
gggaaagccc ctaacctcct gatctacgat gcatccaatt tggttacagg ggtcccatca   180
aggttcagtg gaagtggatc tgggacagat tttactttca ccatcctcag cctgcagcct   240
gaagatattg caacatatta ctgtcaacag tatgatagtc tcctcacttt cggccctggg   300
accaaagtgg atatcaaa                                                 318

<210> SEQ ID NO 89
<211> LENGTH: 106
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Ile Thr Ile Thr Cys Gln Ala Ser Gln Asp Ile Thr Asn Tyr
            20                  25                  30

Leu Asn Trp Tyr Gln Gln Lys Pro Gly Lys Ala Pro Asn Leu Leu Ile
        35                  40                  45

Tyr Asp Ala Ser Asn Leu Val Thr Gly Val Pro Ser Arg Phe Ser Gly
    50                  55                  60

Ser Gly Ser Gly Thr Asp Phe Thr Phe Thr Ile Leu Ser Leu Gln Pro
65                  70                  75                  80

Glu Asp Ile Ala Thr Tyr Tyr Cys Gln Gln Tyr Asp Ser Leu Leu Thr
                85                  90                  95

Phe Gly Pro Gly Thr Lys Val Asp Ile Lys
            100                 105

<210> SEQ ID NO 90
<211> LENGTH: 18
<212> TYPE: DNA
<213> ORGANISM: Homo sapiens

<400> SEQUENCE: 90
caggacatta ccaactat                                                    18

<210> SEQ ID NO 91
<211> LENGTH: 6
<212> TYPE: PRT
<213> ORGANISM: Homo sapiens

<400> SEQUENCE: 91

Gln Asp Ile Thr Asn Tyr
1               5

<210> SEQ ID NO 92
<211> LENGTH: 9
<212> TYPE: DNA
<213> ORGANISM: Homo sapiens

<400> SEQUENCE: 92 gatgcatcc                                                               9

<210> SEQ ID NO 93
<211> LENGTH: 3
<212> TYPE: PRT
<213> ORGANISM: Homo sapiens

<400> SEQUENCE: 93

Asp Ala Ser
1

<210> SEQ ID NO 94
<211> LENGTH: 24
<212> TYPE: DNA
<213> ORGANISM: Homo sapiens

<400> SEQUENCE: 94
caacagtatg atagtctcct cact                                             24

<210> SEQ ID NO 95
<211> LENGTH: 8
<212> TYPE: PRT
<213> ORGANISM: Homo sapiens

<400> SEQUENCE: 95

Gln Gln Tyr Asp Ser Leu Leu Thr
1               5

<210> SEQ ID NO 96
<211> LENGTH: 1359
<212> TYPE: DNA
<213> ORGANISM: Homo sapiens

<400> SEQUENCE: 96

```
gaggtgcagc tggtggagtc ggggggaggt ttggtaaagc ctgggggtc ccttagactc      60
tcctgtgcag cctctggatt cactttcagt accgcctgga tgagctgggt ccgccagtct    120
ccagggaggg ggctggagtg ggttggccgt atgaaaagca agactgatgg tgggacaaca    180
ttctacgctg cacccgtgaa aggcagattc accatctcaa gagatgattc aaaaaacaca    240
ctgtatctgc aaatgaacag cctgaaaacc gaggacacag ccgtttatta ctgtaccaca    300
ggattagtcc cggccttcta taagtactac ggcgtggacg tctggggcca agggaccacg    360
gtcaccgtct cctcagcctc caccaagggc ccatcggtct tccccctggc gccctgctcc    420
aggagcacct ccgagagcac agccgccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcacga gacctacac ctgcaacgta atcacaagc ccagcaacac caaggtggac      660
aagagagttg agtccaaata tggtccccca tgcccaccct gcccagcacc tgagttcctg    720
gggggaccat cagtcttcct gttcccccca aaacccaagg acactctcat gatctcccgg    780
acccctgagg tcacgtgcgt ggtggtggac gtgagccagg aagaccccga ggtccagttc    840
aactggtacg tggatggcgt ggaggtgcat aatgccaaga caaagccgcg ggaggagcag    900
ttcaacagca cgtaccgtgt ggtcagcgtc ctcaccgtcc tgcaccagga ctggctgaac    960
ggcaaggagt acaagtgcaa ggtctccaac aaaggcctcc cgtcctccat cgagaaaacc   1020
atctccaaag ccaaagggca gccccgagag ccacaggtgt acaccctgcc cccatcccag   1080
gaggagatga ccaagaacca ggtcagcctg acctgcctgg tcaaaggctt ctaccccagc   1140
gacatcgccg tggagtggga gagcaatggg cagccggaga caactacaa gaccacgcct    1200
cccgtgctgg actccgacgg ctccttcttc ctctacagca ggctcaccgt ggacaagagc   1260
aggtggcagg aggggaatgt cttctcatgc tccgtgatgc atgaggctct gcacaaccac   1320
tacacacaga gtccctctc cctgtctctg ggtaaatga                           1359
```

<210> SEQ ID NO 97
<211> LENGTH: 452
<212> TYPE: PRT
<213> ORGANISM: Homo sapiens

<400> SEQUENCE: 97

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Ala
            20                  25                  30

```
Trp Met Ser Trp Val Arg Gln Ser Pro Gly Arg Gly Leu Glu Trp Val
        35                  40                  45

Gly Arg Met Lys Ser Lys Thr Asp Gly Gly Thr Thr Phe Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly Leu Val Pro Ala Phe Lys Tyr Tyr Gly Val
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445
```

```
Ser Leu Gly Lys
    450
```

<210> SEQ ID NO 98
<211> LENGTH: 642
<212> TYPE: DNA
<213> ORGANISM: Homo sapiens

<400> SEQUENCE: 98

```
gacatccaga tgacccagtc tccatcctcc ctgtctgcat ctgtaggaga cagaatcacc      60
atcacttgcc aggcgagtca ggacattacc aactatttaa attggtatca gcagaagcca     120
gggaaagccc ctaacctcct gatctacgat gcatccaatt tggttacagg ggtcccatca     180
aggttcagtg aagtggatc tgggacagat tttactttca ccatcctcag cctgcagcct     240
gaagatattg caacatatta ctgtcaacag tatgatagtc tcctcacttt cggccctggg     300
accaaagtgg atatcaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                        642
```

<210> SEQ ID NO 99
<211> LENGTH: 213
<212> TYPE: PRT
<213> ORGANISM: Homo sapiens

<400> SEQUENCE: 99

```
Asp Ile Gln Met Thr Gln Ser Pro Ser Ser Leu Ser Ala Ser Val Gly
1               5                   10                  15

Asp Arg Ile Thr Ile Thr Cys Gln Ala Ser Gln Asp Ile Thr Asn Tyr
            20                  25                  30

Leu Asn Trp Tyr Gln Gln Lys Pro Gly Lys Ala Pro Asn Leu Leu Ile
        35                  40                  45

Tyr Asp Ala Ser Asn Leu Val Thr Gly Val Pro Ser Arg Phe Ser Gly
    50                  55                  60

Ser Gly Ser Gly Thr Asp Phe Thr Phe Thr Ile Leu Ser Leu Gln Pro
65                  70                  75                  80

Glu Asp Ile Ala Thr Tyr Tyr Cys Gln Gln Tyr Asp Ser Leu Leu Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 100
<211> LENGTH: 369
<212> TYPE: DNA
<213> ORGANISM: Homo sapiens

<400> SEQUENCE: 100
gaggtgcagc tggtggagtc tgggggaggc ttggtccagc ctggggggtc cctgagactc      60
tcctgtgcag cctctggatt caccttcaat aactatgcaa tgcactgggt ccgccaggct     120
cccgggaagg gactggaata tgtttcatct attagtagta gtgggggtag cacatattat     180
gaagactctg tgaagggcag attcaccatc tccagagaca attccaagaa cacgctgtat     240
cttcaaatgg gcagcctgag agctgaggac atggctgtgt attactgtgc gagatcattc     300
tatggttcgg ggacttatta tgatactttt gatatgtggg gccaagggac aatggtcacc     360
gtctcttca                                                             369

<210> SEQ ID NO 101
<211> LENGTH: 123
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met His Trp Val Arg Gln Ala Pro Gly Lys Gly Leu Glu Tyr Val
        35                  40                  45

Ser Ser Ile Ser Ser Ser Gly Gly Ser Thr Tyr Tyr Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Ser Phe Tyr Gly Ser Gly Thr Tyr Tyr Asp Thr Phe Asp Met
            100                 105                 110

Trp Gly Gln Gly Thr Met Val Thr Val Ser Ser
        115                 120

<210> SEQ ID NO 102
<211> LENGTH: 24
<212> TYPE: DNA
<213> ORGANISM: Homo sapiens

<400> SEQUENCE: 102
ggattcacct tcaataacta tgca                                             24

<210> SEQ ID NO 103
<211> LENGTH: 8
<212> TYPE: PRT
<213> ORGANISM: Homo sapiens

<400> SEQUENCE: 103

Gly Phe Thr Phe Asn Asn Tyr Ala
1               5

<210> SEQ ID NO 104
<211> LENGTH: 24
<212> TYPE: DNA
<213> ORGANISM: Homo sapiens

<400> SEQUENCE: 104
attagtagta gtgggggtag caca                                          24

<210> SEQ ID NO 105
<211> LENGTH: 8
<212> TYPE: PRT
<213> ORGANISM: Homo sapiens

<400> SEQUENCE: 105

Ile Ser Ser Ser Gly Gly Ser Thr
1               5

<210> SEQ ID NO 106
<211> LENGTH: 48
<212> TYPE: DNA
<213> ORGANISM: Homo sapiens

<400> SEQUENCE: 106
gcgagatcat tctatggttc ggggacttat tatgatactt ttgatatg                48

<210> SEQ ID NO 107
<211> LENGTH: 16
<212> TYPE: PRT
<213> ORGANISM: Homo sapiens

<400> SEQUENCE: 107

Ala Arg Ser Phe Tyr Gly Ser Gly Thr Tyr Tyr Asp Thr Phe Asp Met
1               5                   10                  15

<210> SEQ ID NO 108
<211> LENGTH: 321
<212> TYPE: DNA
<213> ORGANISM: Homo sapiens

<400> SEQUENCE: 108
gacatccaga tgacccagtc tccatcctcc ctgtctgcat ctataggaga cagagtcacc     60
atcacttgcc gggcaagtca gagcattagc aggtatttaa attggtatca gcagaaacca    120
gggaaagccc ctaagctcct gatctatgct gcatccagtt tgcaaagtgg ggtcccatca    180
aggttcagtg ccagtggatc tgggacagat tcactctca ccatcagcag tctgcaacct    240
gaagattttg caacttacta ctgtcaacag agttacagta ccccgttcac ttttggccag    300
gggaccaagc tggagatcaa a                                              321

<210> SEQ ID NO 109
<211> LENGTH: 107
<212> TYPE: PRT
<213> ORGANISM: Homo sapiens

<400> SEQUENCE: 109

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Ser Ile Ser Arg Tyr
                20                  25                  30

Leu Asn Trp Tyr Gln Gln Lys Pro Gly Lys Ala Pro Lys Leu Leu Ile
            35                  40                  45

```
Tyr Ala Ala Ser Ser Leu Gln Ser Gly Val Pro Ser Arg Phe Ser Ala
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Phe
                 85                  90                  95
Thr Phe Gly Gln Gly Thr Lys Leu Glu Ile Lys
            100                 105
```

<210> SEQ ID NO 110
<211> LENGTH: 18
<212> TYPE: DNA
<213> ORGANISM: Homo sapiens

<400> SEQUENCE: 110
cagagcatta gcaggtat                                                   18

<210> SEQ ID NO 111
<211> LENGTH: 6
<212> TYPE: PRT
<213> ORGANISM: Homo sapiens

<400> SEQUENCE: 111

```
Gln Ser Ile Ser Arg Tyr
 1               5
```

<210> SEQ ID NO 112
<211> LENGTH: 27
<212> TYPE: DNA
<213> ORGANISM: Homo sapiens

<400> SEQUENCE: 112
caacagagtt acagtacccc gttcact                                         27

<210> SEQ ID NO 113
<211> LENGTH: 9
<212> TYPE: PRT
<213> ORGANISM: Homo sapiens

<400> SEQUENCE: 113

```
Gln Gln Ser Tyr Ser Thr Pro Phe Thr
 1               5
```

<210> SEQ ID NO 114
<211> LENGTH: 1353
<212> TYPE: DNA
<213> ORGANISM: Homo sapiens

<400> SEQUENCE: 114
gaggtgcagc tggtggagtc tgggggaggc ttggtccagc ctggggggtc cctgagactc     60
tcctgtgcag cctctggatt caccttcaat aactatgcaa tgcactgggt ccgccaggct    120
cccgggaagg gactggaata tgtttcatct attagtagta gtgggggtag cacatattat    180
gaagactctg tgaagggcag attcaccatc tccagagaca attccaagaa cacgctgtat    240
cttcaaatgg gcagcctgag agctgaggac atggctgtgt attactgtgc gagatcattc    300
tatggttcgg ggacttatta tgatactttt gatatgtggg gccaagggac aatggtcacc    360
gtctcttcag cctccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540

```
cagtcctcag gactctactc cctcagcagc gtggtgaccg tgccctccag cagcttgggc    600
acgaagacct acacctgcaa cgtagatcac aagcccagca acaccaaggt ggacaagaga    660
gttgagtcca aatatggtcc cccatgccca ccctgcccag cacctgagtt cctgggggga    720
ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag gcagccccg agagccacag gtgtacaccc tgcccccatc ccaggaggag    1080
atgaccaaga accaggtcag cctgacctgc ctggtcaaag gcttctaccc cagcgacatc   1140
gccgtggagt gggagagcaa tgggcagccg gagaacaact acaagaccac gcctcccgtg   1200
ctggactccg acggctcctt cttcctctac agcaggctca ccgtggacaa gagcaggtgg   1260
caggagggga atgtcttctc atgctccgtg atgcatgagg ctctgcacaa ccactacaca   1320
cagaagtccc tctccctgtc tctgggtaaa tga                                1353
```

<210> SEQ ID NO 115
<211> LENGTH: 450
<212> TYPE: PRT
<213> ORGANISM: Homo sapiens

<400> SEQUENCE: 115

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
            20                  25                  30

Ala Met His Trp Val Arg Gln Ala Pro Gly Lys Gly Leu Glu Tyr Val
        35                  40                  45

Ser Ser Ile Ser Ser Gly Gly Ser Thr Tyr Tyr Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Ser Phe Tyr Gly Ser Gly Thr Tyr Tyr Asp Thr Phe Asp Met
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220
```

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
    450

<210> SEQ ID NO 116
<211> LENGTH: 645
<212> TYPE: DNA
<213> ORGANISM: Homo sapiens

<400> SEQUENCE: 116
gacatccaga tgacccagtc tccatcctcc ctgtctgcat ctataggaga cagagtcacc      60
atcacttgcc gggcaagtca gagcattagc aggtatttaa attggtatca gcagaaacca     120
gggaaagccc ctaagctcct gatctatgct gcatccagtt tgcaaagtgg ggtcccatca     180
aggttcagtg ccagtggatc tgggacagat ttcactctca ccatcagcag tctgcaacct     240
gaagattttg caacttacta ctgtcaacag agttacagta ccccgttcac ttttggccag     300
gggaccaagc tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga gaaacacaaa gtctacgcct gcgaagtcac ccatcagggc     600
ctgagctcgc ccgtcacaaa gagcttcaac aggggagagt gttag                     645

<210> SEQ ID NO 117
<211> LENGTH: 214
<212> TYPE: PRT

<213> ORGANISM: Homo sapiens

<400> SEQUENCE: 117

```
Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Ala
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 118
<211> LENGTH: 342
<212> TYPE: DNA
<213> ORGANISM: Homo sapiens

<400> SEQUENCE: 118

```
caggtgcagc tggtggagtc tgggggagac ttggtcaagc ctgggggtc cctgagactc      60
tcctgtgcaa cctctggatt caccttcagt gactttttaca tgacctggat ccgccaggct   120
ccagggaagg gattggagtg gatttcatat ataagtaata gtgggagtat cgtgaagtac    180
gcagactctg tgaagggccg attcaccatt tccagggata acgccaagaa ctcactgtat    240
ctgcaaatga acagcctgag agccgaggac acggccattt attactgtgc gcggttttat    300
ggtgacagat ggggccaggg aaccctggtc accgtctcct ca                        342
```

<210> SEQ ID NO 119
<211> LENGTH: 114
<212> TYPE: PRT
<213> ORGANISM: Homo sapiens

<400> SEQUENCE: 119

```
Gln Val Gln Leu Val Glu Ser Gly Gly Asp Leu Val Lys Pro Gly Gly
 1               5                  10                  15

Ser Leu Arg Leu Ser Cys Ala Thr Ser Gly Phe Thr Phe Ser Asp Phe
            20                  25                  30
```

```
Tyr Met Thr Trp Ile Arg Gln Ala Pro Gly Lys Gly Leu Glu Trp Ile
            35                  40                  45

Ser Tyr Ile Ser Asn Ser Gly Ser Ile Val Lys Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Ile Tyr Tyr Cys
                 85                  90                  95

Ala Arg Phe Tyr Gly Asp Arg Trp Gly Gln Gly Thr Leu Val Thr Val
            100                 105                 110

Ser Ser

<210> SEQ ID NO 120
<211> LENGTH: 24
<212> TYPE: DNA
<213> ORGANISM: Homo sapiens

<400> SEQUENCE: 120
ggattcacct tcagtgactt ttac                                          24

<210> SEQ ID NO 121
<211> LENGTH: 8
<212> TYPE: PRT
<213> ORGANISM: Homo sapiens

<400> SEQUENCE: 121

Gly Phe Thr Phe Ser Asp Phe Tyr
1               5

<210> SEQ ID NO 122
<211> LENGTH: 24
<212> TYPE: DNA
<213> ORGANISM: Homo sapiens

<400> SEQUENCE: 122
ataagtaata gtgggagtat cgtg                                          24

<210> SEQ ID NO 123
<211> LENGTH: 8
<212> TYPE: PRT
<213> ORGANISM: Homo sapiens

<400> SEQUENCE: 123

Ile Ser Asn Ser Gly Ser Ile Val
1               5

<210> SEQ ID NO 124
<211> LENGTH: 21
<212> TYPE: DNA
<213> ORGANISM: Homo sapiens

<400> SEQUENCE: 124
gcgcggtttt atggtgacag a                                             21

<210> SEQ ID NO 125
<211> LENGTH: 7
<212> TYPE: PRT
<213> ORGANISM: Homo sapiens

<400> SEQUENCE: 125

Ala Arg Phe Tyr Gly Asp Arg
```

<210> SEQ ID NO 126
<211> LENGTH: 321
<212> TYPE: DNA
<213> ORGANISM: Homo sapiens

<400> SEQUENCE: 126
gacatccagt tgacccagtc tccatctttc ctgtctgcat ctgtaggaga cagagtcacc     60
atcacttgct gggccagtca gggcattagc acttttttag cctggtatca gcaaaagccg    120
ggtaaagccc ctaagctcct gatctatgct gcatctactt tacaaagtgg ggtcccatcg    180
cgattcagcg gcagcggatc tgggacagat ttcactctca caatcagcag cctgcagcct    240
gaagattttg caacttatca ctgtcaacaa cttaataatt acccgtggac gttcggccaa    300
gggaccaagg tggaaatcaa a                                              321

<210> SEQ ID NO 127
<211> LENGTH: 107
<212> TYPE: PRT
<213> ORGANISM: Homo sapiens

<400> SEQUENCE: 127

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Thr Phe
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Leu Asn Asn Tyr Pro Trp
                85                  90                  95

Thr Phe Gly Gln Gly Thr Lys Val Glu Ile Lys
            100                 105

<210> SEQ ID NO 128
<211> LENGTH: 18
<212> TYPE: DNA
<213> ORGANISM: Homo sapiens

<400> SEQUENCE: 128
cagggcatta gcactttt                                                   18

<210> SEQ ID NO 129
<211> LENGTH: 6
<212> TYPE: PRT
<213> ORGANISM: Homo sapiens

<400> SEQUENCE: 129

Gln Gly Ile Ser Thr Phe
1               5

<210> SEQ ID NO 130
<211> LENGTH: 9
<212> TYPE: DNA
<213> ORGANISM: Homo sapiens

<400> SEQUENCE: 130

| gctgcatct | 9 |

<210> SEQ ID NO 131
<211> LENGTH: 27
<212> TYPE: DNA
<213> ORGANISM: Homo sapiens

<400> SEQUENCE: 131

| caacaactta ataattaccc gtggacg | 27 |

<210> SEQ ID NO 132
<211> LENGTH: 9
<212> TYPE: PRT
<213> ORGANISM: Homo sapiens

<400> SEQUENCE: 132

Gln Gln Leu Asn Asn Tyr Pro Trp Thr
1               5

<210> SEQ ID NO 133
<211> LENGTH: 1326
<212> TYPE: DNA
<213> ORGANISM: Homo sapiens

<400> SEQUENCE: 133

| caggtgcagc tggtggagtc tgggggagac ttggtcaagc ctgggggtc cctgagactc | 60 |
| tcctgtgcaa cctctggatt caccttcagt gacttttaca tgacctggat ccgccaggct | 120 |
| ccagggaagg gattggagtg gatttcatat ataagtaata gtgggagtat cgtgaagtac | 180 |
| gcagactctg tgaagggccg attcaccatt tccagggata acgccaagaa ctcactgtat | 240 |
| ctgcaaatga acagcctgag agccgaggac acggccattt attactgtgc gcggttttat | 300 |
| ggtgacagat ggggccaggg aaccctggtc accgtctcct cagcctccac caagggccca | 360 |
| tcggtcttcc ccctggcgcc ctgctccagg agcacctccg agagcacagc cgccctgggc | 420 |
| tgcctggtca aggactactt ccccgaaccg gtgacggtgt cgtggaactc aggcgccctg | 480 |
| accagcggcg tgcacacctt cccggctgtc ctacagtcct caggactcta ctccctcagc | 540 |
| agcgtggtga ccgtgccctc agcagcttg gcacgaaga cctacacctg caacgtagat | 600 |
| cacaagccca gcaacaccaa ggtggacaag agagttgagt ccaaatatgg tcccccatgc | 660 |
| ccaccctgcc cagcacctga gttcctgggg ggaccatcag tcttcctgtt ccccccaaaa | 720 |
| cccaaggaca ctctcatgat ctcccggacc cctgaggtca cgtgcgtggt ggtggacgtg | 780 |
| agccaggaag accccgaggt ccagttcaac tggtacgtgg atggcgtgga ggtgcataat | 840 |
| gccaagacaa agccgcggga ggagcagttc aacagcacgt accgtgtggt cagcgtcctc | 900 |
| accgtcctgc accaggactg gctgaacggc aaggagtaca agtgcaaggt ctccaacaaa | 960 |
| ggcctcccgt cctccatcga gaaaaccatc tccaaagcca agggcagcc ccgagagcca | 1020 |
| caggtgtaca ccctgccccc atcccaggag gagatgacca gaaccaggt cagcctgacc | 1080 |
| tgcctggtca aaggcttcta ccccagcgac atcgccgtgg agtgggagag caatgggcag | 1140 |
| ccggagaaca actacaagac cacgcctccc gtgctggact ccgacggctc cttcttcctc | 1200 |
| tacagcaggc tcaccgtgga caagagcagg tggcaggagg ggaatgtctt ctcatgctcc | 1260 |
| gtgatgcatg aggctctgca caaccactac acacagaagt ccctctccct gtctctgggt | 1320 |
| aaatga | 1326 |

```
<210> SEQ ID NO 134
<211> LENGTH: 441
<212> TYPE: PRT
<213> ORGANISM: Homo sapiens

<400> SEQUENCE: 134

Gln Val Gln Leu Val Glu Ser Gly Gly Asp Leu Val Lys Pro Gly Gly
1               5                   10                  15

Ser Leu Arg Leu Ser Cys Ala Thr Ser Gly Phe Thr Phe Ser Asp Phe
            20                  25                  30

Tyr Met Thr Trp Ile Arg Gln Ala Pro Gly Lys Gly Leu Glu Trp Ile
        35                  40                  45

Ser Tyr Ile Ser Asn Ser Gly Ser Ile Val Lys Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Phe Tyr Gly Asp Arg Trp Gly Gln Gly Thr Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
210                 215                 220

Ala Pro Glu Phe Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380
```

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
            405                 410                 415

Phe Ser Cys Ser Val Met His Glu Ala Leu His Asn His Tyr Thr Gln
        420                 425                 430

Lys Ser Leu Ser Leu Ser Leu Gly Lys
        435                 440

<210> SEQ ID NO 135
<211> LENGTH: 645
<212> TYPE: DNA
<213> ORGANISM: Homo sapiens

<400> SEQUENCE: 135
gacatccagt tgacccagtc tccatctttc ctgtctgcat ctgtaggaga cagagtcacc      60
atcacttgct gggccagtca gggcattagc acttttttag cctggtatca gcaaaagccg     120
ggtaaagccc ctaagctcct gatctatgct gcatctactt tacaaagtgg ggtcccatcg     180
cgattcagcg gcagcggatc tgggacagat ttcactctca caatcagcag cctgcagcct     240
gaagattttg caacttatca ctgtcaacaa cttaataatt acccgtggac gttcggccaa     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 136
<211> LENGTH: 214
<212> TYPE: PRT
<213> ORGANISM: Homo sapiens

<400> SEQUENCE: 136

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Thr Phe
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Leu Asn Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
              165                 170                 175

Ser Thr Leu Thr Leu Ser Lys Ala Asp Tyr Glu Lys His Lys Val Tyr
              180                 185                 190

Ala Cys Glu Val Thr His Gln Gly Leu Ser Ser Pro Val Thr Lys Ser
              195                 200                 205

Phe Asn Arg Gly Glu Cys
        210

<210> SEQ ID NO 137
<211> LENGTH: 342
<212> TYPE: DNA
<213> ORGANISM: Homo sapiens

<400> SEQUENCE: 137
caggtgcagc tggtggagtc tgggggaggc ttggtcaagc ctggagggtc cctgagactc      60
tcctgtgaag cctctggatt caccttcaat gacttctata tgacctggat ccgccaggct     120
ccagggaagg gctggagtg gattgcatac atttctaaga gtggtgataa aatgcgttat      180
gcagactctg tgaagggccg attcagcacc tccaggaca acgccaagaa ttcactatcc      240
ttgcaaatga atagcctgag agccgaggac acggccgtgt attattgtgc gagattctac     300
ggtgatatat ggggccaggg aaccctggtc accgtctcct ca                        342

<210> SEQ ID NO 138
<211> LENGTH: 114
<212> TYPE: PRT
<213> ORGANISM: Homo sapiens

<400> SEQUENCE: 138

Gln Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Asn Asp Phe
            20                  25                  30

Tyr Met Thr Trp Ile Arg Gln Ala Pro Gly Lys Gly Leu Glu Trp Ile
        35                  40                  45

Ala Tyr Ile Ser Lys Ser Gly Asp Lys Met Arg Tyr Ala Asp Ser Val
    50                  55                  60

Lys Gly Arg Phe Ser Thr Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Phe Tyr Gly Asp Ile Trp Gly Gln Gly Thr Leu Val Thr Val
            100                 105                 110

Ser Ser

<210> SEQ ID NO 139
<211> LENGTH: 24
<212> TYPE: DNA
<213> ORGANISM: Homo sapiens

<400> SEQUENCE: 139
ggattcacct tcaatgactt ctat                                             24

<210> SEQ ID NO 140
<211> LENGTH: 8
<212> TYPE: PRT
<213> ORGANISM: Homo sapiens

<400> SEQUENCE: 140

Gly Phe Thr Phe Asn Asp Phe Tyr
1               5

<210> SEQ ID NO 141
<211> LENGTH: 24
<212> TYPE: DNA
<213> ORGANISM: Homo sapiens

<400> SEQUENCE: 141
atttctaaga gtggtgataa aatg                                          24

<210> SEQ ID NO 142
<211> LENGTH: 8
<212> TYPE: PRT
<213> ORGANISM: Homo sapiens

<400> SEQUENCE: 142

Ile Ser Lys Ser Gly Asp Lys Met
1               5

<210> SEQ ID NO 143
<211> LENGTH: 21
<212> TYPE: DNA
<213> ORGANISM: Homo sapiens

<400> SEQUENCE: 143
gcgagattct acggtgatat a                                             21

<210> SEQ ID NO 144
<211> LENGTH: 7
<212> TYPE: PRT
<213> ORGANISM: Homo sapiens

<400> SEQUENCE: 144

Ala Arg Phe Tyr Gly Asp Ile
1               5

<210> SEQ ID NO 145
<211> LENGTH: 321
<212> TYPE: DNA
<213> ORGANISM: Homo sapiens

<400> SEQUENCE: 145
gacatccagt tgacccagtc tccatccttc ctgtctgcat ctgtaggaga cagagtcacc    60
atcacttgct gggccagtca ggacattagc agttttttag tctggtatca gcaaaaacca   120
gggaaagccc ctaacctcct gatctatgct catccgcttt gcagagtgg ggtcccatca    180 aggttcagcg gcagtggatc tgggacagaa ttcactctca caatcagcag cctgcagcct   240
gaagattttg caagttatta ctgtgaacag cttaataatt atccgtggac gttcggccaa   300
gggaccaagg tggaaatcaa a                                            321

<210> SEQ ID NO 146
<211> LENGTH: 107
<212> TYPE: PRT
<213> ORGANISM: Homo sapiens

<400> SEQUENCE: 146

Asp Ile Gln Leu Thr Gln Ser Pro Ser Phe Leu Ser Ala Ser Val Gly
1               5                   10                  15

```
Asp Arg Val Thr Ile Thr Cys Trp Ala Ser Gln Asp Ile Ser Ser Phe
             20                  25                  30
Leu Val Trp Tyr Gln Gln Lys Pro Gly Lys Ala Pro Asn Leu Leu Ile
         35                  40                  45
Tyr Ala Ala Ser Ala Leu Gln Ser Gly Val Pro Ser Arg Phe Ser Gly
 50                  55                  60
Ser Gly Ser Gly Thr Glu Phe Thr Leu Thr Ile Ser Ser Leu Gln Pro
65                  70                  75                  80
Glu Asp Phe Ala Ser Tyr Tyr Cys Glu Gln Leu Asn Asn Tyr Pro Trp
                 85                  90                  95
Thr Phe Gly Gln Gly Thr Lys Val Glu Ile Lys
            100                 105
```

<210> SEQ ID NO 147
<211> LENGTH: 18
<212> TYPE: DNA
<213> ORGANISM: Homo sapiens

<400> SEQUENCE: 147
caggacatta gcagtttt                                                     18

<210> SEQ ID NO 148
<211> LENGTH: 6
<212> TYPE: PRT
<213> ORGANISM: Homo sapiens

<400> SEQUENCE: 148

```
Gln Asp Ile Ser Ser Phe
1               5
```

<210> SEQ ID NO 149
<211> LENGTH: 27
<212> TYPE: DNA
<213> ORGANISM: Homo sapiens

<400> SEQUENCE: 149
gaacagctta ataattatcc gtggacg                                           27

<210> SEQ ID NO 150
<211> LENGTH: 9
<212> TYPE: PRT
<213> ORGANISM: Homo sapiens

<400> SEQUENCE: 150

```
Glu Gln Leu Asn Asn Tyr Pro Trp Thr
1               5
```

<210> SEQ ID NO 151
<211> LENGTH: 1326
<212> TYPE: DNA
<213> ORGANISM: Homo sapiens

<400> SEQUENCE: 151
caggtgcagc tggtggagtc tgggggaggc ttggtcaagc ctggagggtc cctgagactc        60
tcctgtgaag cctctggatt caccttcaat gacttctata tgacctggat ccgccaggct       120
ccagggaagg ggctggagtg gattgcatac atttctaaga gtggtgataa aatgcgttat       180
gcagactctg tgaagggccg attcagcacc tccagggaca acgccaagaa ttcactatcc       240
ttgcaaatga atagcctgag agccgaggac acggccgtgt attattgtgc gagattctac       300
ggtgatatat gggccaggg aaccctggtc accgtctcct cagcctccac caagggccca       360

```
tcggtcttcc ccctggcgcc ctgctccagg agcacctccg agagcacagc cgccctgggc    420
tgcctggtca aggactactt ccccgaaccg gtgacggtgt cgtggaactc aggcgccctg    480
accagcggcg tgcacacctt cccggctgtc ctacagtcct caggactcta ctccctcagc    540
agcgtggtga ccgtgccctc cagcagcttg ggcacgaaga cctacacctg caacgtagat    600
cacaagccca gcaacaccaa ggtggacaag agagttgagt ccaaatatgg tcccccatgc    660
ccaccctgcc cagcacctga gttcctgggg ggaccatcag tcttcctgtt ccccccaaaa    720
cccaaggaca ctctcatgat ctcccggacc cctgaggtca cgtgcgtggt ggtggacgtg    780
agccaggaag accccgaggt ccagttcaac tggtacgtgg atggcgtgga ggtgcataat    840
gccaagacaa agccgcggga ggagcagttc aacagcacgt accgtgtggt cagcgtcctc    900
accgtcctgc accaggactg gctgaacggc aaggagtaca agtgcaaggt ctccaacaaa    960
ggcctcccgt cctccatcga gaaaaccatc tccaaagcca agggcagccc cgagagcca   1020 caggtgtaca ccctgccccc atcccaggag gagatgacca gaaccaggt cagcctgacc    1080 tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc tcaccgtgga caagagcagg tggcaggagg ggaatgtctt ctcatgctcc    1260
gtgatgcatg aggctctgca caaccactac acacagaagt ccctctccct gtctctgggt    1320
aaatga                                                              1326
```

<210> SEQ ID NO 152
<211> LENGTH: 441
<212> TYPE: PRT
<213> ORGANISM: Homo sapiens

<400> SEQUENCE: 152

```
Gln Val Gln Leu Val Glu Ser Gly Gly Gly Leu Val Lys Pro Gly Gly
 1               5                  10                  15

Ser Leu Arg Leu Ser Cys Glu Ala Ser Gly Phe Thr Phe Asn Asp Phe
            20                  25                  30

Tyr Met Thr Trp Ile Arg Gln Ala Pro Gly Lys Gly Leu Glu Trp Ile
        35                  40                  45

Ala Tyr Ile Ser Lys Ser Gly Asp Lys Met Arg Tyr Ala Asp Ser Val
    50                  55                  60

Lys Gly Arg Phe Ser Thr Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Phe Tyr Gly Asp Ile Trp Gly Gln Gly Thr Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190
```

```
Lys Thr Tyr Thr Cys Asn Val Asp His Lys Pro Ser Asn Thr Lys Val
            195                 200                 205

Asp Lys Arg Val Glu Ser Lys Tyr Gly Pro Pro Cys Pro Pro Cys Pro
210                 215                 220

Ala Pro Glu Phe Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
            275                 280                 285

Gln Phe Asn Ser Thr Tyr Arg Val Val Ser Val Leu Thr Val Leu His
            290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys
            435                 440

<210> SEQ ID NO 153
<211> LENGTH: 645
<212> TYPE: DNA
<213> ORGANISM: Homo sapiens

<400> SEQUENCE: 153
gacatccagt tgacccagtc tccatccttc ctgtctgcat ctgtaggaga cagagtcacc      60
atcacttgct gggccagtca ggacattagc agttttttag tctggtatca gcaaaaacca    120
gggaaagccc ctaacctcct gatctatgct gcatccgctt tgcagagtgg ggtcccatca    180
aggttcagcg gcagtggatc tgggacagaa ttcactctca caatcagcag cctgcagcct    240
gaagattttg caagttatta ctgtgaacag cttaataatt atccgtggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                     645
```

<210> SEQ ID NO 154
<211> LENGTH: 214
<212> TYPE: PRT
<213> ORGANISM: Homo sapiens

<400> SEQUENCE: 154

```
Asp Ile Gln Leu Thr Gln Ser Pro Ser Phe Leu Ser Ala Ser Val Gly
1               5                  10                  15
Asp Arg Val Thr Ile Thr Cys Trp Ala Ser Gln Asp Ile Ser Ser Phe
            20                  25                  30
Leu Val Trp Tyr Gln Gln Lys Pro Gly Lys Ala Pro Asn Leu Leu Ile
        35                  40                  45
Tyr Ala Ala Ser Ala Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Ser Tyr Tyr Cys Gln Gln Leu Asn Asn Tyr Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 155
<211> LENGTH: 375
<212> TYPE: DNA
<213> ORGANISM: Homo sapiens

<400> SEQUENCE: 155

```
gaggtgcagc tggtggagtc cgggggacgc ttggtacagc ctgggggtc  cctgagactc      60 tcctgtgaag cctctggatt cacgtttagt aattatggca tgacctgggt ccgccaggct     120
ccagggaagg gctgaatg ggtctcagtt attagtggca gtgataatag aaaatactat       180
gcagagtccg tgaagggccg gttcaccatc tccagagaca attccaaaaa cacactatat     240
ctgcaaatga atagcctgag agccgaggac acggccgtct attactgtgc aaaattggga    300
tatagtcgtt cgtccaagga cttctactac ggaatggacg tctggggcca agggaccacg    360
gtcaccgtct cctca                                                     375
```

<210> SEQ ID NO 156
<211> LENGTH: 125
<212> TYPE: PRT
<213> ORGANISM: Homo sapiens

<400> SEQUENCE: 156

-continued

```
Glu Val Gln Leu Val Glu Ser Gly Gly Arg Leu Val Gln Pro Gly Gly
1               5                   10                  15

Ser Leu Arg Leu Ser Cys Glu Ala Ser Gly Phe Thr Phe Ser Asn Tyr
            20                  25                  30

Gly Met Thr Trp Val Arg Gln Ala Pro Gly Lys Gly Leu Glu Trp Val
        35                  40                  45

Ser Val Ile Ser Gly Ser Asp Asn Arg Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Tyr Ser Arg Ser Ser Lys Asp Phe Tyr Tyr Gly Met
            100                 105                 110

Asp Val Trp Gly Gln Gly Thr Thr Val Thr Val Ser Ser
            115                 120                 125
```

<210> SEQ ID NO 157
<211> LENGTH: 24
<212> TYPE: DNA
<213> ORGANISM: Homo sapiens

<400> SEQUENCE: 157
ggattcacgt ttagtaatta tggc          24

<210> SEQ ID NO 158
<211> LENGTH: 8
<212> TYPE: PRT
<213> ORGANISM: Homo sapiens

<400> SEQUENCE: 158

```
Gly Phe Thr Phe Ser Asn Tyr Gly
1               5
```

<210> SEQ ID NO 159
<211> LENGTH: 24
<212> TYPE: DNA
<213> ORGANISM: Homo sapiens

<400> SEQUENCE: 159
attagtggca gtgataatag aaaa          24

<210> SEQ ID NO 160
<211> LENGTH: 8
<212> TYPE: PRT
<213> ORGANISM: Homo sapiens

<400> SEQUENCE: 160

```
Ile Ser Gly Ser Asp Asn Arg Lys
1               5
```

<210> SEQ ID NO 161
<211> LENGTH: 54
<212> TYPE: DNA
<213> ORGANISM: Homo sapiens

<400> SEQUENCE: 161
gcaaaattgg gatatagtcg ttcgtccaag gacttctact acggaatgga cgtc          54

<210> SEQ ID NO 162
<211> LENGTH: 18

<212> TYPE: PRT
<213> ORGANISM: Homo sapiens

<400> SEQUENCE: 162

Ala Lys Leu Gly Tyr Ser Arg Ser Ser Lys Asp Phe Tyr Tyr Gly Met
1               5                   10                  15

Asp Val

<210> SEQ ID NO 163
<211> LENGTH: 339
<212> TYPE: DNA
<213> ORGANISM: Homo sapiens

<400> SEQUENCE: 163
gacatcgtga tgacccagtc tccagactcc ctggctgtgt ctctgggcga gagggccacc    60
atcaactgca agtccagcca gagtgtttta tacaattcca ataataggaa ctacttagtt   120
tggtaccagc agaaaccagg acagtctcct aagttgctca tttactgggc atctacccgg   180
gaatccgggg tccctgaccg gttcagtggc agcgggtctg ggacagattt cactctcacc   240
atcagcagcc tgcaggctga agatgtggca gtgtattact gtcagcaata ttataatgtt   300
ccgtacactt ttggccaggg gaccaagctg gagatcaaa                          339

<210> SEQ ID NO 164
<211> LENGTH: 113
<212> TYPE: PRT
<213> ORGANISM: Homo sapiens

<400> SEQUENCE: 164

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asn Asn Arg Asn Tyr Leu Val Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Val Pro Tyr Thr Phe Gly Gln Gly Thr Lys Leu Glu Ile
            100                 105                 110

Lys

<210> SEQ ID NO 165
<211> LENGTH: 36
<212> TYPE: DNA
<213> ORGANISM: Homo sapiens

<400> SEQUENCE: 165
cagagtgttt tatacaattc caataatagg aactac                              36

<210> SEQ ID NO 166
<211> LENGTH: 12
<212> TYPE: PRT
<213> ORGANISM: Homo sapiens

<400> SEQUENCE: 166

Gln Ser Val Leu Tyr Asn Ser Asn Asn Arg Asn Tyr
1               5                   10

<210> SEQ ID NO 167
<211> LENGTH: 27
<212> TYPE: DNA
<213> ORGANISM: Homo sapiens

<400> SEQUENCE: 167
cagcaatatt ataatgttcc gtacact                                        27

<210> SEQ ID NO 168
<211> LENGTH: 9
<212> TYPE: PRT
<213> ORGANISM: Homo sapiens

<400> SEQUENCE: 168

Gln Gln Tyr Tyr Asn Val Pro Tyr Thr
1               5

<210> SEQ ID NO 169
<211> LENGTH: 1359
<212> TYPE: DNA
<213> ORGANISM: Homo sapiens

<400> SEQUENCE: 169
gaggtgcagc tggtggagtc cggggggacgc ttggtacagc ctggggggtc cctgagactc      60
tcctgtgaag cctctggatt cacgtttagt aattatggca tgacctgggt ccgccaggct     120
ccagggaagg ggctggaatg ggtctcagtt attagtggca gtgataatag aaaatactat     180
gcagagtccg tgaagggccg gttcaccatc tccagagaca attccaaaaa cacactatat     240
ctgcaaatga atagcctgag agccgaggac acggccgtct attactgtgc aaaattggga     300
tatagtcgtt cgtccaagga cttctactac ggaatggacg tctggggcca agggaccacg     360
gtcaccgtct cctcagcctc caccaagggc ccatcggtct tccccctggc gccctgctcc     420
aggagcacct ccgagagcac agccgccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcacga gacctacac ctgcaacgta atcacaagc ccagcaacac caaggtggac     660
aagagagttg agtccaaata tggtccccca tgcccaccct gcccagcacc tgagttcctg     720
gggggaccat cagtcttcct gttcccccca aaacccaagg acactctcat gatctcccgg     780
acccctgagg tcacgtgcgt ggtggtggac gtgagccagg aagaccccga ggtccagttc     840
aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
ggcaaggagt acaagtgcaa ggtctccaac aaaggcctcc cgtcctccat cgagaaaacc    1020
atctccaaag ccaaagggca gccccgagag ccacaggtgt acaccctgcc cccatcccag    1080
gaggagatga ccaagaacca ggtcagcctg acctgcctgg tcaaaggctt ctaccccagc    1140
gacatcgccg tggagtggga gagcaatggg cagccggaga caactacaa gaccacgcct    1200 cccgtgctgg actccgacgg ctccttcttc ctctacagca ggctcaccgt ggacaagagc    1260
aggtggcagg aggggaatgt cttctcatgc tccgtgatgc atgaggctct gcacaaccac    1320
tacacacaga gtccctctc cctgtctctg ggtaaatga                            1359

<210> SEQ ID NO 170
<211> LENGTH: 452
<212> TYPE: PRT
<213> ORGANISM: Homo sapiens

<400> SEQUENCE: 170

```
Glu Val Gln Leu Val Glu Ser Gly Gly Arg Leu Val Gln Pro Gly Gly
1               5                   10                  15

Ser Leu Arg Leu Ser Cys Glu Ala Ser Gly Phe Thr Phe Ser Asn Tyr
            20                  25                  30

Gly Met Thr Trp Val Arg Gln Ala Pro Gly Lys Gly Leu Glu Trp Val
        35                  40                  45

Ser Val Ile Ser Gly Ser Asp Asn Arg Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Tyr Ser Arg Ser Lys Asp Phe Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
        450

<210> SEQ ID NO 171
<211> LENGTH: 663
<212> TYPE: DNA
<213> ORGANISM: Homo sapiens

<400> SEQUENCE: 171
gacatcgtga tgacccagtc tccagactcc ctggctgtgt ctctgggcga gagggccacc      60
atcaactgca agtccagcca gagtgtttta tacaattcca ataataggaa ctacttagtt     120
tggtaccagc agaaaccagg acagtctcct aagttgctca tttactgggc atctacccgg     180
gaatccgggg tccctgaccg gttcagtggc agcgggtctg ggacagattt cactctcacc     240
atcagcagcc tgcaggctga agatgtggca gtgtattact gtcagcaata ttataatgtt     300
ccgtacactt ttggccaggg gaccaagctg gagatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tag                                                                    663

<210> SEQ ID NO 172
<211> LENGTH: 220
<212> TYPE: PRT
<213> ORGANISM: Homo sapiens

<400> SEQUENCE: 172

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asn Asn Arg Asn Tyr Leu Val Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Val Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

| | | | | | | | | | | | | |
|---|---|---|---|---|---|---|---|---|---|---|---|---|
|Glu|Gln|Leu|Lys|Ser|Gly|Thr|Ala|Ser|Val|Val|Cys|Leu|Leu|Asn|Asn|
| |130| | | |135| | | |140| | | |

Glu Gln Leu Lys Ser Gly Thr Ala Ser Val Val Cys Leu Leu Asn Asn
    130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175

Ser Thr Tyr Ser Leu Ser Ser Thr Leu Thr Leu Ser Lys Ala Asp Tyr
            180             185             190

Glu Lys His Lys Val Tyr Ala Cys Glu Val Thr His Gln Gly Leu Ser
            195             200             205

Ser Pro Val Thr Lys Ser Phe Asn Arg Gly Glu Cys
        210             215             220

<210> SEQ ID NO 173
<211> LENGTH: 348
<212> TYPE: DNA
<213> ORGANISM: Homo sapiens

<400> SEQUENCE: 173
gaggtgcagc tggtggagtc tgggggaggt gtggtacggc ctggggggtc cctgagactc      60
tcctgtgcag cctctggatt cacctttgat gattatggca tgagctgggt ccgccaagct     120
ccagggaagg ggctggagtg gatctcttct attaatagga atggtggtag cgcagattat     180
gcagactctg tgaagggccg attcaccatc tccagagaca cgccaagaa ctccctcttt      240 ctgcaaatga gcagtctgag agccgaggac acggccctct atcactgtgc gagcggggag     300
tttcgctttg actactgggg ccagggaacc ctggtcaccg tctcctca                  348

<210> SEQ ID NO 174
<211> LENGTH: 116
<212> TYPE: PRT
<213> ORGANISM: Homo sapiens

<400> SEQUENCE: 174

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Ile
        35                  40                  45

Ser Ser Ile Asn Arg Asn Gly Gly Ser Ala Asp Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Leu Tyr His Cys
            85                  90                  95

Ala Ser Gly Glu Phe Arg Phe Asp Tyr Trp Gly Gln Gly Thr Leu Val
            100                 105                 110

Thr Val Ser Ser
        115

<210> SEQ ID NO 175
<211> LENGTH: 24
<212> TYPE: DNA
<213> ORGANISM: Homo sapiens

<400> SEQUENCE: 175
ggattcacct ttgatgatta tggc                                             24

<210> SEQ ID NO 176
<211> LENGTH: 8
<212> TYPE: PRT
<213> ORGANISM: Homo sapiens

<400> SEQUENCE: 176

Gly Phe Thr Phe Asp Asp Tyr Gly
1               5

<210> SEQ ID NO 177
<211> LENGTH: 24
<212> TYPE: DNA
<213> ORGANISM: Homo sapiens

<400> SEQUENCE: 177
attaatagga atggtggtag cgca                                              24

<210> SEQ ID NO 178
<211> LENGTH: 8
<212> TYPE: PRT
<213> ORGANISM: Homo sapiens

<400> SEQUENCE: 178

Ile Asn Arg Asn Gly Gly Ser Ala
1               5

<210> SEQ ID NO 179
<211> LENGTH: 27
<212> TYPE: DNA
<213> ORGANISM: Homo sapiens

<400> SEQUENCE: 179
gcgagcgggg agtttcgctt tgactac                                           27

<210> SEQ ID NO 180
<211> LENGTH: 9
<212> TYPE: PRT
<213> ORGANISM: Homo sapiens

<400> SEQUENCE: 180

Ala Ser Gly Glu Phe Arg Phe Asp Tyr
1               5

<210> SEQ ID NO 181
<211> LENGTH: 324
<212> TYPE: DNA
<213> ORGANISM: Homo sapiens

<400> SEQUENCE: 181
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                             324

<210> SEQ ID NO 182
<211> LENGTH: 108
<212> TYPE: PRT
<213> ORGANISM: Homo sapiens

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 183
<211> LENGTH: 30
<212> TYPE: DNA
<213> ORGANISM: Homo sapiens

<400> SEQUENCE: 183
caacagagtt acagtacccc tccgatcacc                                    30

<210> SEQ ID NO 184
<211> LENGTH: 10
<212> TYPE: PRT
<213> ORGANISM: Homo sapiens

<400> SEQUENCE: 184

Gln Gln Ser Tyr Ser Thr Pro Pro Ile Thr
1               5                   10

<210> SEQ ID NO 185
<211> LENGTH: 1332
<212> TYPE: DNA
<213> ORGANISM: Homo sapiens

<400> SEQUENCE: 185
gaggtgcagc tggtggagtc tgggggaggt gtggtacggc ctgggggtc cctgagactc      60 tcctgtgcag cctctggatt cacctttgat gattatggca tgagctgggt ccgccaagct    120
ccagggaagg ggctggagtg gatctcttct attaatagga atggtggtag cgcagattat    180
gcagactctg tgaagggccg attcaccatc tccagagaca acgccaagaa ctccctcttt    240
ctgcaaatga gcagtctgag agccgaggac acggccctct atcactgtgc gagcggggag    300
tttcgctttg actactgggg ccagggaacc ctggtcaccg tctcctcagc tccaccaag     360 ggcccatcgg tcttccccct ggcgccctgc tccaggagca cctccgagag cacagccgcc    420
ctgggctgcc tggtcaagga ctacttcccc gaaccggtga cggtgtcgtg aactcaggc     480 gccctgacca gcggcgtgca caccttcccg gctgtcctac agtcctcagg actctactcc    540
ctcagcagcg tggtgaccgt gccctccagc agcttgggca cgaagaccta cacctgcaac    600
gtagatcaca agcccagcaa caccaaggtg gacaagagag ttgagtccaa atatggtccc    660
ccatgcccac cctgcccagc acctgagttc ctggggggac catcagtctt cctgttcccc    720
ccaaaaccca aggacactct catgatctcc cggacccctg aggtcacgtg cgtggtggtg    780

```
gacgtgagcc aggaagaccc cgaggtccag ttcaactggt acgtggatgg cgtggaggtg      840
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca aagccaaagg gcagccccga     1020
gagccacagg tgtacaccct gcccccatcc caggaggaga tgaccaagaa ccaggtcagc     1080
ctgacctgcc tggtcaaagg cttctacccc agcgacatcg ccgtggagtg ggagagcaat     1140
gggcagccgg agaacaacta caagaccacg cctcccgtgc tggactccga cggctccttc     1200
ttcctctaca gcaggctcac cgtggacaag agcaggtggc aggagggaa tgtcttctca     1260 tgctccgtga tgcatgaggc tctgcacaac cactacacac agaagtccct ctccctgtct     1320
ctgggtaaat ga                                                         1332
```

<210> SEQ ID NO 186
<211> LENGTH: 443
<212> TYPE: PRT
<213> ORGANISM: Homo sapiens

<400> SEQUENCE: 186

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Ile
        35                  40                  45

Ser Ser Ile Asn Arg Asn Gly Gly Ser Ala Asp Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Leu Tyr His Cys
                85                  90                  95

Ala Ser Gly Glu Phe Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270
```

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 187
<211> LENGTH: 648
<212> TYPE: DNA
<213> ORGANISM: Homo sapiens

<400> SEQUENCE: 187

```
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag                 648
```

<210> SEQ ID NO 188
<211> LENGTH: 215
<212> TYPE: PRT
<213> ORGANISM: Homo sapiens

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 189
<211> LENGTH: 348
<212> TYPE: DNA
<213> ORGANISM: Homo sapiens

<400> SEQUENCE: 189
gaagtgcagc tggtggagtc tgggggaggc ttggtacagc ctggcaggtc cctgagactc    60
tcctgtgcag cctctggatt caccctggaa gattatgcca tgcactgggt ccggcaagct   120
ccagggaagg gcctggaatg ggtctcaggt attagttgga atagaggtag cacaggctat   180
gcggactctg tgaagggccg attcaccatc tcaagagaca acgccaagaa ctccctgtat   240
ctgcaaatga ccagtctgag agctgaggac acggccttgt attactgtgc aaaaggattc   300
tacagtatgg acgtctgggg ccaagggacc acggtcaccg tctcctca                348

<210> SEQ ID NO 190
<211> LENGTH: 116
<212> TYPE: PRT
<213> ORGANISM: Homo sapiens

<400> SEQUENCE: 190

Glu Val Gln Leu Val Glu Ser Gly Gly Gly Leu Val Gln Pro Gly Arg
 1                5                  10                  15

Ser Leu Arg Leu Ser Cys Ala Ala Ser Gly Phe Thr Leu Glu Asp Tyr
                20                  25                  30

Ala Met His Trp Val Arg Gln Ala Pro Gly Lys Gly Leu Glu Trp Val
            35                  40                  45

Ser Gly Ile Ser Trp Asn Arg Gly Ser Thr Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Thr Ser Leu Arg Ala Glu Asp Thr Ala Leu Tyr Tyr Cys
                85                  90                  95
```

Ala Lys Gly Phe Tyr Ser Met Asp Val Trp Gly Gln Gly Thr Thr Val
            100                 105                 110

Thr Val Ser Ser
        115

<210> SEQ ID NO 191
<211> LENGTH: 24
<212> TYPE: DNA
<213> ORGANISM: Homo sapiens

<400> SEQUENCE: 191
ggattcaccc ttgaagatta tgcc                                          24

<210> SEQ ID NO 192
<211> LENGTH: 8
<212> TYPE: PRT
<213> ORGANISM: Homo sapiens

<400> SEQUENCE: 192

Gly Phe Thr Leu Glu Asp Tyr Ala
1               5

<210> SEQ ID NO 193
<211> LENGTH: 24
<212> TYPE: DNA
<213> ORGANISM: Homo sapiens

<400> SEQUENCE: 193
attagttgga atagaggtag caca                                          24

<210> SEQ ID NO 194
<211> LENGTH: 8
<212> TYPE: PRT
<213> ORGANISM: Homo sapiens

<400> SEQUENCE: 194

Ile Ser Trp Asn Arg Gly Ser Thr
1               5

<210> SEQ ID NO 195
<211> LENGTH: 27
<212> TYPE: DNA
<213> ORGANISM: Homo sapiens

<400> SEQUENCE: 195
gcaaaaggat tctacagtat ggacgtc                                       27

<210> SEQ ID NO 196
<211> LENGTH: 9
<212> TYPE: PRT
<213> ORGANISM: Homo sapiens

<400> SEQUENCE: 196

Ala Lys Gly Phe Tyr Ser Met Asp Val
1               5

<210> SEQ ID NO 197
<211> LENGTH: 1332
<212> TYPE: DNA
<213> ORGANISM: Homo sapiens

<400> SEQUENCE: 197
gaagtgcagc tggtggagtc tgggggaggc ttggtacagc ctggcaggtc cctgagactc    60

```
tcctgtgcag cctctggatt caccottgaa gattatgcca tgcactgggt ccggcaagct    120
ccagggaagg gcctggaatg ggtctcaggt attagttgga atagaggtag cacaggctat    180
gcggactctg tgaagggccg attcaccatc tcaagagaca acgccaagaa ctccctgtat    240
ctgcaaatga ccagtctgag agctgaggac acggccttgt attactgtgc aaaaggattc    300
tacagtatgg acgtctgggg ccaagggacc acggtcaccg tctcctcagc tccaccaag     360 ggcccatcgg tcttccccct ggcgccctgc tccaggagca cctccgagag cacagccgcc    420
ctgggctgcc tggtcaagga ctacttcccc gaaccggtga cggtgtcgtg aactcaggc     480 gccctgacca gcggcgtgca caccttcccg gctgtcctac agtcctcagg actctactcc    540
ctcagcagcg tggtgaccgt gccctccagc agcttgggca cgaagaccta cacctgcaac    600
gtagatcaca agcccagcaa caccaaggtg gacaagagag ttgagtccaa atatggtccc    660
ccatgcccac cctgcccagc acctgagttc ctgggggac catcagtctt cctgttcccc     720
ccaaaaccca aggacactct catgatctcc cggacccctg aggtcacgtg cgtggtggtg    780
gacgtgagcc aggaagaccc cgaggtccag ttcaactggt acgtggatgg cgtggaggtg    840
cataatgcca agacaaagcc gcgggaggag cagttcaaca gcacgtaccg tgtggtcagc    900
gtcctcaccg tcctgcacca ggactggctg aacggcaagg agtacaagtg caaggtctcc    960
aacaaaggcc tcccgtcctc catcgagaaa accatctcca aagccaaagg cagccccga   1020 gagccacagg tgtacaccct gcccccatcc caggaggaga tgaccaagaa ccaggtcagc   1080
ctgacctgcc tggtcaaagg cttctacccc agcgacatcg ccgtggagtg ggagagcaat   1140
gggcagccgg agaacaacta caagaccacg cctcccgtgc tggactccga cggctccttc   1200
ttcctctaca gcaggctcac cgtggacaag agcaggtggc aggagggaa tgtcttctca    1260 tgctccgtga tgcatgaggc tctgcacaac cactacacac agaagtccct ctccctgtct   1320
ctgggtaaat ga                                                      1332
```

<210> SEQ ID NO 198
<211> LENGTH: 443
<212> TYPE: PRT
<213> ORGANISM: Homo sapiens

<400> SEQUENCE: 198

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Leu Glu Asp Tyr
            20                  25                  30

Ala Met His Trp Val Arg Gln Ala Pro Gly Lys Gly Leu Glu Trp Val
        35                  40                  45

Ser Gly Ile Ser Trp Asn Arg Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Leu Tyr Tyr Cys
                85                  90                  95

Ala Lys Gly Phe Tyr Ser Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
    195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
    275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
        420                 425                 430

Thr Gln Lys Ser Leu Ser Leu Ser Leu Gly Lys
    435                 440

<210> SEQ ID NO 199
<211> LENGTH: 363
<212> TYPE: DNA
<213> ORGANISM: Homo sapiens

<400> SEQUENCE: 199
caggtacagc tgcagcagtc aggtccagga ctggtgaagc cctcgcagac cctctcactc        60
acctgtgcca tctccggtga cagtgtctct agcaacattg ctgcttggaa ctggatcagg       120
ctgtccccat cgagaggcct tgagtggctg gaaggacat tcttcaggtc acgtggttt        180 tatgattatt cactatctgt gaaaggtcgc ataaccatca cccagacac atccaagaac       240 cagttctccc tgcacctgaa ctctgtgact cccgaggacg cggctgtgta ttattgtgca       300
agaacggggc gacggtggtc tcttgactac tggggccagg gaaccctggt caccgtctcc       360
tca                                                                    363

<210> SEQ ID NO 200
<211> LENGTH: 121
<212> TYPE: PRT
<213> ORGANISM: Homo sapiens

<400> SEQUENCE: 200

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ile Ala Ala Trp Asn Trp Ile Arg Leu Ser Pro Ser Arg Gly Leu Glu
        35                  40                  45

Trp Leu Gly Arg Thr Phe Phe Arg Ser Thr Trp Phe Tyr Asp Tyr Ser
    50                  55                  60

Leu Ser Val Lys Gly Arg Ile Thr Ile Asn Pro Asp Thr Ser Lys Asn
65                  70                  75                  80

Gln Phe Ser Leu His Leu Asn Ser Val Thr Pro Glu Asp Ala Ala Val
                85                  90                  95

Tyr Tyr Cys Ala Arg Thr Gly Arg Arg Trp Ser Leu Asp Tyr Trp Gly
            100                 105                 110

Gln Gly Thr Leu Val Thr Val Ser Ser
        115                 120

<210> SEQ ID NO 201
<211> LENGTH: 30
<212> TYPE: DNA
<213> ORGANISM: Homo sapiens

<400> SEQUENCE: 201
ggtgacagtg tctctagcaa cattgctgct                                    30

<210> SEQ ID NO 202
<211> LENGTH: 10
<212> TYPE: PRT
<213> ORGANISM: Homo sapiens

<400> SEQUENCE: 202

Gly Asp Ser Val Ser Ser Asn Ile Ala Ala
1               5                   10

<210> SEQ ID NO 203
<211> LENGTH: 27
<212> TYPE: DNA
<213> ORGANISM: Homo sapiens

<400> SEQUENCE: 203
acattcttca ggtccacgtg gttttat                                       27

<210> SEQ ID NO 204
<211> LENGTH: 9
<212> TYPE: PRT
<213> ORGANISM: Homo sapiens

<400> SEQUENCE: 204

Thr Phe Phe Arg Ser Thr Trp Phe Tyr
1               5

<210> SEQ ID NO 205
<211> LENGTH: 33
<212> TYPE: DNA

<213> ORGANISM: Homo sapiens

<400> SEQUENCE: 205
gcaagaacgg ggcgacggtg gtctcttgac tac    33

<210> SEQ ID NO 206
<211> LENGTH: 11
<212> TYPE: PRT
<213> ORGANISM: Homo sapiens

<400> SEQUENCE: 206

Ala Arg Thr Gly Arg Arg Trp Ser Leu Asp Tyr
1               5                   10

<210> SEQ ID NO 207
<211> LENGTH: 1347
<212> TYPE: DNA
<213> ORGANISM: Homo sapiens

<400> SEQUENCE: 207
caggtacagc tgcagcagtc aggtccagga ctggtgaagc cctcgcagac cctctcactc    60
acctgtgcca tctccggtga cagtgtctct agcaacattg ctgcttggaa ctggatcagg   120
ctgtccccat cgagaggcct tgagtggctg ggaaggacat tcttcaggtc acgtggtttt   180
tatgattatt cactatctgt gaaaggtcgc ataaccatca cccagacaca tccaagaac   240
cagttctccc tgcacctgaa ctctgtgact cccgaggacg cggctgtgta ttattgtgca   300
agaacgggc gacggtggtc tcttgactac tggggccagg gaaccctggt caccgtctcc   360
tcagcctcca ccaagggccc atcggtcttc cccctggcgc cctgctccag gagcacctcc   420
gagagcacag ccgccctggg ctgcctggtc aaggactact ccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacgaag   600
acctacacct gcaacgtaga tcacaagccc agcaacacca aggtggacaa gagagttgag   660
tccaaatatg gtccccatg cccacccctgc ccagcacctg agttcctggg gggaccatca   720
gtcttcctgt tccccccaaa acccaaggac actctcatga tctcccggac ccctgaggtc   780
acgtgcgtgg tggtggacgt gagccaggaa gaccccgagg tccagttcaa ctggtacgtg   840
gatggcgtgg aggtgcataa tgccaagaca aagccgcggg aggagcagtt caacagcacg   900
taccgtgtgg tcagcgtcct caccgtcctg caccaggact ggctgaacgg caaggagtac   960
aagtgcaagg tctccaacaa aggcctcccg tcctccatcg agaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                      1347

<210> SEQ ID NO 208
<211> LENGTH: 448
<212> TYPE: PRT
<213> ORGANISM: Homo sapiens

<400> SEQUENCE: 208

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ile Ala Ala Trp Asn Trp Ile Arg Leu Ser Pro Ser Arg Gly Leu Glu
        35                  40                  45

Trp Leu Gly Arg Thr Phe Phe Arg Ser Thr Trp Phe Tyr Asp Tyr Ser
    50                  55                  60

Leu Ser Val Lys Gly Arg Ile Thr Ile Asn Pro Asp Thr Ser Lys Asn
65                  70                  75                  80

Gln Phe Ser Leu His Leu Asn Ser Val Thr Pro Glu Asp Ala Ala Val
                85                  90                  95

Tyr Tyr Cys Ala Arg Thr Gly Arg Arg Trp Ser Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala

```
                420           425           430
Leu His Asn His Tyr Thr Gln Lys Ser Leu Ser Leu Ser Leu Gly Lys
        435                 440                 445

<210> SEQ ID NO 209
<211> LENGTH: 348
<212> TYPE: DNA
<213> ORGANISM: Homo sapiens

<400> SEQUENCE: 209
gaggtgcagc tggtggagtc tgggggaggt gtggtacggc ctgggggtc cctgagactc      60 tcctgtgcaa cctctggatt cacctttgat gattatggca tgagctgggt ccgccaagtt    120
ccagggaagg ggctggagtg ggtctctagt gttaatagga atggtggtac cacagattat    180
gcagactctg tgaagggccg attcaccatc tccagagaca tgccaagag gtcccttttt    240 ctgcaaatga atagtctgag agccgaagac acggccttgt atcactgtgc gacaggggaa    300
cttttctttg actattgggg ccagggaacc ctggtcaccg tctcctca                 348

<210> SEQ ID NO 210
<211> LENGTH: 116
<212> TYPE: PRT
<213> ORGANISM: Homo sapiens

<400> SEQUENCE: 210

Glu Val Gln Leu Val Glu Ser Gly Gly Gly Val Val Arg Pro Gly Gly
1               5                   10                  15

Ser Leu Arg Leu Ser Cys Ala Thr Ser Gly Phe Thr Phe Asp Asp Tyr
            20                  25                  30

Gly Met Ser Trp Val Arg Gln Val Pro Gly Lys Gly Leu Glu Trp Val
        35                  40                  45

Ser Ser Val Asn Arg Asn Gly Gly Thr Thr Asp Tyr Ala Asp Ser Val
    50                  55                  60

Lys Gly Arg Phe Thr Ile Ser Arg Asp Asn Ala Lys Ser Leu
65                  70                  75                  80

Leu Gln Met Asn Ser Leu Arg Ala Glu Asp Thr Ala Leu Tyr His Cys
                85                  90                  95

Ala Thr Gly Glu Leu Phe Phe Asp Tyr Trp Gly Gln Gly Thr Leu Val
            100                 105                 110

Thr Val Ser Ser
        115

<210> SEQ ID NO 211
<211> LENGTH: 24
<212> TYPE: DNA
<213> ORGANISM: Homo sapiens

<400> SEQUENCE: 211
gttaatagga atggtggtac caca                                            24

<210> SEQ ID NO 212
<211> LENGTH: 8
<212> TYPE: PRT
<213> ORGANISM: Homo sapiens

<400> SEQUENCE: 212

Val Asn Arg Asn Gly Gly Thr Thr
1               5
```

<210> SEQ ID NO 213
<211> LENGTH: 27
<212> TYPE: DNA
<213> ORGANISM: Homo sapiens

<400> SEQUENCE: 213
gcgacagggg aactttctt tgactat                                            27

<210> SEQ ID NO 214
<211> LENGTH: 9
<212> TYPE: PRT
<213> ORGANISM: Homo sapiens

<400> SEQUENCE: 214

Ala Thr Gly Glu Leu Phe Phe Asp Tyr
1               5

<210> SEQ ID NO 215
<211> LENGTH: 1332
<212> TYPE: DNA
<213> ORGANISM: Homo sapiens

<400> SEQUENCE: 215
gaggtgcagc tggtggagtc tgggggaggt gtggtacggc ctgggggtc cctgagactc        60 tcctgtgcaa cctctggatt caccttttgat gattatggca tgagctgggt ccgccaagtt    120
ccagggaagg gctggagtg gtctctagt gttaatagga tggtggtac cacagattat        180 gcagactctg tgaagggccg attcaccatc tccagagaca tgccaagag gtccttttt      240 ctgcaaatga atagtctgag agccgaagac acggccttgt atcactgtgc gcagggggaa    300
cttttctttg actattgggg ccagggaacc ctggtcaccg tctcctcagc ctccaccaag    360
ggcccatcgg tcttcccct ggcgccctgc tccaggagca cctccgagag cacagccgcc      420
ctgggctgcc tggtcaagga ctacttcccc gaaccggtga cggtgtcgtg aactcaggc     480 gccctgacca gcggcgtgca caccttcccg gctgtcctac agtcctcagg actctactcc    540
ctcagcagcg tggtgaccgt gccctccagc agcttgggca cgaagaccta cacctgcaac    600
gtagatcaca gcccagcaa caccaaggtg gacaagagag ttgagtccaa atatggtccc     660
ccatgcccac cctgcccagc acctgagttc ctgggggac catcagtctt cctgttcccc    720
ccaaaaccca aggacactct catgatctcc cggacccctg aggtcacgtg cgtggtggtg    780
gacgtgagcc aggaagaccc cgaggtccag ttcaactggt acgtggatgg cgtggaggtg    840
cataatgcca agacaaagcc gcgggaggag cagttcaaca gcacgtaccg tgtggtcagc    900
gtcctcaccg tcctgcacca ggactggctg aacggcaagg agtacaagtg caaggtctcc    960
aacaaaggcc tcccgtcctc catcgagaaa accatctcca aagccaaagg gcagccccga   1020
gagccacagg tgtacaccct gcccccatcc caggaggaga tgaccaagaa ccaggtcagc   1080
ctgacctgcc tggtcaaagg cttctacccc agcgacatcg ccgtggagtg ggagagcaat   1140
gggcagccgg agaacaacta caagaccacg cctcccgtgc tggactccga cggctccttc   1200
ttcctctaca gcaggctcac cgtggacaag agcaggtggc aggaggggaa tgtcttctca   1260
tgctccgtga tgcatgaggc tctgcacaac cactacacac agaagtccct ctccctgtct   1320
ctgggtaaat ga                                                       1332

<210> SEQ ID NO 216
<211> LENGTH: 443
<212> TYPE: PRT
<213> ORGANISM: Homo sapiens

<400> SEQUENCE: 216

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Val | Val | Arg | Pro | Gly | Gly |
| 1 | | | | 5 | | | | | 10 | | | | | 15 | |
| Ser | Leu | Arg | Leu | Ser | Cys | Ala | Thr | Ser | Gly | Phe | Thr | Phe | Asp | Asp | Tyr |
| | | | 20 | | | | | 25 | | | | | 30 | | |
| Gly | Met | Ser | Trp | Val | Arg | Gln | Val | Pro | Gly | Lys | Gly | Leu | Glu | Trp | Val |
| | | 35 | | | | | 40 | | | | | 45 | | | |
| Ser | Ser | Val | Asn | Arg | Asn | Gly | Gly | Thr | Thr | Asp | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ala | Lys | Arg | Ser | Leu | Phe |
| 65 | | | | | 70 | | | | | 75 | | | | | 80 |
| Leu | Gln | Met | Asn | Ser | Leu | Arg | Ala | Glu | Asp | Thr | Ala | Leu | Tyr | His | Cys |
| | | | | 85 | | | | | 90 | | | | | 95 | |
| Ala | Thr | Gly | Glu | Leu | Phe | Phe | Asp | Tyr | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Cys | Ser | Arg | Ser | Thr | Ser | Glu | Ser | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Thr | Val | Pro | Ser | Ser | Ser | Leu | |
| | | | 180 | | | | | 185 | | | | | 190 | | |
| Gly | Thr | Lys | Thr | Tyr | Thr | Cys | Asn | Val | Asp | His | Lys | Pro | Ser | Asn | Thr |
| | | | 195 | | | | | 200 | | | | | 205 | | |
| Lys | Val | Asp | Lys | Arg | Val | Glu | Ser | Lys | Tyr | Gly | Pro | Pro | Cys | Pro | Pro |
| | 210 | | | | | 215 | | | | | 220 | | | | |
| Cys | Pro | Ala | Pro | Glu | Phe | Leu | Gly | Gly | Pro | Ser | Val | Phe | Leu | Phe | Pro |
| 225 | | | | | 230 | | | | | 235 | | | | | 240 |
| Pro | Lys | Pro | Lys | Asp | Thr | Leu | Met | Ile | Ser | Arg | Thr | Pro | Glu | Val | Thr |
| | | | | 245 | | | | | 250 | | | | | 255 | |
| Cys | Val | Val | Val | Asp | Val | Ser | Gln | Glu | Asp | Pro | Glu | Val | Gln | Phe | Asn |
| | | | 260 | | | | | 265 | | | | | 270 | | |
| Trp | Tyr | Val | Asp | Gly | Val | Glu | Val | His | Asn | Ala | Lys | Thr | Lys | Pro | Arg |
| | | 275 | | | | | 280 | | | | | 285 | | | |
| Glu | Glu | Gln | Phe | Asn | Ser | Thr | Tyr | Arg | Val | Val | Ser | Val | Leu | Thr | Val |
| | 290 | | | | | 295 | | | | | 300 | | | | |
| Leu | His | Gln | Asp | Trp | Leu | Asn | Gly | Lys | Glu | Tyr | Lys | Cys | Lys | Val | Ser |
| 305 | | | | | 310 | | | | | 315 | | | | | 320 |
| Asn | Lys | Gly | Leu | Pro | Ser | Ser | Ile | Glu | Lys | Thr | Ile | Ser | Lys | Ala | Lys |
| | | | | 325 | | | | | 330 | | | | | 335 | |
| Gly | Gln | Pro | Arg | Glu | Pro | Gln | Val | Tyr | Thr | Leu | Pro | Pro | Ser | Gln | Glu |
| | | | 340 | | | | | 345 | | | | | 350 | | |
| Glu | Met | Thr | Lys | Asn | Gln | Val | Ser | Leu | Thr | Cys | Leu | Val | Lys | Gly | Phe |
| | | | 355 | | | | | 360 | | | | | 365 | | |
| Tyr | Pro | Ser | Asp | Ile | Ala | Val | Glu | Trp | Glu | Ser | Asn | Gly | Gln | Pro | Glu |
| | 370 | | | | | 375 | | | | | 380 | | | | |
| Asn | Asn | Tyr | Lys | Thr | Thr | Pro | Pro | Val | Leu | Asp | Ser | Asp | Gly | Ser | Phe |
| 385 | | | | | 390 | | | | | 395 | | | | | 400 |
| Phe | Leu | Tyr | Ser | Arg | Leu | Thr | Val | Asp | Lys | Ser | Arg | Trp | Gln | Glu | Gly |

```
                    405                 410                 415
Asn Val Phe Ser Cys Ser Val Met His Glu Ala Leu His Asn His Tyr
        420                 425                 430

Thr Gln Lys Ser Leu Ser Leu Ser Leu Gly Lys
        435                 440

<210> SEQ ID NO 217
<211> LENGTH: 357
<212> TYPE: DNA
<213> ORGANISM: Homo sapiens

<400> SEQUENCE: 217
caggtccagc tggtacagtc tggggctgag gtgaagaagc ctggggcctc agtgaaggtc     60
tcctgcaagg cttctggata caccttcacc ggccactata tgcactgggt gcgacaggcc    120
cctggacaag gcttgagtg gatgggatgg atctaccctc acagtggtca cacaaattat     180
gcaaagaggt ttcagggcag ggtcaccatg accagggaca cgtccatcac tacagcctac    240
atggagctga tcaggctgag atctgacgac acggccgtgt attactgtgc gagaaggagt    300
gggaggtcct ggtatttcga tctgtggggc cgtggcaccc tggtcactgt ctcctca       357

<210> SEQ ID NO 218
<211> LENGTH: 119
<212> TYPE: PRT
<213> ORGANISM: Homo sapiens

<400> SEQUENCE: 218

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Tyr Pro His Ser Gly His Thr Asn Tyr Ala Lys Arg Phe
    50                  55                  60

Gln Gly Arg Val Thr Met Thr Arg Asp Thr Ser Ile Thr Thr Ala Tyr
65                  70                  75                  80

Met Glu Leu Ile Arg Leu Arg Ser Asp Asp Thr Ala Val Tyr Tyr Cys
                85                  90                  95

Ala Arg Arg Ser Gly Arg Ser Trp Tyr Phe Asp Leu Trp Gly Arg Gly
            100                 105                 110

Thr Leu Val Thr Val Ser Ser
        115

<210> SEQ ID NO 219
<211> LENGTH: 24
<212> TYPE: DNA
<213> ORGANISM: Homo sapiens

<400> SEQUENCE: 219
ggatacacct tcaccggcca ctat                                            24

<210> SEQ ID NO 220
<211> LENGTH: 8
<212> TYPE: PRT
<213> ORGANISM: Homo sapiens

<400> SEQUENCE: 220

Gly Tyr Thr Phe Thr Gly His Tyr
```

<210> SEQ ID NO 221
<211> LENGTH: 24
<212> TYPE: DNA
<213> ORGANISM: Homo sapiens

<400> SEQUENCE: 221
atctaccctc acagtggtca caca 24

<210> SEQ ID NO 222
<211> LENGTH: 8
<212> TYPE: PRT
<213> ORGANISM: Homo sapiens

<400> SEQUENCE: 222

Ile Tyr Pro His Ser Gly His Thr
1               5

<210> SEQ ID NO 223
<211> LENGTH: 36
<212> TYPE: DNA
<213> ORGANISM: Homo sapiens

<400> SEQUENCE: 223
gcgagaagga gtgggaggtc ctggtatttc gatctg 36

<210> SEQ ID NO 224
<211> LENGTH: 12
<212> TYPE: PRT
<213> ORGANISM: Homo sapiens

<400> SEQUENCE: 224

Ala Arg Arg Ser Gly Arg Ser Trp Tyr Phe Asp Leu
1               5                   10

<210> SEQ ID NO 225
<211> LENGTH: 324
<212> TYPE: DNA
<213> ORGANISM: Homo sapiens

<400> SEQUENCE: 225
gaaatagttt tgacacagag tcccggcaca ctgtcactct ctcccgggga aagagccacc    60
ttgtcatgta gagcaagtca gtcagtctct agctcttatc tcgcctggta ccagcagaag   120
ccgggacagg ccctagact gctgatctac ggggcaagtt ccagggccac cggaatcccc    180
gaccggttca gtggaagcgg aagcggaacc gattttactt tgacgatttc tagactggag   240
ccagaggatt tcgccgttta ctattgtcaa cagtacggaa gcagccgtg acgtttggc    300
cagggcacga aggtagaaat caag                                          324

<210> SEQ ID NO 226
<211> LENGTH: 108
<212> TYPE: PRT
<213> ORGANISM: Homo sapiens

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105
```

<210> SEQ ID NO 227
<211> LENGTH: 21
<212> TYPE: DNA
<213> ORGANISM: Homo sapiens

<400> SEQUENCE: 227
cagtcagtct ctagctctta t                                            21

<210> SEQ ID NO 228
<211> LENGTH: 7
<212> TYPE: PRT
<213> ORGANISM: Homo sapiens

<400> SEQUENCE: 228

```
Gln Ser Val Ser Ser Ser Tyr
 1               5
```

<210> SEQ ID NO 229
<211> LENGTH: 9
<212> TYPE: DNA
<213> ORGANISM: Homo sapiens

<400> SEQUENCE: 229 ggggcaagt                                                           9

<210> SEQ ID NO 230
<211> LENGTH: 3
<212> TYPE: PRT
<213> ORGANISM: Homo sapiens

<400> SEQUENCE: 230

```
Gly Ala Ser
 1
```

<210> SEQ ID NO 231
<211> LENGTH: 27
<212> TYPE: DNA
<213> ORGANISM: Homo sapiens

<400> SEQUENCE: 231
caacagtacg gaagcagccc gtggacg                                      27

<210> SEQ ID NO 232
<211> LENGTH: 9
<212> TYPE: PRT
<213> ORGANISM: Homo sapiens

<400> SEQUENCE: 232

```
Gln Gln Tyr Gly Ser Ser Pro Trp Thr
 1               5
```

<210> SEQ ID NO 233

<211> LENGTH: 1341
<212> TYPE: DNA
<213> ORGANISM: Homo sapiens

<400> SEQUENCE: 233

```
caggtccagc tggtacagtc tggggctgag gtgaagaagc ctggggcctc agtgaaggtc      60
tcctgcaagg cttctggata caccttcacc ggccactata tgcactgggt gcgacaggcc     120
cctggacaag gcttgagtg gatgggatgg atctaccctc acagtggtca cacaaattat     180
gcaaagaggt ttcagggcag ggtcaccatg accagggaca cgtccatcac tacagcctac     240
atggagctga tcaggctgag atctgacgac acggccgtgt attactgtgc gagaaggagt     300
gggaggtcct ggtatttcga tctgtggggc cgtggcaccc tggtcactgt ctcctcagcc     360
tccaccaagg gcccatcggt cttccccctg gcgccctgct ccaggagcac ctccgagagc     420
acagccgccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac gaagacctac     600
acctgcaacg tagatcacaa gcccagcaac accaaggtgg acaagagagt tgagtccaaa     660
tatggtcccc catgcccacc ctgcccagca cctgagttcc tggggggacc atcagtcttc     720
ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                              1341
```

<210> SEQ ID NO 234
<211> LENGTH: 446
<212> TYPE: PRT
<213> ORGANISM: Homo sapiens

<400> SEQUENCE: 234

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met His Trp Val Arg Gln Ala Pro Gly Gln Gly Leu Glu Trp Met
        35                  40                  45

Gly Trp Ile Tyr Pro His Ser Gly His Thr Asn Tyr Ala Lys Arg Phe
    50                  55                  60

Gln Gly Arg Val Thr Met Thr Arg Asp Thr Ser Ile Thr Thr Ala Tyr
65                  70                  75                  80

Met Glu Leu Ile Arg Leu Arg Ser Asp Asp Thr Ala Val Tyr Tyr Cys
                85                  90                  95

Ala Arg Arg Ser Gly Arg Ser Trp Tyr Phe Asp Leu Trp Gly Arg Gly
```

```
                100             105                 110
Thr Leu Val Thr Val Ser Ser Ala Ser Thr Lys Gly Pro Ser Val Phe
            115                 120             125

Pro Leu Ala Pro Cys Ser Arg Ser Thr Ser Glu Ser Thr Ala Ala Leu
        130                 135             140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 235
<211> LENGTH: 648
<212> TYPE: DNA
<213> ORGANISM: Homo sapiens

<400> SEQUENCE: 235
gaaatagttt tgacacagag tcccggcaca ctgtcactct ctcccgggga aagagccacc      60
ttgtcatgta gagcaagtca gtcagtctct agctcttatc tcgcctggta ccagcagaag     120
ccgggacagg cccctagact gctgatctac ggggcaagtt ccagggccac cggaatcccc     180
```

```
gaccggttca gtggaagcgg aagcggaacc gattttactt tgacgatttc tagactggag        240
ccagaggatt tcgccgttta ctattgtcaa cagtacggaa gcagcccgtg gacgtttggc        300
cagggcacga aggtagaaat caagcgaact gtggctgcac catctgtctt catcttcccg        360
ccatctgatg agcagttgaa atctggaact gcctctgttg tgtgcctgct gaataacttc        420
tatcccagag aggccaaagt acagtggaag gtggataacg ccctccaatc gggtaactcc        480
caggagagtg tcacagagca ggacagcaag gacagcacct acagcctcag cagcaccctg        540
acgctgagca agcagactac gagaaacac aaagtctacg cctgcgaagt cacccatcag        600
ggcctgagct cgcccgtcac aaagagcttc aacaggggag agtgttag                    648
```

```
<210> SEQ ID NO 236
<211> LENGTH: 215
<212> TYPE: PRT
<213> ORGANISM: Homo sapiens

<400> SEQUENCE: 236

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 237
<211> LENGTH: 351
<212> TYPE: DNA
<213> ORGANISM: Homo sapiens

<400> SEQUENCE: 237
gaggtgcagc tggtggagtc tgggggaggg ttggtacagc ctgggggtc cctgggactc        60 tcctgtgcag cctctggatt caccttagc aactatgcca tgagctgggt ccgccaggct        120
ccagggaagg ggctggagtg ggtctcagct gttagtggtg gtggtggtgg cacatactac        180
```

```
gcagactccg tgaagggccg gttcaccatc tccagagaca attccaagaa cacggttctt    240
ctgcaaatga acagcctgag agccgaggac acggccgtat attactgtgc gagaggtcgg    300
actgggggcc ttgactactg ggcccggga accctggtca ccgtctcctc a             351
```

<210> SEQ ID NO 238
<211> LENGTH: 117
<212> TYPE: PRT
<213> ORGANISM: Homo sapiens

<400> SEQUENCE: 238

Glu Val Gln Leu Val Glu Ser Gly Gly Gly Leu Val Gln Pro Gly Gly
1               5                   10                  15

Ser Leu Gly Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Val Ser Gly Gly Gly Gly Thr Tyr Tyr Ala Asp Ser Val
    50                  55                  60

Lys Gly Arg Phe Thr Ile Ser Arg Asp Asn Ser Lys Asn Thr Val Leu
65                  70                  75                  80

Leu Gln Met Asn Ser Leu Arg Ala Glu Asp Thr Ala Val Tyr Tyr Cys
                85                  90                  95

Ala Arg Gly Arg Thr Gly Gly Leu Asp Tyr Trp Gly Pro Gly Thr Leu
            100                 105                 110

Val Thr Val Ser Ser
        115

<210> SEQ ID NO 239
<211> LENGTH: 24
<212> TYPE: DNA
<213> ORGANISM: Homo sapiens

<400> SEQUENCE: 239
ggattcacct ttagcaacta tgcc                                            24

<210> SEQ ID NO 240
<211> LENGTH: 8
<212> TYPE: PRT
<213> ORGANISM: Homo sapiens

<400> SEQUENCE: 240

Gly Phe Thr Phe Ser Asn Tyr Ala
1               5

<210> SEQ ID NO 241
<211> LENGTH: 24
<212> TYPE: DNA
<213> ORGANISM: Homo sapiens

<400> SEQUENCE: 241
gttagtggtg gtggtggtgg caca                                            24

<210> SEQ ID NO 242
<211> LENGTH: 8
<212> TYPE: PRT
<213> ORGANISM: Homo sapiens

<400> SEQUENCE: 242

Val Ser Gly Gly Gly Gly Gly Thr

<210> SEQ ID NO 243
<211> LENGTH: 30
<212> TYPE: DNA
<213> ORGANISM: Homo sapiens

<400> SEQUENCE: 243
gcgagaggtc ggactggggg ccttgactac                                    30

<210> SEQ ID NO 244
<211> LENGTH: 10
<212> TYPE: PRT
<213> ORGANISM: Homo sapiens

<400> SEQUENCE: 244

Ala Arg Gly Arg Thr Gly Gly Leu Asp Tyr
1               5                   10

<210> SEQ ID NO 245
<211> LENGTH: 336
<212> TYPE: DNA
<213> ORGANISM: Homo sapiens

<400> SEQUENCE: 245
gatgttgtga tgactcagtc tcctctctcc ctgcccgtca tctttggaca gccggcctcc    60
atctcctgca ggtcaagtca agcctcgta gacagtgatg gaaacaccta cttgaattgg   120
cttcagcaga ggccaggcca atctccaagg cgcctaattt atgaggtttc taaccgggac   180
tctgggggtcc cagacagatt cagcggcagt gggtcaggca ctgatttcac actgacaatc   240
agcagggtgg aggctgagga tgttggcatt tattactgca tgcaaggtac gcgctggcct   300
cctacttttcg gcggagggac caaggtggag atcaaa                             336

<210> SEQ ID NO 246
<211> LENGTH: 112
<212> TYPE: PRT
<213> ORGANISM: Homo sapiens

<400> SEQUENCE: 246

Asp Val Val Met Thr Gln Ser Pro Leu Ser Leu Pro Val Ile Phe Gly
1               5                   10                  15

Gln Pro Ala Ser Ile Ser Cys Arg Ser Ser Gln Ser Leu Val Asp Ser
                20                  25                  30

Asp Gly Asn Thr Tyr Leu Asn Trp Leu Gln Gln Arg Pro Gly Gln Ser
            35                  40                  45

Pro Arg Arg Leu Ile Tyr Glu Val Ser Asn Arg Asp Ser Gly Val Pro
        50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Gly
                85                  90                  95

Thr Arg Trp Pro Pro Thr Phe Gly Gly Gly Thr Lys Val Glu Ile Lys
                100                 105                 110

<210> SEQ ID NO 247
<211> LENGTH: 33
<212> TYPE: DNA
<213> ORGANISM: Homo sapiens

<400> SEQUENCE: 247

```
caaagcctcg tagacagtga tggaaacacc tac                                    33
```

<210> SEQ ID NO 248
<211> LENGTH: 11
<212> TYPE: PRT
<213> ORGANISM: Homo sapiens

<400> SEQUENCE: 248

```
Gln Ser Leu Val Asp Ser Asp Gly Asn Thr Tyr
1               5                   10
```

<210> SEQ ID NO 249
<211> LENGTH: 9
<212> TYPE: DNA
<213> ORGANISM: Homo sapiens

<400> SEQUENCE: 249

```
gaggtttct                                                                9
```

<210> SEQ ID NO 250
<211> LENGTH: 3
<212> TYPE: PRT
<213> ORGANISM: Homo sapiens

<400> SEQUENCE: 250

```
Glu Val Ser
1
```

<210> SEQ ID NO 251
<211> LENGTH: 27
<212> TYPE: DNA
<213> ORGANISM: Homo sapiens

<400> SEQUENCE: 251

```
atgcaaggta cgcgctggcc tcctact                                           27
```

<210> SEQ ID NO 252
<211> LENGTH: 9
<212> TYPE: PRT
<213> ORGANISM: Homo sapiens

<400> SEQUENCE: 252

```
Met Gln Gly Thr Arg Trp Pro Pro Thr
1               5
```

<210> SEQ ID NO 253
<211> LENGTH: 1335
<212> TYPE: DNA
<213> ORGANISM: Homo sapiens

<400> SEQUENCE: 253

```
gaggtgcagc tggtggagtc tgggggaggg ttggtacagc ctggggggtc cctgggactc        60
tcctgtgcag cctctggatt cacctttagc aactatgcca tgagctgggt ccgccaggct       120
ccagggaagg ggctggagtg ggtctcagct gttagtggtg gtggtggtgg cacatactac       180
gcagactccg tgaagggccg gttcaccatc tccagagaca attccaagaa cacggttctt       240
ctgcaaatga acagcctgag agccgaggac acggccgtat attactgtgc gagaggtcgg       300
actgggggcc ttgactactg gggcccggga accctggtca ccgtctcctc agcctccacc       360
aagggcccat cggtcttccc cctggcgccc tgctccagga gcacctccga gagcacagcc       420
gccctgggct gcctggtcaa ggactacttc cccgaaccgg tgacggtgtc gtggaactca       480
```

```
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttgagtc caaatatggt    660
cccccatgcc caccctgccc agcacctgag ttcctggggg gaccatcagt cttcctgttc    720
cccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtc    960
tccaacaaag gcctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acgcctcccg tgctggactc cgacggctcc   1200
ttcttcctct acagcaggct caccgtggac aagagcaggt ggcaggaggg gaatgtcttc   1260
tcatgctccg tgatgcatga ggctctgcac aaccactaca cacagaagtc cctctccctg   1320
tctctgggta aatga                                                    1335

<210> SEQ ID NO 254
<211> LENGTH: 444
<212> TYPE: PRT
<213> ORGANISM: Homo sapiens

<400> SEQUENCE: 254

Glu Val Gln Leu Val Glu Ser Gly Gly Gly Leu Val Gln Pro Gly Gly
1               5                   10                  15

Ser Leu Gly Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Val Ser Gly Gly Gly Gly Thr Tyr Tyr Ala Asp Ser Val
    50                  55                  60

Lys Gly Arg Phe Thr Ile Ser Arg Asp Asn Ser Lys Asn Thr Val Leu
65                  70                  75                  80

Leu Gln Met Asn Ser Leu Arg Ala Glu Asp Thr Ala Val Tyr Tyr Cys
                85                  90                  95

Ala Arg Gly Arg Thr Gly Gly Leu Asp Tyr Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
```

210                 215                 220
Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440

<210> SEQ ID NO 255
<211> LENGTH: 660
<212> TYPE: DNA
<213> ORGANISM: Homo sapiens

<400> SEQUENCE: 255
gatgttgtga tgactcagtc tcctctctcc ctgcccgtca tctttggaca gccggcctcc     60
atctcctgca ggtcaagtca aagcctcgta gacagtgatg aaacacccta cttgaattgg    120
cttcagcaga ggccaggcca atctccaagg cgcctaattt atgaggtttc taaccgggac    180
tctggggtcc cagacagatt cagcggcagt gggtcaggca ctgatttcac actgacaatc    240
agcagggtgg aggctgagga tgttggcatt tattactgca tgcaaggtac gcgctggcct    300
cctactttcg gcggagggac caaggtggag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 256
<211> LENGTH: 219
<212> TYPE: PRT
<213> ORGANISM: Homo sapiens

<400> SEQUENCE: 256

Asp Val Val Met Thr Gln Ser Pro Leu Ser Leu Pro Val Ile Phe Gly
1               5                   10                  15

Gln Pro Ala Ser Ile Ser Cys Arg Ser Ser Gln Ser Leu Val Asp Ser
            20                  25                  30

Asp Gly Asn Thr Tyr Leu Asn Trp Leu Gln Gln Arg Pro Gly Gln Ser
        35                  40                  45

Pro Arg Arg Leu Ile Tyr Glu Val Ser Asn Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Gly
                85                  90                  95

Thr Arg Trp Pro Pro Thr Phe Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 257
<211> LENGTH: 366
<212> TYPE: DNA
<213> ORGANISM: Homo sapiens

<400> SEQUENCE: 257
gaggtgcagc tggtggagtc tgggggaggt gtggtccggc ctggggggtc cctgagactc     60
tcctgtgcag cctctggatt catctttgat gattatgaca tgagttgggt ccgccaacct    120
ccagggaggg gactggaatg ggtctccggt attgattggt tggtggtac cagaggttat     180 gcagactcta tgaagggccg attcaccatt tccagagaca acgccaagaa ctccctgtat    240
ctgcaaatga acagcctgag agtcgaggac acggccttct attactgtgc gagggggg     300 gctatagtgg gagctgttac tcccttgac tactggggcc agggaaccct ggtcactgtc     360
tcctca                                                              366

<210> SEQ ID NO 258
<211> LENGTH: 122
<212> TYPE: PRT
<213> ORGANISM: Homo sapiens

<400> SEQUENCE: 258

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ile Phe Asp Asp Tyr

```
            20                  25                  30
Asp Met Ser Trp Val Arg Gln Pro Pro Gly Arg Gly Leu Glu Trp Val
         35                  40                  45

Ser Gly Ile Asp Trp Phe Gly Gly Thr Arg Gly Tyr Ala Asp Ser Met
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Phe Tyr Tyr Cys
                 85                  90                  95

Ala Arg Gly Gly Ala Ile Val Gly Ala Val Thr Pro Phe Asp Tyr Trp
             100                 105                 110

Gly Gln Gly Thr Leu Val Thr Val Ser Ser
         115                 120

<210> SEQ ID NO 259
<211> LENGTH: 24
<212> TYPE: DNA
<213> ORGANISM: Homo sapiens

<400> SEQUENCE: 259
ggattcatct ttgatgatta tgac                                              24

<210> SEQ ID NO 260
<211> LENGTH: 8
<212> TYPE: PRT
<213> ORGANISM: Homo sapiens

<400> SEQUENCE: 260

Gly Phe Ile Phe Asp Asp Tyr Asp
1               5

<210> SEQ ID NO 261
<211> LENGTH: 24
<212> TYPE: DNA
<213> ORGANISM: Homo sapiens

<400> SEQUENCE: 261
attgattggt ttggtggtac caga                                              24

<210> SEQ ID NO 262
<211> LENGTH: 8
<212> TYPE: PRT
<213> ORGANISM: Homo sapiens

<400> SEQUENCE: 262

Ile Asp Trp Phe Gly Gly Thr Arg
1               5

<210> SEQ ID NO 263
<211> LENGTH: 45
<212> TYPE: DNA
<213> ORGANISM: Homo sapiens

<400> SEQUENCE: 263
gcgagagggg gggctatagt gggagctgtt actccctttg actac                       45

<210> SEQ ID NO 264
<211> LENGTH: 15
<212> TYPE: PRT
<213> ORGANISM: Homo sapiens

<400> SEQUENCE: 264
```

Ala Arg Gly Gly Ala Ile Val Gly Ala Val Thr Pro Phe Asp Tyr
1               5                   10                  15

<210> SEQ ID NO 265
<211> LENGTH: 321
<212> TYPE: DNA
<213> ORGANISM: Homo sapiens

<400> SEQUENCE: 265
gacatccaga tgacccagtc tccatcctcc ctgtctgcat ctgttggaaa cagagtcacc      60
ctcagttgcc gggcaagtca gagcattaac acctatttaa gttggtatca gcagagacca    120
ggaaaagccc ctaagctcct gatctatgct gcatccagtt tgcaaagtgg ggtcccctca    180
aggttcagtg gcagtggagc tgggacagat tcactctcca ccatcagcag tctgcaacct    240
gaagattttg caacttacta ctgtcaacag agttacagtg cccctctcac tttcggcggt    300
gggaccaagg tggagatcaa a                                              321

<210> SEQ ID NO 266
<211> LENGTH: 107
<212> TYPE: PRT
<213> ORGANISM: Homo sapiens

<400> SEQUENCE: 266

Asp Ile Gln Met Thr Gln Ser Pro Ser Ser Leu Ser Ala Ser Val Gly
1               5                   10                  15

Asn Arg Val Thr Leu Ser Cys Arg Ala Ser Gln Ser Ile Asn Thr Tyr
            20                  25                  30

Leu Ser Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ala Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Leu
                85                  90                  95

Thr Phe Gly Gly Gly Thr Lys Val Glu Ile Lys
            100                 105

<210> SEQ ID NO 267
<211> LENGTH: 18
<212> TYPE: DNA
<213> ORGANISM: Homo sapiens

<400> SEQUENCE: 267
cagagcatta acacctat                                                   18

<210> SEQ ID NO 268
<211> LENGTH: 6
<212> TYPE: PRT
<213> ORGANISM: Homo sapiens

<400> SEQUENCE: 268

Gln Ser Ile Asn Thr Tyr
1               5

<210> SEQ ID NO 269
<211> LENGTH: 27
<212> TYPE: DNA
<213> ORGANISM: Homo sapiens

<400> SEQUENCE: 269
caacagagtt acagtgcccc tctcact    27

<210> SEQ ID NO 270
<211> LENGTH: 9
<212> TYPE: PRT
<213> ORGANISM: Homo sapiens

<400> SEQUENCE: 270

Gln Gln Ser Tyr Ser Ala Pro Leu Thr
1               5

<210> SEQ ID NO 271
<211> LENGTH: 1350
<212> TYPE: DNA
<213> ORGANISM: Homo sapiens

<400> SEQUENCE: 271
gaggtgcagc tggtggagtc tgggggaggt gtggtccggc ctggggggtc cctgagactc    60
tcctgtgcag cctctggatt catctttgat gattatgaca tgagttgggt ccgccaacct   120
ccagggaggg gactggaatg ggtctccggt attgattggt tggtggtac cagaggttat    180
gcagactcta tgaagggccg attcaccatt tccagagaca cgccaagaa ctccctgtat    240
ctgcaaatga acagcctgag agtcgaggac acggccttct attactgtgc gagagggggg    300
gctatagtgg gagctgttac tccctttgac tactggggcc agggaaccct ggtcactgtc    360
tcctcagcct ccaccaaggg cccatcggtc ttccccctgg cgccctgctc caggagcacc    420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccaccc tgcccagcac ctgagttcct ggggggacca    720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc cccatccca ggaggagatg    1080
accaagaacc aggtcagcct gacctgcctg gtcaaaggct tctacccag cgacatcgcc    1140
gtggagtggg agagcaatgg gcagccggag aacaactaca agaccacgcc tcccgtgctg    1200
gactccgacg gctccttctt cctctacagc aggctcaccg tggacaagag caggtggcag    1260
gaggggaatg tcttctcatg ctccgtgatg catgaggctc tgcacaacca ctacacacag    1320
aagtccctct ccctgtctct gggtaaatga                                    1350

<210> SEQ ID NO 272
<211> LENGTH: 449
<212> TYPE: PRT
<213> ORGANISM: Homo sapiens

<400> SEQUENCE: 272

Glu Val Gln Leu Val Glu Ser Gly Gly Gly Val Val Arg Pro Gly Gly

-continued

```
1               5                   10                  15
Ser Leu Arg Leu Ser Cys Ala Ala Ser Gly Phe Ile Phe Asp Asp Tyr
            20                  25                  30

Asp Met Ser Trp Val Arg Gln Pro Gly Arg Gly Leu Glu Trp Val
            35                  40                  45

Ser Gly Ile Asp Trp Phe Gly Thr Arg Gly Tyr Ala Asp Ser Met
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Phe Tyr Tyr Cys
                85                  90                  95

Ala Arg Gly Gly Ala Ile Val Gly Ala Val Thr Pro Phe Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430
```

Ala Leu His Asn His Tyr Thr Gln Lys Ser Leu Ser Leu Ser Leu Gly
        435                 440                 445

Lys

<210> SEQ ID NO 273
<211> LENGTH: 645
<212> TYPE: DNA
<213> ORGANISM: Homo sapiens

<400> SEQUENCE: 273

```
gacatccaga tgacccagtc tccatcctcc ctgtctgcat ctgttggaaa cagagtcacc      60
ctcagttgcc gggcaagtca gagcattaac acctatttaa gttggtatca gcagagacca    120
ggaaaagccc ctaagctcct gatctatgct gcatccagtt tgcaaagtgg ggtcccctca    180
aggttcagtg gcagtggagc tgggacagat ttcactctca ccatcagcag tctgcaacct    240
gaagattttg caacttacta ctgtcaacag agttacagtg ccctctcac tttcggcggt     300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                     645
```

<210> SEQ ID NO 274
<211> LENGTH: 214
<212> TYPE: PRT
<213> ORGANISM: Homo sapiens

<400> SEQUENCE: 274

Asp Ile Gln Met Thr Gln Ser Pro Ser Ser Leu Ser Ala Ser Val Gly
1               5                   10                  15

Asn Arg Val Thr Leu Ser Cys Arg Ala Ser Gln Ser Ile Asn Thr Tyr
            20                  25                  30

Leu Ser Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ala Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205
Phe Asn Arg Gly Glu Cys
        210
```

<210> SEQ ID NO 275
<211> LENGTH: 366
<212> TYPE: DNA
<213> ORGANISM: Homo sapiens

<400> SEQUENCE: 275

```
cagctgcagc tgcaggagtc gggcccagga ctggtgaagc cttcggagac cctgtccctc    60
acctgcactg tctctggtgg ctccatcagc attaagaatt actactgggg ctggatccgt   120
cagcccccag ggaaggggct ggagtggatt gggagtatct attatagtgg gaccacctac   180
tacaacccgt ccctcaagag tcgagtcacc atatccgtag acacgtccaa gaaccagttc   240
tccctgaagc tgagctctgt gaccgccgca gacacggctg tatatcactg tgcgagacat   300
ggatacagct atggtcacgg ctggttcgac ccctgggggcc agggaaccct ggtcaccgtc   360
tcctca                                                               366
```

<210> SEQ ID NO 276
<211> LENGTH: 122
<212> TYPE: PRT
<213> ORGANISM: Homo sapiens

<400> SEQUENCE: 276

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ile Lys
            20                  25                  30
Asn Tyr Tyr Trp Gly Trp Ile Arg Gln Pro Pro Gly Lys Gly Leu Glu
        35                  40                  45
Trp Ile Gly Ser Ile Tyr Tyr Ser Gly Thr Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr His
                85                  90                  95
Cys Ala Arg His Gly Tyr Ser Tyr Gly His Gly Trp Phe Asp Pro Trp
            100                 105                 110
Gly Gln Gly Thr Leu Val Thr Val Ser Ser
        115                 120
```

<210> SEQ ID NO 277
<211> LENGTH: 30
<212> TYPE: DNA
<213> ORGANISM: Homo sapiens

<400> SEQUENCE: 277

```
ggtggctcca tcagcattaa gaattactac                                      30
```

<210> SEQ ID NO 278
<211> LENGTH: 10
<212> TYPE: PRT
<213> ORGANISM: Homo sapiens

<400> SEQUENCE: 278

Gly Gly Ser Ile Ser Ile Lys Asn Tyr Tyr
1               5               10

<210> SEQ ID NO 279
<211> LENGTH: 21
<212> TYPE: DNA
<213> ORGANISM: Homo sapiens

<400> SEQUENCE: 279
atctattata gtgggaccac c                                           21

<210> SEQ ID NO 280
<211> LENGTH: 7
<212> TYPE: PRT
<213> ORGANISM: Homo sapiens

<400> SEQUENCE: 280

Ile Tyr Tyr Ser Gly Thr Thr
1               5

<210> SEQ ID NO 281
<211> LENGTH: 42
<212> TYPE: DNA
<213> ORGANISM: Homo sapiens

<400> SEQUENCE: 281
gcgagacatg gatacagcta tggtcacggc tggttcgacc cc                    42

<210> SEQ ID NO 282
<211> LENGTH: 14
<212> TYPE: PRT
<213> ORGANISM: Homo sapiens

<400> SEQUENCE: 282

Ala Arg His Gly Tyr Ser Tyr Gly His Gly Trp Phe Asp Pro
1               5               10

<210> SEQ ID NO 283
<211> LENGTH: 1350
<212> TYPE: DNA
<213> ORGANISM: Homo sapiens

<400> SEQUENCE: 283
cagctgcagc tgcaggagtc gggcccagga ctggtgaagc cttcggagac cctgtccctc    60
acctgcactg tctctggtgg ctccatcagc attaagaatt actactgggg ctggatccgt   120
cagcccccag ggaaggggct ggagtggatt gggagtatct attatagtgg gaccacctac   180
tacaacccgt ccctcaagag tcgagtcacc atatccgtag acacgtccaa gaaccagttc   240
tccctgaagc tgagctctgt gaccgccgca gacacggctg tatatcactg tgcgagacat   300
ggatacagct atggtcacgg ctggttcgac ccctggggcc agggaaccct ggtcaccgtc   360
tcctcagcct ccaccaaggg cccatcggtc ttccccctgg cgccctgctc caggagcacc   420
tccgagagca gccgccct gggctgcctg gtcaaggact acttccccga accggtgacg   480
gtgtcgtgga actcaggcgc cctgaccagc ggcgtgcaca ccttccccggc tgtcctacag   540 tcctcaggac tctactccct cagcagcgtg gtgaccgtgc cctccagcag cttgggcacg   600
aagacctaca cctgcaacgt agatcacaag cccagcaaca ccaaggtgga cagagagtt   660 gagtccaaat atggtccccc atgcccaccc tgcccagcac ctgagttcct gggggggacca   720 tcagtcttcc tgttcccccc aaaacccaag gacactctca tgatctcccg gacccctgag   780

```
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140 gtggagtggg agagcaatgg gcagccggag aacaactaca agaccacgcc tcccgtgctg   1200
gactccgacg gctccttctt cctctacagc aggctcaccg tggacaagag caggtggcag   1260 gagggggaatg tcttctcatg ctccgtgatg catgaggctc tgcacaacca ctacacacag   1320
aagtccctct ccctgtctct gggtaaatga                                     1350
```

<210> SEQ ID NO 284
<211> LENGTH: 449
<212> TYPE: PRT
<213> ORGANISM: Homo sapiens

<400> SEQUENCE: 284

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Lys
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr His
                85                  90                  95

Cys Ala Arg His Gly Tyr Ser Tyr Gly His Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270
```

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 285
<211> LENGTH: 366
<212> TYPE: DNA
<213> ORGANISM: Homo sapiens

<400> SEQUENCE: 285
caggtacagc tgcagcagtc aggtccagga ctggtaaagc cctcacagac cctctcactc      60
acctgtgaca tctccgggga cagtgtctct agcaacattg ctacttggaa ctggatcagg     120
cagtccccat cgagaggcct tgagtggctg gaaggacat attacaggtc caagtggtat      180
aaagattatg cagtatctgt gaaaagtcga ataaccatca cccagacac atccaagaac      240 cagttctccc tgcaggtgaa ctctgtgact cccgaggaca cggctgtcta ttactgtgca     300
agaatgactg gccgcgcata ctactttgag tactggggcc agggaaccct ggtcaccgtc     360
tcctca                                                                366

<210> SEQ ID NO 286
<211> LENGTH: 122
<212> TYPE: PRT
<213> ORGANISM: Homo sapiens

<400> SEQUENCE: 286

Gln Val Gln Leu Gln Gln Ser Gly Pro Gly Leu Val Lys Pro Ser Gln
1               5                   10                  15

Thr Leu Ser Leu Thr Cys Asp Ile Ser Gly Asp Ser Val Ser Ser Asn
            20                  25                  30

Ile Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Lys Asp Tyr Ala
    50                  55                  60

Val Ser Val Lys Ser Arg Ile Thr Ile Asn Pro Asp Thr Ser Lys Asn
65                  70                  75                  80

```
Gln Phe Ser Leu Gln Val Asn Ser Val Thr Pro Glu Asp Thr Ala Val
                85                  90                  95

Tyr Tyr Cys Ala Arg Met Thr Gly Pro Arg Tyr Tyr Phe Glu Tyr Trp
            100                 105                 110

Gly Gln Gly Thr Leu Val Thr Val Ser Ser
        115                 120

<210> SEQ ID NO 287
<211> LENGTH: 30
<212> TYPE: DNA
<213> ORGANISM: Homo sapiens

<400> SEQUENCE: 287
ggggacagtg tctctagcaa cattgctact                                      30

<210> SEQ ID NO 288
<211> LENGTH: 10
<212> TYPE: PRT
<213> ORGANISM: Homo sapiens

<400> SEQUENCE: 288

Gly Asp Ser Val Ser Ser Asn Ile Ala Thr
1               5                   10

<210> SEQ ID NO 289
<211> LENGTH: 27
<212> TYPE: DNA
<213> ORGANISM: Homo sapiens

<400> SEQUENCE: 289
acatattaca ggtccaagtg gtataaa                                         27

<210> SEQ ID NO 290
<211> LENGTH: 9
<212> TYPE: PRT
<213> ORGANISM: Homo sapiens

<400> SEQUENCE: 290

Thr Tyr Tyr Arg Ser Lys Trp Tyr Lys
1               5

<210> SEQ ID NO 291
<211> LENGTH: 36
<212> TYPE: DNA
<213> ORGANISM: Homo sapiens

<400> SEQUENCE: 291
gcaagaatga ctgggccgcg atactacttt gagtac                               36

<210> SEQ ID NO 292
<211> LENGTH: 12
<212> TYPE: PRT
<213> ORGANISM: Homo sapiens

<400> SEQUENCE: 292

Ala Arg Met Thr Gly Pro Arg Tyr Tyr Phe Glu Tyr
1               5                   10

<210> SEQ ID NO 293
<211> LENGTH: 1350
<212> TYPE: DNA
<213> ORGANISM: Homo sapiens
```

<400> SEQUENCE: 293

```
caggtacagc tgcagcagtc aggtccagga ctggtaaagc cctcacagac cctctcactc      60
acctgtgaca tctccgggga cagtgtctct agcaacattg ctacttggaa ctggatcagg     120
cagtccccat cgagaggcct tgagtggctg ggaaggacat attacaggtc caagtggtat     180
aaagattatg cagtatctgt gaaaagtcga ataaccatca acccagacac atccaagaac     240
cagttctccc tgcaggtgaa ctctgtgact cccgaggaca cggctgtcta ttactgtgca     300
agaatgactg ggccgcgata ctactttgag tactggggcc agggaaccct ggtcaccgtc     360
tcctcagcct ccaccaaggg cccatcggtc ttccccctgg cgccctgctc caggagcacc     420
tccgagagca gccgccct gggctgcctg gtcaaggact acttccccga accggtgacg      480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccaccc tgcccagcac ctgagttcct ggggggacca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag cgacatcgcc    1140
gtggagtggg agagcaatgg gcagccggag aacaactaca agaccacgcc tcccgtgctg    1200
gactccgacg gctccttctt cctctacagc aggctcaccg tggacaagag caggtggcag    1260
gaggggaatg tcttctcatg ctccgtgatg catgaggctc tgcacaacca ctacacacag    1320
aagtccctct ccctgtctct gggtaaatga                                    1350
```

<210> SEQ ID NO 294
<211> LENGTH: 449
<212> TYPE: PRT
<213> ORGANISM: Homo sapiens

<400> SEQUENCE: 294

```
Gln Val Gln Leu Gln Gln Ser Gly Pro Gly Leu Val Lys Pro Ser Gln
1               5                   10                  15

Thr Leu Ser Leu Thr Cys Asp Ile Ser Gly Asp Ser Val Ser Ser Asn
            20                  25                  30

Ile Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Lys Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Val Asn Ser Val Thr Pro Glu Asp Thr Ala Val
                85                  90                  95

Tyr Tyr Cys Ala Arg Met Thr Gly Pro Arg Tyr Tyr Phe Glu Tyr Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
Lys

<210> SEQ ID NO 295
<211> LENGTH: 366
<212> TYPE: DNA
<213> ORGANISM: Homo sapiens

<400> SEQUENCE: 295
gaggtgcagc tggtggagtc tgggggaggt gtggtccggc ctggggggtc cctgagactc      60
tcctgtgcag cctctggatt cacctttgat gattttgaca tgagctgggt ccgccaaggt     120
ccagggaagg ggctggagtg ggtctctggt attaattggc atgggagtag tacaggttat     180
gcagactctg tgaagggccg attcaccatc tccagagaca acgccaagaa ctccctgtat     240
```

```
ctgcaaatga gcagtctgag ggccgaggac acggccttat atcactgtgt gagagggggg    300
actatagtgg gtgccactac tccccttgac tactggggcc agggaaccct ggtcaccgtc    360
tcctca                                                                366
```

<210> SEQ ID NO 296
<211> LENGTH: 122
<212> TYPE: PRT
<213> ORGANISM: Homo sapiens

<400> SEQUENCE: 296

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Phe
            20                  25                  30

Asp Met Ser Trp Val Arg Gln Gly Pro Gly Lys Gly Leu Glu Trp Val
        35                  40                  45

Ser Gly Ile Asn Trp His Gly Ser Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Leu Tyr His Cys
                85                  90                  95

Val Arg Gly Gly Thr Ile Val Gly Ala Thr Thr Pro Leu Asp Tyr Trp
            100                 105                 110

Gly Gln Gly Thr Leu Val Thr Val Ser Ser
        115                 120
```

<210> SEQ ID NO 297
<211> LENGTH: 24
<212> TYPE: DNA
<213> ORGANISM: Homo sapiens

<400> SEQUENCE: 297

```
ggattcacct ttgatgattt tgac                                             24
```

<210> SEQ ID NO 298
<211> LENGTH: 8
<212> TYPE: PRT
<213> ORGANISM: Homo sapiens

<400> SEQUENCE: 298

```
Gly Phe Thr Phe Asp Asp Phe Asp
1               5
```

<210> SEQ ID NO 299
<211> LENGTH: 24
<212> TYPE: DNA
<213> ORGANISM: Homo sapiens

<400> SEQUENCE: 299

```
attaattggc atgggagtag taca                                             24
```

<210> SEQ ID NO 300
<211> LENGTH: 8
<212> TYPE: PRT
<213> ORGANISM: Homo sapiens

<400> SEQUENCE: 300

```
Ile Asn Trp His Gly Ser Ser Thr
1               5
```

<210> SEQ ID NO 301
<211> LENGTH: 45
<212> TYPE: DNA
<213> ORGANISM: Homo sapiens

<400> SEQUENCE: 301
gtgagagggg ggactatagt gggtgccact actccccttg actac                           45

<210> SEQ ID NO 302
<211> LENGTH: 15
<212> TYPE: PRT
<213> ORGANISM: Homo sapiens

<400> SEQUENCE: 302

Val Arg Gly Gly Thr Ile Val Gly Ala Thr Thr Pro Leu Asp Tyr
1               5                   10                  15

<210> SEQ ID NO 303
<211> LENGTH: 321
<212> TYPE: DNA
<213> ORGANISM: Homo sapiens

<400> SEQUENCE: 303
gacatccaga tgacccagtc tccatcctcc ctgtctgcat ctgtaggaga cagagtcacc           60
atgacttgcc gggcaagtcg gaccattagc agctatttaa gttggtatca gcagaaatca          120
gggaaagtcc ctaacctcct gatctttggt gcatccagtt tgcaaagtgg ggtcccatca          180
aggttcagtg ccagtggatc tgggacagat ttcactctca tcatcagcag tctgcaacct          240
gaagattttg caacttacta ctgtcaacag agttacagct cccctctcac tttcggcgga          300
gggaccaagg tggagatcaa a                                                    321

<210> SEQ ID NO 304
<211> LENGTH: 107
<212> TYPE: PRT
<213> ORGANISM: Homo sapiens

<400> SEQUENCE: 304

Asp Ile Gln Met Thr Gln Ser Pro Ser Ser Leu Ser Ala Ser Val Gly
1               5                   10                  15

Asp Arg Val Thr Met Thr Cys Arg Ala Ser Arg Thr Ile Ser Ser Tyr
                20                  25                  30

Leu Ser Trp Tyr Gln Gln Lys Ser Gly Lys Val Pro Asn Leu Leu Ile
            35                  40                  45

Phe Gly Ala Ser Ser Leu Gln Ser Gly Val Pro Ser Arg Phe Ser Ala
        50                  55                  60

Ser Gly Ser Gly Thr Asp Phe Thr Leu Ile Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gly Gly Thr Lys Val Glu Ile Lys
            100                 105

<210> SEQ ID NO 305
<211> LENGTH: 18
<212> TYPE: DNA
<213> ORGANISM: Homo sapiens

<400> SEQUENCE: 305

```
cggaccatta gcagctat                                                    18
```

<210> SEQ ID NO 306
<211> LENGTH: 6
<212> TYPE: PRT
<213> ORGANISM: Homo sapiens

<400> SEQUENCE: 306

Arg Thr Ile Ser Ser Tyr
1               5

<210> SEQ ID NO 307
<211> LENGTH: 9
<212> TYPE: DNA
<213> ORGANISM: Homo sapiens

<400> SEQUENCE: 307

```
ggtgcatcc                                                               9
```

<210> SEQ ID NO 308
<211> LENGTH: 27
<212> TYPE: DNA
<213> ORGANISM: Homo sapiens

<400> SEQUENCE: 308

```
caacagagtt acagctcccc tctcact                                          27
```

<210> SEQ ID NO 309
<211> LENGTH: 9
<212> TYPE: PRT
<213> ORGANISM: Homo sapiens

<400> SEQUENCE: 309

Gln Gln Ser Tyr Ser Ser Pro Leu Thr
1               5

<210> SEQ ID NO 310
<211> LENGTH: 1350
<212> TYPE: DNA
<213> ORGANISM: Homo sapiens

<400> SEQUENCE: 310

```
gaggtgcagc tggtggagtc tgggggaggt gtggtccggc ctgggggtc cctgagactc       60
tcctgtgcag cctctggatt cacctttgat gattttgaca tgagctgggt ccgccaaggt     120
ccagggaagg ggctggagtg gtctctggt attaattggc atgggagtag tacaggttat      180
gcagactctg tgaagggccg attcaccatc tccagagaca cgccaagaa ctccctgtat      240
ctgcaaatga gcagtctgag ggccgaggac acggccttat atcactgtgt gagagggggg    300
actatagtgg gtgccactac tccccttgac tactggggcc agggaaccct ggtcaccgtc    360
tcctcagcct ccaccaaggg cccatcggtc ttccccctgg cgccctgctc caggagcacc    420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccaccc tgcccagcac ctgagttcct ggggggacca    720
tcagtcttcc tgttcccccc aaaacccaag gacactctca tgatctcccg gacccctgag    780
gtcacgtgcg tggtggtgga cgtgagccag gaagacccg aggtccagtt caactggtac    840
```

```
gtggatggcg tggaggtgca taatgccaag acaaagccgc gggaggagca gttcaacagc       900
acgtaccgtg tggtcagcgt cctcaccgtc ctgcaccagg actggctgaa cggcaaggag       960
tacaagtgca aggtctccaa caaaggcctc ccgtcctcca tcgagaaaac catctccaaa      1020 gccaagggc agccccgaga gccacaggtg tacaccctgc ccccatccca ggaggagatg       1080
accaagaacc aggtcagcct gacctgcctg gtcaaaggct tctaccccag cgacatcgcc      1140
gtggagtggg agagcaatgg gcagccggag aacaactaca agaccacgcc tcccgtgctg      1200
gactccgacg gctccttctt cctctacagc aggctcaccg tggacaagag caggtggcag      1260
gaggggaatg tcttctcatg ctccgtgatg catgaggctc tgcacaacca ctacacacag      1320
aagtccctct ccctgtctct gggtaaatga                                       1350
```

<210> SEQ ID NO 311
<211> LENGTH: 449
<212> TYPE: PRT
<213> ORGANISM: Homo sapiens

<400> SEQUENCE: 311

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Phe
            20                  25                  30

Asp Met Ser Trp Val Arg Gln Pro Gly Lys Gly Leu Glu Trp Val
        35                  40                  45

Ser Gly Ile Asn Trp His Gly Ser Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Leu Tyr His Cys
                85                  90                  95

Val Arg Gly Gly Thr Ile Val Gly Ala Thr Thr Pro Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
```

```
            275                 280                 285
Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 312
<211> LENGTH: 645
<212> TYPE: DNA
<213> ORGANISM: Homo sapiens

<400> SEQUENCE: 312
gacatccaga tgacccagtc tccatcctcc ctgtctgcat ctgtaggaga cagagtcacc    60
atgacttgcc gggcaagtcg gaccattagc agctatttaa gttggtatca gcagaaatca   120
gggaaagtcc ctaacctcct gatctttggt gcatccagtt tgcaaagtgg ggtcccatca   180
aggttcagtg ccagtggatc tgggacagat ttcactctca tcatcagcag tctgcaacct   240
gaagattttg caacttacta ctgtcaacag agttacagct cccctctcac tttcggcgga   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag              645

<210> SEQ ID NO 313
<211> LENGTH: 214
<212> TYPE: PRT
<213> ORGANISM: Homo sapiens

<400> SEQUENCE: 313

Asp Ile Gln Met Thr Gln Ser Pro Ser Ser Leu Ser Ala Ser Val Gly
1               5                   10                  15

Asp Arg Val Thr Met Thr Cys Arg Ala Ser Arg Thr Ile Ser Ser Tyr
            20                  25                  30

Leu Ser Trp Tyr Gln Gln Lys Ser Gly Lys Val Pro Asn Leu Leu Ile
```

```
                35                  40                  45
Phe Gly Ala Ser Ser Leu Gln Ser Gly Val Pro Ser Arg Phe Ser Ala
         50                  55                  60
Ser Gly Ser Gly Thr Asp Phe Thr Leu Ile Ile Ser Ser Leu Gln Pro
 65                  70                  75                  80
Glu Asp Phe Ala Thr Tyr Tyr Cys Gln Gln Ser Tyr Ser Ser Pro Leu
                 85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 314
<211> LENGTH: 351
<212> TYPE: DNA
<213> ORGANISM: Homo sapiens

<400> SEQUENCE: 314
gaggtgcagc tggtggagtc tgggggagac ttggtacagc ctgggggtc cctgagactc        60 tcctgtacag cctctggatt cattttagg aactatgcca tgaactgggt ccgccaggct       120
ccagggaagg gctggagtg gttgtcaggt attcttggta gtaatgataa cacatactac       180
gtagactccg tgaagggccg gttcaccatt tctagagaca attccaggaa cacgctgtat       240
ctgcaaatga acagcctgag agccgaggac tcggccgtat attactgtgc aaaaggggac       300
gctgggggct tgactactgg ggccaggga accctggtca ccgtctcctc a                351

<210> SEQ ID NO 315
<211> LENGTH: 117
<212> TYPE: PRT
<213> ORGANISM: Homo sapiens

<400> SEQUENCE: 315

Glu Val Gln Leu Val Glu Ser Gly Gly Asp Leu Val Gln Pro Gly Gly
 1               5                  10                  15
Ser Leu Arg Leu Ser Cys Thr Ala Ser Gly Phe Ile Phe Arg Asn Tyr
             20                  25                  30
Ala Met Asn Trp Val Arg Gln Ala Pro Gly Lys Gly Leu Glu Trp Leu
         35                  40                  45
Ser Gly Ile Leu Gly Ser Asn Asp Asn Thr Tyr Tyr Val Asp Ser Val
     50                  55                  60
Lys Gly Arg Phe Thr Ile Ser Arg Asp Asn Ser Arg Asn Thr Leu Tyr
 65                  70                  75                  80
Leu Gln Met Asn Ser Leu Arg Ala Glu Asp Ser Ala Val Tyr Tyr Cys
```

```
                 85                  90                  95

Ala Lys Gly Asp Ala Gly Gly Phe Asp Tyr Trp Gly Gln Gly Thr Leu
            100                 105                 110

Val Thr Val Ser Ser
        115

<210> SEQ ID NO 316
<211> LENGTH: 24
<212> TYPE: DNA
<213> ORGANISM: Homo sapiens

<400> SEQUENCE: 316
ggattcattt ttaggaacta tgcc                                           24

<210> SEQ ID NO 317
<211> LENGTH: 8
<212> TYPE: PRT
<213> ORGANISM: Homo sapiens

<400> SEQUENCE: 317

Gly Phe Ile Phe Arg Asn Tyr Ala
1               5

<210> SEQ ID NO 318
<211> LENGTH: 24
<212> TYPE: DNA
<213> ORGANISM: Homo sapiens

<400> SEQUENCE: 318
attcttggta gtaatgataa caca                                           24

<210> SEQ ID NO 319
<211> LENGTH: 8
<212> TYPE: PRT
<213> ORGANISM: Homo sapiens

<400> SEQUENCE: 319

Ile Leu Gly Ser Asn Asp Asn Thr
1               5

<210> SEQ ID NO 320
<211> LENGTH: 30
<212> TYPE: DNA
<213> ORGANISM: Homo sapiens

<400> SEQUENCE: 320
gcaaaagggg acgctggggg ctttgactac                                     30

<210> SEQ ID NO 321
<211> LENGTH: 10
<212> TYPE: PRT
<213> ORGANISM: Homo sapiens

<400> SEQUENCE: 321

Ala Lys Gly Asp Ala Gly Gly Phe Asp Tyr
1               5                  10

<210> SEQ ID NO 322
<211> LENGTH: 336
<212> TYPE: DNA
<213> ORGANISM: Homo sapiens

<400> SEQUENCE: 322
```

-continued

```
gatgttgtga tgactcagtc tccactctcc ctgcccgtca tccttggaca gccggcctcc      60
atctcctgca ggtctagtca aagcctcgta tccagtgatg aaacaccta cttgaattgg      120 tttcagcaga ggccaggcca atctccaagg cgcctaattt ataaagtttc taaccgggac     180
tctggggtcc cagacagatt cagcggcagt gggtcaggca ctgatttcac actgaaaatc     240
agcagggtgg aggctgagga tgttgggggct tattactgca tgcaaggttc atactggcct    300 ccgactttg gccaggggac caagctggag atcaaa                                336
```

<210> SEQ ID NO 323
<211> LENGTH: 112
<212> TYPE: PRT
<213> ORGANISM: Homo sapiens

<400> SEQUENCE: 323

```
Asp Val Val Met Thr Gln Ser Pro Leu Ser Leu Pro Val Ile Leu Gly
1               5                   10                  15

Gln Pro Ala Ser Ile Ser Cys Arg Ser Ser Gln Ser Leu Val Ser Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ala Tyr Tyr Cys Met Gln Gly
                85                  90                  95

Ser Tyr Trp Pro Pro Thr Phe Gly Gln Gly Thr Lys Leu Glu Ile Lys
            100                 105                 110
```

<210> SEQ ID NO 324
<211> LENGTH: 33
<212> TYPE: DNA
<213> ORGANISM: Homo sapiens

<400> SEQUENCE: 324

```
caaagcctcg tatccagtga tggaaacacc tac                                   33
```

<210> SEQ ID NO 325
<211> LENGTH: 11
<212> TYPE: PRT
<213> ORGANISM: Homo sapiens

<400> SEQUENCE: 325

```
Gln Ser Leu Val Ser Ser Asp Gly Asn Thr Tyr
1               5                   10
```

<210> SEQ ID NO 326
<211> LENGTH: 9
<212> TYPE: DNA
<213> ORGANISM: Homo sapiens

<400> SEQUENCE: 326

```
aaagtttct                                                              9
```

<210> SEQ ID NO 327
<211> LENGTH: 3
<212> TYPE: PRT
<213> ORGANISM: Homo sapiens

<400> SEQUENCE: 327

Lys Val Ser
1

<210> SEQ ID NO 328
<211> LENGTH: 27
<212> TYPE: DNA
<213> ORGANISM: Homo sapiens

<400> SEQUENCE: 328
atgcaaggtt catactggcc tccgact                                              27

<210> SEQ ID NO 329
<211> LENGTH: 9
<212> TYPE: PRT
<213> ORGANISM: Homo sapiens

<400> SEQUENCE: 329

Met Gln Gly Ser Tyr Trp Pro Pro Thr
1               5

<210> SEQ ID NO 330
<211> LENGTH: 1335
<212> TYPE: DNA
<213> ORGANISM: Homo sapiens

<400> SEQUENCE: 330
gaggtgcagc tggtggagtc tgggggagac ttggtacagc ctgggggtc cctgagactc            60 tcctgtacag cctctggatt cattttagg aactatgcca tgaactgggt ccgccaggct          120
ccagggaagg ggctggagtg gttgtcaggt attcttggta gtaatgataa acatatactac        180 gtagactccg tgaagggccg gttcaccatt tctagagaca attccaggaa cacgctgtat         240
ctgcaaatga acagcctgag agccgaggac tcggccgtat attactgtgc aaaaggggac        300
gctgggggct ttgactactg gggccaggga accctggtca ccgtctcctc agcctccacc        360
aagggcccat cggtcttccc cctggcgccc tgctccagga gcacctccga gagcacagcc        420
gccctgggct gcctggtcaa ggactacttc cccgaaccgg tgacggtgtc gtggaactca        480
ggcgccctga ccagcggcgt gcacaccttc ccggctgtcc tacagtcctc aggactctac        540
tccctcagca gcgtggtgac cgtgccctcc agcagcttgg gcacgaagac ctacacctgc        600
aacgtagatc acaagcccag caacaccaag gtggacaaga gagttgagtc caaatatggt        660
cccccatgcc caccctgccc agcacctgag ttcctggggg gaccatcagt cttcctgttc        720
cccccaaaac ccaaggacac tctcatgatc tcccggaccc ctgaggtcac gtgcgtggtg        780
gtggacgtga gccaggaaga ccccgaggtc cagttcaact ggtacgtgga tggcgtggag        840
gtgcataatg ccaagacaaa gccgcgggag gagcagttca acagcacgta ccgtgtggtc        900
agcgtcctca ccgtcctgca ccaggactgg ctgaacggca aggagtacaa gtgcaaggtc        960
tccaacaaag gcctcccgtc ctccatcgag aaaaccatct ccaaagccaa agggcagccc       1020
cgagagccac aggtgtacac cctgccccca tcccaggagg agatgaccaa gaaccaggtc       1080
agcctgacct gcctggtcaa aggcttctac cccagcgaca tcgccgtgga gtgggagagc       1140
aatgggcagc cggagaacaa ctacaagacc acgcctcccg tgctggactc cgacggctcc       1200
ttcttcctct acagcaggct caccgtggac aagagcaggt ggcaggaggg gaatgtcttc       1260
tcatgctccg tgatgcatga ggctctgcac aaccactaca cacagaagtc cctctccctg       1320
tctctgggta aatga                                                        1335

<210> SEQ ID NO 331
<211> LENGTH: 444
<212> TYPE: PRT
<213> ORGANISM: Homo sapiens

<400> SEQUENCE: 331

```
Glu Val Gln Leu Val Glu Ser Gly Gly Asp Leu Val Gln Pro Gly Gly
1               5                   10                  15

Ser Leu Arg Leu Ser Cys Thr Ala Ser Gly Phe Ile Phe Arg Asn Tyr
            20                  25                  30

Ala Met Asn Trp Val Arg Gln Ala Pro Gly Lys Gly Leu Glu Trp Leu
        35                  40                  45

Ser Gly Ile Leu Gly Ser Asn Asp Asn Thr Tyr Tyr Val Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Ser Ala Val Tyr Tyr Cys
                85                  90                  95

Ala Lys Gly Asp Ala Gly Gly Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 332
<211> LENGTH: 660
<212> TYPE: DNA
<213> ORGANISM: Homo sapiens

<400> SEQUENCE: 332
gatgttgtga tgactcagtc tccactctcc ctgcccgtca tccttggaca gccggcctcc     60
atctcctgca ggtctagtca aagcctcgta tccagtgatg aaacacccta cttgaattgg    120
tttcagcaga ggccaggcca atctccaagg cgcctaattt ataaagtttc taaccgggac    180
tctggggtcc cagacagatt cagcggcagt gggtcaggca ctgatttcac actgaaaatc    240
agcagggtgg aggctgagga tgttggggct tattactgca tgcaaggttc atactggcct    300 ccgactttttg gccaggggac caagctggag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 333
<211> LENGTH: 219
<212> TYPE: PRT
<213> ORGANISM: Homo sapiens

<400> SEQUENCE: 333

Asp Val Val Met Thr Gln Ser Pro Leu Ser Leu Pro Val Ile Leu Gly
1               5                   10                  15

Gln Pro Ala Ser Ile Ser Cys Arg Ser Ser Gln Ser Leu Val Ser Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ala Tyr Tyr Cys Met Gln Gly
                85                  90                  95

Ser Tyr Trp Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln

```
                145                 150                 155                 160
Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 334
<211> LENGTH: 363
<212> TYPE: DNA
<213> ORGANISM: Homo sapiens

<400> SEQUENCE: 334
caggtgcagc tggtggagtc tgggggaggc gtggtcaagc ctgggggtc cctgagactc        60 tcctgtgcag cctctggatt caccttcagt aactctggca ttcactgggt ccgccaggct       120
ccaggcaagg ggctggagtg ggtggcactt atatcatatg ctggaagtaa taaatactat       180
gcagactccg tgaagggccg attcaccatc tccagagaca attccaagaa cacgctgtct       240
ctgcaaatga acagcctgag agctgaggac acggctgtgt attactgtgc gaaagaggtt       300
tggactggaa cttatgattc ttttgatatg tggggccgag gacaatggt caccgtctct       360 tca                                                                    363

<210> SEQ ID NO 335
<211> LENGTH: 121
<212> TYPE: PRT
<213> ORGANISM: Homo sapiens

<400> SEQUENCE: 335

Gln Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Asn Ser
            20                  25                  30

Gly Ile His Trp Val Arg Gln Ala Pro Gly Lys Gly Leu Glu Trp Val
        35                  40                  45

Ala Leu Ile Ser Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Glu Val Trp Thr Gly Thr Tyr Asp Ser Phe Asp Met Trp Gly
            100                 105                 110

Arg Gly Thr Met Val Thr Val Ser Ser
        115                 120

<210> SEQ ID NO 336
<211> LENGTH: 24
<212> TYPE: DNA
<213> ORGANISM: Homo sapiens

<400> SEQUENCE: 336
ggattcacct tcagtaactc tggc                                              24
```

```
<210> SEQ ID NO 337
<211> LENGTH: 8
<212> TYPE: PRT
<213> ORGANISM: Homo sapiens

<400> SEQUENCE: 337

Gly Phe Thr Phe Ser Asn Ser Gly
1               5

<210> SEQ ID NO 338
<211> LENGTH: 24
<212> TYPE: DNA
<213> ORGANISM: Homo sapiens

<400> SEQUENCE: 338
atatcatatg ctggaagtaa taaa                                          24

<210> SEQ ID NO 339
<211> LENGTH: 8
<212> TYPE: PRT
<213> ORGANISM: Homo sapiens

<400> SEQUENCE: 339

Ile Ser Tyr Ala Gly Ser Asn Lys
1               5

<210> SEQ ID NO 340
<211> LENGTH: 42
<212> TYPE: DNA
<213> ORGANISM: Homo sapiens

<400> SEQUENCE: 340
gcgaaagagg tttggactgg aacttatgat tcttttgata tg                      42

<210> SEQ ID NO 341
<211> LENGTH: 14
<212> TYPE: PRT
<213> ORGANISM: Homo sapiens

<400> SEQUENCE: 341

Ala Lys Glu Val Trp Thr Gly Thr Tyr Asp Ser Phe Asp Met
1               5                   10

<210> SEQ ID NO 342
<211> LENGTH: 1347
<212> TYPE: DNA
<213> ORGANISM: Homo sapiens

<400> SEQUENCE: 342
caggtgcagc tggtggagtc tgggggaggc gtggtcaagc ctggggggtc cctgagactc    60
tcctgtgcag cctctggatt caccttcagt aactctggca ttcactgggt ccgccaggct   120
ccaggcaagg ggctggagtg ggtggcactt atatcatatg ctggaagtaa taaatactat   180
gcagactccg tgaagggccg attcaccatc tccagagaca attccaagaa cacgctgtct   240
ctgcaaatga acagcctgag agctgaggac acggctgtgt attactgtgc gaaagaggtt   300
tggactggaa cttatgattc ttttgatatg tggggccgag gacaatggt caccgtctct   360 tcagcctcca ccaagggccc atcggtcttc cccctggcgc cctgctccag gagcacctcc   420
gagagcacag ccgccctggg ctgcctggtc aaggactact ccccgaacc ggtgacggtg   480 tcgtggaact caggcgccct gaccagcggc gtgcacacct tcccggctgt cctacagtcc   540
tcaggactct actccctcag cagcgtggtg accgtgccct ccagcagctt gggcacgaag   600
```

```
acctacacct gcaacgtaga tcacaagccc agcaacacca aggtggacaa gagagttgag      660
tccaaatatg gtcccccatg cccaccctgc ccagcacctg agttcctggg ggaccatca      720 gtcttcctgt tcccccaaa  acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctcaccgtgg acaagagcag gtggcaggag    1260
gggaatgtct tctcatgctc cgtgatgcat gaggctctgc acaaccacta cacacagaag    1320
tccctctccc tgtctctggg taaatga                                        1347

<210> SEQ ID NO 343
<211> LENGTH: 448
<212> TYPE: PRT
<213> ORGANISM: Homo sapiens

<400> SEQUENCE: 343

Gln Val Gln Leu Val Glu Ser Gly Gly Gly Val Val Lys Pro Gly Gly
  1               5                  10                  15

Ser Leu Arg Leu Ser Cys Ala Ala Ser Gly Phe Thr Phe Ser Asn Ser
             20                  25                  30

Gly Ile His Trp Val Arg Gln Ala Pro Gly Lys Gly Leu Glu Trp Val
         35                  40                  45

Ala Leu Ile Ser Tyr Ala Gly Ser Asn Lys Tyr Tyr Ala Asp Ser Val
     50                  55                  60

Lys Gly Arg Phe Thr Ile Ser Arg Asp Asn Ser Lys Asn Thr Leu Ser
 65                  70                  75                  80

Leu Gln Met Asn Ser Leu Arg Ala Glu Asp Thr Ala Val Tyr Tyr Cys
                 85                  90                  95

Ala Lys Glu Val Trp Thr Gly Thr Tyr Asp Ser Phe Asp Met Trp Gly
            100                 105                 110

Arg Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240
```

-continued

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 344
<211> LENGTH: 363
<212> TYPE: DNA
<213> ORGANISM: Homo sapiens

<400> SEQUENCE: 344
gaggtgcagc tggtggagtc tgggggaggc ttggtacagc ctggagggtc cctgagactc      60
tcctgtgcag cctctggatt catcttcagt agttatgaaa tgcattgggt ccgccaggct     120
ccagggaagg ggctggagtg gatttcatac attagtagta gtggtactac catatactac     180
gcagactctg tgaagggccg attcaccatc tccagagaca acgccaagaa ctcactgtat     240
ctgcacatga acagcctgag agccgaggac acggctgttt attactgtac gagagcccgt     300
ataactggaa ctttcgatgt ttttgatatc tggggccaag ggacaatggt caccgtctct     360
tca                                                                   363

<210> SEQ ID NO 345
<211> LENGTH: 121
<212> TYPE: PRT
<213> ORGANISM: Homo sapiens

<400> SEQUENCE: 345

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Glu Met His Trp Val Arg Gln Ala Pro Gly Lys Gly Leu Glu Trp Ile
        35                  40                  45

Ser Tyr Ile Ser Ser Ser Gly Thr Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Met Asn Ser Leu Arg Ala Glu Asp Thr Ala Val Tyr Tyr Cys
                85                  90                  95

Thr Arg Ala Arg Ile Thr Gly Thr Phe Asp Val Phe Asp Ile Trp Gly
            100                 105                 110

Gln Gly Thr Met Val Thr Val Ser Ser
            115                 120

<210> SEQ ID NO 346
<211> LENGTH: 24
<212> TYPE: DNA
<213> ORGANISM: Homo sapiens

<400> SEQUENCE: 346
ggattcatct tcagtagtta tgaa                                          24

<210> SEQ ID NO 347
<211> LENGTH: 8
<212> TYPE: PRT
<213> ORGANISM: Homo sapiens

<400> SEQUENCE: 347

Gly Phe Ile Phe Ser Ser Tyr Glu
1               5

<210> SEQ ID NO 348
<211> LENGTH: 24
<212> TYPE: DNA
<213> ORGANISM: Homo sapiens

<400> SEQUENCE: 348
attagtagta gtggtactac cata                                          24

<210> SEQ ID NO 349
<211> LENGTH: 8
<212> TYPE: PRT
<213> ORGANISM: Homo sapiens

<400> SEQUENCE: 349

Ile Ser Ser Ser Gly Thr Thr Ile
1               5

<210> SEQ ID NO 350
<211> LENGTH: 42
<212> TYPE: DNA
<213> ORGANISM: Homo sapiens

<400> SEQUENCE: 350
acgagagccc gtataactgg aactttcgat gtttttgata tc                      42

<210> SEQ ID NO 351
<211> LENGTH: 14
<212> TYPE: PRT
<213> ORGANISM: Homo sapiens

<400> SEQUENCE: 351

Thr Arg Ala Arg Ile Thr Gly Thr Phe Asp Val Phe Asp Ile
1               5                   10

<210> SEQ ID NO 352
<211> LENGTH: 321
<212> TYPE: DNA
<213> ORGANISM: Homo sapiens

<400> SEQUENCE: 352

```
gacatccaga tgacccagtc tccatcctcc ctgtctgcat ctgtgggaga cagagtcacc    60
atcacttgcc gggcaagtca gagcattagc agctatttaa attggtatca gcagaaacca   120
gggaaagccc ctaagctcct gatctttgct gcatccaatt tacagagtgg ggtcccatca   180
aggttcagtg gcagtagatc tgggacagat ttcactctca ccatcagcag tctgcaacct   240
gaagattttg caacttacta ctgtcaacag aattacaata tcccgtacac ttttggccag   300
gggaccaagc tggagatcaa a                                             321
```

<210> SEQ ID NO 353
<211> LENGTH: 107
<212> TYPE: PRT
<213> ORGANISM: Homo sapiens

<400> SEQUENCE: 353

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Phe Ala Ala Ser Asn Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Asn Ile Pro Tyr
                85                  90                  95

Thr Phe Gly Gln Gly Thr Lys Leu Glu Ile Lys
            100                 105

<210> SEQ ID NO 354
<211> LENGTH: 27
<212> TYPE: DNA
<213> ORGANISM: Homo sapiens

<400> SEQUENCE: 354

```
caacagaatt acaatatccc gtacact                                        27
```

<210> SEQ ID NO 355
<211> LENGTH: 9
<212> TYPE: PRT
<213> ORGANISM: Homo sapiens

<400> SEQUENCE: 355

Gln Gln Asn Tyr Asn Ile Pro Tyr Thr
1               5

<210> SEQ ID NO 356
<211> LENGTH: 1347
<212> TYPE: DNA
<213> ORGANISM: Homo sapiens

<400> SEQUENCE: 356

```
gaggtgcagc tggtggagtc tgggggaggc ttggtacagc ctggagggtc cctgagactc    60
```

```
tcctgtgcag cctctggatt catcttcagt agttatgaaa tgcattgggt ccgccaggct    120
ccagggaagg ggctggagtg gattcatac attagtagta gtggtactac catatactac    180
gcagactctg tgaagggccg attcaccatc tccagagaca acgccaagaa ctcactgtat    240
ctgcacatga acagcctgag agccgaggac acggctgttt attactgtac gagagcccgt    300
ataactggaa ctttcgatgt ttttgatatc tggggccaag ggacaatggt caccgtctct    360
tcagcctcca ccaagggccc atcggtcttc cccctggcgc cctgctccag gagcacctcc    420
gagagcacag ccgccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacgaag    600
acctacacct gcaacgtaga tcacaagccc agcaacacca aggtggacaa gagagttgag    660
tccaaatatg gtcccccatg cccaccctgc ccagcacctg agttcctggg gggaccatca    720
gtcttcctgt tccccccaaa acccaaggac actctcatga tctcccggac ccctgaggtc    780
acgtgcgtgg tggtggacgt gagccaggaa gaccccgagg tccagttcaa ctggtacgtg    840
gatggcgtgg aggtgcataa tgccaagaca aagccgcggg aggagcagtt caacagcacg    900
taccgtgtgg tcagcgtcct caccgtcctg caccaggact ggctgaacgg caaggagtac    960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctcaccgtgg acaagagcag gtggcaggag    1260
gggaatgtct tctcatgctc cgtgatgcat gaggctctgc acaaccacta cacacagaag    1320
tccctctccc tgtctctggg taaatga                                        1347
```

<210> SEQ ID NO 357
<211> LENGTH: 448
<212> TYPE: PRT
<213> ORGANISM: Homo sapiens

<400> SEQUENCE: 357

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Glu Met His Trp Val Arg Gln Ala Pro Gly Lys Gly Leu Glu Trp Ile
        35                  40                  45

Ser Tyr Ile Ser Ser Ser Gly Thr Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Met Asn Ser Leu Arg Ala Glu Asp Thr Ala Val Tyr Tyr Cys
                85                  90                  95

Thr Arg Ala Arg Ile Thr Gly Thr Phe Asp Val Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445

<210> SEQ ID NO 358
<211> LENGTH: 645
<212> TYPE: DNA
<213> ORGANISM: Homo sapiens

<400> SEQUENCE: 358
gacatccaga tgacccagtc tccatcctcc ctgtctgcat ctgtgggaga cagagtcacc     60
atcacttgcc gggcaagtca gagcattagc agctatttaa attggtatca gcagaaacca    120
gggaaagccc ctaagctcct gatctttgct gcatccaatt tacagagtgg ggtcccatca    180
aggttcagtg gcagtagatc tgggacagat ttcactctca ccatcagcag tctgcaacct    240
gaagattttg caacttacta ctgtcaacag aattacaata tcccgtacac ttttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420

```
cccagagagg ccaaagtaca gtggaaggtg ataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                     645
```

<210> SEQ ID NO 359
<211> LENGTH: 214
<212> TYPE: PRT
<213> ORGANISM: Homo sapiens

<400> SEQUENCE: 359

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Phe Ala Ala Ser Asn Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Asn Ile Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 360
<211> LENGTH: 366
<212> TYPE: DNA
<213> ORGANISM: Homo sapiens

<400> SEQUENCE: 360

```
caggtgcagc tgcaggagtc gggcccagga ctggtgaagc cttcacagac cctgtccctc       60
acctgtactg tctctggtgg ctccatcacc agtggcggtt actactggag ctggatccgc      120
cagtacccag gcagggcct ggagtggatt ggttacatct attatagtgg aagacctac       180 tacaatccgt cttttacgag tcgaattacc atatcagtag acacgtctaa gaagcagttc      240
tccctgaaga tgagctctgt gactgccgcg gacacggccg tgtattattg tgcgagagcg      300
ggattcacct ctagtaacgg ctggttcgac ccctggggcc agggaaccct ggtcaccgtc      360
tcctca                                                                 366
```

<210> SEQ ID NO 361
<211> LENGTH: 122
<212> TYPE: PRT
<213> ORGANISM: Homo sapiens

<400> SEQUENCE: 361

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Ser Gly
            20                  25                  30

Gly Tyr Tyr Trp Ser Trp Ile Arg Gln Tyr Pro Gly Gln Gly Leu Glu
        35                  40                  45

Trp Ile Gly Tyr Ile Tyr Tyr Ser Gly Lys Thr Tyr Tyr Asn Pro Ser
50                  55                  60

Phe Thr Ser Arg Ile Thr Ile Ser Val Asp Thr Ser Lys Lys Gln Phe
65                  70                  75                  80

Ser Leu Lys Met Ser Ser Val Thr Ala Ala Asp Thr Ala Val Tyr Tyr
                85                  90                  95

Cys Ala Arg Ala Gly Phe Thr Ser Ser Asn Gly Trp Phe Asp Pro Trp
            100                 105                 110

Gly Gln Gly Thr Leu Val Thr Val Ser Ser
        115                 120

<210> SEQ ID NO 362
<211> LENGTH: 30
<212> TYPE: DNA
<213> ORGANISM: Homo sapiens

<400> SEQUENCE: 362
ggtggctcca tcaccagtgg cggttactac                                      30

<210> SEQ ID NO 363
<211> LENGTH: 10
<212> TYPE: PRT
<213> ORGANISM: Homo sapiens

<400> SEQUENCE: 363

Gly Gly Ser Ile Thr Ser Gly Gly Tyr Tyr
1               5                   10

<210> SEQ ID NO 364
<211> LENGTH: 21
<212> TYPE: DNA
<213> ORGANISM: Homo sapiens

<400> SEQUENCE: 364
atctattata gtgggaagac c                                               21

<210> SEQ ID NO 365
<211> LENGTH: 42
<212> TYPE: DNA
<213> ORGANISM: Homo sapiens

<400> SEQUENCE: 365
gcgagagcgg gattcacctc tagtaacggc tggttcgacc cc                         42

<210> SEQ ID NO 366
<211> LENGTH: 14
<212> TYPE: PRT
<213> ORGANISM: Homo sapiens

<400> SEQUENCE: 366

Ala Arg Ala Gly Phe Thr Ser Ser Asn Gly Trp Phe Asp Pro
1               5                   10

<210> SEQ ID NO 367
<211> LENGTH: 321
<212> TYPE: DNA
<213> ORGANISM: Homo sapiens

<400> SEQUENCE: 367

```
gacatccaga tgacccagtc tccatcctcc ctatctgcat ctgtaggaga cagagtcacc    60
atcacttgcc gggcaagtca gaacattcgc agctatttga attggtatca gcagaaacca   120
gggaaagccc caaaactcct gatctattct gcatccagtt tgcaaagtgg ggtcccatca   180
aggttcagtg gcagtggatc tgggacagat ttcactctca ccatcagcag tctgcaacct   240
gaagattttc caacttacta ctgtcaacag acttacagtt ccccgtggac gttcggccct   300
gggaccaagg tggaaatcaa a                                             321
```

<210> SEQ ID NO 368
<211> LENGTH: 107
<212> TYPE: PRT
<213> ORGANISM: Homo sapiens

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Arg Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Pro Thr Tyr Tyr Cys Gln Gln Thr Tyr Ser Ser Pro Trp
                85                  90                  95

Thr Phe Gly Pro Gly Thr Lys Val Glu Ile Lys
            100                 105

<210> SEQ ID NO 369
<211> LENGTH: 18
<212> TYPE: DNA
<213> ORGANISM: Homo sapiens

<400> SEQUENCE: 369

```
cagaacattc gcagctat                                                  18
```

<210> SEQ ID NO 370
<211> LENGTH: 6
<212> TYPE: PRT
<213> ORGANISM: Homo sapiens

<400> SEQUENCE: 370

Gln Asn Ile Arg Ser Tyr
1               5

<210> SEQ ID NO 371
<211> LENGTH: 9

```
<212> TYPE: DNA
<213> ORGANISM: Homo sapiens

<400> SEQUENCE: 371 tctgcatcc                                                                   9

<210> SEQ ID NO 372
<211> LENGTH: 3
<212> TYPE: PRT
<213> ORGANISM: Homo sapiens

<400> SEQUENCE: 372

Ser Ala Ser
1

<210> SEQ ID NO 373
<211> LENGTH: 27
<212> TYPE: DNA
<213> ORGANISM: Homo sapiens

<400> SEQUENCE: 373
caacagactt acagttcccc gtggacg                                              27

<210> SEQ ID NO 374
<211> LENGTH: 9
<212> TYPE: PRT
<213> ORGANISM: Homo sapiens

<400> SEQUENCE: 374

Gln Gln Thr Tyr Ser Ser Pro Trp Thr
1               5

<210> SEQ ID NO 375
<211> LENGTH: 1350
<212> TYPE: DNA
<213> ORGANISM: Homo sapiens

<400> SEQUENCE: 375
caggtgcagc tgcaggagtc gggcccagga ctggtgaagc cttcacagac cctgtccctc          60
acctgtactg tctctggtgg ctccatcacc agtggcggtt actactggag ctggatccgc         120
cagtacccag gcagggcct ggagtggatt ggttacatct attatagtgg aagacctac           180
tacaatccgt cttttacgag tcgaattacc atatcagtag acacgtctaa gaagcagttc        240
tccctgaaga tgagctctgt gactgccgcg gacacggccg tgtattattg cgagagcg          300
ggattcacct ctagtaacgg ctggttcgac ccctggggcc agggaaccct ggtcaccgtc        360
tcctcagcct ccaccaaggg cccatcggtc ttccccctgg cgccctgctc caggagcacc        420
tccgagagca cagccgccct gggctgcctg gtcaaggact acttccccga accggtgacg        480
gtgtcgtgga actcaggcgc cctgaccagc ggcgtgcaca ccttcccggc tgtcctacag        540
tcctcaggac tctactccct cagcagcgtg gtgaccgtgc cctccagcag cttgggcacg        600
aagacctaca cctgcaacgt agatcacaag cccagcaaca ccaaggtgga caagagagtt        660
gagtccaaat atggtccccc atgcccaccc tgcccagcac ctgagttcct gggggaccca        720
tcagtcttcc tgttcccccc aaaacccaag gacactctca tgatctcccg gacccctgag        780
gtcacgtgcg tggtggtgga cgtgagccag gaagaccccg aggtccagtt caactggtac        840
gtggatggcg tggaggtgca taatgccaag acaaagccgc gggaggagca gttcaacagc        900
acgtaccgtg tggtcagcgt cctcaccgtc ctgcaccagg actggctgaa cggcaaggag        960
```

-continued

```
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctaccccag cgacatcgcc    1140
gtggagtggg agagcaatgg gcagccggag aacaactaca agaccacgcc tcccgtgctg    1200
gactccgacg gctccttctt cctctacagc aggctcaccg tggacaagag caggtggcag    1260 gagggggaatg tcttctcatg ctccgtgatg catgaggctc tgcacaacca ctacacacag    1320
aagtccctct ccctgtctct gggtaaatga                                     1350
```

<210> SEQ ID NO 376
<211> LENGTH: 449
<212> TYPE: PRT
<213> ORGANISM: Homo sapiens

<400> SEQUENCE: 376

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Gly Tyr Tyr Trp Ser Trp Ile Arg Gln Tyr Pro Gly Gln Gly Leu Glu
        35                  40                  45

Trp Ile Gly Tyr Ile Tyr Tyr Ser Gly Lys Thr Tyr Tyr Asn Pro Ser
    50                  55                  60

Phe Thr Ser Arg Ile Thr Ile Ser Val Asp Thr Ser Lys Lys Gln Phe
65                  70                  75                  80

Ser Leu Lys Met Ser Ser Val Thr Ala Ala Asp Thr Ala Val Tyr Tyr
                85                  90                  95

Cys Ala Arg Ala Gly Phe Thr Ser Ser Asn Gly Trp Phe Asp Pro Trp
            100                 105                 110

Gly Gln Gly Thr Leu Val Thr Val Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 377
<211> LENGTH: 645
<212> TYPE: DNA
<213> ORGANISM: Homo sapiens

<400> SEQUENCE: 377
gacatccaga tgacccagtc tccatcctcc ctatctgcat ctgtaggaga cagagtcacc      60
atcacttgcc gggcaagtca gaacattcgc agctatttga attggtatca gcagaaacca     120
gggaaagccc caaaactcct gatctattct gcatccagtt tgcaaagtgg ggtcccatca     180
aggttcagtg gcagtggatc tgggacagat ttcactctca ccatcagcag tctgcaacct     240
gaagattttc aacttactac tgtcaacag acttacagtt ccccgtggac gttcggccct     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 378
<211> LENGTH: 214
<212> TYPE: PRT
<213> ORGANISM: Homo sapiens

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Arg Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Pro Thr Tyr Tyr Cys Gln Gln Thr Tyr Ser Ser Pro Trp
                 85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 379
<211> LENGTH: 268
<212> TYPE: PRT
<213> ORGANISM: Artificial Sequence
<220> FEATURE:
<223> OTHER INFORMATION: Human IL2R extracellular domain expressed with
      a C-terminal myc-myc-hexahistidine tag

<400> SEQUENCE: 379

Leu Asn Thr Thr Ile Leu Thr Pro Asn Gly Asn Glu Asp Thr Thr Ala
 1                   5                  10                  15

Asp Phe Phe Leu Thr Thr Met Pro Thr Asp Ser Leu Ser Val Ser Thr
                 20                  25                  30

Leu Pro Leu Pro Glu Val Gln Cys Phe Val Phe Asn Val Glu Tyr Met
            35                  40                  45

Asn Cys Thr Trp Asn Ser Ser Ser Glu Pro Gln Pro Thr Asn Leu Thr
 50                  55                  60

Leu His Tyr Trp Tyr Lys Asn Ser Asp Asn Asp Lys Val Gln Lys Cys
 65                  70                  75                  80

Ser His Tyr Leu Phe Ser Glu Glu Ile Thr Ser Gly Cys Gln Leu Gln
                 85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205
```

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Glu Gln Lys Leu Ile Ser Glu Glu Asp Leu Gly Gly Glu Gln Lys Leu
            245                 250                 255

Ile Ser Glu Glu Asp Leu His His His His His His
            260                 265

<210> SEQ ID NO 380
<211> LENGTH: 268
<212> TYPE: PRT
<213> ORGANISM: Artificial Sequence
<220> FEATURE:
<223> OTHER INFORMATION: Macaca fascicularis IL2R extracellular domain
      expressed with a C-terminal myc-myc-hexahistidine tag

<400> SEQUENCE: 380

Leu Asn Thr Thr Ile Leu Thr Pro Asn Gly Asn Glu Asp Ala Thr Thr
1               5                   10                  15

Asp Phe Phe Leu Thr Ser Met Pro Thr Asp Ser Leu Ser Val Ser Thr
                20                  25                  30

Leu Pro Leu Pro Glu Val Gln Cys Phe Val Phe Asn Val Glu Tyr Met
            35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu Arg Lys Leu Ser
130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Ser Ser Lys Glu Asn Pro Phe Leu Phe Ala Leu Glu Ala
225                 230                 235                 240

Glu Gln Lys Leu Ile Ser Glu Glu Asp Leu Gly Gly Glu Gln Lys Leu
            245                 250                 255

Ile Ser Glu Glu Asp Leu His His His His His His
            260                 265

<210> SEQ ID NO 381
<211> LENGTH: 473
<212> TYPE: PRT

<213> ORGANISM: Artificial Sequence
<220> FEATURE:
<223> OTHER INFORMATION: Human IL2R extracellular domain expressed with a C-terminal mouse IgG2a Fc tag

<400> SEQUENCE: 381

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
                100                 105                 110

Pro Arg Glu Pro Arg Arg Gln Ala Thr Gln Met Leu Lys Leu Gln Asn
            115                 120                 125

Leu Val Ile Pro Trp Ala Pro Glu Asn Leu Thr Leu His Lys Leu Ser
        130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
210                 215                 220

Gly Ser Asn Thr Ser Lys Glu Asn Pro Phe Leu Phe Ala Leu Glu Ala
225                 230                 235                 240

Glu Pro Arg Gly Pro Thr Ile Lys Pro Cys Pro Pro Cys Lys Cys Pro
                245                 250                 255

Ala Pro Asn Leu Leu Gly Gly Pro Ser Val Phe Ile Phe Pro Pro Lys
            260                 265                 270

Ile Lys Asp Val Leu Met Ile Ser Leu Ser Pro Ile Val Thr Cys Val
        275                 280                 285

Val Val Asp Val Ser Glu Asp Asp Pro Asp Val Gln Ile Ser Trp Phe
290                 295                 300

Val Asn Asn Val Glu Val His Thr Ala Gln Thr Gln Thr His Arg Glu
305                 310                 315                 320

Asp Tyr Asn Ser Thr Leu Arg Val Val Ser Ala Leu Pro Ile Gln His
                325                 330                 335

Gln Asp Trp Met Ser Gly Lys Glu Phe Lys Cys Lys Val Asn Asn Lys
            340                 345                 350

Asp Leu Pro Ala Pro Ile Glu Arg Thr Ile Ser Lys Pro Lys Gly Ser
        355                 360                 365

Val Arg Ala Pro Gln Val Tyr Val Leu Pro Pro Glu Glu Glu Met
370                 375                 380
```

Thr Lys Lys Gln Val Thr Leu Thr Cys Met Val Thr Asp Phe Met Pro
385                 390                 395                 400

Glu Asp Ile Tyr Val Glu Trp Thr Asn Asn Gly Lys Thr Glu Leu Asn
            405                 410                 415

Tyr Lys Asn Thr Glu Pro Val Leu Asp Ser Asp Gly Ser Tyr Phe Met
            420                 425                 430

Tyr Ser Lys Leu Arg Val Glu Lys Lys Asn Trp Val Glu Arg Asn Ser
            435                 440                 445

Tyr Ser Cys Ser Val Val His Glu Gly Leu His Asn His His Thr Thr
            450                 455                 460

Lys Ser Phe Ser Arg Thr Pro Gly Lys
465                 470

<210> SEQ ID NO 382
<211> LENGTH: 159
<212> TYPE: PRT
<213> ORGANISM: Artificial Sequence
<220> FEATURE:
<223> OTHER INFORMATION: D1 domain of human IL-2R extracellular domain
      expressed with a C-terminal myc-myc-hexahistidine tag

<400> SEQUENCE: 382

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
            35                  40                  45

Asn Cys Thr Trp Asn Ser Ser Ser Glu Pro Gln Pro Thr Asn Leu Thr
50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
            85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
            115                 120                 125

Leu Val Ile Glu Gln Lys Leu Ile Ser Glu Glu Asp Leu Gly Gly Glu
    130                 135                 140

Gln Lys Leu Ile Ser Glu Glu Asp Leu His His His His His His
145                 150                 155

<210> SEQ ID NO 383
<211> LENGTH: 116
<212> TYPE: PRT
<213> ORGANISM: Artificial Sequence
<220> FEATURE:
<223> OTHER INFORMATION: D2 domain of human IL2R extracellular domain
      expressed with a C-terminal myc-myc-hexahistidine tag

<400> SEQUENCE: 383

Pro Trp Ala Pro Glu Asn Leu Thr Leu His Lys Leu Ser Glu Ser Gln
1               5                   10                  15

Leu Glu Leu Asn Trp Asn Asn Arg Phe Leu Asn His Cys Leu Glu His
            20                  25                  30

Leu Val Gln Tyr Arg Thr Asp Trp Asp His Ser Trp Thr Glu Gln Ser
            35                  40                  45

Val Asp Tyr Arg His Lys Phe Ser Leu Pro Ser Val Asp Gly Gln Lys
 50                  55                  60

Arg Tyr Thr Phe Arg Val Arg Ser Arg Phe Asn Pro Leu Cys Gly Ser
 65                  70                  75                  80

Ala Gln His Trp Ser Glu Trp Ser Glu Gln Lys Leu Ile Ser Glu Glu
                 85                  90                  95

Asp Leu Gly Gly Glu Gln Lys Leu Ile Ser Glu Glu Asp Leu His His
                100                 105                 110

His His His His
        115

<210> SEQ ID NO 384
<211> LENGTH: 269
<212> TYPE: PRT
<213> ORGANISM: Artificial Sequence
<220> FEATURE:
<223> OTHER INFORMATION: Mouse IL2R extracellular domain expressed with
      a C-terminal myc-myc-hexahistidine tag

<400> SEQUENCE: 384

Trp Ser Ser Lys Val Leu Met Ser Ser Ala Asn Glu Asp Ile Lys Ala
 1                   5                  10                  15

Asp Leu Ile Leu Thr Ser Thr Ala Pro Glu His Leu Ser Ala Pro Thr
                 20                  25                  30

Leu Pro Leu Pro Glu Val Gln Cys Phe Val Phe Asn Ile Glu Tyr Met
             35                  40                  45

Asn Cys Thr Trp Asn Ser Ser Ser Glu Pro Gln Ala Thr Asn Leu Thr
 50                  55                  60

Leu His Tyr Arg Tyr Lys Val Ser Asp Asn Asn Thr Phe Gln Glu Cys
 65                  70                  75                  80

Ser His Tyr Leu Phe Ser Lys Glu Ile Thr Ser Gly Cys Gln Ile Gln
                 85                  90                  95

Lys Glu Asp Ile Gln Leu Tyr Gln Thr Phe Val Val Gln Leu Gln Asp
                100                 105                 110

Pro Gln Lys Pro Gln Arg Arg Ala Val Gln Lys Leu Asn Leu Gln Asn
             115                 120                 125

Leu Val Ile Pro Arg Ala Pro Glu Asn Leu Thr Leu Ser Asn Leu Ser
130                 135                 140

Glu Ser Gln Leu Glu Leu Arg Trp Lys Ser Arg His Ile Lys Glu Arg
145                 150                 155                 160

Cys Leu Gln Tyr Leu Val Gln Tyr Arg Ser Asn Arg Asp Arg Ser Trp
                165                 170                 175

Thr Glu Leu Ile Val Asn His Glu Pro Arg Phe Ser Leu Pro Ser Val
                180                 185                 190

Asp Glu Leu Lys Arg Tyr Thr Phe Arg Val Arg Ser Arg Tyr Asn Pro
             195                 200                 205

Ile Cys Gly Ser Ser Gln Gln Trp Ser Lys Trp Ser Gln Pro Val His
         210                 215                 220

Trp Gly Ser His Thr Val Glu Glu Asn Pro Ser Leu Phe Ala Leu Glu
225                 230                 235                 240

Ala Glu Gln Lys Leu Ile Ser Glu Glu Asp Leu Gly Gly Glu Gln Lys
                245                 250                 255

Leu Ile Ser Glu Glu Asp Leu His His His His His His
                260                 265

<210> SEQ ID NO 385

```
<211> LENGTH: 268
<212> TYPE: PRT
<213> ORGANISM: Artificial Sequence
<220> FEATURE:
<223> OTHER INFORMATION: Rat IL2R extracellular domain expressed with a
      C-terminal myc-myc-hexahistidine tag

<400> SEQUENCE: 385

Trp Ser Ser Lys Val Leu Met Ser Ser Gly Asn Glu Asp Thr Lys Ser
1               5                   10                  15

Asp Leu Leu Thr Ser Met Asp Leu Lys His Leu Ser Val Pro Thr
            20                  25                  30

Leu Pro Leu Pro Glu Val Gln Cys Phe Val Phe Asn Val Glu Tyr Met
            35                  40                  45

Asn Cys Thr Trp Asn Ser Ser Ser Glu Pro Gln Pro Thr Asn Leu Thr
        50                  55                  60

Met His Tyr Arg Tyr Lys Gly Ser Asp Asn Asn Thr Phe Gln Glu Cys
65                  70                  75                  80

Ser His Tyr Leu Phe Ser Lys Glu Ile Thr Ser Gly Cys Gln Ile Gln
                85                  90                  95

Lys Glu Asp Ile Gln Leu Tyr Gln Thr Phe Val Val Gln Leu Gln Asp
            100                 105                 110

Pro Gln Lys Pro Gln Arg Arg Ala Glu Gln Lys Leu Asn Leu Gln Asn
            115                 120                 125

Leu Val Ile Pro Trp Ala Pro Glu Asn Leu Thr Leu Tyr Asn Leu Ser
        130                 135                 140

Glu Ser Gln Val Glu Leu Arg Trp Lys Ser Arg Tyr Ile Glu Arg Cys
145                 150                 155                 160

Leu Gln Tyr Leu Val Gln Tyr Arg Ser Asn Arg Asp Arg Ser Trp Thr
                165                 170                 175

Glu Gln Ile Val Asp His Glu Pro Arg Phe Ser Leu Pro Ser Val Asp
            180                 185                 190

Glu Gln Lys Leu Tyr Thr Phe Arg Val Arg Ser Arg Phe Asn Pro Ile
            195                 200                 205

Cys Gly Ser Thr Gln Gln Trp Ser Lys Trp Ser Gln Pro Ile His Trp
        210                 215                 220

Gly Ser His Thr Ala Glu Glu Asn Pro Ser Leu Phe Ala Leu Glu Ala
225                 230                 235                 240

Glu Gln Lys Leu Ile Ser Glu Glu Asp Leu Gly Gly Glu Gln Lys Leu
                245                 250                 255

Ile Ser Glu Glu Asp Leu His His His His His His
            260                 265

<210> SEQ ID NO 386
<211> LENGTH: 5
<212> TYPE: PRT
<213> ORGANISM: Artificial Sequence
<220> FEATURE:
<223> OTHER INFORMATION: G4S linker

<400> SEQUENCE: 386

Gly Gly Gly Gly Ser
1               5
```

ANTI-IL2 RECEPTOR GAMMA ANTIGEN-BINDING PROTEINS

This application claims the benefit of U.S. Provisional Patent Application No. 62/799,851, filed Feb. 1, 2019, which is herein incorporated by reference in its entirety.

The sequence listing of the present application is submitted electronically as an ASCII formatted sequence listing with a file name "179227_01301_10561_seqlist_st25_28345_1.txt", creation date of Jan. 29, 2020, and a size of 295205 bytes. This sequence listing submitted is part of the specification and is hereby incorporated by reference in its entirety.

FIELD OF THE INVENTION

The present invention relates to antibodies that bind to the anti-IL2 receptor gamma protein and method of use thereof, e.g., to treat or prevent diseases.

BACKGROUND OF THE INVENTION

The common cytokine receptor gamma chain (γc) was first identified as the third chain of the interleukin-2 (IL-2) receptor complex and named IL-2Rγ. The same subunit was identified as part of several other cytokine receptors complexes: IL-4, IL-7, IL-9, IL-15, and IL-21, and therefore may be referred to as γc (common cytokine receptor gamma chain). The γc is involved in the signal transduction of these cytokine receptors as well as ligand binding.

Binding of a cytokine to its receptor activates Janus kinase (JAK)-family protein tyrosine kinases JAK1 and JAK3 and triggers the transphosphorylation of JAK1 and JAK3 on tyrosines. JAK1 is associated with the unique a or 13 chain and JAK3 with the γc of the receptor. The phosphorylated JAKs can in turn activate the signal transducer and activator of transcription (STAT) proteins, which together form the JAK/STAT signaling pathway. The phosphorylation of STATs causes dimerization of STATs, which now adopt a high-affinity DNA-binding activity and translocate to the nucleus. Here, they act as transcription factors inducing the transcription of target genes.

The γc gene (IL2RG) is located on chromosome Xq13. IL-2Rγ is mutated in patients with X-linked severe combined immunodeficiency (X-SCID). Patients with this disease present with profound immunodeficiency due to lack of T, NK and fully mature B cells.

IL-7, -9 and -15 have been linked to psoriasis and rheumatoid arthritis (Pathak, The expanding role of IL-7 and thymic stromal lymphopoietin as therapeutic target for rheumatoid arthritis. Expert Opin Ther Targets. 18(5):581-94 (2014); Hughes-Austin et al., Multiple cytokines and chemokines are associated with rheumatoid arthritis-related autoimmunity in first-degree relatives without rheumatoid arthritis: Studies of the Aetiology of Rheumatoid Arthritis (SERA), Ann Rheum Dis.; 72(6):901-7 (2013); Dantas et al., Increased Serum Interleukin-9 Levels in Rheumatoid Arthritis and Systemic Lupus Erythematosus: Pathogenic Role or Just an Epiphenomenon?, Dis Markers. 2015; 2015:519638; Yang et al., Therapeutic potential of IL-15 in rheumatoid arthritis, Hum Immunol. 2015 November; 76(11):812-8; Lesiak et al., Are interleukin-15 and -22 a new pathogenic factor in pustular palmoplantar psoriasis?, Postepy Dermatol Alergol. 33(5):336-339 (2016); Raeber et al., The role of cytokines in T-cell memory in health and disease, Immunol Rev. 283(1):176-193 (2018)).

IL-4 and IL-9 blockade have been shown to improve asthma symptoms in mice (Generoso et al., Prospects for Monoclonal Antibody Therapy in Pediatric Asthma, Curr Allergy Asthma Rep. 18(9):45 (2018); Tashkin & Wechsler, Role of eosinophils in airway inflammation of chronic obstructive pulmonary disease, Int J Chron Obstruct Pulmon Dis. 13:335-349 (2018); Buzney et al., Asthma and Atopic Dermatitis: A Review of Targeted Inhibition of Interleukin-4 and Interleukin-13 As Therapy for Atopic Disease, J Drugs Dermatol. 15(2):165-71 (2016); Lloyd & Harker, Epigenetic Control of Interleukin-9 in Asthma, N Engl J Med. 379(1): 87-89 (2018); Neurath & Finotto, IL-9 signaling as key driver of chronic inflammation in mucosal immunity, Cytokine Growth Factor Rev. 29:93-9 (2016)).

IL-21 is connected with various inflammatory disorders including Crohn's disease and rheumatoid arthritis. (Holm et al., Evaluating IL-21 as a Potential Therapeutic Target in Crohn's Disease, Gastroenterol Res Pract. 2018:5962624 (2018); Dinesh & Rasool Multifaceted role of IL-21 in rheumatoid arthritis: Current understanding and future perspectives, J Cell Physiol. 233(5):3918-3928 (2018)).

SUMMARY OF THE INVENTION

The present invention provides isolated antigen-binding proteins (e.g., antibodies or antigen-binding fragments thereof, for example, which are monospecific or multispecific) characterized by one or more of the following: Binds to human IL2Rγ at 25° C. with a $K_D$ of about $2.75 \times 10^{-9}$ M to about $3.36 \times 10^{-7}$ M; Binds to human IL2Rγ at 37° C. with a $K_D$ of about $6.42 \times 10^{-9}$ M to about $3.53 \times 10^{-7}$ M; or binds with a $K_D$ of less than about $3.53 \times 10^{-7}$ M; Binds to Macaca fascicularis IL-2Rγ at 25° C. with a $K_D$ of about $3.18 \times 10^{-9}$ M to about $2.38 \times 10^{-7}$ M; Binds to Macaca fascicularis IL-2Rγ at 37° C. with a $K_D$ of about $8.29 \times 10^{-9}$M to about $3.20 \times 10^{-7}$M; or binds with a $K_D$ of less than about $3.20 \times 10^{-7}$M; Binds to human IL2Rγ at 25° C. with a $K_D$ of about $2.45 \times 10^{-9}$ M to about $1.20 \times 10^{-8}$ M; or binds with a $K_D$ of less than about $1.20 \times 10^{-8}$ M; Binds to human IL2Rγ at 37° C. with a $K_D$ of about $1.86 \times 10^{-11}$ M to about $3.00 \times 10^{-8}$ M; or binds with a $K_D$ of less than about $3.00 \times 10^{-8}$ M; Binds to mouse IL2Rγ at 25° C. with a $K_D$ of about $1.84 \times 10^{-8}$ M, $3.76 \times 10^{-9}$ M, $1.08 \times 10^{-7}$ M, $2.17 \times 10^{-8}$ M, $6.02 \times 10^{-9}$ M or $7.93 \times 10^{-8}$ M; or does not bind detectably; Binds to mouse IL2Rγ at 37° C. with a $K_D$ of about $5.59 \times 10^{-8}$ M, $6.11 \times 10^{-9}$ M, $3.87 \times 10^{-7}$ M, $5.16 \times 10^{-8}$ M, $8.70 \times 10^{-9}$ M or $2.15 \times 10^{-7}$ M; or does not bind detectably; Binds to human IL2Rγ domain 1 at 25° C. with a $K_D$ of about $3.32 \times 10^{-9}$ M to about $1.97 \times 10^{-7}$ M; or does not bind detectably; Binds to human IL2Rγ domain 1 at 37° C. with a $K_D$ of about $4.13 \times 10^{-9}$ M to about $2.25 \times 10^{-7}$ M; or does not bind detectably; Binds to human IL2Rγ domain 2 at 25° C. with a $K_D$ of about $2.91 \times 10^{-7}$ M to about $5.35 \times 10^{-10}$; or does not bind detectably; Binds to human IL2Rγ domain 2 at 37° C. with a $K_D$ of about $1.14 \times 10^{-8}$ or about $1.27 \times 10^{-8}$; or does not bind detectably; Blocks STAT phosphorylation in T-cells which is induced by IL-2, IL-4, IL7, IL-15 and/or IL-21; Blocks STAT phosphorylation in mast cells which is induced by IL-9; Reduces the number of human immune cells which were injected into a mouse; Reduces the levels of serum human cytokines and/or mouse serum cytokines in mice having human immune cells; Does not bind detectably to mouse or rat IL2Rγ; Protects mice from weight loss and/or death due to GvHD in a GvHD mouse model; Blocks binding of a hybrid receptor comprising IL2Rγ complexed with a cytokine-specific receptor subunit from binding to IL-2, IL-4, IL-7, IL-9, IL-15 and/or IL-21; and/or reduces the number of CD45+ cells, B-cells, T-cells and/or NK cells (but, optionally, not, for example, neutrophils) in the blood or serum of a subject. Antibodies and antigen-binding fragments that bind specifically to IL2Rγ, which are variants of any of the antibodies or fragments whose sequences are specifically set forth herein, and which are characterized by one or more of the traits set forth above, form part of the present invention.

The present invention also provides an isolated antigen-binding protein, e.g., which is an antibody or antigen-binding fragment thereof, that (i) specifically binds to the same epitope on IL2Rγ as a reference antibody or antigen-binding fragment thereof; or (ii) competes for binding to IL2Rγ polypeptide with a reference antibody or antigen-binding fragment thereof, wherein the reference antibody or antigen-binding fragment thereof comprises: (a) a heavy chain immunoglobulin or variable region thereof that comprises CDR-H1, CDR-H2 and CDR-H3 of a heavy chain immunoglobulin or variable region thereof that comprises the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; or a variant thereof; and/or (b) a light chain immunoglobulin or variable region thereof that comprises CDR-L1, CDR-L2 and CDR-L3 of a light chain immunoglobulin or variable region thereof that comprises the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378; or a variant thereof. In an embodiment of the invention, the reference antibody or fragment is pre-bound to the IL2Rg antigen before the antigen-binding protein is added and evaluated for binding. In an embodiment of the invention, antigen-binding protein is pre-bound to the antigen before the reference antibody or fragment is added and evaluated for binding.

The present invention also provides an isolated antigen-binding protein (e.g., antibody or antigen-binding fragment thereof) comprising: (a) a heavy chain immunoglobulin or variable region thereof that comprises CDR-H1, CDR-H2 and CDR-H3 of a heavy chain immunoglobulin or variable region thereof that comprises the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; or a variant thereof; and/or (b) a light chain immunoglobulin or variable region thereof that comprises CDR-L1, CDR-L2 and CDR-L3 of a light chain immunoglobulin or variable region thereof that comprises the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378; or a variant thereof.

In an embodiment of the invention comprises (a) a heavy chain immunoglobulin or variable region thereof comprising an amino acid sequence having at least 90% amino acid sequence identity to the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; and/or (b) a light chain immunoglobulin or variable region thereof comprising an amino acid sequence having at least 90% amino acid sequence identity to the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378. For example, in an embodiment of the invention, the antigen-binding protein comprises (a) a heavy chain immunoglobulin or variable region thereof comprising the CDR-H1, CDR-H2 and CDR-H3 of a heavy chain immunoglobulin or variable region thereof comprising an amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376 and at least 90% amino acid sequence identity to the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376; and/or (b) an light chain immunoglobulin or variable region thereof comprising the CDR-L1, CDR-L2 and CDR-L3 of a light chain immunoglobulin or variable region thereof comprising an amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378 and at least 90% amino acid sequence identity to the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378.

In an embodiment of the invention, the antigen-binding protein comprises:
(i) the heavy chain set of CDRs: CDR-H1 comprising the amino acid sequence set forth in SEQ ID NO: 4; CDR-H2 comprising the amino acid sequence set forth in SEQ ID NO: 6; and CDR-H3 comprising the amino acid sequence set forth in SEQ ID NO: 8; and/or CDR-H1 comprising the amino acid sequence set forth in SEQ ID NO: 24; CDR-H2 comprising the amino acid sequence set forth in SEQ ID NO: 26; and CDR-H3 comprising the amino acid sequence set forth in SEQ ID NO: 28; and/or CDR-H1 comprising the amino acid sequence set forth in SEQ ID NO: 44; CDR-H2 comprising the amino acid sequence set forth in SEQ ID NO: 46; and CDR-H3 comprising the amino acid sequence set forth in SEQ ID NO: 48; and/or CDR-H1 comprising the amino acid sequence set forth in SEQ ID NO: 64; CDR-H2 comprising the amino acid sequence set forth in SEQ ID NO: 66; and CDR-H3 comprising the amino acid sequence set forth in SEQ ID NO: 68; and/or CDR-H1 comprising the amino acid sequence set forth in SEQ ID NO: 83; CDR-H2 comprising the amino acid sequence set forth in SEQ ID NO: 85; and CDR-H3 comprising the amino acid sequence set forth in SEQ ID NO: 87; and/or CDR-H1 comprising the amino acid sequence set forth in SEQ ID NO: 103; CDR-H2 comprising the amino acid sequence set forth in SEQ ID NO: 105; and CDR-H3 comprising the amino acid sequence set forth in SEQ ID NO: 107; and/or CDR-H1 comprising the amino acid sequence set forth in SEQ ID NO: 121; CDR-H2 comprising the amino acid sequence set forth in SEQ ID NO: 123; and CDR-H3 comprising the amino acid sequence set forth in SEQ ID NO: 125; and/or CDR-H1 comprising the amino acid sequence set forth in SEQ ID NO: 140; CDR-H2 comprising the amino acid sequence set forth in SEQ ID NO: 142; and CDR-H3 comprising the amino acid sequence set forth in SEQ ID NO: 144; and/or CDR-H1 comprising the amino acid sequence set forth in SEQ ID NO: 158; CDR-H2 comprising the amino acid sequence set forth in SEQ ID NO: 160; and CDR-H3 comprising the amino acid sequence set forth in SEQ ID NO: 162; and/or CDR-H1 comprising the amino acid sequence set forth in SEQ ID NO: 176; CDR-H2 comprising the amino acid sequence set forth in SEQ ID NO: 178; and CDR-H3 comprising the amino acid sequence set forth in SEQ ID NO: 180; and/or CDR-H1 comprising the amino acid sequence set forth in SEQ ID NO: 192; CDR-H2 comprising the amino acid sequence set forth in SEQ ID NO: 194; and CDR-H3 comprising the amino acid sequence set forth in SEQ ID NO: 196; and/or CDR-H1 comprising the amino acid sequence set forth in SEQ ID NO: 202; CDR-H2 comprising the amino acid sequence set forth in SEQ ID NO: 204; and CDR-H3 comprising the amino acid sequence set forth in SEQ ID NO: 206; and/or CDR-H1 comprising the amino acid sequence set forth in SEQ ID NO: 176; CDR-H2 comprising the amino acid sequence set forth in SEQ ID NO: 212; and CDR-H3 comprising the amino acid sequence set forth in SEQ ID NO: 214; and/or CDR-H1 comprising the amino acid sequence set forth in SEQ ID NO: 220; CDR-H2 comprising the amino acid sequence set forth in SEQ ID NO: 222; and CDR-H3 comprising the amino acid sequence set forth in SEQ ID NO: 224; and/or CDR-H1 comprising the amino acid sequence set forth in SEQ ID NO: 240; CDR-H2 comprising the amino acid sequence set forth in SEQ ID NO: 242; and CDR-H3 comprising the amino acid sequence set forth in SEQ ID NO: 244; and/or CDR-H1 comprising the amino acid sequence set forth in SEQ ID NO: 260; CDR-H2 comprising the amino acid sequence set forth in SEQ ID NO: 262; and CDR-H3 comprising the amino acid sequence set forth in SEQ ID NO: 264; and/or CDR-H1 comprising the amino acid sequence set forth in SEQ ID NO: 278; CDR-H2 comprising the amino acid sequence set forth in SEQ ID NO: 280; and CDR-H3 comprising the amino acid sequence set forth in SEQ ID NO: 282; and/or CDR-H1 comprising the amino acid sequence set forth in SEQ ID NO: 288; CDR-H2 comprising the amino acid sequence set forth in SEQ ID NO: 290; and CDR-H3 comprising the amino acid sequence set forth in SEQ ID NO: 292; and/or CDR-H1 comprising the amino acid sequence set forth in SEQ ID NO: 298; CDR-H2 comprising the amino acid sequence set forth in SEQ ID NO: 300; and CDR-H3 comprising the amino acid sequence set forth in SEQ ID NO: 302; and/or CDR-H1 comprising the amino acid sequence set forth in SEQ ID NO: 317; CDR-H2 comprising the amino acid sequence set forth in SEQ ID NO: 319; and CDR-H3 comprising the amino acid sequence set forth in SEQ ID NO: 321; and/or CDR-H1 comprising the amino acid sequence set forth in SEQ ID NO: 337; CDR-H2 comprising the amino acid sequence set forth in SEQ ID NO: 339; and CDR-H3 comprising the amino acid sequence set forth in SEQ ID NO: 341; and/or CDR-H1 comprising the amino acid sequence set forth in SEQ ID NO: 347; CDR-H2 comprising the amino acid sequence set forth in SEQ ID NO: 349; and CDR-H3 comprising the amino acid sequence set forth in SEQ ID NO: 351; and/or CDR-H1 comprising the amino acid sequence set forth in SEQ ID NO: 363; CDR-H2 comprising the amino acid sequence set forth in SEQ ID NO: 66; and CDR-H3 comprising the amino acid sequence set forth in SEQ ID NO: 366; and/or (ii) the light chain set of CDRs: CDR-L1 comprising the amino acid sequence set forth in SEQ ID NO: 12; CDR-L2 comprising the amino acid sequence set forth in SEQ ID NO: 14; and CDR-L3 comprising the amino acid sequence set forth in SEQ ID NO: 16; and/or CDR-L1 comprising the amino acid sequence set forth in SEQ ID NO: 32; CDR-L2 comprising the amino acid sequence set forth in SEQ ID NO: 34; and CDR-L3 comprising the amino acid sequence set forth in SEQ ID NO: 36; and/or CDR-L1 comprising the amino acid sequence set forth in SEQ ID NO: 52; CDR-L2 comprising the amino acid sequence set forth in SEQ ID NO: 54; and CDR-L3 comprising the amino acid sequence set forth in SEQ ID NO: 56; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 75; and/or CDR-L1 comprising the amino acid sequence set forth in SEQ ID NO: 91; CDR-L2 comprising the amino acid sequence set forth in SEQ ID NO: 93; and CDR-L3 comprising the amino acid sequence set forth in SEQ ID NO: 95; and/or CDR-L1 comprising the amino acid sequence set forth in SEQ ID NO: 111; CDR-L2 comprising the amino acid sequence set forth in SEQ ID NO: 54; and CDR-L3 comprising the amino acid sequence set forth in SEQ ID NO: 113; and/or CDR-L1 comprising the amino acid sequence set forth in SEQ ID NO: 129; CDR-L2 comprising the amino acid sequence set forth in SEQ ID NO: 54; and CDR-L3 comprising the amino acid sequence set forth in SEQ ID NO: 132; and/or CDR-L1 comprising the amino acid sequence set forth in SEQ ID NO: 148; CDR-L2 comprising the amino acid sequence set forth in SEQ ID NO: 54; and CDR-L3 comprising the amino acid sequence set forth in SEQ ID NO: 150; and/or CDR-L1 comprising the amino acid sequence set forth in SEQ ID NO: 166; CDR-L2 comprising the amino acid sequence set forth in SEQ ID NO: 14; and CDR-L3 comprising the amino acid sequence set forth in SEQ ID NO: 168; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 228; CDR-L2 comprising the amino acid sequence set forth in SEQ ID NO: 230; and CDR-L3 comprising the amino acid sequence set forth in SEQ ID NO: 232; and/or CDR-L1 comprising the amino acid sequence set forth in SEQ ID NO: 248; CDR-L2 comprising the amino acid sequence set forth in SEQ ID NO: 250; and CDR-L3 comprising the amino acid sequence set forth in SEQ ID NO: 252; and/or CDR-L1 comprising the amino acid sequence set forth in SEQ ID NO: 268; CDR-L2 comprising the amino acid sequence set forth in SEQ ID NO: 54; and CDR-L3 comprising the amino acid sequence set forth in SEQ ID NO: 270; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 306; CDR-L2 comprising the amino acid sequence set forth in SEQ ID NO: 230; and CDR-L3 comprising the amino acid sequence set forth in SEQ ID NO: 309; and/or CDR-L1 comprising the amino acid sequence set forth in SEQ ID NO: 325; CDR-L2 comprising the amino acid sequence set forth in SEQ ID NO: 327; and CDR-L3 comprising the amino acid sequence set forth in SEQ ID NO: 329; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 184; and/or CDR-L1 comprising the amino acid sequence set forth in SEQ ID NO: 72; CDR-L2 comprising the amino acid sequence set forth in SEQ ID NO: 54; and CDR-L3 comprising the amino acid sequence set forth in SEQ ID NO: 355; and/or CDR-L1 comprising the amino acid sequence set forth in SEQ ID NO: 370; CDR-L2 comprising the amino acid sequence set forth in SEQ ID NO: 372; and CDR-L3 comprising the amino acid sequence set forth in SEQ ID NO: 374.

In an embodiment of the invention, the antigen-binding protein of the present invention comprises the heavy chain set of CDRs and the light chain set of CDRs as follows:
(i) a heavy chain variable region comprising a CDR-H1 comprising the amino acid sequence set forth in SEQ ID NO: 4; a CDR-H2 comprising the amino acid sequence set forth in SEQ ID NO: 6; and a CDR-H3 comprising the amino acid sequence set forth in SEQ ID NO: 8; and a light chain variable region comprising a CDR-L1 comprising the amino acid sequence set forth in SEQ ID NO: 12; a CDR-L2 comprising the amino acid sequence set forth in SEQ ID NO: 14; and a CDR-L3 comprising the amino acid sequence set forth in SEQ ID NO: 16; (ii) a heavy chain variable region comprising a CDR-H1 comprising the amino acid sequence set forth in SEQ ID NO: 24; a CDR-H2 comprising the amino acid sequence set forth in SEQ ID NO: 26; and a CDR-H3 comprising the amino acid sequence set forth in SEQ ID NO: 28; and a light chain variable region comprising a CDR-L1 comprising the amino acid sequence set forth in SEQ ID NO: 32; a CDR-L2 comprising the amino acid sequence set forth in SEQ ID NO: 34; and a CDR-L3 comprising the amino acid sequence set forth in SEQ ID NO: 36; (iii) a heavy chain variable region comprising a CDR-H1 comprising the amino acid sequence set forth in SEQ ID NO: 44; a CDR-H2 comprising the amino acid sequence set forth in SEQ ID NO: 46; and a CDR-H3 comprising the amino acid sequence set forth in SEQ ID NO: 48; and a light chain variable region comprising a CDR-L1 comprising the amino acid sequence set forth in SEQ ID NO: 52; a CDR-L2 comprising the amino acid sequence set forth in SEQ ID NO: 54; and a CDR-L3 comprising the amino acid sequence set forth in SEQ ID NO: 56; (iv) a heavy chain variable region comprising a CDR-H1 comprising the amino acid sequence set forth in SEQ ID NO: 64; a CDR-H2 comprising the amino acid sequence set forth in SEQ ID NO: 66; and a CDR-H3 comprising the amino acid sequence set forth in SEQ ID NO: 68; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 75; (v) a heavy chain variable region comprising a CDR-H1 comprising the amino acid sequence set forth in SEQ ID NO: 83; a CDR-H2 comprising the amino acid sequence set forth in SEQ ID NO: 85; and a CDR-H3 comprising the amino acid sequence set forth in SEQ ID NO: 87; and a light chain variable region comprising a CDR-L1 comprising the amino acid sequence set forth in SEQ ID NO: 91; a CDR-L2 comprising the amino acid sequence set forth in SEQ ID NO: 93; and a CDR-L3 comprising the amino acid sequence set forth in SEQ ID NO: 95; (vi) a heavy chain variable region comprising a CDR-H1 comprising the amino acid sequence set forth in SEQ ID NO: 103; a CDR-H2 comprising the amino acid sequence set forth in SEQ ID NO: 105; and a CDR-H3 comprising the amino acid sequence set forth in SEQ ID NO: 107; and a light chain variable region comprising a CDR-L1 comprising the amino acid sequence set forth in SEQ ID NO: 111; a CDR-L2 comprising the amino acid sequence set forth in SEQ ID NO: 54; and a CDR-L3 comprising the amino acid sequence set forth in SEQ ID NO: 113; (vi) a heavy chain variable region comprising a CDR-H1 comprising the amino acid sequence set forth in SEQ ID NO: 121; a CDR-H2 comprising the amino acid sequence set forth in SEQ ID NO: 123; and a CDR-H3 comprising the amino acid sequence set forth in SEQ ID NO: 125; and a light chain variable region comprising a CDR-L1 comprising the amino acid sequence set forth in SEQ ID NO: 129; a CDR-L2 comprising the amino acid sequence set forth in SEQ ID NO: 54; and a CDR-L3 comprising the amino acid sequence set forth in SEQ ID NO: 132; (vii) a heavy chain variable region comprising a CDR-H1 comprising the amino acid sequence set forth in SEQ ID NO: 140; a CDR-H2 comprising the amino acid sequence set forth in SEQ ID NO: 142; and a CDR-H3 comprising the amino acid sequence set forth in SEQ ID NO: 144; and a light chain variable region comprising a CDR-L1 comprising the amino acid sequence set forth in SEQ ID NO: 148; a CDR-L2 comprising the amino acid sequence set forth in SEQ ID NO: 54; and a CDR-L3 comprising the amino acid sequence set forth in SEQ ID NO: 150; (viii) a heavy chain variable region comprising a CDR-H1 comprising the amino acid sequence set forth in SEQ ID NO: 158; a CDR-H2 comprising the amino acid sequence set forth in SEQ ID NO: 160; and a CDR-H3 comprising the amino acid sequence set forth in SEQ ID NO: 162; and a light chain variable region comprising a CDR-L1 comprising the amino acid sequence set forth in SEQ ID NO: 166; a CDR-L2 comprising the amino acid sequence set forth in SEQ ID NO: 14; and a CDR-L3 comprising the amino acid sequence set forth in SEQ ID NO: 168; (ix) a heavy chain variable region comprising a CDR-H1 comprising the amino acid sequence set forth in SEQ ID NO: 176; a CDR-H2 comprising the amino acid sequence set forth in SEQ ID NO: 178; and a CDR-H3 comprising the amino acid sequence set forth in SEQ ID NO: 180; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (x) a heavy chain variable region comprising a CDR-H1 comprising the amino acid sequence set forth in SEQ ID NO: 192; a CDR-H2 comprising the amino acid sequence set forth in SEQ ID NO: 194; and a CDR-H3 comprising the amino acid sequence set forth in SEQ ID NO: 196; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xi) a heavy chain variable region comprising a CDR-H1 comprising the amino acid sequence set forth in SEQ ID NO: 202; a CDR-H2 comprising the amino acid sequence set forth in SEQ ID NO: 204; and a CDR-H3 comprising the amino acid sequence set forth in SEQ ID NO: 206; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xii) a heavy chain variable region comprising a CDR-H1 comprising the amino acid sequence set forth in SEQ ID NO: 176; a CDR-H2 comprising the amino acid sequence set forth in SEQ ID NO: 212; and a CDR-H3 comprising the amino acid sequence set forth in SEQ ID NO: 214; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xiii) a heavy chain variable region comprising a CDR-H1 comprising the amino acid sequence set forth in SEQ ID NO: 220; a CDR-H2 comprising the amino acid sequence set forth in SEQ ID NO: 222; and a CDR-H3 comprising the amino acid sequence set forth in SEQ ID NO: 224; and a light chain variable region comprising a CDR-L1 comprising the amino acid sequence set forth in SEQ ID NO: 228; a CDR-L2 comprising the amino acid sequence set forth in SEQ ID NO: 230; and a CDR-L3 comprising the amino acid sequence set forth in SEQ ID NO: 232; (xiv) a heavy chain variable region comprising a CDR-H1 comprising the amino acid sequence set forth in SEQ ID NO: 240; a CDR-H2 comprising the amino acid sequence set forth in SEQ ID NO: 242; and a CDR-H3 comprising the amino acid sequence set forth in SEQ ID NO: 244; and a light chain variable region comprising a CDR-L1 comprising the amino acid sequence set forth in SEQ ID NO: 248; a CDR-L2 comprising the amino acid sequence set forth in SEQ ID NO: 250; and a CDR-L3 comprising the amino acid sequence set forth in SEQ ID NO: 252; (xv) a heavy chain variable region comprising a CDR-H1 comprising the amino acid sequence set forth in SEQ ID NO: 260; a CDR-H2 comprising the amino acid sequence set forth in SEQ ID NO: 262; and a CDR-H3 comprising the amino acid sequence set forth in SEQ ID NO: 264; and a light chain variable region comprising a CDR-L1 comprising the amino acid sequence set forth in SEQ ID NO: 268; a CDR-L2 comprising the amino acid sequence set forth in SEQ ID NO: 54; and a CDR-L3 comprising the amino acid sequence set forth in SEQ ID NO: 270; (xvi) a heavy chain variable region comprising a CDR-H1 comprising the amino acid sequence set forth in SEQ ID NO: 278; a CDR-H2 comprising the amino acid sequence set forth in SEQ ID NO: 280; and a CDR-H3 comprising the amino acid sequence set forth in SEQ ID NO: 282; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xvii) a heavy chain variable region comprising a CDR-H1 comprising the amino acid sequence set forth in SEQ ID NO: 288; a CDR-H2 comprising the amino acid sequence set forth in SEQ ID NO: 290; and a CDR-H3 comprising the amino acid sequence set forth in SEQ ID NO: 292; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xviii) a heavy chain variable region comprising a CDR-H1 comprising the amino acid sequence set forth in SEQ ID NO: 298; a CDR-H2 comprising the amino acid sequence set forth in SEQ ID NO: 300; and a CDR-H3 comprising the amino acid sequence set forth in SEQ ID NO: 302; and a light chain variable region comprising a CDR-L1 comprising the amino acid sequence set forth in SEQ ID NO: 306; a CDR-L2 comprising the amino acid sequence set forth in SEQ ID NO: 230; and a CDR-L3 comprising the amino acid sequence set forth in SEQ ID NO: 309; (xix) a heavy chain variable region comprising a CDR-H1 comprising the amino acid sequence set forth in SEQ ID NO: 317; a CDR-H2 comprising the amino acid sequence set forth in SEQ ID NO: 319; and a CDR-H3 comprising the amino acid sequence set forth in SEQ ID NO: 321; and a light chain variable region comprising a CDR-L1 comprising the amino acid sequence set forth in SEQ ID NO: 325; a CDR-L2 comprising the amino acid sequence set forth in SEQ ID NO: 327; and a CDR-L3 comprising the amino acid sequence set forth in SEQ ID NO: 329; (xx) a heavy chain variable region comprising a CDR-H1 comprising the amino acid sequence set forth in SEQ ID NO: 337; a CDR-H2 comprising the amino acid sequence set forth in SEQ ID NO: 339; and a CDR-H3 comprising the amino acid sequence set forth in SEQ ID NO: 341; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 184; (xxi) a heavy chain variable region comprising a CDR-H1 comprising the amino acid sequence set forth in SEQ ID NO: 347; a CDR-H2 comprising the amino acid sequence set forth in SEQ ID NO: 349; and a CDR-H3 comprising the amino acid sequence set forth in SEQ ID NO: 351; and a light chain variable region comprising a CDR-L1 comprising the amino acid sequence set forth in SEQ ID NO: 72; a CDR-L2 comprising the amino acid sequence set forth in SEQ ID NO: 54; and a CDR-L3 comprising the amino acid sequence set forth in SEQ ID NO: 355; (xxii) a heavy chain variable region comprising a CDR-H1 comprising the amino acid sequence set forth in SEQ ID NO: 363; a CDR-H2 comprising the amino acid sequence set forth in SEQ ID NO: 66; and a CDR-H3 comprising the amino acid sequence set forth in SEQ ID NO: 366; and a light chain variable region comprising a CDR-L1 comprising the amino acid sequence set forth in SEQ ID NO: 370; a CDR-L2 comprising the amino acid sequence set forth in SEQ ID NO: 372; and a CDR-L3 comprising the amino acid sequence set forth in SEQ ID NO: 374.

Complexes including an antigen-binding protein of the present invention bound to an IL2Rγ polypeptide or antigenic fragment thereof are also part of the present invention.

The present invention also provides a method for making an antigen-binding protein (e.g., antibody or antigen-binding fragment thereof) or an immunoglobulin chain thereof (e.g., $V_H$, $V_L$, HC or LC) comprising: (a) introducing one or more polynucleotides (or a vector comprising such a polynucleotide) encoding one or more immunoglobulin chains of said antigen-binding protein into a host cell (e.g., a CHO cell); (b) culturing the host cell under conditions favorable to expression of the polynucleotide; and (c) optionally, isolating the antigen-binding protein or immunoglobulin chain from the host cell and/or medium in which the host cell is grown. An antigen-binding protein or immunoglobulin chain which is a product of such a method also forms part of the present invention.

The present invention also provides a polypeptide comprising: (a) CDR-H1, CDR-H2, and CDR-H3 of a heavy chain immunoglobulin or variable region thereof that comprises the amino acid sequence set forth in SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 and/or 376, or a variant thereof; and/or (b) CDR-L1, CDR-L2, and CDR-L3 of a light chain immunoglobulin or variable region thereof that comprises the amino acid sequence set forth in SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 and/or 378, or a variant thereof; or (c) the amino acid sequence set forth in a member selected from the group consisting of SEQ ID NO: 1-378, or a variant thereof. The present invention also provides a polynucleotide encoding one or more of such polypeptides or a vector comprising such a polynucleotide (e.g., a plasmid).

The present invention also provides a host cell (e.g., a CHO cell) comprising the antigen-binding protein (e.g., antibody or antigen-binding fragment thereof) or immunoglobulin chain (e.g., $V_H$, $V_L$, HC or LC) or polypeptide or polynucleotide or vector set forth herein.

The present invention also provides a composition or kit comprising one or more of the antigen-binding proteins set forth herein (e.g., antibody or antigen-binding fragment thereof) optionally in association with a further therapeutic agent (e.g., anti-inflammatory agent, an anti-TNFα antibody or binding protein, infliximab, adalimumab, etanercept, golimumab, a corticoid, prednisolone, methylprednisolone, antithymocyte globulin, alemtuzumab, dacluzimab, extracorporeal photphoresis, mycophenolate mofetil, sirolimus, pentostatin, mesenchyman stem cells, inolimomab, denileukin or basiliximab).

The present invention further provides a pharmaceutical formulation comprising the antigen-binding protein set forth herein (e.g., antibody or antigen-binding fragment thereof) and a pharmaceutically acceptable carrier and, optionally, a further therapeutic agent (e.g., anti-inflammatory agent, an anti-TNFα antibody or binding protein, infliximab, adalimumab, etanercept, golimumab, a corticoid, prednisolone, methylprednisolone, antithymocyte globulin, alemtuzumab, daclizumab, extracorporeal photphoresis, mycophenolate mofetil, tacrolimus, cyclosporine, sirolimus, pentostatin, mesenchyman stem cells, inolimomab, denileukin or basiliximab).

The present invention also provides a vessel or injection device (e.g., a vial, syringe, pre-filled syringe or autoinjector) comprising the antigen-binding protein or composition (e.g., pharmaceutical formulation) set forth herein.

The present invention also provides a method for administering antigen-binding protein or composition set forth herein to a subject (e.g., a human) comprising introducing, e.g., injecting (e.g., subcutaneously, intravenously or intramuscularly), said antigen-binding protein or composition into the body of the subject. The present invention also provides a method for treating or preventing an IL2Rγ-mediated disease or condition (e.g., graft versus host disease, organ transplant rejection, skin transplant rejection, heart transplant rejection, lung transplant rejection, kidney transplant rejection, liver transplant rejection, birdshot chorioretinopathy, multiple sclerosis, uveitis, an autoimmune disease, Type I diabetes, multiple sclerosis, rheumatoid arthritis, systemic lupus erythematosus, and/or myasthenia gravis), in a subject in need thereof, comprising administering, e.g., injecting, an effective amount of antigen-binding protein or composition set forth herein.

The present invention also provides a method for: blocking STAT phosphorylation in an peripheral blood mononuclear cell (e.g., a T-cell) induced by a cytokine (e.g., IL-2, IL-4, IL-7, IL-15 and/or IL-21); blocking STAT (e.g., STAT3) phosphorylation in a mast cell induced by a cytokine (e.g., IL-9); reducing serum levels of interferon-gamma, tumor necrosis factor-alpha, IL-6, IL-8, IL-10 and/or mKC/GRO (e.g., in a subject that has received a transplant); blocking JAK-STAT-mediated (e.g., STAT3) intracellular signaling (e.g., in an NK cell), induced by a cytokine in the IL2Rγ family (e.g., IL-2, IL-4, IL-7, IL-9, IL-15 and/or IL-21); and/or reducing the serum levels of CD45+ immune cells, NK cells, T-cells and/or B-cells (e.g., excluding neutrophils), in a subject, comprising administering, to the subject, an effective amount of anti-IL2Rγ antigen-binding protein set forth herein or composition thereof or formulation thereof. In an embodiment of the invention, the subject suffers from an IL2Rγ-mediated disease or condition, e.g., graft versus host disease, organ transplant rejection, b-islet cell graft rejection, skin transplant rejection, heart transplant rejection, lung transplant rejection, kidney transplant rejection, liver transplant rejection, birdshot chorioretinopathy, multiple sclerosis, uveitis, an autoimmune disease, Type I diabetes, multiple sclerosis, rheumatoid arthritis, systemic lupus erythematosus, myasthenia gravis, aplastic anemia, atopic dermatitis, asthma, a mast cell activation disorder, mast cell activation syndrome (MCAS), systemic mastocytosis (SM) and/or mast cell leukemia (MCL).

DETAILED DESCRIPTION OF THE INVENTION

Figure 1:
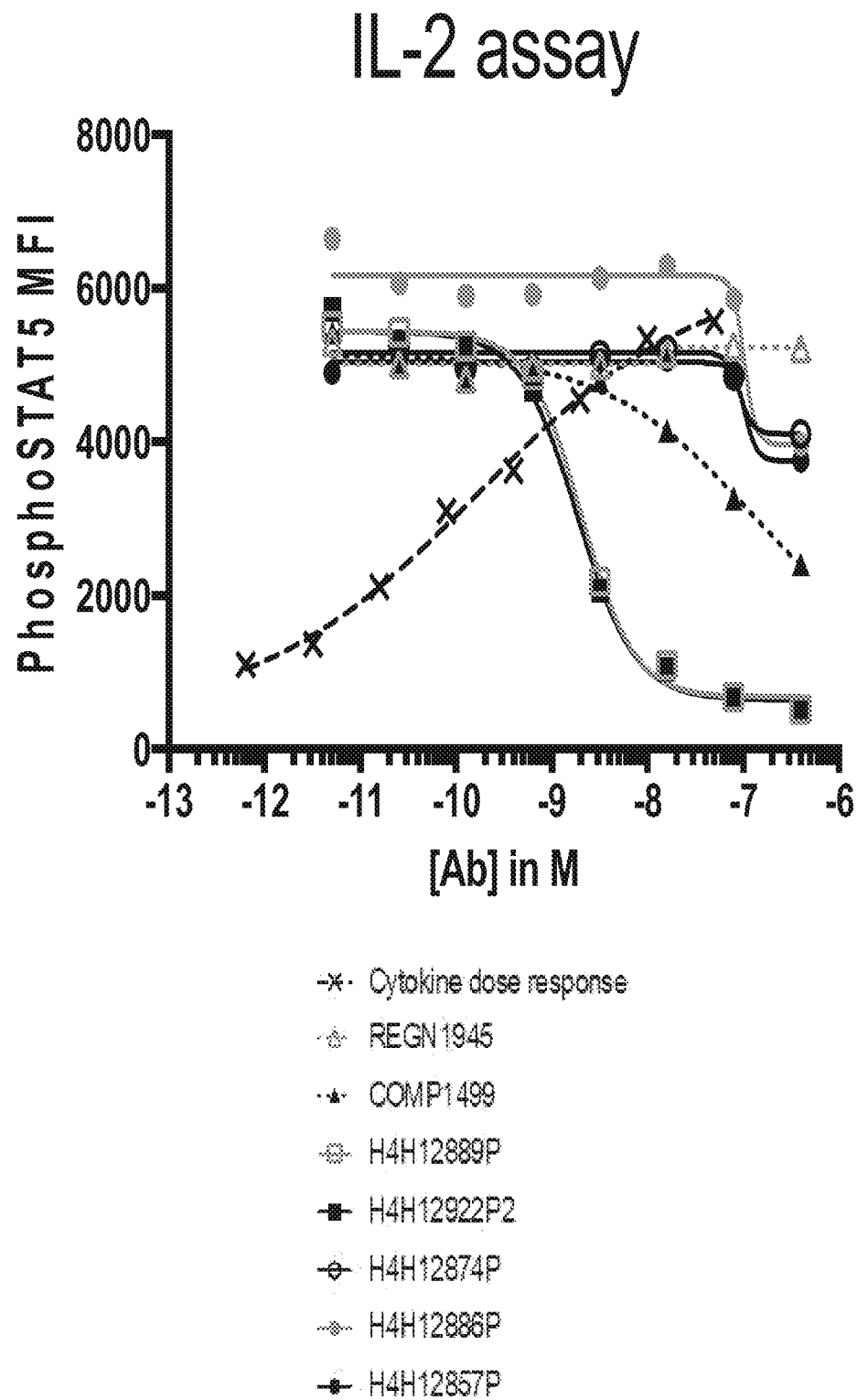
FIG. 1(A) is a graph showing blocking of human IL-2-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
FIG. 1(B) is a graph showing blocking of human IL-4-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
FIG. 1(C) is a graph showing blocking of human IL-7-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
FIG. 1(D) is a graph showing blocking of human IL-15-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
FIG. 1(E) is a graph showing blocking of human IL-21-induced STAT phosphorylation in human CD4+ T cells by various concentrations of anti-IL-2R gamma antibodies H4H12857P, H4H12874P, H4H12886P, H4H12889P and H4H12922P2; and antibodies REGN1945 and COMP1499.
Figure 1:
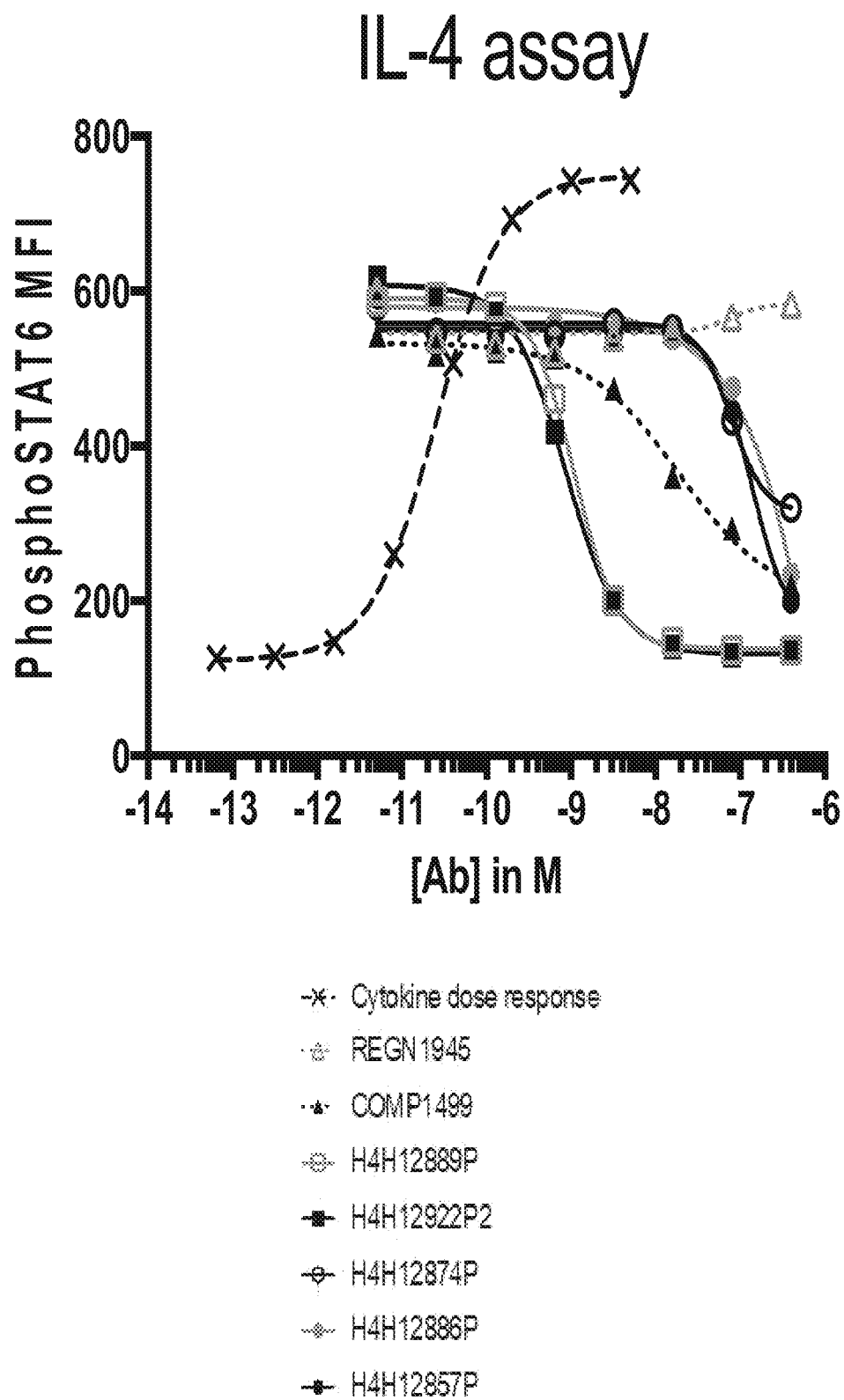
Figure 1:
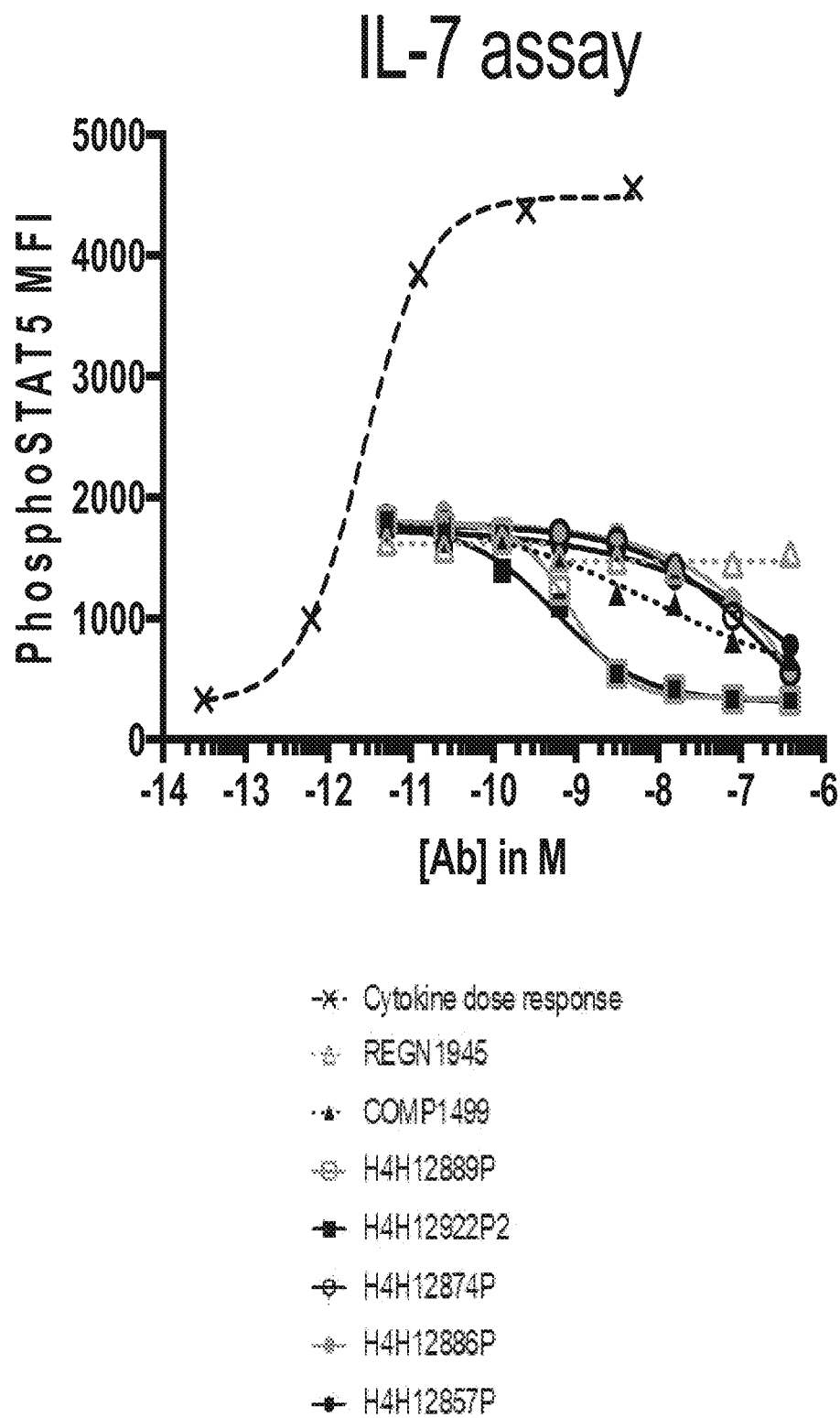
Figure 1:
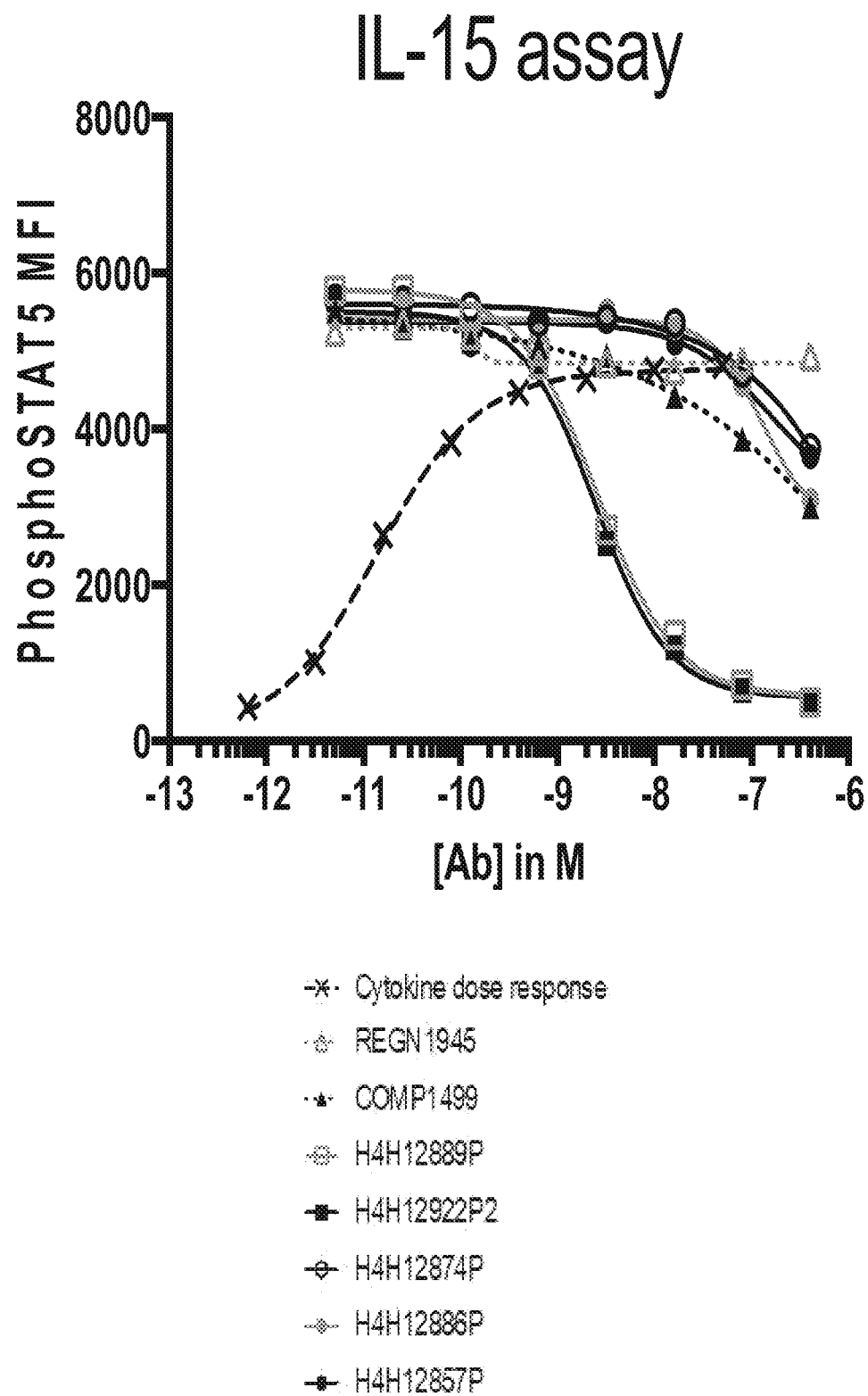
Figure 1:
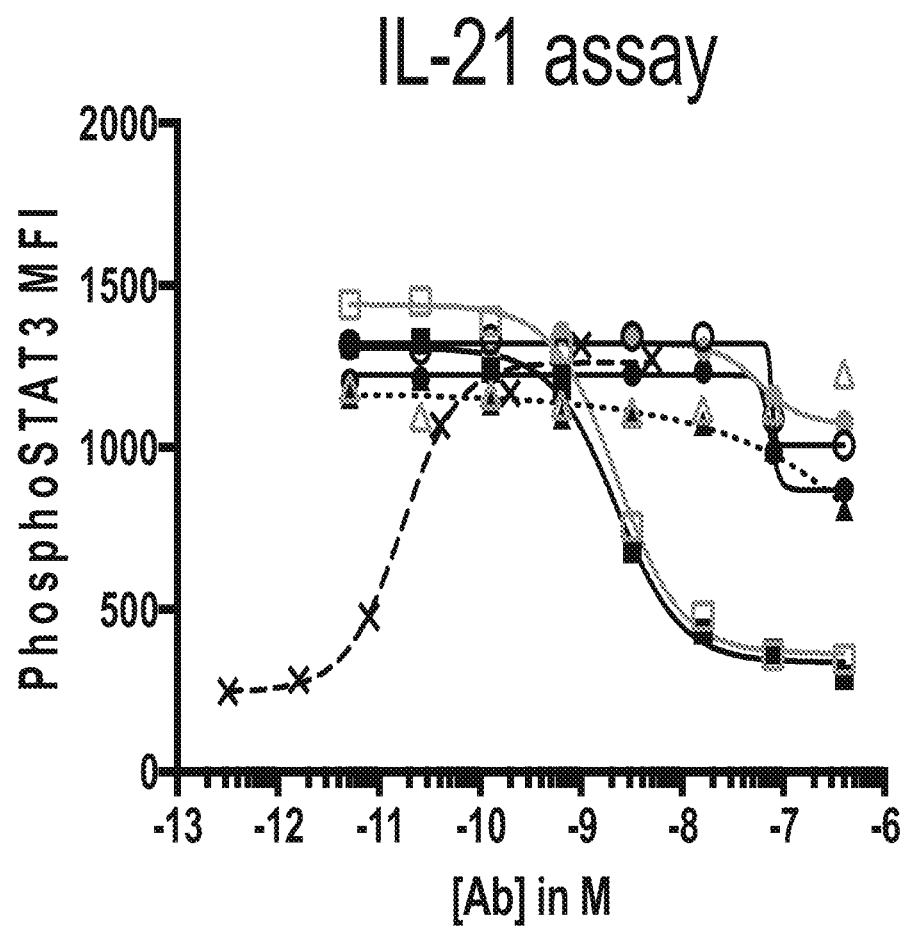

The present invention provides antibodies and antigen-binding fragments thereof that specifically bind to human and *Macaca fascicularis* IL2Rγ and exhibit exceptional biological activity, especially with respect to blockage of cytokine-induced STAT phosphorylation in T-cells and blockage of graft vs host disease in an applicable mouse model.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994).

IL-2Rγ

Interleukin-2 receptor subunit gamma is also known as CD132; common cytokine receptor γc-chain; IL-2RG; IL-2Rg; IL2Rgamma; IL-2Rγ, IMD4; P64: SCIDX; or SCIDX1. IL2Rγ is a subunit which is common to several interleukin receptors including IL-2R, IL-4R, IL-7R, IL-9R, IL-15R and IL21R.

In an embodiment of the invention, human IL2Rγ is encoded by the nucleotide sequence set forth under Genbank accession no. NM_000206. In an embodiment of the invention, human IL2Rγ comprises the amino acid sequence set forth under Genbank accession no. NP 000197.

Antigen-Binding Proteins

The present invention provides antigen-binding proteins, such as antibodies (e.g., human antibodies, monoclonal antibodies and recombinant antibodies) and antigen-binding fragments thereof, that specifically bind to IL2Rγ protein or an antigenic fragment thereof (e.g., the extracellular domain of IL2Rγ). Antigen-binding proteins that bind to the same epitope on IL2Rγ as, or compete for binding to IL2Rγ with any of the antigen-binding proteins set forth herein, are also part of the present invention.

The present invention also provides any polypeptide that includes an amino acid sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 75, 77, 79, 81, 83, 85, 87, 89, 91, 93, 95, 97, 99, 101, 103, 105, 107, 109, 111, 113, 115, 117, 119, 121, 123, 125, 127, 129, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 309, 311, 313, 315, 317, 319, 321, 323, 325, 327, 329, 331, 333, 335, 337, 339, 341, 343, 345, 347, 349, 351, 353, 355, 357, 359, 361, 363, 366, 368, 370, 372, 374, 376 and/or 378 or a variant thereof. Optionally, the polypeptide is fused to one or more other polypeptides, e.g., a human Fc (e.g., a human IgG such as an IgG1 or IgG4 (e.g., comprising a S108P mutation)).

The term "antibody", as used herein, refers to immunoglobulin molecules comprising four polypeptide chains, two heavy chains (HCs) and two light chains (LCs) inter-connected by disulfide bonds (i.e., "full antibody molecules") (e.g. IgG)—for example H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2. In an embodiment of the invention, each antibody heavy chain (HC) comprises a heavy chain variable region ("HCVR" or "$V_H$") (e.g., SEQ ID NO: 2, 22, 42, 62, 81, 101, 119, 138, 156, 174, 190, 200, 210, 218, 238, 258, 276, 286, 296, 315, 335, 345 or 361 or a variant thereof) and a heavy chain constant region (including domains $C_H1$, $C_H2$ and $C_H3$); and each antibody light chain (LC) comprises a light chain variable region ("LCVR or "$V_L$") (e.g., SEQ ID NO: 10, 30, 50, 70, 89, 109, 127, 146, 164, 182, 226, 246, 266, 304, 323, 353 or 368 or a variant thereof) and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883. Thus, the present invention includes antibodies and antigen-binding fragments including the CDRs of a $V_H$ and the CDRs of a $V_L$, which $V_H$ and $V_L$ comprise amino acid sequences as set forth herein (or a variant thereof), wherein the CDRs are as defined according to Kabat and/or Chothia.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) F(ab')2 fragments; (iii) Fd fragments (heavy chain portion of a Fab fragment cleaved with papain); (iv) Fv fragments (a $V_H$ or $V_L$); and (v) single-chain Fv (scFv) molecules; consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies and small modular immunopharmaceuticals (SMIPs), are also encompassed within the expression "antigen-binding fragment," as used herein. In an embodiment of the invention, the antigen-binding fragment comprises three or more CDRs of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 (e.g., CDR-H1, CDR-H2 and CDR-H3; or CDR-L1, CDR-L2 and CDR-L3).

In an embodiment of the invention, an antigen-binding protein of the present invention (e.g., an antibody or antigen-binding fragment thereof) includes a heavy chain immunoglobulin that comprises a $V_H$ (e.g., an HC) including the combination of heavy chain CDRs (CDR-H1, CDR-H2 and CDR-H3) set forth below in Table A.

TABLE A

Heavy Chain CDRs in Immunoglobulins of the Present Invention.

| CDR-H combination | CDR-H1 | CDR-H2 | CDR-H3 |
|---|---|---|---|
| 1 | 4 | 6 | 8 |
| 2 | 24 | 26 | 28 |
| 3 | 44 | 46 | 48 |
| 4 | 64 | 66 | 68 |
| 5 | 83 | 85 | 87 |

TABLE A-continued

Heavy Chain CDRs in Immunoglobulins of the Present Invention.

| CDR-H combination | CDR-H1 | CDR-H2 | CDR-H3 |
|---|---|---|---|
| 6 | 103 | 105 | 107 |
| 7 | 121 | 123 | 125 |
| 8 | 140 | 142 | 144 |
| 9 | 158 | 160 | 162 |
| 10 | 176 | 178 | 180 |
| 11 | 192 | 194 | 196 |
| 12 | 202 | 204 | 206 |
| 13 | 176 | 212 | 214 |
| 14 | 220 | 222 | 224 |
| 15 | 240 | 242 | 244 |
| 16 | 260 | 262 | 264 |
| 17 | 278 | 280 | 282 |
| 18 | 288 | 290 | 292 |
| 19 | 298 | 300 | 302 |
| 20 | 317 | 319 | 321 |
| 21 | 337 | 339 | 341 |
| 22 | 347 | 349 | 351 |
| 23 | 363 | 66 | 366 |

*Numbers correspond to an amino acid sequence set forth in that SEQ ID NO and/or a light chain immunoglobulin that comprises a $V_L$ (e.g., a LC) including the combination of light chain CDRs (CDR-L1, CDR-L2 and CDR-L3) set forth below in Table B.

TABLE B

Light Chain CDRs in Immunoglobulins of the Present Invention.

| CDR-L combination | CDR-L1 | CDR-L2 | CDR-L3 |
|---|---|---|---|
| 1 | 12 | 14 | 16 |
| 2 | 32 | 34 | 36 |
| 3 | 52 | 54 | 56 |
| 4 | 72 | 54 | 75 |
| 5 | 91 | 93 | 95 |
| 6 | 111 | 54 | 113 |
| 7 | 129 | 54 | 132 |
| 8 | 148 | 54 | 150 |
| 9 | 166 | 14 | 168 |

TABLE B-continued

Light Chain CDRs in Immunoglobulins of the Present Invention.

| CDR-L combination | CDR-L1 | CDR-L2 | CDR-L3 |
|---|---|---|---|
| 10 | 72 | 54 | 184 |
| 11 | 228 | 230 | 232 |
| 12 | 248 | 250 | 252 |
| 13 | 268 | 54 | 270 |
| 14 | 306 | 230 | 309 |
| 15 | 325 | 327 | 329 |
| 16 | 72 | 54 | 355 |
| 17 | 370 | 372 | 374 |

*Numbers correspond to an amino acid sequence set forth in that SEQ ID NO

In an embodiment of the invention, an antigen-binding protein of the present invention (e.g., an antibody or antigen-binding fragment thereof) includes a heavy and light chain immunoglobulin that comprises a $V_H$ (e.g., an HC) and a $V_L$ (e.g., a LC), respectively, including the combination of heavy and light chain CDRs (CDR-H1, CDR-H2 and CDR-H3; and CDR-L1, CDR-L2 and CDR-L3) set forth below in Table C.

TABLE C

Heavy and Light Chain CDRs in Immunoglobulins of the Present Invention.

| CDR combination | CDR-H1 | CDR-H2 | CDR-H3 | CDR-L1 | CDR-L2 | CDR-L3 |
|---|---|---|---|---|---|---|
| 1 | 4 | 6 | 8 | 12 | 14 | 16 |
| 2 | 24 | 26 | 28 | 32 | 34 | 36 |
| 3 | 44 | 46 | 48 | 52 | 54 | 56 |
| 4 | 64 | 66 | 68 | 72 | 54 | 75 |
| 5 | 83 | 85 | 87 | 91 | 93 | 95 |
| 6 | 103 | 105 | 107 | 111 | 54 | 113 |
| 7 | 121 | 123 | 125 | 129 | 54 | 132 |
| 8 | 140 | 142 | 144 | 148 | 54 | 150 |
| 9 | 158 | 160 | 162 | 166 | 14 | 168 |
| 10 | 176 | 178 | 180 | 72 | 54 | 184 |
| 11 | 192 | 194 | 196 | 72 | 54 | 184 |
| 12 | 202 | 204 | 206 | 72 | 54 | 184 |
| 13 | 176 | 212 | 214 | 72 | 54 | 184 |
| 14 | 220 | 222 | 224 | 228 | 230 | 232 |
| 15 | 240 | 242 | 244 | 248 | 250 | 252 |
| 16 | 260 | 262 | 264 | 268 | 54 | 270 |
| 17 | 278 | 280 | 282 | 72 | 54 | 184 |
| 18 | 288 | 290 | 292 | 72 | 54 | 184 |
| 19 | 298 | 300 | 302 | 306 | 230 | 309 |
| 20 | 317 | 319 | 321 | 325 | 327 | 329 |
| 21 | 337 | 339 | 341 | 72 | 54 | 184 |
| 22 | 347 | 349 | 351 | 72 | 54 | 355 |
| 23 | 363 | 66 | 366 | 370 | 372 | 374 |

*Numbers correspond to an amino acid sequence set forth in that SEQ ID NO

The present invention includes an antigen-binding protein (e.g., an antibody or antigen-binding fragment thereof) comprising polypeptide pairs that comprise the following $V_H$ and $V_L$ amino acid sequences:

SEQ ID NO: 2 and SEQ ID NO: 10;
SEQ ID NO: 22 and SEQ ID NO: 30;
SEQ ID NO: 42 and SEQ ID NO: 50;
SEQ ID NO: 62 and SEQ ID NO: 70;
SEQ ID NO: 81 and SEQ ID NO: 89;
SEQ ID NO: 101 and SEQ ID NO: 109;
SEQ ID NO: 119 and SEQ ID NO: 127;
SEQ ID NO: 138 and SEQ ID NO: 146;
SEQ ID NO: 156 and SEQ ID NO: 164;

SEQ ID NO: 174 and SEQ ID NO: 182;
SEQ ID NO: 190 and SEQ ID NO: 182;
SEQ ID NO: 200 and SEQ ID NO: 182;
SEQ ID NO: 210 and SEQ ID NO: 182;
SEQ ID NO: 218 and SEQ ID NO: 226;
SEQ ID NO: 238 and SEQ ID NO: 246;
SEQ ID NO: 258 and SEQ ID NO: 266;
SEQ ID NO: 276 and SEQ ID NO: 182;
SEQ ID NO: 286 and SEQ ID NO: 182;
SEQ ID NO: 296 and SEQ ID NO: 304;
SEQ ID NO: 315 and SEQ ID NO: 323;
SEQ ID NO: 335 and SEQ ID NO: 182;
SEQ ID NO: 345 and SEQ ID NO: 353; or
SEQ ID NO: 361 and SEQ ID NO: 368.

The present invention includes an antigen-binding protein (e.g., an antibody or antigen-binding fragment thereof) comprising the following amino acid sequence pairs encoding a HC and LC:
SEQ ID NO: 18 and SEQ ID NO: 20;
SEQ ID NO: 38 and SEQ ID NO: 40;
SEQ ID NO: 58 and SEQ ID NO: 60;
SEQ ID NO: 77 and SEQ ID NO: 79;
SEQ ID NO: 97 and SEQ ID NO: 99;
SEQ ID NO: 115 and SEQ ID NO: 117;
SEQ ID NO: 134 and SEQ ID NO: 136;
SEQ ID NO: 152 and SEQ ID NO: 154;
SEQ ID NO: 170 and SEQ ID NO: 172;
SEQ ID NO: 186 and SEQ ID NO: 188;
SEQ ID NO: 198 and SEQ ID NO: 188;
SEQ ID NO: 208 and SEQ ID NO: 188;
SEQ ID NO: 216 and SEQ ID NO: 188;
SEQ ID NO: 234 and SEQ ID NO: 236;
SEQ ID NO: 254 and SEQ ID NO: 256;
SEQ ID NO: 272 and SEQ ID NO: 274;
SEQ ID NO: 284 and SEQ ID NO: 188;
SEQ ID NO: 294 and SEQ ID NO: 188;
SEQ ID NO: 311 and SEQ ID NO: 313;
SEQ ID NO: 331 and SEQ ID NO: 333;
SEQ ID NO: 343 and SEQ ID NO: 188;
SEQ ID NO: 357 and SEQ ID NO: 359; or
SEQ ID NO: 376 and SEQ ID NO: 378.

Embodiments of the present invention also include antigen-binding proteins, e.g., anti-IL2Rγ antibodies and antigen-binding fragments thereof, that comprise immunoglobulin $V_H$s and $V_L$s; or HCs and LCs, which comprise a variant amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise the amino acid sequences set forth herein. Thus, in such embodiments, the CDRs within variant antigen-binding proteins are not, themselves, variants.

The present invention includes monoclonal anti-IL2Rγ antigen-binding proteins, e.g., antibodies and antigen-binding fragments thereof, as well as monoclonal compositions comprising a plurality of isolated monoclonal antigen-binding proteins. The term "monoclonal antibody" or "mAb", as used herein, refers to a member of a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-IL2Rγ antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4 (e.g., comprising a S228P and/or S108P mutation)) or IgM. In an embodiment of the invention, an antigen-binding protein, e.g., antibody or antigen-binding fragment, comprises a light chain constant domain, e.g., of the type kappa or lambda. The present invention includes antigen-binding proteins comprising the variable domains set forth herein (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) which are linked to a heavy and/or light chain constant domain, e.g., as set forth above.

The term "human" antigen-binding protein, such as an antibody or antigen-binding fragment, as used herein, includes antibodies and fragments having variable and constant regions derived from human germline immunoglobulin sequences whether in a human cell or grafted into a non-human cell, e.g., a mouse cell. See e.g., U.S. Pat. Nos. 8,502,018, 6,596,541 or 5,789,215. The human antibodies and antigen-binding fragments of the invention may, in an embodiment of the invention, include amino acid residues not encoded by human germline immunoglobulin sequences (e.g., having mutations introduced by random or site-specific mutagenesis in vitro or by somatic mutation in vivo), for example in the CDRs and, in particular, CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject. The present invention includes human antigen-binding proteins (e.g., antibodies or antigen-binding fragments thereof such as H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

The present invention includes anti-IL2Rγ chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (see e.g., U.S. Pat. No. 4,816,567; and Morrison et al., (1984) Proc. Natl. Acad. Sci. USA 81: 6851-6855). The present invention includes chimeric antibodies comprising the variable domains which are set forth herein (e.g., from H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2;

H4H12922P2; H4H12924P2; H4H12926P2; H4H12927P2; H4H12934P2; H4H13538P; H4H13541P; H4H13544P2; or H4H13545P2).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a host cell (e.g., Chinese hamster ovary (CHO) cell) or cellular expression system or isolated from a recombinant combinatorial human antibody library. The present invention includes recombinant antigen-binding proteins as set forth herein (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

An antigen-binding fragment of an antibody will, in an embodiment of the invention, comprise at least one variable domain. The variable domain may be of any size or amino acid composition and will generally comprise at least one (e.g., 3) CDR(s), which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ and/or $V_L$ domain which are bound non-covalently.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; OD $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). The present invention includes an antigen-binding fragment of an anti-gen-binding protein set forth herein, for example, H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2.

Antigen-binding proteins (e.g., antibodies and antigen-binding fragments) may be monospecific or multi-specific (e.g., bispecific). Multispecific antigen-binding proteins are discussed further herein. The present invention includes monospecific as well as multispecific (e.g., bispecific) anti-gen-binding fragments comprising one or more variable domains from an antigen-binding protein that is specifically set forth herein (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

The term "specifically binds" or "binds specifically" refers to those antigen-binding proteins (e.g., antibodies or antigen-binding fragments thereof) having a binding affinity to an antigen, such as IL2Rγ protein, expressed as $K_D$, of at least about $10^{-7}$ M (e.g., $10^{-8}$ M, $10^{-9}$ M, $10^{-10}$M, $10^{-11}$ M or $10^{-12}$ M), as measured by real-time, label free bio-layer interferometry assay, for example, at 25° C. or 37° C., e.g., an Octet® HTX biosensor, or by surface plasmon resonance, e.g., BIACORE™, or by solution-affinity ELISA. The present invention includes antigen-binding proteins that specifically bind to IL2Rγ protein. In an embodiment of the invention, an anti-IL2Rγ antigen-binding protein comprises a $K_D$ value, for binding to human and/or mouse and/or *Macaca fascicularis* and/or rat IL2Rγ or a domain thereof, which value is set forth in any of Tables 3-1 to 3-12. "Anti-IL2Rgamma" refers to an antigen-binding protein (or other molecule), for example an antibody or antigen-binding fragment thereof, that binds specifically to IL2Rgamma.

"Isolated" antigen-binding proteins (e.g., antibodies or antigen-binding fragments thereof), polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antigen-binding protein may further be at least partially free of expression system components such as biological molecules from a host cell or of the growth medium thereof. Generally, the term "isolated" is not intended to refer to a complete absence of such biological molecules (e.g., minor or insignificant amounts of impurity may remain) or to an absence of water, buffers, or salts or to components of a pharmaceutical formulation that includes the antigen-binding proteins (e.g., antibodies or antigen-binding fragments).

The present invention includes antigen-binding proteins, e.g., antibodies or antigen-binding fragments, that bind to the same epitope as an antigen-binding protein of the present invention (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2).

An antigen is a molecule, such as a peptide (e.g., IL2R gamma or a fragment thereof (an antigenic fragment)), to which, for example, an antibody binds. The specific region on an antigen that an antibody recognizes and binds to is called the epitope. Antigen-binding proteins (e.g., antibodies) of the present invention that specifically bind to such antigens are part of the present invention.

The term "epitope" refers to an antigenic determinant (e.g., on IL2Rγ) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" may also refer to a site on an antigen to which B and/or T cells respond and/or to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes to which antigen-binding proteins of the present invention bind may be included in fragments of IL2Rγ, e.g., human IL2Rγ, for example the ectodomain, domain 1 or domain 2 thereof. Antigen-binding proteins (e.g., antibodies) of the present invention that bind to such epitopes are part of the present invention.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) interacts is hydrogen/deuterium exchange detected by mass spectrometry. See, e.g., Ehring (1999) Analytical Biochemistry 267: 252-259; Engen and Smith (2001) Anal. Chem. 73: 256A-265A.

The present invention includes antigen-binding proteins that compete for binding to IL2Rγ, e.g., a variant IL2Rγ epitope as discussed herein, with an antigen-binding protein of the present invention, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2. The term "competes" as used herein, refers to an antigen-binding protein (e.g., antibody or antigen-binding fragment thereof) that binds to an antigen (e.g., IL2Rγ) and inhibits or blocks the binding of another antigen-binding protein (e.g., antibody or antigen-binding fragment thereof) to the antigen. Unless otherwise stated, the term also includes competition between two antigen-binding proteins e.g., antibodies, in both orientations, i.e., a first antibody that binds antigen and blocks binding by a second antibody and vice versa. Thus, in an embodiment of the invention, competition occurs in one such orientation. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping or non-overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. Also, binding competition between anti-IL2Rγ antigen-binding proteins (e.g., monoclonal antibodies (mAbs)) can be determined using a real time, label-free bio-layer interferometry assay on an Octet RED384 biosensor (Pall ForteBio Corp.).

Typically, an antibody or antigen-binding fragment of the invention which is modified in some way retains the ability to specifically bind to IL2Rγ, e.g., retains at least 10% of its IL2Rγ binding activity (when compared to the parental antibody) when that activity is expressed on a molar basis. Preferably, an antibody or antigen-binding fragment of the invention retains at least 20%, 50%, 70%, 80%, 90%, 95% or 100% or more of the IL2Rγ binding affinity as the parental antibody. It is also intended that an antibody or antigen-binding fragment of the invention may include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., an H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 $V_H$, $V_L$, HC or LC or CDR thereof comprising the amino acid sequence specifically set forth herein), refers to a polypeptide comprising an amino acid sequence that is at least about 70-99.9% (e.g., at least 70, 72, 74, 75, 76, 79, 80, 81, 82, 83, 84, 85, 86, 87, 88, 89, 90, 91, 92, 93, 94, 95, 96, 97, 98, 99, 99.5 or 99.9%) identical or similar to a referenced amino acid sequence that is set forth herein (e.g., any of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 75, 77, 79, 81, 83, 85, 87, 89, 91, 93, 95, 97, 99, 101, 103, 105, 107, 109, 111, 113, 115, 117, 119, 121, 123, 125, 127, 129, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 309, 311, 313, 315, 317, 319, 321, 323, 325, 327, 329, 331, 333, 335, 337, 339, 341, 343, 345, 347, 349, 351, 353, 355, 357, 359, 361, 363, 366, 368, 370, 372, 374, 376 or 378); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

Moreover, a variant of a polypeptide may include a polypeptide such as an immunoglobulin chain (e.g., an H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 $V_H$, $V_L$, HC or LC or CDR thereof) which may include the amino acid sequence of the reference polypeptide whose amino acid sequence is specifically set forth herein but for one or more (e.g., 1, 2, 3, 4, 5, 6, 7, 8, 9 or 10) mutations, e.g., one or more missense mutations (e.g., conservative substitutions), non-sense mutations, deletions, or insertions. For example, the present invention includes anti-IL2Rγ antigen-binding proteins which include an immunoglobulin light chain (or $V_L$) variant comprising the amino acid sequence set forth in SEQ ID NO: 10 but having one or more of such mutations and/or an immunoglobulin heavy chain (or $V_H$) variant comprising the amino acid sequence set forth in SEQ ID NO: 2 but having one or more of such mutations. In an embodiment of the invention, an anti-IL2Rγ antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

A "conservatively modified variant" or a "conservative substitution", e.g., of an immunoglobulin chain set forth herein, refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 ($4^{th}$ Ed.)). In addition, substitutions of structurally or functionally similar amino acids are less likely to significantly disrupt biological activity. The present invention includes anti-IL2Rγ antigen-binding proteins comprising such conservatively modified variant immunoglobulin chains.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Alternatively, a conservative replacement is any change having a positive value in the PAM250 log-likelihood matrix disclosed in Gonnet et al. (1992) Science 256: 1443-45.

Anti-IL2Rγ antigen-binding proteins set forth herein, e.g., comprising variant immunoglobulin chains, may exhibit one or more of the following properties:

Binds to human IL2Rγ (e.g., a fusion thereof such as a myc-myc-His6 fusion) at 25° C. with a $K_D$ of about $2.75 \times 10^{-9}$ M to about $3.36 \times 10^{-7}$ M;

Binds to human IL2Rγ (e.g., a fusion thereof such as a myc-myc-His6 fusion) at 37° C. with a $K_D$ of about $6.42 \times 10^{-9}$ M to about $3.53 \times 10^{-7}$ M (or binds with a $K_D$ of less than about $3.53 \times 10^{-7}$ M);

Binds to *Macaca fascicularis* IL-2Rγ (e.g., a fusion thereof such as a myc-myc-His6 fusion) at 25° C. with a $K_D$ of about $3.18 \times 10^{-9}$ M to about $2.38 \times 10^{-7}$ M;

Binds to *Macaca fascicularis* IL-2Rγ (e.g., a fusion thereof such as a myc-myc-His6 fusion) at 37° C. with a $K_D$ of about $8.29 \times 10^{-9}$ M to about $3.20 \times 10^{-7}$ M (or binds with a $K_D$ of less than about $3.20 \times 10^{-7}$ M);

Binds to human IL2Rγ (e.g., a fusion thereof such as to a C-terminal mouse IgG2a Fc tag) at 25° C. with a $K_D$ of about $2.45 \times 10^{-9}$ M to about $1.20 \times 10^{-8}$ M (or binds with a $K_D$ of less than about $1.20 \times 10^{-8}$ M);

Binds to human IL2Rγ (e.g., a fusion thereof such as to a C-terminal mouse IgG2a Fc tag) at 37° C. with a $K_D$ of about $1.86 \times 10^{-11}$ M to about $3.00 \times 10^{-8}$ M (or binds with a $K_D$ of less than about $3.00 \times 10^{-8}$ M);

Binds to mouse IL2Rγ (e.g., a fusion thereof such as a myc-myc-His6 fusion) at 25° C. with a $K_D$ of about $1.84 \times 10^{-8}$ M, $3.76 \times 10^{-9}$ M, $1.08 \times 10^{-7}$ M, $2.17 \times 10^{-8}$ M, $6.02 \times 10^{-9}$ M or $7.93 \times 10^{-8}$ M (or binds does not bind);

Binds to mouse IL2Rγ (e.g., a fusion thereof such as a myc-myc-His6 fusion) at 37° C. with a $K_D$ of about $5.59 \times 10^{-8}$ M, $6.11 \times 10^{-9}$ M, $3.87 \times 10^{-7}$ M, $5.16 \times 10^{-8}$ M, $8.70 \times 10^{-9}$ M or $2.15 \times 10^{-7}$ M (or binds does not bind);

Binds to human IL2Rγ domain 1 (e.g., a fusion thereof such as a myc-myc-His6 fusion) at 25° C. with a $K_D$ of about $3.32 \times 10^{-9}$ M to about $1.97 \times 10^{-7}$ M (or binds does not bind);

Binds to human IL2Rγ domain 1 (e.g., a fusion thereof such as a myc-myc-His6 fusion) at 37° C. with a $K_D$ of about $4.13 \times 10^{-9}$ M to about $2.25 \times 10^{-7}$ M (or binds does not bind);

Binds to human IL2Rγ domain 2 (e.g., a fusion thereof such as a myc-myc-His6 fusion) at 25° C. with a $K_D$ of about $2.91 \times 10^{-7}$ M to about $5.35 \times 10^{-10}$ (or binds does not bind);

Binds to human IL2Rγ domain 2 (e.g., a fusion thereof such as a myc-myc-His6 fusion) at 37° C. with a $K_D$ of about $1.14 \times 10^{-8}$ or about $1.27 \times 10^{-8}$ (or binds does not bind);

Blocks STAT phosphorylation in T-cells (e.g., human CD4+ T cells), for example which is induced by IL-2 (e.g., at about 10 nM), IL-4 (e.g., at about 50 pM), IL7 (e.g., at about 1 pM), IL-15 (e.g., at about 0.5 nM) and/or IL-21 (e.g., at about 50 pM), e.g. at an IC$_{50}$ of about 1 nM to about 0.5 nM;

Blocks STAT phosphorylation in mast cells (e.g., differentiated human mast cells), for example which is induced by IL-9 (e.g., at about 2 nM), e.g., with an IC$_{50}$ of about $4\times10^{-10}$ M;

Reduces the number of human immune cells (e.g., human PBMCs (peripheral blood mononuclear cells), for example, human CD45+ cells, human T cells, human CD4+ T cells and/or human CD8+ T cells) in a mouse after injection with human peripheral blood mononuclear cells (PBMCs) (e.g., NOD-scid IL2rγ null (NSG) mouse);

Reduces the levels of serum human cytokines (e.g., human IFN-γ, human TNFα, human IL-6, human IL-8 and/or human IL-10) and/or mouse cytokines (e.g., mouse TNFα, mouse IL-6, mouse KC/GRO and/or mouse IL-10) in mice (e.g., NOD-scid IL2rγ null (NSG) mouse) in a mouse after injection with human peripheral blood mononuclear cells (PBMCs);

Competes for binding to human IL-2Rγ, for example, on a cell surface (e.g., tagged with a C-terminal myc-myc-hexahistidine tag), with any one or more anti-IL2Rγ antibodies set forth herein;

Binds to the same epitope on IL2Rγ, for example, on a cell surface (e.g., tagged with a C-terminal myc-myc-hexahistidine tag) as any one or more anti-IL2Rγ antibodies set forth herein;

Does not bind detectably to mouse or rat IL2Rγ (e.g., as measured by Biacore at 37° C.);

Protects mice from weight loss and/or death due to GvHD in a GvHD mouse model;

Blocks binding of a hybrid receptor comprising IL2Rγ complexed with a cytokine-specific receptor subunit from binding to a cytokine such as IL-2, IL-4, IL-7, IL-9, IL-15 and/or IL-21; and/or Inhibits IL2Rγ intracellular signaling (e.g., in a human B-lymphocyte cell or human natural killer cell) through the JAK-STAT pathway, e.g., which is induced by IL2, IL4, IL7, IL9, ID 5 and/or IL21, for example, as measured by luciferase expression in a cell including a luciferase gene operably linked to a STAT3 response element.

"H4H12857P"; "H4H12858P"; "H4H12859P"; "H4H12863P"; "H4H12874P"; "H4H12871P"; "H4H12884P"; "H4H12886P"; "H4H12889P"; "H4H12890P"; "H4H12899P"; "H4H12900P"; "H4H12908P"; "H4H12913P2"; "H4H12922P2"; "H4H12924P2"; "H4H12926P2"; "H4H12927P2"; "H4H12934P2"; "H4H13538P"; "H4H13541P"; "H4H13544P2"; or "H4H13545P2", unless otherwise stated, refer to anti-IL2Rγ antigen-binding proteins, e.g., antibodies and antigen-binding fragments thereof (including multispecific antigen-binding proteins), comprising an immunoglobulin heavy chain or variable region thereof (V$_H$) comprising the amino acid sequence specifically set forth herein for H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 (e.g., SEQ ID NO: 2, 18, 22, 38, 42, 58, 62, 77, 81, 97, 101, 115, 119, 134, 138, 152, 156, 170, 174, 186, 190, 198, 200, 208, 210, 216, 218, 234, 238, 254, 258, 272, 276, 284, 286, 294, 296, 311, 315, 331, 335, 343, 345, 357, 361 or 376) (or a variant thereof), and/or an immunoglobulin light chain or variable region thereof (V$_L$) comprising the amino acid sequence specifically set forth herein for H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 (e.g., SEQ ID NO: 10, 20, 30, 40, 50, 60, 70, 79, 89, 99, 109, 117, 127, 136, 146, 154, 164, 172, 182, 188, 226, 236, 246, 256, 266, 274, 304, 313, 323, 333, 353, 359, 368 or 378) (or a variant thereof), respectively; and/or that comprise a heavy chain or V$_H$ that comprises the CDRs thereof (CDR-H1 (or a variant thereof), CDR-H2 (or a variant thereof) and CDR-H3 (or a variant thereof)) and/or a light chain or V$_L$ that comprises the CDRs thereof (CDR-L1 (or a variant thereof), CDR-L2 (or a variant thereof) and CDR-L3 (or a variant thereof)). In an embodiment of the invention, the V$_H$ is linked to an IgG constant heavy chain domain, for example, human IgG constant heavy chain domain (e.g., IgG1 or IgG4 (e.g., comprising the S228P and/or S108P mutation)) and/or the V$_L$ is linked to a light chain constant domain, for example a human light chain constant domain (e.g., lambda or kappa constant light chain domain). Polynucleotides encoding one or more of any such immunoglobulin chains (e.g., V$_H$, V$_L$, HC and/or LC) forms part of the present invention.

The present invention includes "neutralizing" or "antagonist" anti-IL2Rγ antigen-binding proteins (e.g., antibody or antigen-binding fragment) which includes molecules that inhibit an activity of IL2Rγ (e.g., binding of a hybrid receptor comprising IL2Rγ complexed with a cytokine-specific receptor subunit from binding to a cytokine such as IL-2, IL-4, IL-7, IL-9, IL-15 and/or IL-21) to any detectable degree.

Antibodies and antigen-binding fragments of the present invention (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) comprise immunoglobulin chains including the amino acid sequences specifically set forth herein (and variants thereof) as well as cellular and in vitro post-translational modifications to the antibody or fragment. For example, the present invention includes antibodies and antigen-binding fragments thereof that specifically bind to IL2Rγ comprising heavy and/or light chain amino acid sequences set forth herein as well as antibodies and fragments wherein one or more asparagine, serine and/or threonine residues is glycosylated, one or more asparagine residues is deamidated, one or more residues (e.g., Met, Trp and/or His) is oxidized, the N-terminal glutamine is pyroglutamate (pyroE) and/or the C-terminal lysine or other amino acid is missing.

The present invention provides a vessel (e.g., a plastic or glass vial, e.g., with a cap or a chromatography column, hollow bore needle or a syringe cylinder) comprising an anti-IL2Rγ antigen-binding protein of the present invention, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2;

H4H12926P2; H4H12927P2; H4H12934P2; H4H13538P; H4H13541P; H4H13544P2; or H4H13545P2.

The present invention also provides an injection device comprising one or more antigen-binding proteins (e.g., antibody or antigen-binding fragment) that bind specifically to IL2Rγ, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, or a pharmaceutical formulation thereof. The injection device may be packaged into a kit. An injection device is a device that introduces a substance into the body of a subject via a parenteral route, e.g., intraocular, intravitreal, intramuscular, subcutaneous or intravenous. For example, an injection device may be a syringe or an auto-injector (e.g., pre-filled with the pharmaceutical formulation) which, for example, includes a cylinder or barrel for holding fluid to be injected (e.g., comprising the antibody or fragment or a pharmaceutical formulation thereof), a needle for piecing skin, blood vessels or other tissue for injection of the fluid; and a plunger for pushing the fluid out of the cylinder and through the needle bore and into the body of the subject.

The present invention further provides methods for administering an anti-IL2Rγ antigen-binding protein of the present invention, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, to a subject, comprising introducing the antigen-binding protein into the body of the subject (e.g., a human), for example, parenterally. For example, the method comprises piercing the body of the subject with a needle of a syringe and injecting the antigen-binding protein into the body of the subject, e.g., into the vein, artery, eye, muscular tissue or subcutis of the subject.

Polynucleotides and Methods of Making

A polynucleotide includes DNA and RNA. The present invention includes any polynucleotide of the present invention, for example, encoding an immunoglobulin $V_H$, $V_L$, CDR-H, CDR-L, HC or LC of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, optionally, which is operably linked to a promoter or other expression control sequence. For example, the present invention provides any polynucleotide (e.g., DNA) that includes a nucleotide sequence set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 74, 76, 78, 80, 82, 84, 86, 88, 90, 92, 94, 96, 98, 100, 102, 104, 106, 108, 110, 112, 114, 116, 118, 120, 122, 124, 126, 128, 130, 131, 133, 135, 137, 139, 141, 143, 145, 147, 149, 151, 153, 155, 157, 159, 161, 163, 165, 167, 169, 171, 173, 175, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 308, 310, 312, 314, 316, 318, 320, 322, 324, 326, 328, 330, 332, 334, 336, 338, 340, 342, 344, 346, 348, 350, 352, 354, 356, 358, 360, 362, 364, 365, 367, 369, 371, 373, 375 or 377. In an embodiment of the invention, a polynucleotide of the present invention is fused to a secretion signal sequence. Polypeptides encoded by such polynucleotides are also within the scope of the present invention.

In general, a "promoter" or "promoter sequence" is a DNA regulatory region capable of binding an RNA polymerase in a cell (e.g., directly or through other promoter-bound proteins or substances) and initiating transcription of a coding sequence. A promoter may be operably linked to other expression control sequences, including enhancer and repressor sequences and/or with a polynucleotide of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the beta-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal4 promoter, the ADC (alcohol dehydrogenase) promoter, PGK (phosphoglycerol kinase) promoter or the alkaline phosphatase promoter.

A polynucleotide encoding a polypeptide is "operably linked" to a promoter or other expression control sequence when, in a cell or other expression system, the sequence directs RNA polymerase mediated transcription of the coding sequence into RNA, preferably mRNA, which then may be RNA spliced (if it contains introns) and, optionally, translated into a protein encoded by the coding sequence.

The present invention includes a polynucleotide comprising the following polynucleotide pairs encoding a $V_H$ and $V_L$:

SEQ ID NO: 1 and SEQ ID NO: 9;
SEQ ID NO: 21 and SEQ ID NO: 29;
SEQ ID NO: 41 and SEQ ID NO: 49;
SEQ ID NO: 61 and SEQ ID NO: 69;
SEQ ID NO: 80 and SEQ ID NO: 88;
SEQ ID NO: 100 and SEQ ID NO: 108;
SEQ ID NO: 118 and SEQ ID NO: 126;
SEQ ID NO: 137 and SEQ ID NO: 145;
SEQ ID NO: 155 and SEQ ID NO: 163;
SEQ ID NO: 173 and SEQ ID NO: 181;
SEQ ID NO: 189 and SEQ ID NO: 181;
SEQ ID NO: 199 and SEQ ID NO: 181;
SEQ ID NO: 209 and SEQ ID NO: 181;
SEQ ID NO: 217 and SEQ ID NO: 225;
SEQ ID NO: 237 and SEQ ID NO: 245;
SEQ ID NO: 257 and SEQ ID NO: 265;
SEQ ID NO: 275 and SEQ ID NO: 181;
SEQ ID NO: 285 and SEQ ID NO: 181;
SEQ ID NO: 295 and SEQ ID NO: 303;
SEQ ID NO: 314 and SEQ ID NO: 322;
SEQ ID NO: 334 and SEQ ID NO: 181;
SEQ ID NO: 344 and SEQ ID NO: 352; or
SEQ ID NO: 360 and SEQ ID NO: 367.

The present invention includes a polynucleotide comprising the following polynucleotide sets which encode a CDR-H1, CDR-H2, CDR-H3, CDR-L1, CDR-L2 and CDR-L3:
SEQ ID NOs: 3, 5, 7, 11, 13 and 15;
SEQ ID NOs: 23, 25, 27, 31, 33 and 35;
SEQ ID NOs: 43, 45, 47, 51, 53 and 55;
SEQ ID NOs: 63, 65, 67, 71, 73 and 74;
SEQ ID NOs: 82, 84, 86, 90, 92 and 94;
SEQ ID NOs: 102, 104, 106, 110, 73 and 112;
SEQ ID NOs: 120, 122, 124, 128, 130 and 131;
SEQ ID NOs: 139, 141, 143, 147, 73 and 149;
SEQ ID NOs: 157, 159, 161, 165, 13 and 167;
SEQ ID NOs: 175, 177, 179, 71, 73 and 183;
SEQ ID NOs: 191, 193, 195, 71, 73 and 183;
SEQ ID NOs: 201, 203, 205, 71, 73 and 183;
SEQ ID NOs: 175, 211, 213, 71, 73 and 183;
SEQ ID NOs: 219, 221, 223, 227, 229 and 231;
SEQ ID NOs: 239, 241, 243, 247, 249 and 251;
SEQ ID NOs: 259, 261, 263, 267, 73 and 269;
SEQ ID NOs: 277, 279, 281, 71, 73 and 183;
SEQ ID NOs: 287, 289, 291, 71, 73 and 183;
SEQ ID NOs: 297, 299, 301, 305, 307 and 308;
SEQ ID NOs: 316, 318, 320, 324, 326 and 328;
SEQ ID NOs: 336, 338, 340, 71, 73 and 183;
SEQ ID NOs: 346, 348, 350, 71, 73 and 354; or
SEQ ID NOs: 362, 364, 365, 369, 371 and 373.

The present invention includes a polynucleotide comprising the following polynucleotide pairs encoding a HC and LC:
SEQ ID NO: 17 and SEQ ID NO: 19;
SEQ ID NO: 37 and SEQ ID NO: 39;
SEQ ID NO: 57 and SEQ ID NO: 59;
SEQ ID NO: 76 and SEQ ID NO: 78;
SEQ ID NO: 96 and SEQ ID NO: 98;
SEQ ID NO: 114 and SEQ ID NO: 116;
SEQ ID NO: 133 and SEQ ID NO: 135;
SEQ ID NO: 151 and SEQ ID NO: 153;
SEQ ID NO: 169 and SEQ ID NO: 171;
SEQ ID NO: 185 and SEQ ID NO: 187;
SEQ ID NO: 197 and SEQ ID NO: 187;
SEQ ID NO: 207 and SEQ ID NO: 187;
SEQ ID NO: 215 and SEQ ID NO: 187;
SEQ ID NO: 233 and SEQ ID NO: 235;
SEQ ID NO: 253 and SEQ ID NO: 255;
SEQ ID NO: 271 and SEQ ID NO: 273;
SEQ ID NO: 283 and SEQ ID NO: 187;
SEQ ID NO: 293 and SEQ ID NO: 187;
SEQ ID NO: 310 and SEQ ID NO: 312;
SEQ ID NO: 330 and SEQ ID NO: 332;
SEQ ID NO: 342 and SEQ ID NO: 187;
SEQ ID NO: 356 and SEQ ID NO: 358; or
SEQ ID NO: 375 and SEQ ID NO: 377.

The present invention includes polynucleotides encoding immunoglobulin polypeptide chains which are variants of those whose nucleotide sequence is specifically set forth herein. A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, -2; gap costs: linear). In an embodiment of the invention, a variant of a nucleotide sequence specifically set forth herein comprises one or more (e.g., 1, 2, 3, 4, 5, 6, 7, 8, 9, 10, 11 or 12) point mutations, insertions (e.g., in frame insertions) or deletions (e.g., in frame deletions) of one or more nucleotides. Such mutations may, in an embodiment of the invention, be missense or nonsense mutations. In an embodiment of the invention, such a variant polynucleotide encodes an immunoglobulin polypeptide chain which can be incorporated into an anti-IL2Rγ antigen-binding protein, i.e., such that the protein retains specific binding to IL2Rγ.

Eukaryotic and prokaryotic host cells, including mammalian cells, may be used as hosts for expression of an anti-IL2Rγ antigen-binding protein (e.g., antibody or antigen-binding fragment thereof). Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia, Pichia pastoris, Pichia finlandica, Pichia trehalophila, Pichia koclamae, Pichia membranaefaciens, Pichia minuta (Ogataea minuta, Pichia lindnen), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. The present invention includes an isolated host cell (e.g., a CHO cell or any type of host cell set forth above) comprising an antigen-binding protein, a $V_H$, $V_L$, HC, LC or CDRs thereof (or variant thereof), such as H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2; and/or a polynucleotide encoding one or more immunoglobulin chains thereof (e.g., as discussed herein).

The present invention also includes a cell which is expressing IL2Rγ or an antigenic fragment or fusion thereof (e.g., His$_6$, Fc and/or myc) which is bound by an antigen-binding protein of the present invention (e.g., an antibody or antigen-binding fragment thereof), for example, H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, for example, wherein the cell is in the body of a subject or is in vitro.

In addition, the present invention also provides a complex comprising an anti-IL2Rγ antigen-binding protein, e.g., antibody or antigen-binding fragment thereof, as discussed herein complexed with IL2Rγ polypeptide or an antigenic fragment thereof or fusion thereof and/or with a secondary antibody or antigen-binding fragment thereof (e.g., detectably labeled secondary antibody) that binds specifically to the anti-IL2Rγ antibody or fragment. In an embodiment of the invention, the complex is in vitro (e.g., is immobilized to a solid substrate) or is in the body of a subject.

Recombinant anti-IL2Rγ antigen-binding proteins, e.g., antibodies and antigen-binding fragments, disclosed herein may also be produced in an *E. coli*/T7 expression system. In this embodiment, polynucleotides encoding the anti-IL2Rγ antibody immunoglobulin molecules of the invention (e.g., HC, LC, $V_H$ and/or $V_L$ or CDRs thereof of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21 DE3) comprising expressing T7 RNA polymerase in the cell which also includes a polynucleotide encoding an immunoglobulin chain (e.g., including the nucleotide sequence in any one or more of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 74, 76, 78, 80, 82, 84, 86, 88, 90, 92, 94, 96, 98, 100, 102, 104, 106, 108, 110, 112, 114, 116, 118, 120, 122, 124, 126, 128, 130, 131, 133, 135, 137, 139, 141, 143, 145, 147, 149, 151, 153, 155, 157, 159, 161, 163, 165, 167, 169, 171, 173, 175, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 308, 310, 312, 314, 316, 318, 320, 322, 324, 326, 328, 330, 332, 334, 336, 338, 340, 342, 344, 346, 348, 350, 352, 354, 356, 358, 360, 362, 364, 365, 367, 369, 371, 373, 375 or 377; or a variant thereof) that is operably linked to a T7 promoter. For example, in an embodiment of the invention, a bacterial host cell, such as an *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952,496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455. Thus, the present invention includes recombinant methods for making an anti-IL2Rγ antigen-binding protein, such as an antibody or antigen-binding fragment thereof of the present invention, or an immunoglobulin chain thereof, comprising (i) introducing, into a host cell, one or more polynucleotides (e.g., including the nucleotide sequence in any one or more of SEQ ID NOs: 1, 9, 17, 19, 21, 29, 37, 39, 41, 49, 57, 59, 61, 69, 76, 78, 80, 88, 96, 98, 100, 108, 114, 116, 118, 126, 133, 135, 137, 145, 151, 153, 155, 163, 169, 171, 173, 181, 185, 187, 189, 197, 199, 207, 209, 215, 217, 225, 233, 235, 237, 245, 253, 255, 257, 265, 271, 273, 275, 283, 285, 293, 295, 303, 310, 312, 314, 322, 330, 332, 334, 342, 344, 352, 356, 358, 360, 367, 375 or 377; or a variant thereof) encoding light and/or heavy immunoglobulin chains of the antigen-binding protein, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, for example, wherein the polynucleotide is in a vector; and/or integrates into the host cell chromosome and/or is operably linked to a promoter; (ii) culturing the host cell (e.g., CHO or *Pichia* or *Pichia pastoris*) under conditions favorable to expression of the polynucleotide and, (iii) optionally, isolating the antigen-binding protein (e.g., antibody or antigen-binding fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods of the present invention include those wherein only a heavy immunoglobulin chain or only a light immunoglobulin chain or both (e.g., any of those discussed herein including mature fragments and/or variable domains thereof) are expressed in a cell. Such single chains are useful, for example, as intermediates in the expression of an antibody or antigen-binding fragment that includes such a chain. For example, the present invention also includes anti-IL2Rγ antigen-binding proteins, such as antibodies and antigen-binding fragments thereof which are the product of the production methods set forth herein, and, optionally, the purification methods set forth herein.

In an embodiment of the invention, a method for making an anti-IL2Rγ antigen-binding protein, e.g., antibody or antigen-binding fragment thereof, includes a method of purifying the antigen-binding protein, e.g., by column chromatography, precipitation and/or filtration. As discussed, the product of such a method also forms part of the present invention.

Preparation of Human Antibodies

The anti-IL2Rγ antibodies of the present invention can be fully human antibodies. Methods for generating monoclonal antibodies, including fully human monoclonal antibodies are known in the art. Any such known methods can be used in the context of the present invention to make human antibodies that specifically bind to human IL2Rγ.

Using VELOCIMMUNE™ technology, for example, or any other similar known method for generating fully human monoclonal antibodies, high affinity chimeric antibodies to IL2Rγ are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-IL2Rγ antibody. While the constant region selected may vary according to specific use, high affinity antigen-binding and target specificity characteristics reside in the variable region. In certain instances, fully human anti-IL2Rγ antibodies are isolated directly from antigen-positive B cells. See, for example, U.S. Pat. No. 6,596,541, Regeneron Pharmaceuticals, VELOCIMMUNE®.

Anti-IL2Rγ Antibodies Comprising Fc Variants

According to certain embodiments of the present invention, anti-IL2Rγ antibodies are provided comprising an Fc domain comprising one or more mutations which enhance or diminish antibody binding to the FcRn receptor, e.g., at acidic pH as compared to neutral pH. For example, the present invention includes anti-IL2Rγ antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal.

Non-limiting examples of such Fc modifications include, e.g., a modification at position:
  250 (e.g., E or Q);
  250 and 428 (e.g., L or F);
  252 (e.g., L/Y/F/W or T),
  254 (e.g., S or T), and/or
  256 (e.g., S/R/Q/E/D or T);
and/or a modification at position:
  428 and/or 433 (e.g., H/L/R/S/P/Q or K), and/or
  434 (e.g., H/F or Y);
and/or a modification at position:
  250 and/or 428;
and/or a modification at position:
  307 or 308 (e.g., 308F, V308F), and/or
  434.

In an embodiment of the invention, the modification comprises:
  a 428L (e.g., M428L) and 434S (e.g., N434S) modification;
  a 428L, 259I (e.g., V259I), and 308F (e.g., V308F) modification;
  a 433K (e.g., H433K) and a 434 (e.g., 434Y) modification;
  a 252, 254, and 256 (e.g., 252Y, 254T, and 256E) modification;
  a 250Q and 428L modification (e.g., T250Q and M428L); and/or
  a 307 and/or 308 modification (e.g., 308F or 308P).

For example, the present invention includes anti-IL2Rγ antibodies comprising an Fc domain comprising one or more pairs or groups of mutations selected from the group consisting of:
  250Q and 248L (e.g., T250Q and M248L);
  252Y, 254T and 256E (e.g., M252Y, S254T and T256E);
  428L and 434S (e.g., M428L and N434S); and
  433K and 434F (e.g., H433K and N434F).

In an embodiment of the invention, the heavy chain constant domain is γ4 comprising an S228P and/or S108P mutation. See Angal et al. A single amino acid substitution abolishes the heterogeneity of chimeric mouse/human (IgG4) antibody, Mol Immunol. 1993 January; 30(1):105-108.

All possible combinations of the foregoing Fc domain mutations, and other mutations within the antibody variable domains disclosed herein, are contemplated within the scope of the present invention.

The anti-IL2Rγ antibodies of the present invention may comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US2014/0171623; U.S. Pat. No. 8,697,396; US2014/0134162; WO2014/043361, the disclosures of which are hereby incorporated by reference in their entireties. Methods of constructing antibodies or other antigen-binding fusion proteins comprising a modified Fc domain as described herein are known in the art.

Multispecific Antigen-Binding Proteins

The present invention includes anti-IL2Rγ antigen-binding proteins, e.g., antibodies and antigen-binding fragments thereof, as well as methods of use thereof and methods of making such antigen-binding proteins. The term "anti-IL2Rγ" or "anti-IL2Rgamma" antigen-binding protein, e.g., antibodies or antigen-binding fragments, includes multispecific (e.g., bispecific or biparatopic) molecules that include at least one first antigen-binding domain that specifically binds to IL2Rγ (e.g., an antigen-binding domain from H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2;

H4H12926P2; H4H12927P2; H4H12934P2; H4H13538P; H4H13541P; H4H13544P2; or H4H13545P2) and at least one second antigen-binding domain that binds to a different antigen or to an epitope in IL2Rγ which is different from that of the first antigen-binding domain. In an embodiment of the invention, the first and second epitopes overlap. In another embodiment of the invention, the first and second epitopes do not overlap.

Multispecific binding refers to binding to two or more different epitopes which may be on the same or on different antigens. Multispecific includes bispecific, trispecific and tetraspecific.

"H4H12857P"; "H4H12858P"; "H4H12859P"; "H4H12863P"; "H4H12874P"; "H4H12871P"; "H4H12884P"; "H4H12886P"; "H4H12889P"; "H4H12890P"; "H4H12899P"; "H4H12900P"; "H4H12908P"; "H4H12913P2"; "H4H12922P2"; "H4H12924P2"; "H4H12926P2"; "H4H12927P2"; "H4H12934P2"; "H4H13538P"; "H4H13541P"; "H4H13544P2"; or "H4H13545P2" includes multispecific molecules, e.g., antibodies or antigen-binding fragments, that include the HCDRs and LCDRs, $V_H$ and $V_L$, or HC and LC of "H4H12857P"; "H4H12858P"; "H4H12859P"; "H4H12863P"; "H4H12874P"; "H4H12871P"; "H4H12884P"; "H4H12886P"; "H4H12889P"; "H4H12890P"; "H4H12899P"; "H4H12900P"; "H4H12908P"; "H4H12913P2"; "H4H12922P2"; "H4H12924P2"; "H4H12926P2"; "H4H12927P2"; "H4H12934P2"; "H4H13538P"; "H4H13541P"; "H4H13544P2"; or "H4H13545P2", respectively and one or more antigen-binding domains that bind to a different epitope.

In an embodiment of the invention, an antigen-binding domain that bind specifically to IL2Rγ, which may be included in a multispecific molecule, comprise:

(1)
(i) a heavy chain variable domain ($V_H$) sequence that comprises CDR-H1, CDR-H2 and CDR-H3 from an immunoglobulin heavy chain comprising an amino acid sequence selected from: SEQ ID NOs: 2, 22, 42, 62, 81, 101, 119, 138, 156, 174, 190, 200, 210, 218, 238, 258, 276, 286, 296, 315, 335, 345 and 361 (or a variant thereof), and
(ii) a light chain variable domain ($V_L$) sequence that comprises CDR-L1, CDR-L2 and CDR-L3 from an immunoglobulin light chain comprising an amino acid sequence selected from: SEQ ID NOs: 10, 30, 50, 70, 89, 109, 127, 146, 164, 182, 226, 246, 266, 304, 323, 353 and 368 (or a variant thereof);
or,
(2)
(i) a heavy chain variable domain ($V_H$) comprising an amino acid sequence selected from: SEQ ID NOs: 2, 22, 42, 62, 81, 101, 119, 138, 156, 174, 190, 200, 210, 218, 238, 258, 276, 286, 296, 315, 335, 345 and 361 (or a variant thereof); and
(ii) a light chain variable domain ($V_L$) comprising an amino acid sequence selected from: SEQ ID NOs: 10, 30, 50, 70, 89, 109, 127, 146, 164, 182, 226, 246, 266, 304, 323, 353 and 368 (or a variant thereof);
and
one or more antigen-binding domains that bind to a different epitope.

In one embodiment of the invention, a bispecific antigen-binding fragment comprises a first scFv (e.g., comprising $V_H$ and $V_L$ of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) having binding specificity for a first epitope (e.g., IL2Rγ) and a second scFv having binding specificity for a second, different epitope. For example, in an embodiment of the invention, the first and second scFv are tethered with a linker, e.g., a peptide linker (e.g., a GS linker such as (GGGGS)$_n$ (SEQ ID NO: 386) wherein n is, for example, 1, 2, 3, 4, 5, 6, 7, 8, 9 or 10).

Other bispecific antigen-binding fragments include an F(ab)$_2$ of a bispecific IgG antibody which comprises the heavy and light chain CDRs of H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2 and of another antibody that binds to a different epitope.

Immunoconjugates

The invention encompasses anti-IL2Rγ antigen-binding proteins, e.g., antibodies or antigen-binding fragments, conjugated to another moiety, e.g., a therapeutic moiety (an "immunoconjugate"). In an embodiment of the invention, an anti-IL2Rγ antigen-binding protein, e.g., antibody or antigen-binding fragment, is conjugated to any of the further therapeutic agents set forth herein. As used herein, the term "immunoconjugate" refers to an antigen-binding protein, e.g., an antibody or antigen-binding fragment, which is chemically or biologically linked to another antigen-binding protein, a drug, a radioactive agent, a reporter moiety, an enzyme, a peptide, a protein or a therapeutic agent.

Administration and Treatment

The present invention provides methods for treating or preventing an IL2Rγ-mediated disease or condition, in a subject, comprising administering a therapeutically effective dose of anti-IL2Rg antigen-binding protein (H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) to the subject.

An "IL2Rγ-mediated disease or condition" any disease condition whose symptoms are mediated by the activities of one or more of the cytokines IL-2, IL-4, IL-7, IL-9, IL-15 and IL-21 and/or receptors which bind such cytokines; for example, autoimmunity and/or inflammation mediated by such cytokines and/or receptors. For example, IL2Rγ-mediated diseases or conditions include graft versus host disease (GvHD), organ transplant rejection (e.g., transplant of skin (skin graft), b-islet cell graft, transplant of heart, transplant of lung, transplant of kidney and/or transplant of liver), birdshot chorioretinopathy, multiple sclerosis, uveitis, autoimmune diseases (e.g., Type I diabetes, multiple sclerosis, rheumatoid arthritis, systemic lupus erythematosus, and myasthenia gravis), aplastic anemia; atopic dermatitis; asthma; and mast cell activation disorders (e.g., mast cell activation syndrome (MCAS), systemic mastocytosis (SM) or mast cell leukemia (MCL)).

The present invention also includes a method for administering an antigen-binding protein (e.g., antibody or antigen-binding fragment thereof) that binds specifically to IL2Rγ, such as H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, to a subject, e.g., with an IL2Rγ-mediated disease or condition, comprising introducing the antigen-binding protein into the body of the subject, e.g., by injection.

GvHD is a condition that might occur after an allogeneic transplant. For example, in GvHD, donated bone marrow or peripheral blood stem cells may view the recipient's body as foreign, and the donated cells/bone marrow attack the body. GvHD may occur, for example, following hematopoietic cell transplantation (HCT; e.g., in a subject suffering from acute myeloid leukemia (AML) or acute lymphocytic leukemia (ALL)) and/or a myelodysplastic syndrome or a myeloproliferative neoplasm), a transfusion, thymus transplantation or in patients with thymoma. Types of GvHD include steroid-refractory GvHD, acute graft versus host disease (aGvHD) and chronic graft versus host disease (cGvHD). An allogeneic transplant recipient might experience either aGvHD or cGvHD or both forms, or neither. The present invention includes methods for treating or preventing GvHD (of any kind), in a subject, comprising administering a therapeutically effective dosage of an anti-IL2Rγ antigen-binding protein to the subject.

Symptoms of aGvHD may include skin rash or reddened areas on the skin (signs of aGvHD of the skin); yellow discoloration of the skin and/or eyes, and abnormal blood test results (signs of aGvHD of the liver); nausea, vomiting, diarrhea, or abdominal cramping (signs of aGvHD in the gastrointestinal tract, or "gut"); and/or increased dryness/irritation of the eyes (signs of GvHD of the eyes).

Symptoms of cGvHD may include rash, raised, or discolored areas, skin thickening or tightening (signs of cGvHD of the skin); abdominal swelling, yellow discoloration of the skin and/or eyes, and abnormal blood test results (signs of cGvHD of the liver); dry eyes or vision changes (signs of cGvHD of the eyes); dry mouth, white patches inside the mouth, pain or sensitivity to spicy foods (signs of oral cGvHD, of the mouth); shortness of breath or changes seen on your chest X-ray (signs of dry cough pulmonary cGvHD—of the lungs); difficulty swallowing, pain with swallowing, or weight loss (signs of cGvHD of the gastrointestinal tract or "gut"); fatigue, muscle weakness, or pain (signs of neuromuscular cGvHD, of the nerves and muscles); and/or increased need to urinate (urinary frequency), burning or bleeding with urination, vaginal dryness/tightening, or penile dysfunction (signs of cGvHD of the genitourinary system, bladder, or sexual organs).

Organ transplant rejection is the rejection of a transplanted organ by the immune system of the recipient. Hyper-acute rejection occurs within a few minutes of transplant, acute rejection office within a week to 3 months after transplant and chronic rejection takes place over many years. Organs which are transplanted include, for example, solid organs such as skin, pancreas, kidney, liver, heart and lung. The present invention includes methods for treating or preventing organ transplant (of any kind), in a subject, comprising administering a therapeutically effective dosage of an anti-IL2Rγ antigen-binding protein to the subject.

Birdshot chorioretinopathy is a rare form of posterior uveitis—an inflammation of the uvea, the part of the eye that provides the retina with most of its blood supply. Birdshot chorioretinopathy may be caused by autoimmunity. Symptoms of birdshot chorioretinopathy may include night blindness, problems with color vision, sensitivity to bright lights, seeing flashing lights, distortions in vision, pain in the eyes and loss of depth perception and/or peripheral vision. The present invention includes methods for treating or preventing birdshot chorioretinopathy or uveitis, in a subject, comprising administering a therapeutically effective dosage of an anti-IL2Rγ antigen-binding protein to the subject, e.g., by intraocular administration, e.g., intravitreal injection.

The present invention also provides a method for treating or preventing any autoimmune disease or condition by inhibiting IL2Rγ. Blocking of signaling of one or more cytokines in the γc family may be beneficial in patients suffering from autoimmunity due to inhibitor effects on secretion of inflammatory cytokines and production of autoantibodies. Multiple sclerosis (MS) is a disease of the brain and spinal cord (central nervous system (CNS)), wherein the immune system attacks the nerve fiber myelin sheath and causes communication problems between your brain and the rest of your body. Eventually, the disease can cause the nerves themselves to deteriorate or become permanently damaged. Rheumatoid arthritis (RA) is an autoimmune disease in which the body's immune system attacks the joints. This creates inflammation that causes the tissue that lines the inside of joints (the synovium) to thicken, resulting in swelling and pain in and around the joints. Psoriasis is an autoimmune disease with a primary presentation affecting the skin. Inflammation can also affect the joints, vascular system, and eyes of people with psoriasis. Type 1 diabetes is an autoimmune disease wherein the immune system attacks the insulin-producing beta cells in the pancreas and destroys them. The pancreas then produces little or no insulin. Systemic lupus erythematosus (SLE) is a systemic autoimmune disease that occurs when the body's immune system attacks its own tissues and organs. Inflammation caused by lupus can affect many different body systems—including your joints, skin, kidneys, blood cells, brain, heart and lungs. Myasthenia gravis is an autoimmune disease wherein antibodies block the receptors for acetylcholine at the neuromuscular junction, which prevents the muscle from contracting. In most individuals with myasthenia gravis, this is caused by antibodies to the acetylcholine receptor itself. However, antibodies to other proteins, such as MuSK (Muscle-Specific Kinase) protein, can also lead to impaired transmission at the neuromuscular junction. The present invention includes methods for treating or preventing an autoimmune disorder or condition (e.g., multiple sclerosis or any other central nervous system inflammation, rheumatoid arthritis, psoriasis, Type I diabetes, systemic lupus erythematosus and/or myasthenia gravis), in a subject, comprising administering a therapeutically effective dosage of an anti-IL2Rγ antigen-binding protein to the subject.

An effective or therapeutically effective dose of anti-IL2Rγ antigen-binding protein, e.g., antibody or antigen-binding fragment, for treating or preventing an IL2Rγ-mediated disease or condition refers to the amount of the antigen-binding protein sufficient to alleviate one or more signs and/or symptoms of the disease or condition in the treated subject, whether by inducing the regression or elimination of such signs and/or symptoms or by inhibiting the progression of such signs and/or symptoms. In an embodiment of the invention, an effective or therapeutically effective dose of anti-IL2Rγ antigen-binding protein is about 0.05-50 mg/kg of body weight. The dose amount may vary depending upon the age and the size of a subject to be administered, target disease, conditions, route of administration, and the like. In certain embodiments, the initial dose may be followed by administration of a second or a plurality of subsequent doses of antigen-binding protein in an amount that can be approximately the same or less or more than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of an IL2Rγ-mediated disease. The subject may have an IL2Rγ-mediated disease or be predisposed to developing such a disease.

"Preventing" an IL2Rγ-mediated disease or condition refers, as it relates to use of an anti-IL2Rγ antigen-binding protein of the present invention, to administration to a subject prior to manifestation of the disease or condition in the body of the subject so as to stop such manifestation from occurring.

Combinations and Pharmaceutical Formulation

The present invention provides compositions that include anti-IL2Rγ antigen-binding proteins in association with one or more ingredients; as well as methods of use thereof and methods of making such compositions. Pharmaceutic formulations comprising an anti-IL2Rγ antigen-binding protein and a pharmaceutically acceptable carrier or excipient are part of the present invention.

To prepare pharmaceutical formulations of the anti-IL2Rγ antigen-binding proteins, e.g., antibodies and antigen-binding fragments thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical formulation is sterile. Such compositions are part of the present invention.

Pharmaceutical formulations of the present invention include an anti-IL2Rγ antigen-binding protein and a pharmaceutically acceptable carrier including, for example, water, buffering agents, preservatives and/or detergents.

The scope of the present invention includes desiccated, e.g., freeze-dried, compositions comprising an anti-IL2Rγ antigen-binding protein, e.g., antibody or antigen-binding fragment thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), or a pharmaceutical formulation thereof that includes a pharmaceutically acceptable carrier but substantially lacks water.

In a further embodiment of the invention, a further therapeutic agent that is administered to a subject in association with an anti-IL2Rγ antigen-binding protein, e.g., antibody or antigen-binding fragment thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), disclosed herein is administered to the subject in accordance with the Physicians' Desk Reference 2003 (Thomson Healthcare; 57$^{th}$ edition (Nov. 1, 2002)).

The mode of administration of an anti-IL2Rγ antigen-binding protein or composition thereof can vary. Routes of administration include parenteral, non-parenteral, oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, intraocular, intravitreal, transdermal or intra-arterial.

The present invention provides methods for administering an anti-IL2Rγ antigen-binding protein, e.g., antibody or antigen-binding fragment thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2) to a subject, comprising introducing the protein or a pharmaceutical formulation thereof into the body of the subject. For example, in an embodiment of the invention, the method comprises piercing the body of the subject, e.g., with a needle of a syringe, and injecting the antigen-binding protein or a pharmaceutical formulation thereof into the body of the subject, e.g., into the eye, vein, artery, muscular tissue or subcutis of the subject.

The present invention provides a vessel (e.g., a plastic or glass vial, e.g., with a cap or a chromatography column, hollow bore needle or a syringe cylinder) comprising any of the anti-IL2Rγ antigen-binding proteins, e.g., antibodies or antigen-binding fragments thereof (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), or a pharmaceutical formulation comprising a pharmaceutically acceptable carrier thereof.

The present invention includes combinations including an anti-IL2Rγ antigen-binding protein, e.g., antibody or antigen-binding fragment thereof of the present invention (e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2), in association with one or more further therapeutic agents. The anti-IL2Rγ antigen-binding protein and the further therapeutic agent can be in a single composition or in separate compositions. For example, in an embodiment of the invention, the further therapeutic agent is an immunosuppressive drug. In an embodiment of the invention, the further therapeutic agent is an anti-TNFα antibody or binding protein (e.g., infliximab, adalimumab, etanercept or golimumab), tacrolimus, cyclosporine, a corticoid, prednisolone, methylprednisolone, antithymocyte globulin, alemtuzumab, daclizumab, extracorporeal photophoresis, mycophenolate mofetil, sirolimus, pentostatin, mesenchyman stem cells, inolimomab, denileukin, a multispecific (e.g., bispecific) antibody or antigen-binding fragment thereof that binds BCMA (B-cell maturation antigen) and CD3 and/or basiliximab.

Methods for treating or preventing an IL2Rγ-mediated disease in a subject in need of said treatment or prevention by administering an anti-IL2Rγ antigen-binding protein, e.g., H4H12857P; H4H12858P; H4H12859P; H4H12863P; H4H12874P; H4H12871P; H4H12884P; H4H12886P; H4H12889P; H4H12890P; H4H12899P; H4H12900P; H4H12908P; H4H12913P2; H4H12922P2; H4H12924P2; H4H12926P2; H4H12927P2; H4H12934P2; H4H13538P; H4H13541P; H4H13544P2; or H4H13545P2, in association with a further therapeutic agent are part of the present invention.

The term "in association with" indicates that components, an anti-IL2Rγ antigen-binding protein, e.g., antibody or antigen-binding fragment thereof of the present invention, along with another agent such as methotrexate, can be formulated into a single composition, e.g., for simultaneous delivery, or formulated separately into two or more compositions (e.g., a kit including each component). Components administered in association with each another can be administered to a subject at a different time than when the other component is administered; for example, each administration may be given non-simultaneously (e.g., separately or sequentially) at intervals over a given period of time. Separate components administered in association with each another may also be administered sequentially, though essentially simultaneously, during the same administration session. Moreover, the separate components administered in association with each another may be administered to a subject by the same or by a different route.

EXAMPLES

The following examples are put forth so as to provide those of ordinary skill in the art with a complete disclosure and description of how to make and use the methods and compositions of the invention, and are not intended to limit the scope of what the inventors regard as their invention.

Example 1: Identification and Isolation of Anti-IL2Rγ Antibodies

Anti-IL2Rγ antibodies were obtained by immunizing a VELOCIMMUNE® mouse (i.e., an engineered mouse comprising DNA encoding human immunoglobulin heavy and kappa light chain variable regions) with an IL2Rγ protein immunogen comprising the extracellular sequence (ecto domain) of IL2Rγ.

Specifically, the immunogen, human IL2Rg ecto-mmh, comprised:
  Amino acids (1-240): Human IL2Rg ecto (L23-A262 of NP_000197.1), and
  Amino acids (241-268): Myc-Myc-Hexahistadine tag (underlined);
comprising the amino acid sequence:

(SEQ ID NO: 379)
LNTTILTPNGNEDTTADFFLTTMPTDSLSVSTLPLPEVQCFVFNVEYMNC
TWNSSSEPQPTNLTLHYWYKNSDNDKVQKCSHYLFSEEITSGCQLQKKEI
HLYQTFVVQLQDPREPRRQATQMLKLQNLVIPWAPENLTLHKLSESQLEL
NWNNRFLNHCLEHLVQYRTDWDHSWTEQSVDYRHKFSLPSVDGQKRYTFR
VRSRFNPLCGSAQHWSEWSHPIHWGSNTSKENPFLFALEA<u>EQKLISEEDL</u>
<u>GGEQKLISEEDLHHHHHH</u>
*Expressed with mROR signal sequence The antibody immune response was monitored by a IL2Rγ-specific immunoassay. Fully human anti-IL2Rγ antibodies were isolated and purified.

TABLE 1-1

Anti-IL2Rγ VH, VK and CDR Amino Acid Sequence Summary*.

| Name | VH | | CDR1 | | CDR2 | | CDR3 | | VK | |
|---|---|---|---|---|---|---|---|---|---|---|
| | DNA | PEP | DNA | PEP | DNA | PEP | DNA | PEP | DNA | PEP |
| H4H12859P | 1 | 2 | 3 | 4 | 5 | 6 | 7 | 8 | 9 | 10 |
| H4H12863P | 21 | 22 | 23 | 24 | 25 | 26 | 27 | 28 | 29 | 30 |
| H4H12874P | 41 | 42 | 43 | 44 | 45 | 46 | 47 | 48 | 49 | 50 |
| H4H12884P | 61 | 62 | 63 | 64 | 65 | 66 | 67 | 68 | 69 | 70 |
| H4H12886P | 80 | 81 | 82 | 83 | 84 | 85 | 86 | 87 | 88 | 89 |
| H4H12890P | 100 | 101 | 102 | 103 | 104 | 105 | 106 | 107 | 108 | 109 |
| H4H12899P | 118 | 119 | 120 | 121 | 122 | 123 | 124 | 125 | 126 | 127 |
| H4H12900P | 137 | 138 | 139 | 140 | 141 | 142 | 143 | 144 | 145 | 146 |
| H4H12908P | 155 | 156 | 157 | 158 | 159 | 160 | 161 | 162 | 163 | 164 |
| H4H12913P2 | 173 | 174 | 175 | 176 | 177 | 178 | 179 | 180 | 181 | 182 |
| H4H12924P2 | 189 | 190 | 191 | 192 | 193 | 194 | 195 | 196 | 181 | 182 |
| H4H12926P2 | 199 | 200 | 201 | 202 | 203 | 204 | 205 | 206 | 181 | 182 |
| H4H12927P2 | 209 | 210 | 175 | 176 | 211 | 212 | 213 | 214 | 181 | 182 |
| H4H12934P2 | 217 | 218 | 219 | 220 | 221 | 222 | 223 | 224 | 225 | 226 |
| H4H13538P | 237 | 238 | 239 | 240 | 241 | 242 | 243 | 244 | 245 | 246 |
| H4H13541P | 257 | 258 | 259 | 260 | 261 | 262 | 263 | 264 | 265 | 266 |
| H4H13544P2 | 275 | 276 | 277 | 278 | 279 | 280 | 281 | 282 | 181 | 182 |
| H4H13545P2 | 285 | 286 | 287 | 288 | 289 | 290 | 291 | 292 | 181 | 182 |
| REGN9432 (H4H12857P) | 295 | 296 | 297 | 298 | 299 | 300 | 301 | 302 | 303 | 304 |
| REGN9433 (H4H12858P) | 314 | 315 | 316 | 317 | 318 | 319 | 320 | 321 | 322 | 323 |

TABLE 1-1-continued

Anti-IL2Rγ VH, VK and CDR Amino Acid Sequence Summary*.

| | | | | | | | | | |
|---|---|---|---|---|---|---|---|---|---|
| REGN7256 (H4H12922P2) | 334 | 335 | 336 | 337 | 338 | 339 | 340 | 341 | 181 | 182 |
| REGN7257 (H4H12889P) | 344 | 345 | 346 | 347 | 348 | 349 | 350 | 351 | 352 | 353 |
| REGN9434 (H4H12871P) | 360 | 361 | 362 | 363 | 364 | 66 | 365 | 366 | 367 | 368 |

| | CDR1 | | CDR2 | | CDR3 | | HC | | LC | |
|---|---|---|---|---|---|---|---|---|---|---|
| Name | DNA | PEP | DNA | PEP | DNA | PEP | DNA | PEP | DNA | PEP |
| H4H12859P | 11 | 12 | 13 | 14 | 15 | 16 | 17 | 18 | 19 | 20 |
| H4H12863P | 31 | 32 | 33 | 34 | 35 | 36 | 37 | 38 | 39 | 40 |
| H4H12874P | 51 | 52 | 53 | 54 | 55 | 56 | 57 | 58 | 59 | 60 |
| H4H12884P | 71 | 72 | 73 | 54 | 74 | 75 | 76 | 77 | 78 | 79 |
| H4H12886P | 90 | 91 | 92 | 93 | 94 | 95 | 96 | 97 | 98 | 99 |
| H4H12890P | 110 | 111 | 73 | 54 | 112 | 113 | 114 | 115 | 116 | 117 |
| H4H12899P | 128 | 129 | 130 | 54 | 131 | 132 | 133 | 134 | 135 | 136 |
| H4H12900P | 147 | 148 | 73 | 54 | 149 | 150 | 151 | 152 | 153 | 154 |
| H4H12908P | 165 | 166 | 13 | 14 | 167 | 168 | 169 | 170 | 171 | 172 |
| H4H12913P2 | 71 | 72 | 73 | 54 | 183 | 184 | 185 | 186 | 187 | 188 |
| H4H12924P2 | 71 | 72 | 73 | 54 | 183 | 184 | 197 | 198 | 187 | 188 |
| H4H12926P2 | 71 | 72 | 73 | 54 | 183 | 184 | 207 | 208 | 187 | 188 |
| H4H12927P2 | 71 | 72 | 73 | 54 | 183 | 184 | 215 | 216 | 187 | 188 |
| H4H12934P2 | 227 | 228 | 229 | 230 | 231 | 232 | 233 | 234 | 235 | 236 |
| H4H13538P | 247 | 248 | 249 | 250 | 251 | 252 | 253 | 254 | 255 | 256 |
| H4H13541P | 267 | 268 | 73 | 54 | 269 | 270 | 271 | 272 | 273 | 274 |
| H4H13544P2 | 71 | 72 | 73 | 54 | 183 | 184 | 283 | 284 | 187 | 188 |
| H4H13545P2 | 71 | 72 | 73 | 54 | 183 | 184 | 293 | 294 | 187 | 188 |
| REGN9432 (H4H12857P) | 305 | 306 | 307 | 230 | 308 | 309 | 310 | 311 | 312 | 313 |
| REGN9433 (H4H12858P) | 324 | 325 | 326 | 327 | 328 | 329 | 330 | 331 | 332 | 333 |
| REGN7256 (H4H12922P2) | 71 | 72 | 73 | 54 | 183 | 184 | 342 | 343 | 187 | 188 |
| REGN7257 (H4H12889P) | 71 | 72 | 73 | 54 | 354 | 355 | 356 | 357 | 358 | 359 |
| REGN9434 (H4H12871P) | 369 | 370 | 371 | 372 | 373 | 374 | 375 | 376 | 377 | 378 |

*Numbers refer to SEQ ID NOs corresponding to the indicated sequence.

TABLE 1-2

Anti-IL2Rγ Heavy Chain and Light Chain Amino Acid Sequence Summary*.

| | HC | | LC | |
|---|---|---|---|---|
| Name | DNA | PEP | DNA | PEP |
| H4H12859P | 17 | 18 | 19 | 20 |
| H4H12863P | 37 | 38 | 39 | 40 |
| H4H12874P | 57 | 58 | 59 | 60 |
| H4H12884P | 76 | 77 | 78 | 79 |
| H4H12886P | 96 | 97 | 98 | 99 |
| H4H12890P | 114 | 115 | 116 | 117 |
| H4H12899P | 133 | 134 | 135 | 136 |
| H4H12900P | 151 | 152 | 153 | 154 |
| H4H12908P | 169 | 170 | 171 | 172 |
| H4H12913P2 | 185 | 186 | 187 | 188 |
| H4H12924P2 | 197 | 198 | 187 | 188 |
| H4H12926P2 | 207 | 208 | 187 | 188 |
| H4H12927P2 | 215 | 216 | 187 | 188 |
| H4H12934P2 | 233 | 234 | 235 | 236 |
| H4H13538P | 253 | 254 | 255 | 256 |
| H4H13541P | 271 | 272 | 273 | 274 |
| H4H13544P2 | 283 | 284 | 187 | 188 |
| H4H13545P2 | 293 | 294 | 187 | 188 |
| REGN9432 (H4H12857P) | 310 | 311 | 312 | 313 |
| REGN9433 (H4H12858P) | 330 | 331 | 332 | 333 |
| REGN7256 (H4H12922P2) | 342 | 343 | 187 | 188 |
| REGN7257 (H4H12889P) | 356 | 357 | 358 | 359 |
| REGN9434 (H4H12871P) | 375 | 376 | 377 | 378 |

*Numbers refer to SEQ ID NOs corresponding to the indicated sequence.

The amino acid sequences of anti-IL2Rγ antibody heavy and light immunoglobulin chains are set forth below (CDRs underscored; variable regions in bold font).

H4H12857P
Heavy chain
(SEQ ID NO: 311)

EVQLVESGGGVVRPGGSLRLSCAAS<u>GFTFDDFDMS</u>WVRQGPGKGLEWVSG<u>INWHGSST</u>GYADSVKGRFTISRDNAKNSLY

LQMSSLRAEDTALYHC<u>VRGGTIVGATTPLDY</u>WGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

```
SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain
                                                                            (SEQ ID NO: 313)
DIQMTQSPSSLSASVGDRVTMTCRAS<u>RTISSYL</u>SWYQQKSGKVPNLLIF<u>GAS</u>SLQSGVPSRFSASGSTDFTLIISSLQP

EDFATYYC<u>QQSYSSPLT</u>FGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12858P
Heavy chain
                                                                            (SEQ ID NO: 331)
EVQLVESGGDLVQPGGSLRLSCTAS<u>GFIFRNYAMN</u>WVRQAPGKGLEWLSG<u>ILGSNDNT</u>YYVDSVKGRFTISRDNSRNTLY

LQMNSLRAEDSAVYYC<u>AKGDAGGFDY</u>WGQGTLVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTKVDKRVESKYGPPCPPCPAPEFLGGPSVFLF

PPKPKDTLMISRTPEVTCVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

Light chain
                                                                            (SEQ ID NO: 333)
DVVMTQSPLSLPVILGQPASISCRSS<u>QSLVSSDGNTYLN</u>WFQQRPGQSPRRLIY<u>KVS</u>NRDSGVPDRFSGSGSGTDFTLKI

SRVEAEDVGAYYC<u>MQGSYWPPT</u>FGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

H4H12859P
Heavy chain
                                                                            (SEQ ID NO: 18)
QVQLVQSGAEVKKPGASVRVSCKAS<u>GYTFTDYDIH</u>WVRQAPGHGLEWMG<u>WINPNSGGTN</u>YAQKFQGRVTMTRDTSISTVY

MDLSRLRSDDTAVYYC<u>ARADYSSSYYYYGMDV</u>WGQGTTVTVSSASTKGPSVFPLAPCSRSTSESTAALGCLVKDYFPEPV

TVSWNSGALTSGVHTFPAVLQSSGLYSLSSVVTVPSSSLGTKTYTCNVDHKPSNTKVDKRVESKYGPPCPPCPAPEFLGG

PSVFLFPPKPKDTLMISRTPEVTCVVVDVSQEDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

Light chain
                                                                            (SEQ ID NO: 20)
DIVMTQSPDSLAVSLGERATINCKSS<u>QSVLYSSKNKNYL</u>SWYQQKPGQPPKLLIY<u>WAS</u>TREFGVPDRFSGRGSGTDFTLT

ISSLQAEDVAVYYC<u>QQYYTTPYT</u>FGQGTKLEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

H4H12863P
Heavy chain
                                                                            (SEQ ID NO: 38)
QVQLVESGGGVVQPGRSLRLSCTAS<u>GFTFRSYDMY</u>WVRQAPGKGLEWVS<u>VITYDGNNK</u>YYADSVKGRFTISRDNSKNTLF

LQMSSLRPEDTAVYYC<u>AKRGLIWVGESFDY</u>WGQGTLVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain
                                                                            (SEQ ID NO: 40)
DIQMTQSPSTLSASVGDRVTITCRAS<u>QSINSWLA</u>WYQQKPGKAPNLLIY<u>KAS</u>SLESGVPSRFSGSGSGTEFTLTISSLQP DDFATYYC<u>QQYKSYSWT</u>FGQGTKVEIKRTVAAPSVFIFPPSDEQLKSGTASVVCLLNNFYPREAKVQWKVDNALQSGNSQ
```

ESVTEQDSKDSTYSLSSTLTLSKADYEKHKVYACEVTHQGLSSPVTKSFNRGEC

H4H12874P
Heavy chain
(SEQ ID NO: 58)

QVQLVESGGGVVQPGRSLRLSCAAS<u>GFNFRNFGMH</u>WVRQAPGKGLEWVAG<u>ILYDGSSK</u>YYADSVKDRFTISRDNSKNTLF

LQMNSLRAEDTAMYYC<u>AKEEDTAMVPFDS</u>WGPGTLVTVSSASTKGPSVFPLAPCSRSTSESTAALGCLVKDYFPEPVTVS

WNSGALTSGVHTFPAVLQSSGLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

Light chain
(SEQ ID NO: 60)

DIQLTQSPSFLSASVGDRVTITCWAS<u>QGISSY</u>LAWYQQKPGKAPTLLIY<u>AAS</u>TLQSGVPSRFSGSGSGTEFTLTISSLQP

EDFASYYC<u>QQLKSYPLT</u>FGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12871P
Heavy chain
(SEQ ID NO: 376)

QVQLQESGPGLVKPSQTLSLTCTVS<u>GGSITSGGYY</u>WSWIRQYPGQGLEWIGY<u>IYYSGKT</u>YYNPSFTSRITISVDTSKKQF

SLKMSSVTAADTAVYYC<u>ARAGFTSSNGWFDP</u>WGQGTLVTVSSASTKGPSVFTLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain
(SEQ ID NO: 378)

DIQMTQSPSSLSASVGDRVTITCRAS<u>QNIRSY</u>LNWYQQKPGKAPKLLIY<u>SAS</u>SLQSGVPSRFSGSGSGTDFTLTISSLQP

EDFPTYYC<u>QQTYSSPWT</u>FGPGTKVEIKRTVAAPSVFIFPPSDEQLKSGTASVVCLLNNEYPREAKVQWKVDNALQSGNSQ

ESVTEQDSKDSTYSLSSTLTLSKADYEKHKVYACEVTHQGLSSPVTKSFNRGEC

H4H12884P
Heavy chain
(SEQ ID NO: 77)

QVQLQESGPGLVKPSQTLSLTCTVS<u>GGSISSGGYY</u>WSWIRQHPGKGLEWIGF<u>IYYSGKT</u>YYNPSLKSRLTISVDTSKSQF

SLKLRSVTAADTAVYYC<u>ARLGYTNSAGWFDP</u>WGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain
(SEQ ID NO: 79)

DIQMTQSPSSLSASVGDRVTITCRAS<u>QSISSY</u>LNWYQQKPGKAPNLLIY<u>AAS</u>SLQSGVPSRFSGSGSGTDFTLTISSLQP

EDLATYYC<u>QQSYTTPFT</u>FGPGTKVDIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H12886P
Heavy chain
(SEQ ID NO: 97)

EVQLVESGGGLVKPGGSLRLSCAAS<u>GFTFSTAWMS</u>WVRQSPGRGLEWVGR<u>MKSKTDGGTT</u>FYAAPVKGRFTISRDDSKNT

LYLQMNSLKTEDTAVYYC<u>TTGLVPAFYKYYGVDV</u>WGQGTTVTVSSASTKGPSVFTLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAPEFL

```
GGPSVFLFPPKPKDTLMISRTPEVTCVVVDVSQEDPEVQFNWYVDGVEVHNAKTKPREEQFNSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSLGK
```

Light chain
(SEQ ID NO: 99)

```
DIQMTQSPSSLSASVGDRITITCQASQDITNYLNWYQQKPGKAPNLLIYDASNLVTGVPSRFSGSGSGTDFTFTILSLQP

EDIATYYCQQYDSLLTFGPGTKVDIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC
```

H4H12889P
Heavy chain
(SEQ ID NO: 357)

```
EVQLVESGGGLVQPGGSLRLSCAASGFIFSSYEMHWVRQAPGKGLEWISYISSSGTTIYYADSVKGRFTISRDNAKNSLY

LHMNSLRAEDTAVYYCTRARITGTFDVFDIWGQGTMVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
```

Light chain
(SEQ ID NO: 359)

```
DIQMTQSPSSLSASVGDRVTITCRASQSISSYLNWYQQKPGKAPKLLIFAASNLQSGVPSRFSGSRSGTDFTLTISSLQP

EDFATYYCQQNYNIPYTFGQGTKLEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

H4H12890P
Heavy chain
(SEQ ID NO: 115)

```
EVQLVESGGGLVQPGGSLRLSCAASGFTFNNYAMHWVRQAPGKGLEYVSSISSSGGSTYYEDSVKGRFTISRDNSKNTLY

LQMGSLRAEDMAVYYCARSFYGSGTYYDTFDMWGQGTMVTVSSASTKGPSVFTLAPCSRSTSESTAALGCLVKDYFPEPV

TVSWNSGALTSGVHTFPAVLQSSGLYSLSSVVTVPSSSLGTKTYTCNVDHKPSNTKVDKRVESKYGPPCPPCPAPEFLGG

PSVFLFPPKPKDTLMISRTPEVTCVVVDVSQEDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK
```

Light chain
(SEQ ID NO: 117)

```
DIQMTQSPSSLSASIGDRVTITCRASQSISRYLNWYQQKPGKAPKLLIYAASSLQSGVPSRFSASGSGTDFTLTISSLQP

EDFATYYCQQSYSTPFTFGQGTKLEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

H4H12899P
Heavy chain
(SEQ ID NO: 134)

```
QVQLVESGGDLVKPGGSLRLSCATSGFTFSDFYMTWIRQAPGKGLEWISYISNSGSIVKYADSVKGRFTISRDNAKNSLY

LQMNSLRAEDTAIYYCARFYGDRWGQGTLVTVSSASTKGPSVFPLAPCSRSTSESTAALGCLVKDYFPEPVTVSWNSGAL

TSGVHTFPAVLQSSGLYSLSSVVTVPSSSLGTKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQFNSTYRVVSVLTVLHQDWLNGKEYKCKVSNK

GLPSSIEKTISKAKGQPREPQVYTLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK
```

Light chain
(SEQ ID NO: 136)

```
DIQLTQSPSFLSASVGDRVTITCWASQGISTFLAWYQQKPGKAPKLLIYAASTLQSGVPSRFSGSGSGTDFTLTISSLQP

EDFATYHCQQLNNYPWTFGQGTKVEIKRTVAAPSVFIFPPSDEQLKSGTASVVCLLNNFYPREAKVQWKVDNALQSGNSQ
```

-continued

ESVTEQDSKDSTYSLSSTLTLSKADYEKHKVYACEVTHQGLSSPVTKSFNRGEC

H4H12900P
Heavy chain
(SEQ ID NO: 152)
QVQLVESGGGLVKPGGSLRLSCEAS<u>GFTFNDFYMT</u>WIRQAPGKGLEWIAY<u>ISKSGDKMR</u>YADSVKGRFSTSRDNAKNSLS
LQMNSLRAEDTAVYYC<u>ARFYGDI</u>WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYGPPCPPCPAPEFLGGPSVFLFPPK
PKDTLMISRTPEVTCVVVDVSQEDPEVQFNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK Light chain
(SEQ ID NO: 154)
DIQLTQSPSFLSASVGDRVTITCWAS<u>QDISSFL</u>VWYQQKPGKAPNLLIY<u>AAS</u>ALQSGVPSRFSGSGSGTEFTLTISSLQP
EDFASYYC<u>EQLNNYPWT</u>FGQGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC H4H12908P
Heavy chain
(SEQ ID NO: 170)
EVQLVESGGRLVQPGGSLRLSCEAS<u>GFTFSNYGMT</u>WVRQAPGKGLEWVS<u>ISGSDNRK</u>YYAESVKGRFTISRDNSKNTLY
LQMNSLRAEDTAVYYC<u>AKLGYSRSSKDFYYGMDV</u>WGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGK Light chain
(SEQ ID NO: 172)
DIVMTQSPDSLAVSLGERATINCKSS<u>QSVLYNSNNRNY</u>LVWYQQKPGQSPKLLIY<u>WAS</u>TRESGVPDRFSGSGSGTDFTLT
ISSLQAEDVAVYYC<u>QQYYNVPYT</u>FGQGTKLEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC H4H12913P2
Heavy chain
(SEQ ID NO: 186)
EVQLVESGGGVVRPGGSLRLSCAAS<u>GFTFDDYGMS</u>WVRQAPGKGLEWISS<u>INRNGGSA</u>DYADSVKGRFTISRDNAKNSLF
LQMSSLRAEDTALYHC<u>ASGEFRFDY</u>WGQGTLVTVSSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESNGQPENNYKTTPPVLDSDGSF
FLYSRLTVDKSRWQEGNVFSCSVMHEALHNHYTQKSLSLSLGK Light chain
(SEQ ID NO: 188)
DIQMTQSPSSLSASVGDRVTITCRAS<u>QSISSYL</u>NWYQQKPGKAPKLLIY<u>AAS</u>SLQSGVPSRFSGSGSGTDFTLTISSLQP
EDFATYYC<u>QQSYSTPPIT</u>FGQGTRLEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC H4H12922P2
Heavy chain
(SEQ ID NO: 343)
QVQLVESGGGVVKPGGSLRLSCAAS<u>GFTFSNSGIH</u>WVRQAPGKGLEWVAL<u>ISYAGSNK</u>YYADSVKGRFTISRDNSKNTLS
LQMNSLRAEDTAVYYC<u>AKEVWTGTYDSFDM</u>WGRGTMVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDKRVESKYGPPCPPCPAPEFLGGPS
VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain
(SEQ ID NO: 188)

DIQMTQSPSSLSASVGDRVTITCRAS<u>QSISSY</u>LNWYQQKPGKAPKLLIY<u>AAS</u>SLQSGVPSRFSGSGSGTDFTLTISSLQP

EDFATYYC<u>QQSYSTPPIT</u>FGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12924P2
Heavy chain
(SEQ ID NO: 198)

EVQLVESGGGLVQPGRSLRLSCAAS<u>GFTLEDYAMH</u>WVRQAPGKGLEWVSG<u>ISWNRGST</u>GYADSVKGRFTISRDNAKNSLY

LQMTSLRAEDTALYYC<u>AKGFYSMDV</u>WGQGTTVTVSSASTKGPSVFPLAPCSRSTSESTAALGCLVKDYFPEPVTVSWNSG

ALTSGVHTFPAVLQSSGLYSLSSVVTVPSSSLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

Light chain
(SEQ ID NO: 188)

DIQMTQSPSSLSASVGDRVTITCRAS<u>QSISSY</u>LNWYQQKPGKAPKLLIY<u>AAS</u>SLQSGVPSRFSGSGSGTDFTLTISSLQP

EDFATYYC<u>QQSYSTPPIT</u>FGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12926P2
Heavy chain
(SEQ ID NO: 208)

QVQLQQSGPGLVKPSQTLSLTCAIS<u>GDSVSSNIAA</u>WNWIRLSPSRGLEWLGR<u>TFFRSTWFY</u>DYSLSVKGRITINPDTSKN

QFSLHLNSVTPEDAAVYYC<u>ARTGRRWSLDY</u>WGQGTLVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain
(SEQ ID NO: 188)

DIQMTQSPSSLSASVGDRVTITCRAS<u>QSISSY</u>LNWYQQKPGKAPKLLIY<u>AAS</u>SLQSGVPSRFSGSGSGTDFTLTISSLQP

EDFATYYC<u>QQSYSTPPIT</u>FGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12927P2
Heavy chain
(SEQ ID NO: 216)

EVQLVESGGGVVRPGGSLRLSCATS<u>GFTFDDYGMS</u>WVRQVPGKGLEWVSS<u>VNRNGGTT</u>DYADSVKGRFTISRDNAKRSLF

LQMNSLRAEDTALYHC<u>ATGELFFDY</u>WGQGTLVTVSSASTKGPSVFPLAPCSRSTSESTAALGCLVKDYFPEPVTVSWNSG

ALTSGVHTFPAVLQSSGLYSLSSVVTVPSSSLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK

Light chain
(SEQ ID NO: 188)

DIQMTQSPSSLSASVGDRVTITCRAS<u>QSISSY</u>LNWYQQKPGKAPKLLIY<u>AAS</u>SLQSGVPSRFSGSGSGTDFTLTISSLQP

EDFATYYC<u>QQSYSTPPIT</u>FGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H12934P2
Heavy chain
(SEQ ID NO: 234)
QVQLVQSGAEVKKPGASVKVSCKAS<u>GYTFTGHYMH</u>WVRQAPGQGLEWMG<u>WIYPHSGHTNYAKRFQG</u>RVTMTRDTSITTAY
MELIRLRSDDTAVYYC<u>ARRSGRSWYFDL</u>WGRGTLVTVSSASTKGPSVFPLAPCSRSTSESTAALGCLVKDYFPEPVTVSW
NSGALTSGVHTFPAVLQSSGLYSLSSVVTVPSSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLGK Light chain
(SEQ ID NO: 236)
EIVLTQSPGTLSLSPGERATLSCRAS<u>QSVSSSY</u>LAWYQQKPGQAPRLLIY<u>GAS</u>SRATGIPDRFSGSGSGTDFTLTISRLE
PEDFAVYYC<u>QQYGSSPWT</u>FGQGTKVEIKRTVAAPSVFIFPPSDEQLKSGTASVVCLLNNFYPREAKVQWKVDNALQ SGN S
QESVTEQDSKDSTYSLSSTLTLSKADYEKHKVYACEVTHQGLSSPVTKSFNRGEC H4H13538P
Heavy chain
(SEQ ID NO: 254)
EVQLVESGGGLVQPGGSLGLSCAAS<u>GFTFSNYAMS</u>WVRQAPGKGLEWVSA<u>VSGGGGGT</u>YYADSVKGRFTISRDNSKNTVL
LQMNSLRAEDTAVYYC<u>ARGRTGGLDY</u>WGPGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRVESKYGPPCPPCPAPEFLGGPSVFLF
PPKPKDTLMISRTPEVTCVVVDVSQEDPEVQFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK Light chain
(SEQ ID NO: 256)
DVVMTQSPLSLPVIFGQPASISCRSS<u>QSLVDSDGNTY</u>LNWLQQRPGQSPRRLIY<u>EVS</u>NRDSGVPDRFSGSGSGTDFTLTI
SRVEAEDVGIYYC<u>MQGTRWPPT</u>FGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC H4H13541P
Heavy chain
(SEQ ID NO: 272)
EVQLVESGGGVVRPGGSLRLSCAAS<u>GFIFDDYDMS</u>WVRQPPGRGLEWVSG<u>IDWFGGTRGYADSMKG</u>RFTISRDNAKNSLY
LQMNSLRVEDTAFYYC<u>ARGGAIVGAVTPFDY</u>WGQGTLVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTKVDKRVESKYGPPCPPCPAPEFLGGP
SVFLFPPKPKDTLMISRTPEVTCVVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK Light chain
(SEQ ID NO: 274)
DIQMTQSPSSLSASVGNRVTLSCRAS<u>QSINTY</u>LSWYQQRPGKAPKLLIY<u>AAS</u>SLQSGVPSRFSGSGAGTDFTLTISSLQP
EDFATYYC<u>QQSYSAPLT</u>FGGGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC H4H13544P2
Heavy chain
(SEQ ID NO: 284)
QLQLQESGPGLVKPSETLSLTCTVS<u>GGSISIKNYY</u>WGWIRQPPGKGLEWIGS<u>IYYSGTTYYNPSLKS</u>RVTISVDTSKNQF
SLKLSSVTAADTAVYHC<u>ARHGYSYGHGWFDP</u>WGQGTLVTVSSASTKGPSVFTLAPCSRSTSESTAALGCLVKDYFPEPVT
VSWNSGALTSGVHTFPAVLQSSGLYSLSSVVTVPSSSLGTKTYTCNVDHKPSNTKVDKRVESKYGPPCPPCPAPEFLGGP -continued

```
SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain
                                                                    (SEQ ID NO: 188)
DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H13545P2
Heavy chain
                                                                    (SEQ ID NO: 294)
QVQLQQSGPGLVKPSQTLSLTCDISGDSVSSNIATWNWIRQSPSRGLEWLGRTYYRSKWYKDYAVSVKSRITINPDTSKN

QFSLQVNSVTPEDTAVYYCARMTGPRYYFEYWGQGTLVTVSSASTKGPSVFTLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Light chain
                                                                    (SEQ ID NO: 188)
DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC
```
*Antibodies referred to in these Example are those having immunoglobulin chains with the amino acid sequences specifically set forth in Example 1.

Example 2: Surface Plasmon Resonance Binding Assays

The dissociation rate constant ($k_d$) for binding of IL-2Rγ reagents to purified anti-IL2Rγ monoclonal antibodies was determined using a real-time surface plasmon resonance based Biacore 4000 biosensor platform. All binding studies were performed at 25° C. and 37° C. using two running buffers, (i) 1.9 mM NaH$_2$PO$_4$, 8.1 mM Na$_2$HPO$_4$, 2.7 mM KCl, 137 mM NaCl, 0.03% NaN$_3$, 0.05% v/v Surfactant Tween-20, pH7.4 (PBS-T-pH7.4), and (ii) 8.8 mM NaH$_2$PO$_4$, 1.2 mM Na$_2$HPO$_4$, 2.7 mM KCl, 137 mM NaCl, 0.03% NaN$_3$, 0.05% v/v Surfactant Tween-20, pH6.0 (PBS-T-pH6.0). The CM5 Biacore sensor surface derivatized by amine coupling with monoclonal mouse anti-human Fc antibody (GE, Catalog #BR-1008-39) was used to capture anti-IL2Rγ monoclonal antibodies expressed with human IgG4 Fc. All the IL2Rγ reagents were expressed with a C-terminal myc-myc-hexahistidine tag (subsequently referred to with a -MMH suffix). Different concentrations of human IL2Rγ extracellular domain expressed with a C-terminal myc-myc-hexahistidine tag (hIL-2Rg-MMH; SEQ ID NO: 379) or *Macaca fascicularis* IL2Rγ extracellular domain expressed with a C-terminal myc-myc-hexahistidine tag (mfIL-2Rg-MMH; SEQ ID NO: 380) were prepared in PBS-T-pH7.4 running buffer (100 nM-11.11 nM; 3-fold serial dilution) and injected for 4 minutes at a flow rate of 30 µL/minute. The dissociation of bound IL-2Rg-MMH was performed in PBS-T-pH7.4 or PBS-T-pH6.0 running buffers for 6 minutes.

Dissociation rate constants ($k_d$) in two running buffers were determined by fitting the real-time binding sensorgrams to a 1:1 binding model using Scrubber 2.0c curve-fitting software. Values of dissociation rate for anti-Hemojuvelin mAb binding to hIL-2RG-MMH and mfIL-2RG-MMH at 25° C. and 37° C. in PBS-T-pH7.4 and PBS-T-pH6.0 is shown in Table 2-1 through Table 2-8.

TABLE 2-1

Dissociation Rate Constants of Anti-IL-2Rγ mAbs Binding to hIL-2Rg-MMH at 25° C. in PBS-T-pH 7.4.

| mAb Captured | mAb Capture Level (RU) | 100 nM Ag Bound (RU) | kd (1/s) | $t^{1/2}$ (min) |
|---|---|---|---|---|
| H4H13538P | 167 ± 0.3 | 82 | 1.39E−04 | 83 |
| H4H13541P | 195 ± 0.7 | 72 | 1.65E−04 | 70 |
| H4H13544P2 | 273 ± 0.2 | 57 | 6.02E−04 | 19 |
| H4H13545P2 | 319 ± 0.1 | 15 | 2.13E−02 | 0.5 |
| H4H12924P2 | 331 ± 0.4 | 124 | 4.79E−04 | 24 |
| H4H12926P2 | 413 ± 0.6 | 29 | 1.33E−02 | 0.9 |
| H4H12913P2 | 218 ± 0.6 | 56 | 3.03E−04 | 38 |
| H4H12922P2 | 408 ± 1.1 | 164 | 2.04E−04 | 57 |
| H4H12857P | 266 ± 0.4 | 79 | 1.70E−04 | 68 |
| H4H12858P | 272 ± 1.8 | 111 | 1.84E−04 | 63 |
| H4H12859P | 344 ± 0.7 | 54 | 1.11E−03 | 10 |
| H4H12863P | 422 ± 0.8 | 151 | 1.72E−04 | 67 |
| H4H12871P | 413 ± 0.6 | 121 | 5.96E−04 | 19 |
| H4H12874P | 275 ± 0.3 | 72 | 1.62E−04 | 71 |
| H4H12884P | 530 ± 1.4 | 161 | 6.40E−04 | 18 |
| H4H12886P | 303 ± 0.7 | 113 | 1.55E−04 | 75 |
| H4H12889P | 360 ± 0.7 | 118 | 1.38E−04 | 84 |
| H4H12890P | 336 ± 0.6 | 72 | 1.92E−04 | 60 |
| H4H12899P | 327 ± 2.2 | 118 | 1.74E−04 | 66 |
| H4H12900P | 348 ± 1.9 | 130 | 1.75E−04 | 66 |
| H4H12908P | 402 ± 1.5 | 31 | 1.77E−04 | 65 |
| H4H12927P2 | 271 ± 0.5 | 36 | 1.63E−03 | 7 |
| H4H12934P2 | 602 ± 1.4 | 87 | 3.41E−03 | 3.4 |

TABLE 2-2

Dissociation Rate Constants of Anti-IL-2Rg mAbs Binding to hIL-2Rg-MMH at 25° C. in PBS-T-pH 6.0.

| mAb Captured | mAb Capture Level (RU) | 100 nM Ag Bound (RU) | kd (1/s) | $t^{1/2}$ (min) |
|---|---|---|---|---|
| H4H13538P | 203 ± 1.5 | 93 | 4.17E−04 | 28 |
| H4H13541P | 192 ± 0.3 | 66 | 4.69E−04 | 25 |
| H4H13544P2 | 259 ± 0.3 | 45 | 1.75E−03 | 7 |
| H4H13545P2 | 278 ± 0.9 | 11 | 3.34E−02 | 0.3 |
| H4H12924P2 | 381 ± 1 | 136 | 3.67E−03 | 3 |
| H4H12926P2 | 410 ± 0.6 | 24 | 2.97E−02 | 0.4 |
| H4H12913P2 | 203 ± 0.4 | 43 | 1.05E−03 | 11 |
| H4H12922P2 | 349 ± 0.7 | 126 | 1.18E−03 | 10 |
| H4H12857P | 318 ± 1.2 | 88 | 5.49E−04 | 21 |
| H4H12858P | 265 ± 0.7 | 103 | 3.77E−04 | 31 |
| H4H12859P | 324 ± 1 | 39 | 5.03E−03 | 2.3 |
| H4H12863P | 366 ± 0.8 | 116 | 7.62E−04 | 15 |
| H4H12871P | 454 ± 1.2 | 129 | 1.36E−03 | 8 |
| H4H12874P | 272 ± 0.7 | 66 | 7.24E−04 | 16 |
| H4H12884P | 516 ± 1 | 135 | 1.99E−03 | 6 |
| H4H12886P | 250 ± 1.3 | 84 | 6.34E−04 | 18 |
| H4H12889P | 409 ± 1.2 | 130 | 4.37E−04 | 26 |
| H4H12890P | 330 ± 0.5 | 64 | 6.36E−04 | 18 |
| H4H12899P | 301 ± 2.2 | 96 | 5.68E−04 | 20 |
| H4H12900P | 280 ± 1 | 101 | 6.92E−04 | 17 |
| H4H12908P | 450 ± 5.3 | 34 | 5.05E−04 | 23 |
| H4H12927P2 | 267 ± 0.5 | 30 | 4.99E−03 | 2.3 |
| H4H12934P2 | 601 ± 1.6 | 71 | 1.32E−02 | 0.9 |

TABLE 2-3

Dissociation Rate Constants of Anti-IL-2Rγ mAbs Binding to hIL-2Rg-MMH at 37° C. in PBS-T-pH 7.4.

| mAb Captured | mAb Capture Level (RU) | 100 nM Ag Bound (RU) | kd (1/s) | $t^{1/2}$ (min) |
|---|---|---|---|---|
| H4H13538P | 255 ± 1.2 | 110 | 5.99E−04 | 19 |
| H4H13541P | 281 ± 1.8 | 98 | 5.32E−04 | 22 |
| H4H13544P2 | 371 ± 1.5 | 54 | 4.10E−03 | 2.8 |
| H4H13545P2 | 408 ± 2.2 | 7 | IC | IC |
| H4H12924P2 | 463 ± 1.2 | 133 | 3.02E−03 | 4 |
| H4H12926P2 | 533 ± 0.5 | 14 | 3.08E−02 | 0.4 |
| H4H12913P2 | 318 ± 0.2 | 82 | 1.16E−03 | 10 |
| H4H12922P2 | 552 ± 0.7 | 184 | 7.73E−04 | 15 |
| H4H12857P | 388 ± 2.1 | 117 | 6.21E−04 | 19 |
| H4H12858P | 378 ± 3.4 | 141 | 6.61E−04 | 17 |
| H4H12859P | 476 ± 2 | 55 | 4.54E−03 | 2.5 |
| H4H12863P | 544 ± 2 | 176 | 6.72E−04 | 17 |
| H4H12871P | 536 ± 0.8 | 139 | 1.11E−03 | 10 |
| H4H12874P | 381 ± 0.3 | 99 | 5.72E−04 | 20 |
| H4H12884P | 691 ± 1.9 | 171 | 1.51E−03 | 8 |
| H4H12886P | 420 ± 0.6 | 146 | 5.19E−04 | 22 |
| H4H12889P | 502 ± 1.6 | 147 | 6.36E−04 | 18 |
| H4H12890P | 450 ± 1.4 | 90 | 6.61E−04 | 17 |
| H4H12899P | 460 ± 3.5 | 158 | 6.68E−04 | 17 |
| H4H12900P | 475 ± 3.3 | 162 | 7.11E−04 | 16 |
| H4H12908P | 530 ± 3.3 | 54 | 6.71E−04 | 17 |
| H4H12927P2 | 377 ± 1.8 | 23 | 9.82E−03 | 1.2 |
| H4H12934P2 | 763 ± 1.3 | 63 | 1.61E−02 | 0.7 |

TABLE 2-4

Dissociation Rate Constants of Anti-IL-2Rγ mAbs Binding to hIL-2Rg-MMH at 37° C. in PBS-T-pH 6.0.

| mAb Captured | mAb Capture Level (RU) | 100 nM Ag Bound (RU) | kd (1/s) | $t^{1/2}$ (min) |
|---|---|---|---|---|
| H4H13538P | 284 ± 1.4 | 120 | 1.48E−03 | 8 |
| H4H13541P | 284 ± 0.7 | 95 | 1.58E−03 | 7 |
| H4H13544P2 | 335 ± 1.6 | 39 | 8.27E−03 | 1.4 |
| H4H13545P2 | 364 ± 1 | 6 | IC | IC |
| H4H12924P2 | 506 ± 1.2 | 133 | 1.43E−02 | 0.8 |
| H4H12926P2 | 549 ± 0.4 | 14 | 3.12E−02 | 0.4 |
| H4H12913P2 | 277 ± 1.1 | 59 | 3.83E−03 | 3 |
| H4H12922P2 | 486 ± 3.2 | 147 | 3.74E−03 | 3 |
| H4H12857P | 429 ± 1.7 | 123 | 2.07E−03 | 6 |
| H4H12858P | 372 ± 2.6 | 136 | 1.72E−03 | 7 |
| H4H12859P | 424 ± 1.4 | 36 | 1.32E−02 | 0.9 |
| H4H12863P | 485 ± 0.5 | 145 | 2.26E−03 | 5 |
| H4H12871P | 566 ± 1.1 | 141 | 2.46E−03 | 5 |
| H4H12874P | 381 ± 0.4 | 91 | 2.61E−03 | 4 |
| H4H12884P | 634 ± 3.1 | 136 | 3.79E−03 | 3.0 |
| H4H12886P | 350 ± 1.6 | 115 | 2.16E−03 | 5 |
| H4H12889P | 538 ± 1.2 | 153 | 1.88E−03 | 6 |
| H4H12890P | 447 ± 1 | 82 | 2.86E−03 | 4 |
| H4H12899P | 400 ± 2.9 | 125 | 2.19E−03 | 5 |
| H4H12900P | 393 ± 1.8 | 133 | 2.71E−03 | 4 |
| H4H12908P | 566 ± 4.2 | 52 | 1.63E−03 | 7 |
| H4H12927P2 | 374 ± 0.9 | 19 | 2.39E−02 | 0.5 |
| H4H12934P2 | 712 ± 3.7 | 51 | 2.97E−02 | 0.4 |

TABLE 2-5

Dissociation Rate Constants of Anti-IL-2Rγ mAbs Binding to mfIL-2Rg-MMH at 25° C. in PBS-T-pH 7.4.

| mAb Captured | mAb Capture Level (RU) | 100 nM Ag Bound (RU) | kd (1/s) | $t^{1/2}$ (min) |
|---|---|---|---|---|
| H4H13538P | 167 ± 0.7 | 94 | 1.79E−04 | 65 |
| H4H13541P | 194 ± 0.3 | 80 | 2.22E−04 | 52 |
| H4H13544P2 | 272 ± 0.8 | 67 | 5.84E−04 | 20 |
| H4H13545P2 | 317 ± 0.5 | 30 | 7.51E−03 | 1.5 |
| H4H12924P2 | 330 ± 0.2 | 130 | 3.85E−04 | 30 |
| H4H12926P2 | 411 ± 1.4 | 43 | 7.82E−03 | 1.5 |
| H4H12913P2 | 218 ± 0.2 | 57 | 2.72E−04 | 43 |
| H4H12922P2 | 406 ± 0.1 | 168 | 1.91E−04 | 61 |
| H4H12857P | 264 ± 0.8 | 80 | 1.81E−04 | 64 |
| H4H12858P | 269 ± 0.7 | 111 | 1.71E−04 | 68 |
| H4H12859P | 342 ± 0.6 | 51 | 8.71E−04 | 13 |
| H4H12863P | 418 ± 1 | 155 | 1.94E−04 | 59 |
| H4H12871P | 411 ± 0.9 | 125 | 4.81E−04 | 24 |
| H4H12874P | 276 ± 0.6 | 73 | 1.64E−04 | 70 |
| H4H12884P | 528 ± 0.6 | 160 | 5.16E−04 | 22 |
| H4H12886P | 302 ± 0.4 | 113 | 1.75E−04 | 66 |
| H4H12889P | 358 ± 0.5 | 123 | 1.57E−04 | 74 |
| H4H12890P | 335 ± 1.2 | 71 | 2.03E−04 | 57 |
| H4H12899P | 325 ± 0.8 | 117 | 1.67E−04 | 69 |
| H4H12900P | 345 ± 0.4 | 129 | 1.75E−04 | 66 |
| H4H12908P | 399 ± 1.2 | 37 | 2.08E−04 | 56 |
| H4H12927P2 | 270 ± 0.3 | 38 | 9.84E−04 | 12 |
| H4H12934P2 | 601 ± 0.7 | 89 | 3.05E−03 | 3.8 |

TABLE 2-6

Dissociation Rate Constants of Anti-IL-2Rγ mAbs Binding to mfIL-2Rg-MMH at 25° C. in PBS-T-pH 6.0.

| mAb Captured | mAb Capture Level (RU) | 100 nM Ag Bound (RU) | kd (1/s) | $t^{1/2}$ (min) |
|---|---|---|---|---|
| H4H13538P | 202 ± 0.2 | 96 | 4.39E−04 | 26 |
| H4H13541P | 192 ± 0.5 | 69 | 4.97E−04 | 23 |
| H4H13544P2 | 258 ± 0.5 | 52 | 1.70E−03 | 7 |
| H4H13545P2 | 278 ± 1.1 | 20 | 9.35E−03 | 1.2 |
| H4H12924P2 | 381 ± 0.7 | 131 | 3.05E−03 | 4 |
| H4H12926P2 | 410 ± 1.1 | 32 | 1.85E−02 | 0.6 |
| H4H12913P2 | 203 ± 0.8 | 44 | 9.92E−04 | 12 |
| H4H12922P2 | 349 ± 0.7 | 129 | 1.11E−03 | 10 |
| H4H12857P | 317 ± 1 | 80 | 5.01E−04 | 23 |
| H4H12858P | 263 ± 0.6 | 100 | 3.85E−04 | 30 |

TABLE 2-6-continued

Dissociation Rate Constants of Anti-IL-2Rγ mAbs Binding to mfIL-2Rg-MMH at 25° C. in PBS-T-pH 6.0.

| mAb Captured | mAb Capture Level (RU) | 100 nM Ag Bound (RU) | kd (1/s) | $t^{1/2}$ (min) |
|---|---|---|---|---|
| H4H12859P | 323 ± 0.5 | 37 | 4.13E−03 | 2.8 |
| H4H12863P | 365 ± 1.9 | 118 | 7.61E−04 | 15 |
| H4H12871P | 455 ± 3.6 | 128 | 1.16E−03 | 10 |
| H4H12874P | 272 ± 0.6 | 64 | 7.29E−04 | 16 |
| H4H12884P | 513 ± 2.1 | 133 | 1.59E−03 | 7 |
| H4H12886P | 251 ± 0.2 | 83 | 6.82E−04 | 17 |
| H4H12889P | 408 ± 1.6 | 126 | 4.34E−04 | 27 |
| H4H12890P | 329 ± 0.5 | 60 | 6.68E−04 | 17 |
| H4H12899P | 300 ± 0.7 | 95 | 7.03E−04 | 16 |
| H4H12900P | 280 ± 0.4 | 100 | 6.71E−04 | 17 |
| H4H12908P | 445 ± 0.8 | 34 | 4.88E−04 | 24 |
| H4H12927P2 | 267 ± 0.1 | 30 | 3.20E−03 | 3.6 |
| H4H12934P2 | 597 ± 2.5 | 64 | 1.01E−02 | 1.1 |

TABLE 2-7

Dissociation Rate Constants of Anti-IL-2Rγ mAbs Binding to mfIL-2Rg-MMH at 37° C. in PBS-T-pH 7.4.

| mAb Captured | mAb Capture Level (RU) | 100 nM Ag Bound (RU) | kd (1/s) | $t^{1/2}$ (min) |
|---|---|---|---|---|
| H4H13538P | 254 ± 0.3 | 119 | 5.10E−04 | 23 |
| H4H13541P | 280 ± 0.6 | 100 | 5.12E−04 | 23 |
| H4H13544P2 | 368 ± 1.1 | 58 | 3.62E−03 | 3.2 |
| H4H13545P2 | 406 ± 1 | 17 | IC | IC |
| H4H12924P2 | 461 ± 0.5 | 133 | 2.67E−03 | 4 |
| H4H12926P2 | 529 ± 2.1 | 25 | 2.79E−02 | 0.4 |
| H4H12913P2 | 318 ± 0.6 | 76 | 8.94E−04 | 13 |
| H4H12922P2 | 548 ± 1.1 | 185 | 6.93E−04 | 17 |
| H4H12857P | 386 ± 0.7 | 111 | 5.53E−04 | 21 |
| H4H12858P | 374 ± 0.9 | 143 | 5.42E−04 | 21 |
| H4H12859P | 473 ± 1 | 47 | 3.97E−03 | 2.9 |
| H4H12863P | 542 ± 1 | 177 | 6.06E−04 | 19 |
| H4H12871P | 532 ± 1 | 143 | 1.02E−03 | 11 |
| H4H12874P | 381 ± 0.5 | 92 | 5.41E−04 | 21 |
| H4H12884P | 690 ± 1.3 | 171 | 1.47E−03 | 8 |
| H4H12886P | 418 ± 0.6 | 145 | 4.71E−04 | 25 |
| H4H12889P | 500 ± 1.3 | 147 | 5.78E−04 | 20 |
| H4H12890P | 448 ± 0.1 | 82 | 6.24E−04 | 19 |
| H4H12899P | 458 ± 0.8 | 160 | 5.52E−04 | 21 |
| H4H12900P | 474 ± 1.1 | 166 | 6.23E−04 | 19 |
| H4H12908P | 527 ± 0.8 | 55 | 5.14E−04 | 22 |
| H4H12927P2 | 374 ± 0.4 | 27 | 5.96E−03 | 1.9 |
| H4H12934P2 | 762 ± 1.1 | 70 | 1.24E−02 | 0.9 |

TABLE 2-8

Dissociation Rate Constants of Anti-IL-2Rγ mAbs Binding to mfIL-2Rg-MMH at 37° C. in PBS-T-pH 6.0.

| mAb Captured | mAb Capture Level (RU) | 100 nM Ag Bound (RU) | kd (1/sf) | $t^{1/2}$ (min) |
|---|---|---|---|---|
| H4H13538P | 282 ± 0.4 | 122 | 1.39E−03 | 8 |
| H4H13541P | 282 ± 1.4 | 91 | 1.50E−03 | 8 |
| H4H13544P2 | 334 ± 1.1 | 43 | 7.81E−03 | 1.5 |
| H4H13545P2 | 364 ± 0.2 | 13 | IC | IC |
| H4H12924P2 | 506 ± 0.7 | 126 | 1.24E−02 | 0.9 |
| H4H12926P2 | 548 ± 1.5 | 20 | 3.03E−02 | 0.4 |
| H4H12913P2 | 277 ± 1.1 | 54 | 2.96E−03 | 4 |
| H4H12922P2 | 483 ± 1 | 146 | 3.44E−03 | 3.4 |
| H4H12857P | 426 ± 0.6 | 109 | 1.78E−03 | 6 |
| H4H12858P | 369 ± 2.2 | 134 | 1.55E−03 | 7 |
| H4H12859P | 423 ± 1 | 31 | 1.23E−02 | 0.9 |
| H4H12863P | 482 ± 0.8 | 141 | 2.08E−03 | 6 |
| H4H12871P | 565 ± 1.4 | 141 | 2.27E−03 | 5 |
| H4H12874P | 380 ± 0.6 | 82 | 2.55E−03 | 5 |
| H4H12884P | 633 ± 2.4 | 135 | 3.35E−03 | 3.4 |
| H4H12886P | 349 ± 0.7 | 109 | 1.97E−03 | 6 |
| H4H12889P | 537 ± 0.7 | 148 | 1.83E−03 | 6 |
| H4H12890P | 447 ± 0.5 | 71 | 2.76E−03 | 4 |
| H4H12899P | 398 ± 1.4 | 122 | 2.11E−03 | 5 |
| H4H12900P | 390 ± 1.5 | 130 | 2.77E−03 | 4 |
| H4H12908P | 561 ± 0.3 | 52 | 1.31E−03 | 9 |
| H4H12927P2 | 372 ± 0.9 | 22 | 1.29E−02 | 0.9 |
| H4H12934P2 | 711 ± 3.2 | 50 | 2.65E−02 | 0.4 |

Example 3: Binding Kinetics

Equilibrium dissociation constants ($K_D$ values) for IL-2Rγ binding to purified anti-IL2Rγ monoclonal antibodies were determined using a Biacore 4000 instrument equipped with a real-time surface plasmon resonance biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore sensor surface was first derivatized by amine coupling with a monoclonal mouse anti-human Fc antibody (GE, #BR-1008-39) to capture anti-IL2Rγ monoclonal antibodies.

Binding studies were performed on the following IL-2Rγ reagents:

Human IL2Rγ extracellular domain expressed with a C-terminal myc-myc-hexahistidine tag (hIL-2Rg-MMH; SEQ ID NO: 379), comprising
Amino acids (1-240): Human IL2Rg ecto (L23-A262 of NP_000197.1)
Amino acids (241-268): Myc-Myc-Hexahistadine tag (underlined)
comprising the amino acid sequence:

LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR

VRSRFNPLCGSAQHWSEWSHPIHWGSNTSKENPFLFALEA<u>EQKLISEEDL</u>

<u>GGEQKLISEEDLHHHHHH</u>
*Expressed with mROR signal sequence

*Macaca fascicularis* IL2Rγ extracellular domain expressed with a C-terminal myc-myc-hexahistidine tag (mfIL-2Rg-MMH; SEQ ID NO: 380), comprising
Amino acids (1-240): *Macaca fascicularis* IL2Rg ecto (L23-A262 of XP 005593949.1)
Amino acids (241-268): Myc-Myc-Hexahistadine tag (underlined)
comprising the amino acid sequence:

LNTTILTPNGNEDATTDFFLTSMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLRKLSESQLEL

```
NWNNRFLNHCLEHLVQYRTDWDHSWTEQSVDYRHKFSLPSVDGQKRYTFR

VRSRFNPLCGSAQHWSEWSHPIHWGSNSSKENPFLFALEAEQKLISEEDL

GGEQKLISEEDLHHHHHH
```

Human IL2Rγ extracellular domain expressed with a C-terminal mouse IgG2a Fc tag (hIL-2Rg-mFc; SEQ ID NO: 381), comprising
Amino acids (1-240): Human IL2Rg ecto (L23-A262 of NP_000197.1)
Amino acids (241-473): Mouse IgG2a Fc tag (underlined)
comprising the amino acid sequence:

```
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR

VRSRFNPLCGSAQHWSEWSHPIHWGSNTSKENPFLFALEAEPRGPTIKPC

PPCKCPAPNLLGGPSVFIFPPKIKDVLMISLSPIVTCVVVDVSEDDPDVQ

ISWFVNNVEVHTAQTQTHREDYNSTLRVVSALPIQHQDWMSGKEFKCKVN

NKDLPAPIERTISKPKGSVRAPQVYVLPPPEEEMTKKQVTLTCMVTDFMP

EDIYVEWTNNGKTELNYKNTEPVLDSDGSYFMYSKLRVEKKNWVERNSYS

CSVVHEGLHNHHTTKSFSRTPGK
*Expressed with mROR signal sequence
```

D1 domain of human IL-2Rγ extracellular domain expressed with a C-terminal myc-myc-hexahistidine tag (hIL-2Rg_D1-MMH; SEQ ID NO: 382), comprising
Amino acids (1-131): Human IL2Rg domain 1 (L23-1153 of NP_000197.1)
Amino acids (132-159): Myc-Myc-Hexahistadine tag (underlined)
comprising the amino acid sequence:

```
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIEQKLISEEDLGGEQKLISE

EDLHHHHHH
*Expressed with mROR signal sequence
```

D2 domain of human IL-2Rγ extracellular domain expressed with a C-terminal myc-myc-hexahistidine tag (hIL-2Rg_D2-MMH; SEQ ID NO: 383), comprising
Amino acids (1-88): Human IL2Rg Domain 2 (P154-S241 of NP_000197.1)
Amino acids (89-116): Myc-Myc-Hexahistadine tag (underlined)
comprising the amino acid sequence:

```
PWAPENLTLHKLSESQLELNWNNRFLNHCLEHLVQYRTDWDHSWTEQSVD

YRHKFSLPSVDGQKRYTFRVRSRFNPLCGSAQHWSEWSEQKLISEEDLGG

EQKLISEEDLHHHHHH
*Expressed with mROR signal sequence
```

Mouse IL2Rγ extracellular domain expressed with a C-terminal myc-myc-hexahistidine tag (mIL-2Rg-MMH; SEQ ID NO: 384), comprising
Amino acids (1-241): Mouse IL2Rg ecto (W23-A263 of NP_038591.1)
Amino acids (242-269): Myc-Myc-Hexahistadine tag (underlined)
comprising the amino acid sequence:

```
WSSKVLMSSANEDIKADLILTSTAPEHLSAPTLPLPEVQCFVFNIEYMNC

TWNSSSEPQATNLTLHYRYKVSDNNTFQECSHYLFSKEITSGCQIQKEDI

QLYQTFVVQLQDPQKPQRRAVQKLNLQNLVIPRAPENLTLSNLSESQLEL

RWKSRHIKERCLQYLVQYRSNRDRSWTELIVNHEPRFSLPSVDELKRYTF

RVRSRYNPICGSSQQWSKWSQPVHWGSHTVEENPSLFALEAEQKLISEED

LGGEQKLISEEDLHHHHHH
```

Rat IL2Rγ extracellular domain expressed with a C-terminal myc-myc-hexahistidine tag (rIL-2Rg-MMH; SEQ ID NO: 385), comprising
Amino acids (1-240): Rat IL2Rg ecto (W23-A262 of NP_543165.1)
Amino acids (241-268): Myc-Myc-Hexahistadine tag (underlined)
comprising the amino acid sequence:

```
WSSKVLMSSGNEDTKSDLLLTSMDLKHLSVPTLPLPEVQCFVFNVEYMNC

TWNSSSEPQPTNLTMHYRYKGSDNNTFQECSHYLFSKEITSGCQIQKEDI

QLYQTFVVQLQDPQKPQRRAEQKLNLQNLVIPWAPENLTLYNLSESQVEL

RWKSRYIERCLQYLVQYRSNRDRSWTEQIVDHEPRFSLPSVDEQKLYTFR

VRSRFNPICGSTQQWSKWSQPIHWGSHTAEENPSLFALEAEQKLISEEDL

GGEQKLISEEDLHHHHHH
*Expressed with mROR signal sequence
```

Different concentrations of IL2Rγ reagents were prepared in HBS-ET running buffer (100 nM-6.25 nM; 4-fold serial dilution or 50 nM-3.125 nM; 4-fold serial dilution for hIL-2Rg-mFc) and injected over anti-human Fc captured anti-IL2Rγ monoclonal antibody surface for 4 minutes at a flow rate of 30 μL/minute. The dissociation of monoclonal antibody bound IL2Rγ reagents were monitored for 8-10 minutes in HBS-ET running buffer. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives ($t_{1/2}$) were calculated from the kinetic rate constants as:

$$K_D(M) = \frac{kd}{ka}, \text{ and } t\frac{1}{2}(\min) = \frac{\ln(2)}{60*kd}$$

The kinetic parameters for binding of various IL-2Rγ reagents to different IL2Rγ monoclonal antibodies at 25° C. and 37° C. are shown in Tables 3-1 through 3-14.

TABLE 3-1

Binding kinetics parameters of hIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 183 ± 1 | 56 | 8.19E+04 | 2.25E−04 | 2.75E−09 | 51 |
| H4H12858P | 181 ± 0.3 | 67 | 2.57E+05 | 3.16E−04 | 1.23E−09 | 37 |
| H4H12859P | 195 ± 0.4 | 27 | 3.66E+04 | 3.21E−03 | 8.76E−08 | 4 |
| H4H12863P | 283 ± 4.7 | 91 | 2.26E+05 | 3.84E−04 | 1.70E−09 | 30 |
| H4H12871P | 291 ± 4 | 77 | 1.99E+05 | 1.00E−03 | 5.03E−09 | 12 |
| H4H12874P | 199 ± 0.8 | 57 | 8.52E+04 | 3.05E−04 | 3.57E−09 | 38 |
| H4H12884P | 367 ± 2.1 | 84 | 1.99E+05 | 1.39E−03 | 6.96E−09 | 8 |
| H4H12886P | 166 ± 0.6 | 60 | 1.34E+05 | 2.70E−04 | 2.02E−09 | 43 |
| H4H12889P | 215 ± 0.5 | 64 | 2.98E+05 | 4.20E−04 | 1.41E−09 | 28 |
| H4H12890P | 219 ± 1.8 | 48 | 6.79E+04 | 3.33E−04 | 4.91E−09 | 35 |
| H4H12899P | 189 ± 0.7 | 61 | 1.82E+05 | 4.58E−04 | 2.51E−09 | 25 |
| H4H12900P | 248 ± 1.4 | 79 | 2.93E+05 | 3.79E−04 | 1.29E−09 | 30 |
| H4H12908P | 266 ± 1.1 | 19 | 3.31E+04 | 2.85E−04 | 8.61E−09 | 41 |
| H4H12913P2 | 182 ± 0.5 | 42 | 6.20E+04 | 6.91E−04 | 1.12E−08 | 17 |
| H4H12922P2 | 218 ± 0.7 | 79 | 2.97E+05 | 3.86E−04 | 1.30E−09 | 30 |
| H4H12924P2 | 237 ± 0.5 | 78 | 3.22E+05 | 1.74E−03 | 5.38E−09 | 7 |
| H4H12926P2 | 239 ± 0.5 | 13 | 2.00E+05 | 2.64E−02 | 1.32E−07 | 0.4 |
| H4H12927P2 | 151 ± 0.5 | 18 | 5.75E+04 | 5.55E−03 | 9.65E−08 | 2.1 |
| H4H12934P2 | 363 ± 1.1 | 33 | 9.48E+04 | 1.06E−02 | 1.12E−07 | 1.1 |
| H4H13538P | 154 ± 0.4 | 68 | 2.22E+05 | 2.27E−04 | 1.02E−09 | 51 |
| H4H13541P | 199 ± 1 | 72 | 1.05E+05 | 2.52E−04 | 2.41E−09 | 46 |
| H4H13544P2 | 274 ± 0.9 | 51 | 4.72E+04 | 1.35E−03 | 2.87E−08 | 9 |
| H4H13545P2 | 322 ± 1.1 | 12 | 1.71E+05 | 5.75E−02 | 3.36E−07 | 0.2 |

TABLE 3-2

Binding kinetics parameters of hIL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 95 ± 0.6 | 23 | 1.54E+05 | 9.86E−04 | 6.42E−09 | 12 |
| H4H12858P | 169 ± 4.5 | 57 | 3.86E+05 | 1.74E−03 | 4.52E−09 | 7 |
| H4H12859P | 177 ± 4.9 | 18 | 6.90E+04 | 1.29E−02 | 1.87E−07 | 0.9 |
| H4H12863P | 273 ± 7 | 77 | 3.67E+05 | 1.51E−03 | 4.11E−09 | 8 |
| H4H12871P | 266 ± 5.5 | 61 | 2.50E+05 | 2.66E−03 | 1.06E−08 | 4 |
| H4H12874P | 184 ± 4.4 | 52 | 1.20E+05 | 1.25E−03 | 1.04E−08 | 9 |
| H4H12884P | 319 ± 6.2 | 62 | 2.57E+05 | 3.36E−03 | 1.31E−08 | 3.4 |
| H4H12886P | 151 ± 4.4 | 52 | 6.19E+04 | 9.56E−04 | 1.54E−08 | 12 |
| H4H12889P | 125 ± 1.6 | 32 | 4.65E+05 | 1.85E−03 | 3.99E−09 | 6 |
| H4H12890P | 134 ± 1.2 | 27 | 9.51E+04 | 1.33E−03 | 1.40E−08 | 9 |
| H4H12899P | 114 ± 1.7 | 36 | 3.42E+05 | 2.49E−03 | 7.27E−09 | 5 |
| H4H12900P | 183 ± 2.2 | 43 | 5.03E+05 | 1.84E−03 | 3.66E−09 | 6 |
| H4H12908P | 169 ± 2 | 16 | 4.83E+04 | 1.41E−03 | 2.92E−08 | 8 |
| H4H12913P2 | 114 ± 1.6 | 24 | 1.04E+05 | 3.48E−03 | 3.34E−08 | 3.3 |
| H4H12922P2 | 130 ± 1.7 | 44 | 4.07E+05 | 1.05E−03 | 2.58E−09 | 11 |
| H4H12924P2 | 142 ± 2.1 | 26 | 8.71E+05 | 1.57E−02 | 1.80E−08 | 0.7 |
| H4H12926P2 | 105 ± 1.5 | 2 | NB * | NB * | NB * | NB * |
| H4H12927P2 | 74 ± 1.1 | 5 | NB * | NB * | NB * | NB * |
| H4H12934P2 | 221 ± 2.3 | 9 | 2.16E+05 | 7.63E−02 | 3.53E−07 | 0.2 |
| H4H13538P | 231 ± 1.5 | 99 | 3.19E+05 | 1.08E−03 | 3.40E−09 | 11 |
| H4H13541P | 282 ± 2.1 | 103 | 1.56E+05 | 7.80E−04 | 5.01E−09 | 15 |
| H4H13544P2 | 366 ± 1.8 | 49 | 7.60E+04 | 7.82E−03 | 1.03E−07 | 1.5 |
| H4H13545P2 | 410 ± 1.9 | 7 | 6.11E+05 | 6.91E−02 | 1.13E−07 | 0.2 |

* NB indicates that no binding was observed under the current experimental conditions.

TABLE 3-3

Binding kinetics parameters of mfIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 183 ± 1.4 | 42 | 7.17E+04 | 2.28E−04 | 3.18E−09 | 51 |
| H4H12858P | 179 ± 0.3 | 58 | 1.14E+05 | 2.69E−04 | 2.36E−09 | 43 |
| H4H12859P | 193 ± 0.3 | 17 | 4.03E+04 | 5.07E−03 | 1.26E−07 | 2.3 |
| H4H12863P | 280 ± 5.1 | 81 | 1.89E+05 | 3.60E−04 | 1.91E−09 | 32 |
| H4H12871P | 288 ± 2.8 | 72 | 1.74E+05 | 9.05E−04 | 5.19E−09 | 13 |
| H4H12874P | 196 ± 0.9 | 50 | 7.15E+04 | 3.06E−04 | 4.28E−09 | 38 |
| H4H12884P | 364 ± 1.7 | 82 | 1.74E+05 | 1.21E−03 | 6.98E−09 | 10 |
| H4H12886P | 165 ± 0.8 | 57 | 1.09E+05 | 2.66E−04 | 2.45E−09 | 43 |
| H4H12889P | 214 ± 0.2 | 59 | 2.33E+05 | 4.04E−04 | 1.74E−09 | 29 |
| H4H12890P | 218 ± 0.4 | 37 | 6.06E+04 | 3.13E−04 | 5.16E−09 | 37 |
| H4H12899P | 188 ± 0.7 | 54 | 1.02E+05 | 4.07E−04 | 4.01E−09 | 28 |
| H4H12900P | 246 ± 1.2 | 71 | 2.32E+05 | 3.35E−04 | 1.44E−09 | 34 |

TABLE 3-3-continued

Binding kinetics parameters of mfIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12908P | 268 ± 4.1 | 14 | 3.22E+04 | 2.37E−04 | 7.37E−09 | 49 |
| H4H12913P2 | 180 ± 0.8 | 34 | 4.49E+04 | 6.33E−04 | 1.41E−08 | 18 |
| H4H12922P2 | 217 ± 0.3 | 76 | 2.35E+05 | 3.86E−04 | 1.64E−09 | 30 |
| H4H12924P2 | 235 ± 0.6 | 73 | 2.51E+05 | 1.65E−03 | 6.58E−09 | 7 |
| H4H12926P2 | 236 ± 1.2 | 11 | 2.44E+05 | 2.61E−02 | 1.07E−07 | 0.4 |
| H4H12927P2 | 151 ± 0.4 | 12 | 2.88E+04 | 6.86E−03 | 2.38E−07 | 1.7 |
| H4H12934P2 | 362 ± 1.6 | 31 | 9.27E+04 | 1.14E−02 | 1.23E−07 | 1.0 |
| H4H13538P | 154 ± 0.6 | 81 | 1.33E+05 | 3.04E−04 | 2.28E−09 | 38 |
| H4H13541P | 198 ± 0.3 | 82 | 1.70E+05 | 3.15E−04 | 1.85E−09 | 37 |
| H4H13544P2 | 274 ± 0.6 | 60 | 5.17E+04 | 1.27E−03 | 2.46E−08 | 9 |
| H4H13545P2 | 322 ± 1.4 | 26 | 9.78E+04 | 1.40E−02 | 1.43E−07 | 0.8 |

TABLE 3-4

Binding kinetics parameters of mfIL-2Rg-MMH binding to IL-2Rγ monoclonal antibodies at 37 ± C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 93 ± 1 | 18 | 1.30E+05 | 1.08E−03 | 8.29E−09 | 11 |
| H4H12858P | 155 ± 3.6 | 47 | 3.09E+05 | 1.48E−03 | 4.77E−09 | 8 |
| H4H12859P | 162 ± 3.9 | 10 | 6.28E+04 | 2.01E−02 | 3.20E−07 | 0.6 |
| H4H12863P | 253 ± 2.1 | 63 | 2.66E+05 | 1.47E−03 | 5.51E−09 | 8 |
| H4H12871P | 246 ± 5.1 | 55 | 2.06E+05 | 2.61E−03 | 1.27E−08 | 4 |
| H4H12874P | 169 ± 3.6 | 43 | 9.33E+04 | 1.16E−03 | 1.24E−08 | 10 |
| H4H12884P | 296 ± 5.3 | 59 | 2.00E+05 | 3.21E−03 | 1.61E−08 | 4 |
| H4H12886P | 138 ± 3.2 | 47 | 4.78E+04 | 8.46E−04 | 1.77E−08 | 14 |
| H4H12889P | 118 ± 1.4 | 29 | 3.69E+05 | 1.71E−03 | 4.63E−09 | 7 |
| H4H12890P | 128 ± 1.5 | 20 | 9.36E+04 | 1.31E−03 | 1.40E−08 | 9 |
| H4H12899P | 107 ± 1.6 | 31 | 3.22E+05 | 2.16E−03 | 6.71E−09 | 5 |
| H4H12900P | 175 ± 2.2 | 38 | 4.83E+05 | 1.54E−03 | 3.18E−09 | 8 |
| H4H12908P | 162 ± 2.7 | 13 | 3.71E+04 | 1.48E−03 | 3.98E−08 | 8 |
| H4H12913P2 | 109 ± 1.3 | 20 | 7.93E+04 | 2.96E−03 | 3.73E−08 | 4 |
| H4H12922P2 | 124 ± 1.7 | 44 | 3.08E+05 | 1.29E−03 | 4.18E−09 | 9 |
| H4H12924P2 | 135 ± 1.9 | 24 | 6.62E+05 | 1.37E−02 | 2.07E−08 | 0.8 |
| H4H12926P2 | 100 ± 1.2 | 1 | NB * | NB * | NB * | NB * |
| H4H12927P2 | 71 ± 1 | 1 | NB * | NB * | NB * | NB * |
| H4H12934P2 | 212 ± 2.3 | 7 | 5.73E+05 | 7.59E−02 | 1.32E−07 | 0.2 |

TABLE 3-4-continued

Binding kinetics parameters of mfIL-2Rg-MMH binding to IL-2Rγ monoclonal antibodies at 37 ± C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H13538P | 231 ± 1.9 | 115 | 1.69E+05 | 9.32E−04 | 5.50E−09 | 12 |
| H4H13541P | 281 ± 0.6 | 111 | 1.06E+05 | 7.55E−04 | 7.10E−09 | 15 |
| H4H13544P2 | 363 ± 1.6 | 60 | 1.18E+05 | 6.12E−03 | 5.21E−08 | 1.9 |
| H4H13545P2 | 409 ± 1.3 | 21 | 1.46E+05 | 1.29E−02 | 8.86E−08 | 0.9 |

* NB indicates that no binding was observed under the current experimental conditions.

TABLE 3-5

Binding kinetics parameters of hIL-2Rg-mFc binding to IL-2Rγ monoclonal antibodies at 25° C.

| mAb Captured | mAb Capture Level (RU) | 50 nM Ag Bound | ka (1/Ms) | kd (1/s) | $K_D$ (M) | $t_{1/2}$ (min) |
|---|---|---|---|---|---|---|
| H4H12857P | 180 ± 0.5 | 20 | 3.11E+04 | 7.62E−05 | 2.45E−09 | 152 |
| H4H12858P | 175 ± 1.2 | 46 | 1.16E+05 | 9.94E−05 | 8.55E−10 | 116 |
| H4H12859P | 190 ± 1.1 | 5 | NB * | NB * | NB * | NB * |
| H4H12863P | 280 ± 0.6 | 115 | 3.99E+05 | 3.41E−05 | 8.53E−11 | 339 |
| H4H12871P | 284 ± 2.7 | 103 | 3.63E+05 | 5.22E−05 | 1.44E−10 | 221 |
| H4H12874P | 193 ± 0.9 | 15 | 2.00E+04 | 8.35E−05 | 4.18E−09 | 138 |
| H4H12884P | 359 ± 2 | 112 | 3.55E+05 | 4.02E−05 | 1.13E−10 | 287 |
| H4H12886P | 162 ± 1.1 | 23 | 5.34E+04 | 6.70E−05 | 1.26E−09 | 172 |
| H4H12889P | 209 ± 0.9 | 69 | 3.47E+05 | 1.55E−05 | 4.47E−11 | 746 |
| H4H12890P | 213 ± 0.2 | 12 | NB * | NB * | NB * | NB * |
| H4H12899P | 184 ± 0.6 | 1 | NB * | NB * | NB * | NB * |
| H4H12900P | 241 ± 2.6 | 4 | NB * | NB * | NB * | NB * |
| H4H12908P | 261 ± 1.5 | 11 | 7.62E+04 | 1.00E−05 # | 1.31E−10 | 1155 |
| H4H12913P2 | 177 ± 0.3 | 12 | 4.12E+04 | 5.34E−05 | 1.30E−09 | 216 |
| H4H12922P2 | 213 ± 1 | 82 | 3.10E+05 | 1.75E−05 | 5.64E−11 | 661 |
| H4H12924P2 | 232 ± 1.8 | 28 | 7.26E+04 | 4.11E−04 | 5.66E−09 | 28 |
| H4H12926P2 | 232 ± 0.9 | 46 | 1.85E+05 | 9.62E−04 | 5.21E−09 | 12 |
| H4H12927P2 | 147 ± 0.2 | 7 | NB * | NB * | NB * | NB * |
| H4H12934P2 | 357 ± 1.7 | 75 | 1.67E+05 | 3.94E−04 | 2.36E−09 | 29 |
| H4H13538P | 157 ± 0.1 | 38 | 1.17E+05 | 1.16E−04 | 9.96E−10 | 99 |
| H4H13541P | 199 ± 0.5 | 24 | 4.92E+04 | 8.84E−05 | 1.80E−09 | 131 |
| H4H13544P2 | 274 ± 0.3 | 63 | 1.11E+05 | 2.46E−04 | 2.21E−09 | 47 |
| H4H13545P2 | 321 ± 1.1 | 64 | 1.75E+05 | 2.11E−03 | 1.20E−08 | 5 |

* NB indicates that no binding was observed under the current experimental conditions.
# indicates no dissociation was observed under the current experimental condition and the $k_d$ value was manually fixed at 1.00E−05 s⁻¹

TABLE 3-6

Binding kinetics parameters of hIL-2Rg-mFc binding to IL-2Rγ monoclonal antibodies at 37° C.

| mAb Captured | mAb Capture Level (RU) | 50 nM Ag Bound | ka (1/Ms) | kd (1/s) | $K_D$ (M) | $t\frac{1}{2}$ (min) |
|---|---|---|---|---|---|---|
| H4H12857P | 83 ± 0.8 | 12 | IC $ | IC $ | IC $ | IC $ |
| H4H12858P | 126 ± 2.1 | 37 | 1.67E+05 | 2.50E−04 | 1.49E−09 | 46 |
| H4H12859P | 130 ± 2.2 | 5 | NB * | NB * | NB * | NB * |
| H4H12863P | 216 ± 4.1 | 93 | 5.37E+05 | 1.00E−05 # | 1.86E−11 | 1155 |
| H4H12871P | 205 ± 2.9 | 81 | 4.73E+05 | 2.39E−05 | 5.05E−11 | 484 |
| H4H12874P | 138 ± 2.3 | 14 | 3.30E+04 | 1.00E−05 # | 3.03E−10 | 1155 |
| H4H12884P | 246 ± 3.6 | 85 | 4.86E+05 | 2.69E−05 | 5.54E−11 | 429 |
| H4H12886P | 111 ± 2 | 19 | 7.08E+03 | 9.09E−05 | 1.28E−08 | 127 |
| H4H12889P | 101 ± 1.5 | 39 | 2.38E+05 | 1.00E05 # | 4.20E−11 | 1155 |
| H4H12890P | 112 ± 1.2 | 8 | NB * | NB * | NB * | NB * |
| H4H12899P | 91 ± 1.6 | 2 | NB * | NB * | NB * | NB * |
| H4H12900P | 158 ± 2.1 | 4 | NB * | NB * | NB * | NB * |
| H4H12908P | 140 ± 2.3 | 8 | 1.93E+04 | 1.00E−05 # | 5.18E−10 | 1155 |
| H4H12913P2 | 95 ± 1 | 9 | 7.32E+04 | 1.85E−04 | 2.53E−09 | 62 |
| H4H12922P2 | 107 ± 1 | 47 | 2.23E+05 | 1.00E−05 # | 4.48E−11 | 1155 |
| H4H12924P2 | 118 ± 1.3 | 13 | 1.50E+04 | 1.83E−04 | 1.22E−08 | 63 |
| H4H12926P2 | 87 ± 1.1 | 11 | 2.04E+05 | 3.26E−03 | 1.60E−08 | 4 |
| H4H12927P2 | 63 ± 0.7 | 4 | NB * | NB * | NB * | NB * |
| H4H12934P2 | 189 ± 1.5 | 39 | 1.85E+05 | 5.90E−04 | 3.19E−09 | 20 |
| H4H13538P | 233 ± 0.9 | 70 | 1.44E+05 | 1.87E−04 | 1.29E−09 | 62 |
| H4H13541P | 281 ± 0.5 | 42 | 5.60E+04 | 1.22E−04 | 2.18E−09 | 94 |
| H4H13544P2 | 361 ± 2.6 | 88 | 1.26E+05 | 8.01E−04 | 6.33E−09 | 14 |
| H4H13545P2 | 408 ± 1.5 | 59 | 2.46E+05 | 7.37E−03 | 3.00E−08 | 1.6 |

* NB indicates that no binding was observed under the current experimental conditions.
# indicates no dissociation was observed under the current experimental condition and the $k_d$ value was manually fixed at 1.00E−05 s$^{-1}$

TABLE 3-7

Binding kinetics parameters of mIL-2Rg-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | $t\frac{1}{2}$ (min) |
|---|---|---|---|---|---|---|
| H4H12857P | 178 ± 0.1 | 5 | NB * | NB * | NB * | NB * |
| H4H12858P | 175 ± 0.4 | 2 | NB * | NB * | NB * | NB * |
| H4H12859P | 190 ± 1.1 | 2 | NB * | NB * | NB * | NB * |
| H4H12863P | 271 ± 3 | 2 | NB * | NB * | NB * | NB * |
| H4H12871P | 281 ± 88 | 0 | NB * | NB * | NB * | NB * |
| H4H12874P | 191 ± 05 | 1 | NB * | NB * | NB * | NB * |
| H4H12884P | 357 ± 3 | 2 | NB * | NB * | NB * | NB * |
| H4H12886P | 160 ± 1.2 | 2 | NB * | NB * | NB * | NB * |
| H4H12889P | 208 ± 0.3 | 1 | NB * | NB * | NB * | NB * |
| H4H12890P | 212 ± 0.8 | 1 | NB * | NB * | NB * | NB * |
| H4H12899P | 183 ± 0 | 51 | 9.06E+04 | 1.67E−03 | 1.84E−08 | 7 |
| H4H12900P | 240 ± 0.6 | 76 | 1.24E+05 | 4.67E−04 | 3.76E−09 | 25 |
| H4H12908P | 262 ± 6.7 | 25 | 3.41E+04 | 3.67E−03 | 1.08E−07 | 3.1 |
| H4H12913P2 | 176 ± 0.5 | 1 | NB * | NB * | NB * | NB * |
| H4H12922P2 | 213 ± 1.8 | 2 | NB * | NB * | NB * | NB * |
| H4H12924P2 | 230 ± 0.3 | 2 | NB * | NB * | NB * | NB * |
| H4H12926P2 | 231 ± 04 | 0 | NB * | NB * | NB * | NB * |
| H4H12927P2 | 147 ± 0.2 | 1 | NB * | NB * | NB * | NB * |
| H4H12934P2 | 354 ± 2.1 | 0 | NB * | NB * | NB * | NB * |
| H4H13538P | 157 ± 0.5 | 4 | NB * | NB * | NB * | NB * |
| H4H13541P | 199 ± 0.7 | 5 | NB * | NB * | NB * | NB * |
| H4H13544P2 | 273 ± 0.3 | 3 | NB * | NB * | NB * | NB * |
| H4H13545P2 | 322 ± 0.6 | 4 | NB * | NB * | NB * | NB * |

* NB indicates that no binding was observed under the current experimental conditions.

TABLE 3-8

Binding kinetics parameters of mIL-2Rg-MMH binding to IL-2Rγ monoclonal antibodies at 37° C.

| mAb Captured | mAb Capture Level (RU) | 100 nM Ag Bound | ka (1/Ms) | kd (1/s) | K$_D$ (M) | t½ (min) |
|---|---|---|---|---|---|---|
| H4H12857P | 80 ± 0.2 | 1 | NB * | NB * | NB * | NB * |
| H4H12858P | 120 ± 0.8 | 0 | NB * | NB * | NB * | NB * |
| H4H12859P | 123 ± 0.5 | 0 | NB * | NB * | NB * | NB * |
| H4H12863P | 208 ± 2.1 | 0 | NB * | NB * | NB * | NB * |
| H4H12871P | 196 ± 1.3 | −1 | NB * | NB * | NB * | NB * |
| H4H12874P | 132 ± 1.3 | 0 | NB * | NB * | NB * | NB * |
| H4H12884P | 235 ± 1.3 | 1 | NB * | NB * | NB * | NB * |
| H4H12886P | 105 ± 0.8 | −2 | NB * | NB * | NB * | NB * |
| H4H12889P | 97 ± 0.8 | 0 | NB * | NB * | NB * | NB * |
| H4H12890P | 108 ± 0.9 | 1 | NB * | NB * | NB * | NB * |
| H4H12899P | 87 ± 0.4 | 19 | 1.93E+05 | 1.08E−02 | 5.59E−08 | 1.1 |
| H4H12900P | 154 ± 0.6 | 32 | 5.19E+05 | 3.17E−03 | 6.11E−09 | 4 |
| H4H12908P | 135 ± 0.1 | 6 | 7.57E+04 | 2.93E−02 | 3.87E−07 | 0.4 |
| H4H12913P2 | 91 ± 0 | 0 | NB * | NB * | NB * | NB * |
| H4H12922P2 | 104 ± 0.9 | 2 | NB * | NB * | NB * | NB * |
| H4H12924P2 | 114 ± 0.5 | −1 | NB * | NB * | NB * | NB * |
| H4H12926P2 | 84 ± 0.5 | 0 | NB * | NB * | NB * | NB * |
| H4H12927P2 | 61 ± 0 | 1 | NB * | NB * | NB * | NB * |
| H4H12934P2 | 182 ± 0.5 | −1 | NB * | NB * | NB * | NB * |
| H4H13538P | 232 ± 0.8 | 5 | NB * | NB * | NB * | NB * |
| H4H13541P | 281 ± 0.4 | 4 | NB * | NB * | NB * | NB * |
| H4H13544P2 | 361 ± 2.7 | 4 | NB * | NB * | NB * | NB * |
| H4H13545P2 | 407 ± 0.4 | 2 | NB * | NB * | NB * | NB * |

* NB indicates that no binding was observed under the current experimental conditions.

TABLE 3-9

Binding kinetics parameters of rat IL-2Rg-MMH binding to IL-2Rγ monoclonal antibodies at 25° C.

| mAb Captured | mAb Capture Level (RU) | 100 nM Ag Bound | ka (1/Ms) | kd (1/s) | K$_D$ (M) | t½(min) |
|---|---|---|---|---|---|---|
| H4H12857P | 178 ± 0.5 | 1 | NB * | NB * | NB * | NB * |
| H4H12858P | 174 ± 0 | 0 | NB * | NB * | NB * | NB * |
| H4H12859P | 190 ± 1 | 2 | NB * | NB * | NB * | NB * |
| H4H12863P | 279 ± 1.6 | 1 | NB * | NB * | NB * | NB * |
| H4H12871P | 283 ± 0.4 | 1 | NB * | NB * | NB * | NB * |
| H4H12874P | 191 ± 0.6 | 1 | NB * | NB * | NB * | NB * |
| H4H12884P | 355 ± 1.3 | 4 | NB * | NB * | NB * | NB * |
| H4H12886P | 160 ± 0.9 | 3 | NB * | NB * | NB * | NB * |
| H4H12889P | 208 ± 0.2 | 1 | NB * | NB * | NB * | NB * |
| H4H12890P | 211 ± 0.2 | 0 | NB * | NB * | NB * | NB * |
| H4H12899P | 183 ± 0.4 | 39 | 7.04E+04 | 1.53E−03 | 2.17E−08 | 8 |
| H4H12900P | 239 ± 0.8 | 57 | 1.03E+05 | 6.19E−04 | 6.02E−09 | 19 |
| H4H12908P | 261 ± 0.3 | 19 | 2.98E+04 | 2.37E−03 | 7.93E−08 | 5 |
| H4H12913P2 | 176 ± 0.3 | 1 | NB * | NB * | NB * | NB * |
| H4H12922P2 | 213 ± 0.1 | 3 | NB * | NB * | NB * | NB * |
| H4H12924P2 | 229 ± 0.8 | 3 | NB * | NB * | NB * | NB * |
| H4H12926P2 | 230 ± 0.6 | 2 | NB * | NB * | NB * | NB * |
| H4H12927P2 | 147 ± 0 | 2 | NB * | NB * | NB * | NB * |
| H4H12934P2 | 354 ± 6.6 | 1 | NB * | NB * | NB * | NB * |
| H4H13538P | 157 ± 0.2 | 3 | NB * | NB * | NB * | NB * |
| H4H13541P | 198 ± 0 | 4 | NB * | NB * | NB * | NB * |
| H4H13544P2 | 274 ± 0.1 | 3 | NB * | NB * | NB * | NB * |
| H4H13545P2 | 320 ± 1 | 4 | NB * | NB * | NB * | NB * |

* NB indicates that no binding was observed under the current experimental conditions.

TABLE 3-10

Binding kinetics parameters of rat IL-2Rg-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 79 ± 0.8 | 1 | NB * | NB * | NB * | NB * |
| H4H12858P | 117 ± 1.2 | 0 | NB * | NB * | NB * | NB * |
| H4H12859P | 121 ± 1.3 | 1 | NB * | NB * | NB * | NB * |
| H4H12863P | 199 ± 3.7 | 0 | NB * | NB * | NB * | NB * |
| H4H12871P | 190 ± 3.4 | 1 | NB * | NB * | NB * | NB * |
| H4H12874P | 128 ± 0.9 | 3 | NB * | NB * | NB * | NB * |
| H4H12884P | 231 ± 1.5 | 4 | NB * | NB * | NB * | NB * |
| H4H12886P | 103 ± 0.6 | 4 | NB * | NB * | NB * | NB * |
| H4H12889P | 95 ± 0.7 | 2 | NB * | NB * | NB * | NB * |
| H4H12890P | 107 ± 0.6 | 0 | NB * | NB * | NB * | NB * |
| H4H12899P | 86 ± 1.3 | 16 | 1.46E+05 | 7.53E−03 | 5.16E−08 | 1.5 |
| H4H12900P | 152 ± 0.3 | 27 | 4.17E+05 | 3.63E−03 | 8.70E−09 | 3.2 |
| H4H12908P | 134 ± 1.3 | 8 | 3.89E+04 | 8.35E−03 | 2.15E−07 | 1.4 |
| H4H12913P2 | 90 ± 0.5 | 3 | NB * | NB * | NB * | NB * |
| H4H12922P2 | 102 ± 0.3 | 5 | NB * | NB * | NB * | NB * |
| H4H12924P2 | 113 ± 0.7 | 3 | NB * | NB * | NB * | NB * |
| H4H12926P2 | 83 ± 0.8 | 2 | NB * | NB * | NB * | NB * |
| H4H12927P2 | 60 ± 0.2 | 1 | NB * | NB * | NB * | NB * |
| H4H12934P2 | 180 ± 1.4 | 0 | NB * | NB * | NB * | NB * |
| H4H13538P | 233 ± 0.3 | 5 | NB * | NB * | NB * | NB * |
| H4H13541P | 282 ± 0.1 | 5 | NB * | NB * | NB * | NB * |
| H4H13544P2 | 361 ± 2.2 | 4 | NB * | NB * | NB * | NB * |
| H4H13545P2 | 408 ± 0.7 | 3 | NB * | NB * | NB * | NB * |

* NB indicates that no binding was observed under the current experimental conditions.

TABLE 3-11

Binding kinetics parameters of hIL-2Rg_D1-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 181 ± 0.7 | 0 | NB * | NB * | NB * | NB * |
| H4H12858P | 178 ± 0.2 | 1 | NB * | NB * | NB * | NB * |
| H4H12859P | 192 ± 0.4 | 0 | NB * | NB * | NB * | NB * |
| H4H12863P | 291 ± 4.5 | 55 | 1.14E+05 | 5.38E−04 | 4.74E−09 | 21 |
| H4H12871P | 287 ± 3.2 | 47 | 9.40E+04 | 1.11E−03 | 1.18E−08 | 10 |
| H4H12874P | 196 ± 1.2 | 0 | NB * | NB * | NB * | NB * |
| H4H12884P | 364 ± 0.5 | 51 | 1.66E+05 | 1.96E−03 | 1.18E−08 | 6 |
| H4H12886P | 164 ± 0.7 | 0 | NB * | NB * | NB * | NB * |
| H4H12889P | 213 ± 0.6 | 38 | 2.00E+05 | 1.07E−03 | 5.34E−09 | 11 |
| H4H12890P | 217 ± 0.6 | 1 | NB * | NB * | NB * | NB * |
| H4H12899P | 187 ± 0.4 | 0 | NB * | NB * | NB * | NB * |
| H4H12900P | 246 ± 1.9 | 0 | NB * | NB * | NB * | NB * |
| H4H12908P | 264 ± 2.5 | 1 | NB * | NB * | NB * | NB * |
| H4H12913P2 | 180 ± 0.6 | 0 | NB * | NB * | NB * | NB * |
| H4H12922P2 | 216 ± 0.4 | 50 | 2.52E+05 | 8.39E−04 | 3.32E−09 | 14 |
| H4H12924P2 | 234 ± 1 | 1 | NB * | NB * | NB * | NB * |
| H4H12926P2 | 235 ± 0.5 | 8 | 1.40E+05 | 2.73E−02 | 1.95E−07 | 0.4 |
| H4H12927P2 | 150 ± 0.4 | 0 | NB * | NB * | NB * | NB * |
| H4H12934P2 | 359 ± 2.9 | 15 | 5.53E+04 | 1.09E−02 | 1.97E−07 | 1.1 |
| H4H13538P | 155 ± 0.8 | 2 | NB * | NB * | NB * | NB * |
| H4H13541P | 199 ± 0.2 | 2 | NB * | NB * | NB * | NB * |
| H4H13544P2 | 273 ± 0.7 | 24 | 3.58E+04 | 2.07E−03 | 5.78E−08 | 6 |
| H4H13545P2 | 322 ± 0.6 | 8 | NB * | NB * | NB * | NB * |

* NB indicates that no binding was observed under the current experimental conditions.

TABLE 3-12

Binding kinetics parameters of hIL-2Rg_D1-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 88 ± 0.5 | 1 | NB * | NB * | NB * | NB * |
| H4H12858P | 143 ± 2.7 | 1 | NB * | NB * | NB * | NB * |
| H4H12859P | 149 ± 3.4 | 0 | NB * | NB * | NB * | NB * |
| H4H12863P | 237 ± 7.1 | 39 | 2.54E+05 | 2.21E−03 | 8.69E−09 | 5 |
| H4H12871P | 231 ± 3.5 | 33 | 1.70E+05 | 3.60E−03 | 2.12E−08 | 3.2 |
| H4H12874P | 157 ± 3.2 | 1 | NB * | NB * | NB * | NB * |
| H4H12884P | 276 ± 5.1 | 32 | 1.34E+05 | 4.42E−03 | 3.29E−08 | 2.6 |
| H4H12886P | 127 ± 2.5 | 0 | NB * | NB * | NB * | NB * |
| H4H12889P | 112 ± 1.3 | 16 | 2.54E+05 | 5.07E−03 | 2.00E−08 | 2.3 |
| H4H12890P | 122 ± 1.1 | 2 | NB * | NB * | NB * | NB * |
| H4H12899P | 101 ± 1.4 | 1 | NB * | NB * | NB * | NB * |
| H4H12900P | 169 ± 1.7 | 2 | NB * | NB * | NB * | NB * |
| H4H12908P | 153 ± 1.8 | 0 | NB * | NB * | NB * | NB * |
| H4H12913P2 | 104 ± 1.2 | 1 | NB * | NB * | NB * | NB * |
| H4H12922P2 | 118 ± 1.4 | 26 | 4.07E+05 | 1.68E−03 | 4.13E−09 | 7 |
| H4H12924P2 | 129 ± 1.6 | −1 | NB * | NB * | NB * | NB * |
| H4H12926P2 | 96 ± 1.3 | 2 | NB * | NB * | NB * | NB * |
| H4H12927P2 | 68 ± 0.7 | 1 | NB * | NB * | NB * | NB * |
| H4H12934P2 | 204 ± 1.8 | 4 | 9.21E+05 | 1.09E−01 | 1.19E−07 | 0.1 |
| H4H13538P | 231 ± 0.6 | 2 | NB * | NB * | NB * | NB * |
| H4H13541P | 282 ± 0.3 | 2 | NB * | NB * | NB * | NB * |
| H4H13544P2 | 363 ± 1.8 | 22 | 4.64E+04 | 1.05E−02 | 2.25E−07 | 1.1 |
| H4H13545P2 | 408 ± 0.9 | 4 | NB * | NB * | NB * | NB * |

* NB indicates that no binding was observed under the current experimental conditions.

TABLE 3-13

Binding kinetics parameters of hIL-2Rg_D2-MMH binding to IL-2Rγ monoclonal antibodies at 25° C.

| mAb Captured | mAb Capture Level (RU) | 100 nM Ag Bound | ka (1/Ms) | kd (1/s) | $K_D$ (M) | t½ (min) |
|---|---|---|---|---|---|---|
| H4H12857P | 181 ± 1 | 6 | 2.60E+05 | 7.56E−02 | 2.91E−07 | 0.2 |
| H4H12858P | 177 ± 0.3 | 0 | NB * | NB * | NB * | NB * |
| H4H12859P | 191 ± 0.6 | −1 | NB * | NB * | NB * | NB * |
| H4H12863P | 281 ± 1.7 | 0 | NB * | NB * | NB * | NB * |
| H4H12871P | 285 ± 1.2 | 0 | NB * | NB * | NB * | NB * |
| H4H12874P | 194 ± 1.3 | 10 | 2.03E+05 | 4.35E−02 | 2.14E−07 | 0.3 |
| H4H12884P | 360 ± 1.2 | 1 | NB * | NB * | NB * | NB * |
| H4H12886P | 162 ± 0.5 | 35 | 2.76E+05 | 1.48E−04 | 5.35E−10 | 78 |
| H4H12889P | 211 ± 0.5 | 0 | NB * | NB * | NB * | NB * |
| H4H12890P | 215 ± 0.4 | −1 | NB * | NB * | NB * | NB * |
| H4H12899P | 186 ± 1 | −1 | NB * | NB * | NB * | NB * |
| H4H12900P | 244 ± 0.6 | 0 | NB * | NB * | NB * | NB * |
| H4H12908P | 263 ± 1.5 | −1 | NB * | NB * | NB * | NB * |
| H4H12913P2 | 179 ± 0.4 | 37 | 2.56E+05 | 7.08E−04 | 2.76E−09 | 16 |
| H4H12922P2 | 215 ± 1 | 2 | NB * | NB * | NB * | NB * |
| H4H12924P2 | 233 ± 1.1 | 1 | NB * | NB * | NB * | NB * |
| H4H12926P2 | 233 ± 0.4 | 0 | NB * | NB * | NB * | NB * |
| H4H12927P2 | 149 ± 0.5 | 14 | 2.38E+05 | 1.66E−02 | 6.99E−08 | 0.7 |
| H4H12934P2 | 358 ± 0.6 | −1 | NB * | NB * | NB * | NB * |
| H4H13538P | 156 ± 0.5 | 6 | NB * | NB * | NB * | NB * |
| H4H13541P | 199 ± 0.2 | 10 | NB * | NB * | NB * | NB * |
| H4H13544P2 | 273 ± 0.3 | 5 | NB * | NB * | NB * | NB * |
| H4H13545P2 | 321 ± 0.3 | 5 | NB * | NB * | NB * | NB * |

* NB indicates that no binding was observed under the current experimental conditions.

TABLE 3-14

Binding kinetics parameters of hIL-2Rg_D2-MMH binding to IL-2Rγ monoclonal antibodies at 37° C.

| mAb Captured | mAb Capture Level (RU) | 100 nM Ag Bound | ka (1/Ms) | kd (1/s) | $K_D$ (M) | $t^{1/2}$ (min) |
|---|---|---|---|---|---|---|
| H4H12857P | 85 ± 0.5 | 0 | NB * | NB * | NB * | NB * |
| H4H12858P | 134 ± 2 | −1 | NB * | NB * | NB * | NB * |
| H4H12859P | 140 ± 2 | −1 | NB * | NB * | NB * | NB * |
| H4H12863P | 226 ± 4.4 | −1 | NB * | NB * | NB * | NB * |
| H4H12871P | 217 ± 3.4 | −1 | NB * | NB * | NB * | NB * |
| H4H12874P | 147 ± 2.4 | 2 | NB * | NB * | NB * | NB * |
| H4H12884P | 261 ± 3.8 | 2 | NB * | NB * | NB * | NB * |
| H4H12886P | 119 ± 1.9 | 26 | 3.31E+04 | 3.77E−04 | 1.14E−08 | 31 |
| H4H12889P | 106 ± 1.2 | 0 | NB * | NB * | NB * | NB * |
| H4H12890P | 117 ± 1.5 | 1 | NB * | NB * | NB * | NB * |
| H4H12899P | 96 ± 1.4 | 0 | NB * | NB * | NB * | NB * |
| H4H12900P | 164 ± 2.3 | 1 | NB * | NB * | NB * | NB * |
| H4H12908P | 145 ± 2.6 | −1 | NB * | NB * | NB * | NB * |
| H4H12913P2 | 99 ± 0.9 | 16 | 2.66E+05 | 3.37E−03 | 1.27E−08 | 3.4 |
| H4H12922P2 | 113 ± 1.4 | 3 | NB * | NB * | NB * | NB * |
| H4H12924P2 | 124 ± 1.6 | 0 | NB * | NB * | NB * | NB * |
| H4H12926P2 | 91 ± 1.3 | 0 | NB * | NB * | NB * | NB * |
| H4H12927P2 | 66 ± 0.5 | 2 | NB * | NB * | NB * | NB * |
| H4H12934P2 | 196 ± 2.9 | −1 | NB * | NB * | NB * | NB * |
| H4H13538P | 234 ± 4.8 | 6 | NB * | NB * | NB * | NB * |
| H4H13541P | 282 ± 0.6 | 7 | NB * | NB * | NB * | NB * |
| H4H13544P2 | 363 ± 2 | 4 | NB * | NB * | NB * | NB * |
| H4H13545P2 | 409 ± 0.6 | 3 | NB * | NB * | NB * | NB * |

* NB indicates that no binding was observed under the current experimental conditions.

Example 4: Octet Cross-Competition Between Different Anti-IL-2Rγ Monoclonal Antibodies Binding competition between a panel of anti-IL2Rγ monoclonal antibodies was determined using a real time, label-free bio-layer interferometry assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH 7.4 (HBS-EBT) buffer using a plate shaker speed of 1000 rpm. To assess whether 2 antibodies competed with one another for binding to their respective epitopes on human IL2Rγ extracellular domain expressed with a C-terminal myc-myc-hexahistidine tag (hIL-2Rg-MMH; SEQ ID: 379), anti-Penta-His antibody coated Octet biosensor tips (Fortebio Inc, #18-5122) were used to capture ~0.27 nM hIL-2Rg-MMH by submerging the biosensor tips for 3 minutes in wells containing 10 µg/mL hIL-2Rg-MMH. The antigen captured biosensor tips were then saturated with a first anti-IL2Rγ monoclonal antibody (subsequently referred to as mAb-1) by dipping into wells containing 50 µg/mL mAb-1 for 300 seconds. The biosensor tips were then subsequently dipped into wells containing 50 µg/mL of a second anti-IL2Rγ monoclonal antibody (subsequently referred to as mAb-2) for 240 seconds. Biosensor tips were washed in HBS-ETB buffer between every step of the experiment. The real-time binding response was monitored over the entire course of the experiment and the binding response at the end of every step was recorded. The response of mAb-2 binding to hIL-2Rg-MMH pre-complexed with mAb-1 was compared and competitive/non-competitive behavior of different anti-IL2Rγ monoclonal antibodies was determined as shown in Table 4-1.

TABLE 4-1

Cross-competition between anti-IL-2Rg monoclonal antibodies.

| mAb-1 | mAb-2 Competing with mAb-1 |
|---|---|
| H4H12889P | H4H12922P2 |
| H4H12922P2 | H4H12889P |
| H4H12863P | H4H12871P |
|  | H4H12884P |
|  | H4H12926P2 |
|  | H4H12934P2 |
| H4H12871P | H4H12863P |
|  | H4H12884P |
|  | H4H12926P2 |
|  | H4H12934P2 |
| H4H12884P | H4H12863P |
|  | H4H12871P |
|  | H4H12926P2 |
|  | H4H12934P2 |
| H4H12926P2 | H4H12863P |
|  | H4H12871P |
|  | H4H12884P |
|  | H4H12934P2 |
| H4H12934P2 | H4H12863P |
|  | H4H12871P |
|  | H4H12884P |
|  | H4H12926P2 |
| H4H12899P | H4H12900P |
|  | H4H12908P |
|  | H4H12858P |
| H4H12900P | H4H12899P |
|  | H4H12908P |
|  | H4H12858P |
| H4H12908P | H4H12899P |
|  | H4H12900P |
|  | H4H12858P |
| H4H12858P | H4H12899P |
|  | H4H12900P |
|  | H4H12908P |
| H4H12924P2 | H4H12899P |
|  | H4H12900P |
|  | H4H12908P |
|  | H4H12858P |

TABLE 4-1-continued

Cross-competition between anti-IL-2Rg monoclonal antibodies.

| mAb-1 | mAb-2 Competing with mAb-1 |
|---|---|
|  | H4H12890P |
|  | H4H12859P |
|  | H4H12857P |
|  | H4H12874P |
|  | H4H12886P |
|  | H4H12913P2 |
|  | H4H12927P2 |
| H4H12890P | H4H12924P2 |
|  | H4H12859P |
|  | H4H12857P |
|  | H4H12874P |
|  | H4H12886P |
|  | H4H12913P2 |
|  | H4H12927P2 |
| H4H12859P | H4H12924P2 |
|  | H4H12890P |
|  | H4H12857P |
|  | H4H12874P |
|  | H4H12886P |
|  | H4H12913P2 |
|  | H4H12927P2 |
| H4H12857P | H4H12924P2 |
|  | H4H12890P |
|  | H4H12859P |
|  | H4H12874P |
|  | H4H12886P |
|  | H4H12913P2 |
|  | H4H12927P2 |
| H4H12874P | H4H12924P2 |
|  | H4H12890P |
|  | H4H12859P |
|  | H4H12857P |
|  | H4H12886P |
|  | H4H12913P2 |
|  | H4H12927P2 |
| H4H12886P | H4H12924P2 |
|  | H4H12890P |
|  | H4H12859P |
|  | H4H12857P |
|  | H4H12874P |
|  | H4H12913P2 |
|  | H4H12927P2 |
| H4H12913P2 | H4H12924P2 |
|  | H4H12890P |
|  | H4H12859P |
|  | H4H12857P |
|  | H4H12874P |
|  | H4H12886P |
|  | H4H12927P2 |
| H4H12927P2 | H4H12924P2 |
|  | H4H12890P |
|  | H4H12859P |
|  | H4H12857P |
|  | H4H12874P |
|  | H4H12886P |
|  | H4H12913P2 |

Example 5: Flow Cytometry Analysis of STAT Phosphorylation in Human CD4+ T Cells (Human PBMCs)

To assess the in vitro characteristics of IL2Rγ antibodies of the invention, their ability to block CD4+ T cell activation induced by IL-2, IL-4, IL-7, IL-15 and IL-21 was measured by flow cytometry (BD™ Phosflow assay). BD™ Phosflow allows simultaneous analysis of intracellular phosphoprotein (such as STAT proteins) and cell surface markers to analyze cell signaling in discrete subpopulations of cells. This technology was used to analyze STAT phosphorylation in human CD4+ T cells upon stimulation with cytokines from the gamma c family.

Human peripheral blood mononuclear cells (PBMCs) were isolated from fresh whole blood (Bioreclammation-IVT) by density gradient centrifugation. K2 EDTA whole blood was diluted 1:1 in X-VIVO™ 15 media (Lonza), added to SepMate tubes (StemCell) containing FicollPaque-PLUS (Healthcare) and centrifuged to separate PBMCs. The above layer containing the PBMCs was transferred to a new tube and washed twice with DPBS (Life Technologies). PBMCs were then resuspended in X-VIVO™ 15 media at a concentration of ~$5.0 \times 10^6$ cells/mL, plated in 96-well plates (50 uL of cells/well; 250,000 cells/well) and incubated at 37° C. for 2 hours before adding the cytokines and antibodies.

Serial dilutions of antibodies (1:5) were prepared in pre-warmed X-VIVO™ 15 media and were added to the cells (50 uL), with final antibody concentrations starting from 400 nM. Fixed cytokine concentrations were prepared in pre-warmed X-VIVO™ 15 media and were added to the cells (100 uL), with a final concentration of 1 pM for IL-7 (R&D Systems), 50 pM for IL-4 (R&D Systems) and IL-21 (eBioscience), 0.5 nM for IL-15 (R&D Systems) and 10 nM IL-2 (R&D Systems); with a final volume per well of 200 uL.

For cytokine dose responses, serial dilutions for each cytokine (1:5) were also prepared in pre-warmed X-VIVO™ 15 media, with final cytokine concentrations starting from 5 nM for IL-4, IL-7 and IL-21, or from 50 nM for IL-2 and IL-15. First, 50 uL of X-VIVO™ 15 media were added to the cells followed by 100 uL of serial dilutions of cytokines, for a total volume per well of 200 uL. After addition of cytokines and antibodies to the cells, they were incubated at 37° C. for 15 minutes to allow PBMCs activation (STAT phosphorylation). The stimulation was then stopped by addition of 200 uL of warm Cytofix (BD) to each well, and cells were incubated for 10 minutes at 37° C. (fixation step). Cells were then washed twice with Stain Buffer (BD) and kept overnight at 4° C. The next day, cells were centrifuged and permeabilized by slowly adding 100 uL of cold Perm Buffer III (BD) to the pellets. Cells were incubated at 4° C. for 30 minutes, then washed twice with Stain Buffer. To enable the analysis of the CD4+ T cell population used to measure STAT phosphorylation, cells were stained with a mix of human FcR binding inhibitor (eBioscience; 1/10), anti-CD33-PE (BD; 1/200) anti-CD4-PacificBlue (BD; 1/200), anti-CD3-PECy7 (BD; 1/200) and the relevant anti-phospho-STAT-AlexaFluor647 (BD), prepared in Stain Buffer:

Anti-phosphoSTAT3 (1/10): for cells stimulated with IL-21,
Anti-phosphoSTAT5 (1/20): for cells stimulated with IL-2, IL-7 and IL-15,
Anti-phosphoSTAT6 (1/10): for cells stimulated with IL-4.

The samples were held at room temperature for 1 hour in the dark. The cells were then centrifuged and washed twice with Stain Buffer. Sample data were acquired on a LSR Fortessa X-20 cell analyzer using the HTS attachment (BD). Data analysis was performed using FlowJo X Software (Tree Star, OR). CD4+ T cells were defined as intact cells, singlets, CD33−, CD3+, CD4+; and STAT phosphorylation was analyzed within this cell population (MFI=mean fluorescence intensity).

Both H4H12889P and H4H12922P2 similarly and efficiently blocked STAT phosphorylation induced by all the cytokines tested in this assay (IL-2, IL-4, IL-7, IL-15 and IL-21), while H4H12874P, H4H12886P, H4H12857P as well as the comparator antibody COMP1499 (anti-IL2Rγ antibody CP.B8, see US2002/0028202) only partially blocked or didn't block cytokine-induced STAT phosphorylation.

TABLE 5-1

Anti-IL-2Rγ antibodies H4H12889P and H4H12922P2 blocking human IL-2-, IL-4-, IL7-, IL-15- and IL-21-induced STAT phosphorylation in human CD4+ T cells.

| IC50 [M] | IL-2 | IL-4 | IL-7 | IL-15 | IL-21 |
|---|---|---|---|---|---|
| Constant | 10 nM | 50 pM | 1 pM | 0.5 nM | 50 pM |
| H4H12889P | 2.06E−09 | 1.10E−09 | 8.92E−10 | 2.55E−09 | 2.28E−09 |
| H4H12922P2 | 1.87E−09 | 8.54E−10 | 5.80E−10 | 2.46E−09 | 2.21E−09 |

*IC50 values measured for two antibodies are shown with various interleukins at the indicated concentrations.

See also FIG. 1 (A-E) wherein the level of STAT phosphorylation at each concentration of antibody tested is determined.

Example 6: Flow Cytometry Analysis of STAT3 Phosphorylation in In Vitro Differentiated Human Mast Cells To assess the in vitro characteristics of anti-IL2Rγ antibodies of the invention, their ability to block human mast cell activation induced by IL-9 was measured by flow cytometry (BD™ Phosflow assay). We used this technology to look at STAT3 phosphorylation in in vitro differentiated human mast cells upon stimulation with human IL-9.

Briefly, human mast cells were in vitro generated from bone marrow CD133+ progenitor cells cultured in StemSpan serum free medium supplemented with human SCF, IL-6 and IL-3 for 6 weeks.

Human mast cells were resuspended in X-VIVO™ 15 media at a concentration of ~4.0×10$^6$ cells/mL, plated in 96-well plates (50 uL of cells/well; 200,000 cells/well) and incubated at 37° C. for 2 hours before adding the cytokines and antibodies.

Serial dilutions of antibodies (1:5) were prepared in pre-warmed X-VIVO™ 15 media and were added to the cells (50 uL), with final antibody concentrations starting from 400 nM. A fixed IL-9 (R&D) concentration was prepared in pre-warmed X-VIVO™ 15 media and was added to the cells (100 uL), with a final concentration of 2 nM; with a final volume per well of 200 uL.

For the cytokine dose response, serial dilutions of IL-9 (1:5) were also prepared in pre-warmed X-VIVO™ 15 media with final cytokine concentrations starting from 100 nM. First, 50 uL of X-VIVO™ 15 media were added to the cells followed by 100 uL of serial dilutions of cytokines, for a total volume per well of 200 uL.

After addition of cytokines and antibodies to the cells, they were incubated at 37° C. for 15 minutes to allows mast cell activation (as measured by STAT3 phosphorylation). The stimulation was then stopped by addition of 200 uL of warm Cytofix (BD) to each well, and cells were incubated for 10 minutes at 37° C. (fixation step). Cells were then washed twice with Stain Buffer (BD) and kept overnight at 4° C. The next day, cells were centrifuged and permeabilized by slowly adding 100 uL of cold Perm Buffer III (BD) to the pellets. Cells were incubated at 4° C. for 30 minutes, then washed twice with Stain Buffer. Mast cells were then stained with a mix of human FcR binding inhibitor (eBioscience; 1/10), anti-c-Kit-PE (BD; 1/100) and anti-phospho-STAT3-AlexaFluor647 (BD; 1/10), prepared in Stain Buffer.

The samples were held at room temperature for 1 hour in the dark. The cells were then centrifugated and washed twice with Stain Buffer. Sample data were acquired on a LSR Fortessa X-20 cell analyzer using the HTS attachment (BD). Data analysis was performed using FlowJo X Software (Tree Star, OR). Mast cells were defined as intact cells, singlets, c-Kit+; and STAT3 phosphorylation was analyzed within this cell population (MFI=mean fluorescence intensity).

Both H4H12889P and H4H12922P2 similarly and efficiently blocked STAT3 phosphorylation induced by IL-9.

TABLE 6-1

Anti-IL-2Ry antibodies H4H12889P and H4H12922P2 blocking human IL-9- induced STAT3 phosphorylation in in vitro differentiated human mast cells.

| IC50 [M] | IL-9 |
|---|---|
| Constant | 2 nM |
| H4H12889P | 4.41E−10 |
| H4H12922P2 | 4.16E−10 |

*IC50 values measured for two antibodies are shown when IL-9 concentration was 2 nM.

Figure 2:
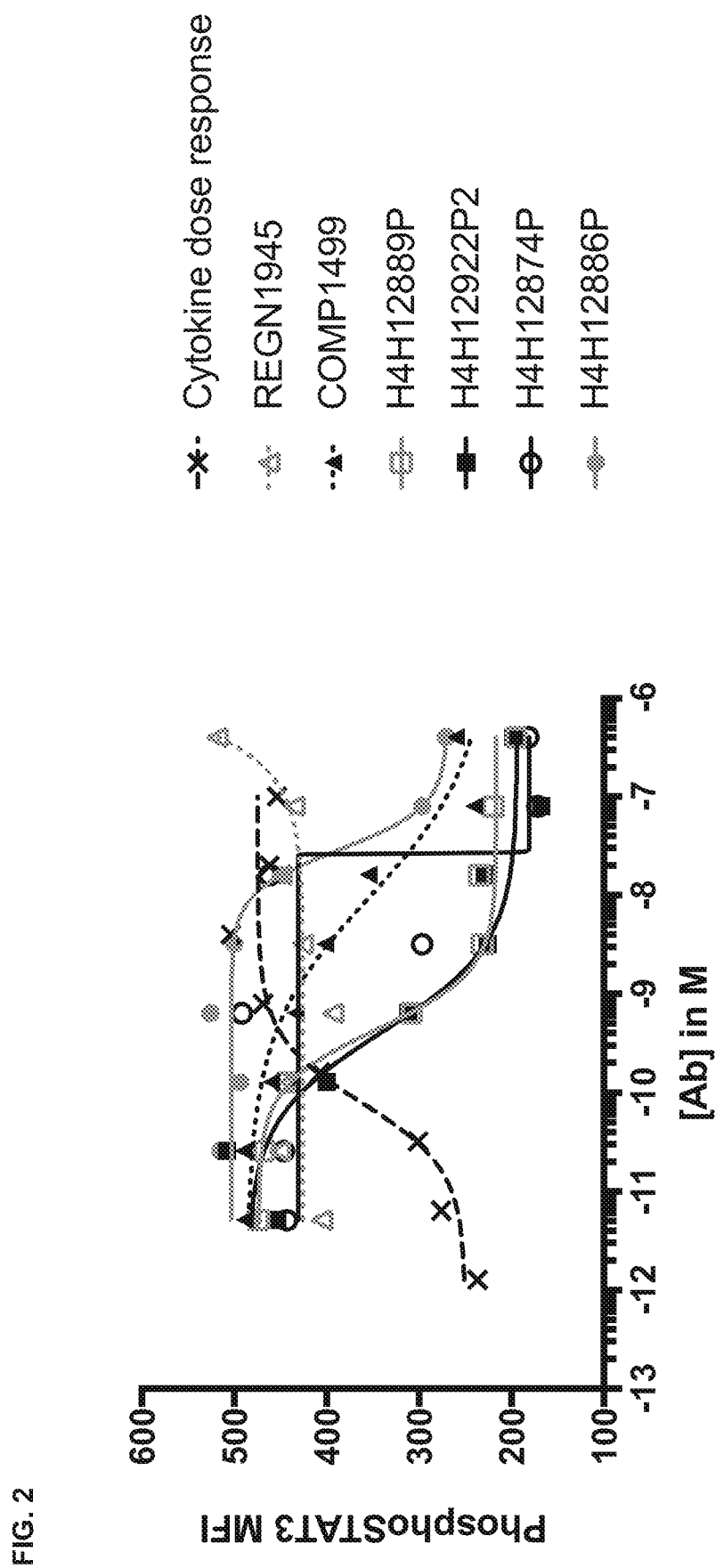
FIG. 2. Blocking human IL-9-induced STAT3 phosphorylation in in vitro differentiated human mast cells by anti-IL-2Rgamma antibodies H4H12874P, H4H12886P, H4H12889P, H4H12922P2; and antibodies COMP1499 and REGN1945.

See also FIG. 2 wherein the level of IL-9 induced STAT phosphorylation at each concentration of antibody tested is determined.

Example 7: Monoclonal Antibody Testing in In Vivo Model; Xenogeneic Acute Graft Versus Host Disease Model to Assess the Blocking Activity of IL-2Rgamma Antibodies as a Therapeutic Treatment To determine the effect of our anti-IL2Rγ antibodies, H4H12889P and H4H12922P2, along with the comparator IL-2Rγ antibody COMP1499, in a relevant in vivo model, a xenogeneic acute Graft versus Host Disease (GvHD) study was conducted. Briefly, to induce GvHD in mice, human peripheral blood mononuclear cells (huPBMCs) were injected into NOD-scid IL2rγ$^{null}$ (NSG) mice (Jackson Lab). Upon engraftment, human immune cells recognize the mouse host as xenogeneic and mount a vigorous immune response against its tissues.

In this experiment, NSG mice (Jackson Lab) were retro-orbitally injected with 10 million huPBMCs (ReachBio) resuspended in DPBS (10 million cells/100 uL; 5 groups of 10 mice each). Briefly, human PBMCs were thawed the day of the injection in IMDM medium (Irvine Scientific) supplemented with 10% FBS (Seradigm) and incubated 2h at 37° C. in this supplemented medium. Cells were then washed in DPBS (Life Technologies) and resuspended at 10 million cells/100 uL for injection. A control group (10 mice) was retro-orbitally injected with 100 uL of PBS. Four groups of huPBMC-engrafted NSG mice were injected subcutaneously with 25 mg/kg of either H4H12889P, H4H12922P2, COMP1499, or an isotype control antibody (REGN1945; a human anti-*Felis domesticus* Fel d1 antibody (IgG4 (S108P)/kappa)) starting 3 weeks after huPBMC injection and then twice per week for 6 weeks. The experiment was terminated at day 161 post-huPBMC engraftment by sacrificing the remaining mice. Experimental dosing and treatment protocol for groups of mice are shown in Table 7-1.

TABLE 7-1

Experimental dosing and treatment protocol for groups of mice.

| Group | NSG mice | huPBMC injection | Antibody |
|---|---|---|---|
| 1 | 10 | None | None |
| 2 | 10 | 10 million | None |
| 3 | 10 | 10 million | Isotype control antibody (REGN1945) |
| 4 | 10 | 10 million | IL-2Rγ antibody (COMP1499) |
| 5 | 10 | 10 million | IL-2Rγ antibody (H4H12889P) |
| 6 | 10 | 10 million | IL-2Rγ antibody (H4H12922P2) |

During the full length of the experiment, mice were monitored twice weekly for weight loss and death (to assess the effect of therapeutic antibodies on survival). Human cell engraftment in blood as well as serum mouse and human cytokine levels were assessed at different timepoints, as shown in Table 7-2.

TABLE 7-2

Blood/serum collection dates and readouts.

| Day post huPBMC injection | Serum cytokine levels | Blood human cells |
|---|---|---|
| 14 | | + |
| 20 | + | |
| 35 | | + |
| 42 | + | |
| 56 | | + |
| 62 | + | |
| 104 | | + |
| 112 | + | |
| 148 | + | |
| 168 | | + |

Figure 3:
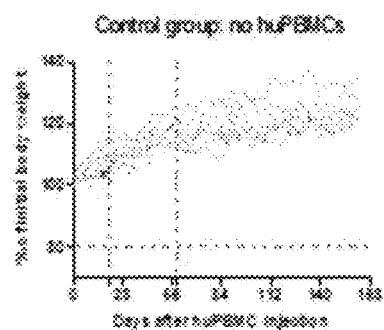
FIG. 3(A) is a graph showing percentage of initial body weight of mice in control experiments of mice not having human PBMCs.
FIG. 3(B) is a graph showing percentage of initial body weight of mice, having human PBMCs, in control experiments of mice administered no antibody.
FIG. 3(C) is a graph showing percentage of initial body weight of mice, having human PBMCs, in control experiments of mice administered isotype control antibody over time. The start of antibody injection on day 21 and the end of antibody injection on day 59 are indicated by dashed lines.
FIG. 3(D) is a graph showing percentage of initial body weight of mice, having human PBMCs, administered antibody COMP1499 over time. The start of antibody injection on day 21 and the end of antibody injection on day 59 are indicated by dashed lines.
FIG. 3(E) is a graph showing percentage of initial body weight of mice, having human PBMCs, administered anti-IL2R gamma antibody H4H12889P over time. The start of antibody injection on day 21 and the end of antibody injection on day 59 are indicated by dashed lines.
FIG. 3(F) is a graph showing percentage of initial body weight of mice, having human PBMCs, administered anti-IL2R gamma antibody H4H12922P2 over time. The start of antibody injection on day 21 and the end of antibody injection on day 59 are indicated by dashed lines.
Figure 3:
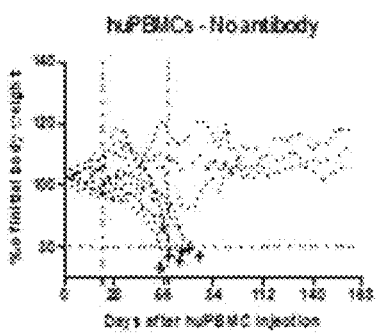
Figure 3:
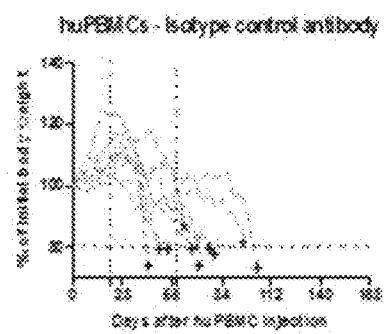
Figure 3:
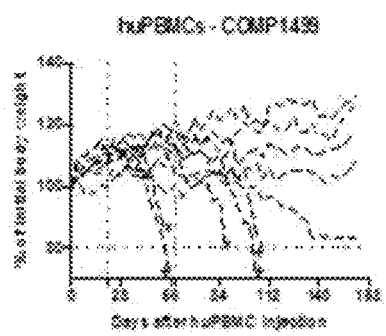
Figure 3:
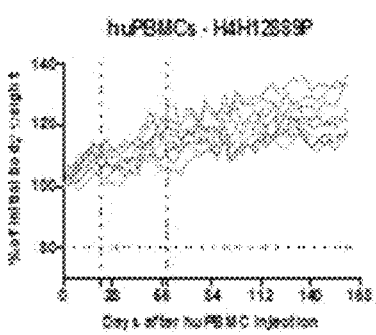
Figure 3:
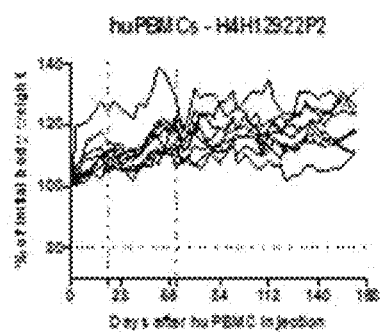
Figure 4:
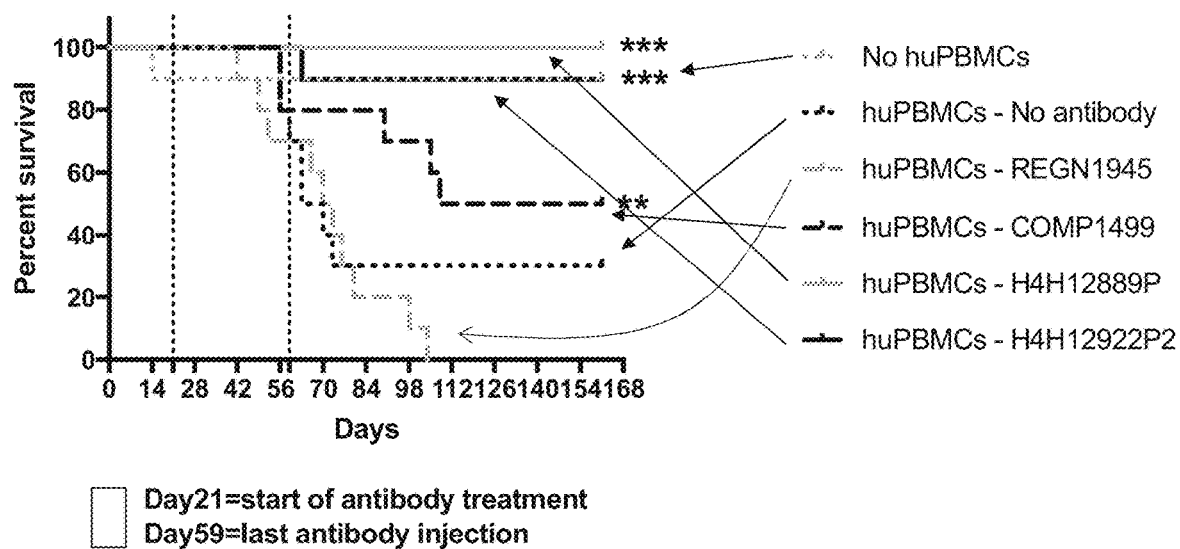
FIG. 4. Survival over time of mice injected with anti-IL2Rgamma antibodies H4H12889P and H4H12922P2, antibody COMP1499, antibody REGN1945 and no antibody are shown. No huPBMCs group is not depicted. Differences in animal survival relative to the isotype control antibody group were analyzed by a Mantel-Cox log-rank test. A P value<0.05 was considered statistically significant. , P value<0.0021; **, P value<0.0001. The start of antibody injection on day 21 and the end of antibody injection on day 59 are indicated by dashed lines.

During the full length of the experiment, mice were monitored twice weekly for weight loss (FIG. 3 (A-F); % of initial body weight at the day of huPBMC engraftment) and death (FIG. 4; to assess the effect of therapeutic antibodies on survival). Animals showing a weight loss of 20% of initial body weight were euthanized.

Blood samples from mice were collected into Microtainer tubes (BD, Cat #3659740) at different timepoints after huPBMC injection and human cell engraftment was assessed by looking at human absolute cell numbers in the blood by flow cytometry. Briefly, 50 uL of each blood sample were incubated in ACK lysis buffer (Gibco) for 5 min at room temperature to lyse red blood cells. Cells were then washed in DPBS, stained with LIVE/DEAD fixable dead stain (Invitrogen), washed in MACS buffer (Miltenyi Biotec), and labelled with a mix of antibodies (anti-human CD45, anti-human CD3, anti-human CD4 and anti-human CD8 [BD] diluted 1/50 in brilliant stain buffer [BD], together with human and mouse Fc inhibitor antibodies [eBioscience and BD, respectively]) used to identify human CD45$^+$ cells, T cells, CD4$^+$ T cells and CD8$^+$ T cells. Finally, samples were washed in MACS buffer, fixed in BD CytoFix (BD) and then resuspended in MACS buffer containing CountBright beads (Life Technologies) in order to calculate absolute cell numbers in each sample. Sample data were acquired on a LSR Fortessa X-20 cell analyzer using the HTS attachment (BD). Data analysis was performed using FlowJo X Software (Tree Star, OR). Human CD45$^+$ T cells were defined as live cells, singlets, CD45$^+$, and within this population CD4$^+$ T cells and CD8$^+$ T cells were further defined as CD3$^+$, CD4$^+$ and CD3$^+$, CD8$^+$, respectively.

TABLE 7-3

Blood human immune cells at day 35 and 56 post huPBMC injection (Mean ± SD in cells/uL of blood).

| Group: | CD45$^+$ cells | | T cells | | CD4$^+$ T cells | | CD8$^+$ T cells | |
|---|---|---|---|---|---|---|---|---|
| | D35 | D56 | D35 | D56 | D35 | D56 | D35 | D56 |
| 1. No huPBMCs | 0.07 ± 0.11 (n = 8) *** | 0.29 ± 0.37 (n = 8) *** | 0.02 ± 0.04 (n = 8) *** | 0.15 ± 0.36 (n = 8) *** | 0.01 ± 0.03 (n = 8) *** | 0.10 ± 0.28 (n = 8) *** | 0 ± 0 (n = 8) *** | 0.03 ± 0.08 (n = 8) *** |
| 2. huPBMCs- No antibody | 1801 ± 1910 (n = 8) | 5047 ± 6745 (n = 8) | 1722 ± 1784 (n = 8) | 5037 ± 6732 (n = 8) | 724 ± 800 (n = 8) | 3053 ± 4427 (n = 8) | 772.6 ± 865.2 (n = 8) | 1446 ± 1856 (n = 8) |
| 3. huPBMCs- Isotype control antibody | 2626 ± 2648 (n = 9) | 2549 ± 2094 (n = 6) | 2622 ± 2646 (n = 9) | 2544 ± 2090 (n = 6) | 1810 ± 2005 (n = 9) | 1505 ± 1354 (n = 6) | 638.6 ± 622 (n = 9) | 830.3 ± 706.1 (n = 6) |
| 4. huPBMCs- COMP1499 | 549.5 ± 637.5 (n = 10) | 2526 ± 5130 (n = 8) | 547.7 ± 636.1 (n = 10) | 2524 ± 5127 (n = 8) | 354.1 ± 415.2 (n = 10) | 2018 ± 4633 (n = 8) | 123.9 ± 130 (n = 10) | 370.1 ± 341.6 (n = 8) |
| 5. huPBMCs- H4H12889P | 7.79 ± 8.32 (n = 9) *** | 9.29 ± 18.16 (n = 10) ** | 7.57 ± 8.10 (n = 9) *** | 9.13 ± 18.16 (n = 10) ** | 5.33 ± 5.57 (n = 9) *** | 3.28 ± 3.57 (n = 10) ** | 1.49 ± 2.05 (n = 9) ** | 5.41 ± 14.71 (n = 10) ** |

TABLE 7-3-continued

Blood human immune cells at day 35 and 56 post huPBMC injection
(Mean ± SD in cells/uL of blood).

| | CD45+ cells | | T cells | | CD4+ T cells | | CD8+ T cells | |
|---|---|---|---|---|---|---|---|---|
| Group: | D35 | D56 | D35 | D56 | D35 | D56 | D35 | D56 |
| 6. huPBMCs-H4H12922P2 | 48.4 ± 65.76 (n = 10) * | 119.1 ± 301.5 (n = 10) | 48.14 ± 65.71 (n = 10) * | 118.8 ± 301.1 (n = 10) | 39.33 ± 57.03 (n = 10) * | 43.73 ± 82.06 (n = 10) | 6.71 ± 8.50 (n = 10) * | 73.6 ± 217.7 (n = 10) |

Note:
Statistical significance determined by Kruskal-Wallis One-way ANOVA with Dunn's multiple comparison post-hoc test is indicated (* = p < 0.05,  = p < 0.01, * = p < 0.001, compared to groups 3: huPBMCs-Isotype control antibody).
n = number of mice analyzed.

Figure 5:
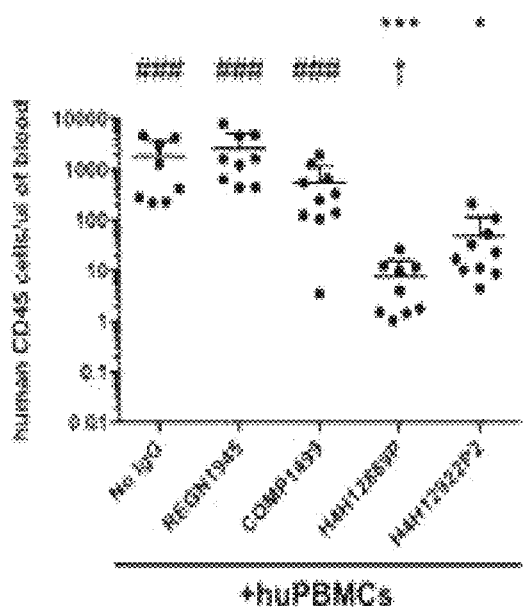
FIG. 5(A) is a graph showing absolute human cell numbers of human CD45 cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs—No IgG"; *, significantly different from group "huPBMCs—REGN1945". Each symbol represents a mouse. Zero values were arbitrarily changed by a value of 0.01 for graphing purposes (logarithmic scale).
FIG. 5(B) is a graph showing absolute human cell numbers of human T-cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs—No IgG"; *, significantly different from group "huPBMCs—REGN1945". Each symbol represents a mouse. Zero values were arbitrarily changed by a value of 0.01 for graphing purposes (logarithmic scale).
FIG. 5(C) is a graph showing absolute human cell numbers of human CD4 T-cells cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs—No IgG"; *, significantly different from group "huPBMCs—REGN1945". Each symbol represents a mouse. Zero values were arbitrarily changed by a value of 0.01 for graphing purposes (logarithmic scale).
FIG. 5(D) is a graph showing absolute human cell numbers of human CD8 T-cells in the blood at day 35 post huPBMC injection of mice administered no antibody (No IgG), REGN1945, COMP1499 or anti-IL2R gamma antibody H4H12889P or H4H12922P2. Group "No huPBMCs" is not shown; #, significantly different from group "No huPBMCs"; †, significantly different from group "huPBMCs—No IgG"; *, significantly different from group "huPBMCs—REGN1945". Each symbol represents a mouse. Zero values were arbitrarily changed by a value of 0.01 for graphing purposes (logarithmic scale).
Figure 5:
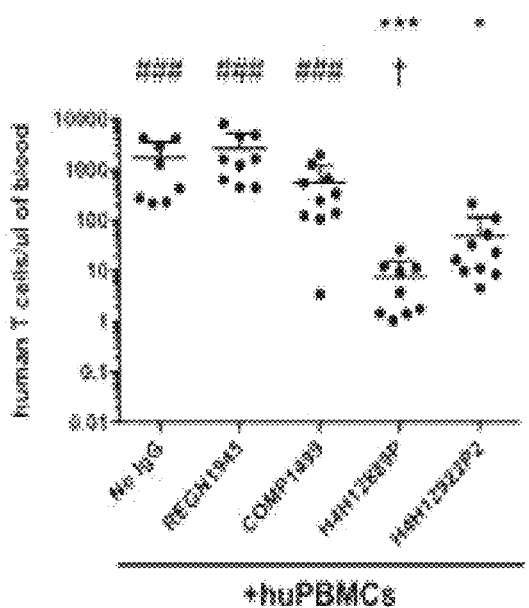
Figure 5:
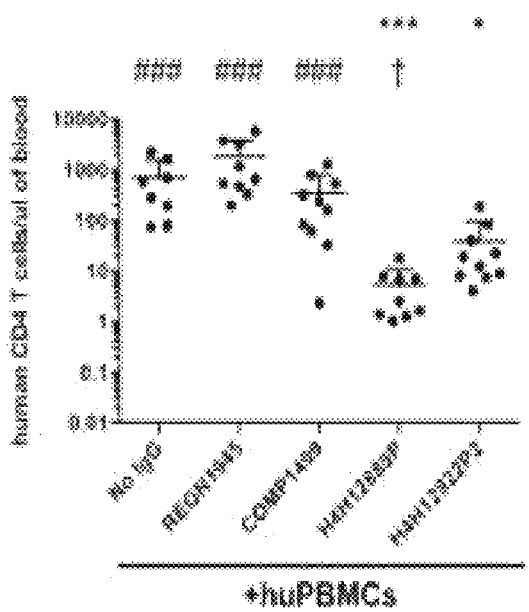
Figure 5:
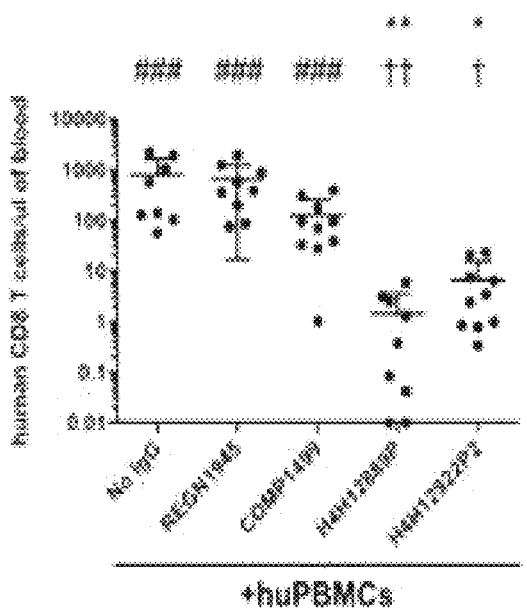
Figure 6:
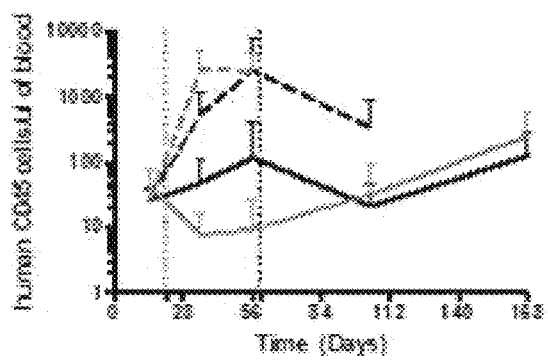
FIG. 6(A) is a graph showing blood counts of human CD45+ cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.
FIG. 6(B) is a graph showing blood counts of human T cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.
FIG. 6(C) is a graph showing blood counts of human CD4+ T cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.
FIG. 6(D) is a graph showing blood counts of human CD8+ T cells over time in mice administered anti-IL2R gamma antibody H4H12889P or H4H12922P2; or COMP1499 or isotype control antibody. The start of antibody injection on day 21 and the end of antibody injection on day 59 are indicated by dashed lines.
Figure 6:
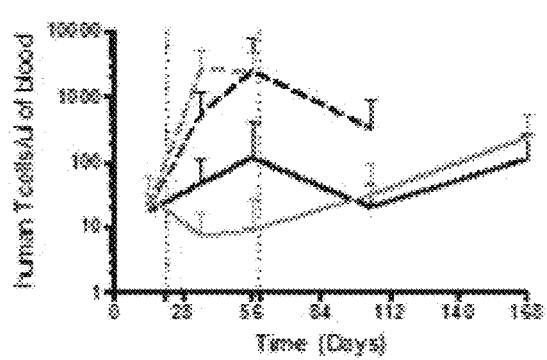
Figure 6:
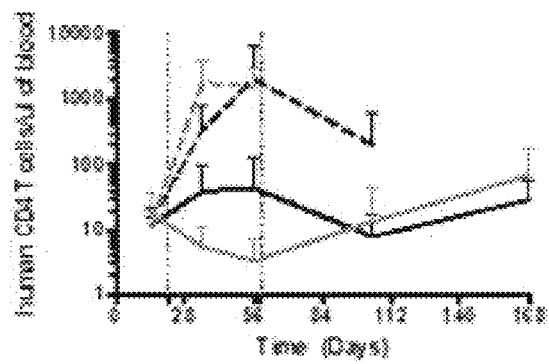
Figure 6:
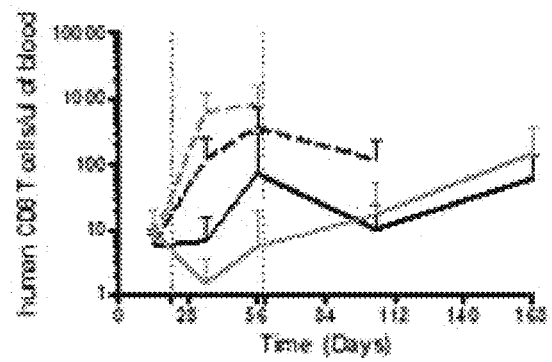

As an example, absolute human cell numbers in the blood at day 35 post huPBMC injection are shown in FIG. 5 (A-D). Blood counts of human CD45+ cells, T cells, CD4+ T cells and CD8+ T cells during time are shown in FIG. 6 (A-D).

Serum from mice was collected at different days after huPBMC injection and serum levels of mouse and human cytokines were assessed. Briefly, whole blood was collected into Microtainer tubes (BD, Cat #365967) and was allowed to clot by leaving it undisturbed at room temperature for at least 30 minutes. Clotted blood and cells were pelleted by centrifuging at 15,000×g for 10 minutes at 4° C. The resulting supernatant, designated serum, was transferred into clean plates and cytokine concentrations in the serum were measured using two Proinflammatory (mouse and human) multiplex immunoassay kits (Meso Scale Discovery), according to the manufacturer's instructions. PBS containing 0.05% (w/v) Tween-20 (Life Technologies) was used to wash the plates. Electrochemiluminescence was immediately read on a MSD Spector instrument. Data analysis was performed using FlowJo X Software (Tree Star, OR).

TABLE 7-4

Serum human cytokine concentrations at day 42 and 62 post huPBMC injection
(Mean ± SD in pg/mL).

| | hIFN-γ | | hTNFα | | hIL-6 | | hIL-8 | | hIL-10 | |
|---|---|---|---|---|---|---|---|---|---|---|
| Group: | D42 | D62 | D42 | D62 | D42 | D62 | D42 | D62 | D42 | D62 |
| 1. No huPBMCs | 0.62 ± 0.74 (n = 9) *** | 0.50 ± 0.94 (n = 9) *** | 0.04 ± 0.13 (n = 9) *** | 0.09 ± 0.15 (n = 9) ** | 0.02 ± 0.03 (n = 9) *** | 0.06 ± 0.04 (n = 9) ** | 0.05 ± 0.06 (n = 9) *** | 0.06 ± 0.10 (n = 9) *** | 0.00 ± 0.00 (n = 9) *** | 0.04 ± 0.05 (n = 9) *** |
| 2. huPBMCs-No antibody | 14617 ± 14370 (n = 10) | 18851 ± 11943 (n = 7) | 14.8 ± 10.09 (n = 10) | 13.25 ± 7.33 (n = 7) | 0.79 ± 0.58 (n = 10) | 0.32 ± 0.22 (n = 7) | 10.36 ± 10.1 (n = 10) | 4.70 ± 4.42 (n = 7) | 12.57 ± 7.70 (n = 10) | 8.17 ± 4.08 (n = 7) |
| 3. huPBMCs-Isotype control antibody | 14143 ± 6273 (n = 10) | 15369 ± 7915 (n = 7) | 14.2 ± 6.38 (n = 10) | 12.33 ± 5.86 (n = 7) | 2.28 ± 3.99 (n = 10) | 0.74 ± 0.49 (n = 7) | 8.89 ± 3.91 (n = 10) | 5.38 ± 2.97 (n = 7) | 16.39 ± 9.93 (n = 10) | 9.11 ± 4.25 (n = 7) |
| 4. huPBMCs-COMP1499 | 8891 ± 10438 (n = 10) | 8568 ± 8388 (n = 8) | 7.18 ± 6.16 (n = 10) | 6.61 ± 6.35 (n = 8) | 0.85 ± 0.65 (n = 10) | 0.25 ± 0.20 (n = 8) | 5.64 ± 5.06 (n = 10) | 2.73 ± 2.52 (n = 8) | 6.74 ± 4.41 (n = 10) | 8.17 ± 5.59 (n = 8) |
| 5. huPBMCs-H4H12889P | 418.6 ± 1315 (n = 10) *** | 126.1 ± 361.2 (n = 10) ** | 0.53 ± 1.67 (n = 10) *** | 0.20 ± 0.38 (n = 10) ** | 0.08 ± 0.12 (n = 10) *** | 0.05 ± 0.04 (n = 10) *** | 1.65 ± 1.61 (n = 10) ** | 0.3 ± 0.36 (n = 10) ** | 0.57 ± 1.79 (n = 10) *** | 0.49 ± 0.88 (n = 10) ** |
| 6. huPBMCs-H4H12922P2 | 31.66 ± 32.61 (n = 10) * | 42.86 ± 33.48 (n = 10) | 0.08 ± 0.18 (n = 10) *** | 0.22 ± 0.25 (n = 10) * | 0.12 ± 0.06 (n = 10) * | 0.06 ± 0.06 (n = 10) ** | 0.59 ± 0.43 (n = 10) | 0.42 ± 0.35 (n = 10) | 0.48 ± 0.55 (n = 10) ** | 0.65 ± 0.38 (n = 10) |

Note:
Statistical significance determined by Kruskal-Wallis One-way ANOVA with Dunn's multiple comparison post-hoc test is indicated (* = p < 0.05,  = p < 0.01, * = p < 0.001, compared to groups 3: huPBMCs-Isotype control antibody).
n = number of mice analyzed.

TABLE 7-5

Serum mouse cytokine concentrations at day 42 and 62 post huPBMC injection (Mean ± SD in pg/mL).

| Group: | mTNFα D42 | mTNFα D62 | mIL-6 D42 | mIL-6 D62 | mKC/GRO D42 | mKC/GRO D62 | mIL-10 D42 | mIL-10 D62 |
|---|---|---|---|---|---|---|---|---|
| 1. No huPBMCs | 5.31 ± 1.35 (n = 9) * | 9.44 ± 9.63 (n = 9) | 13.14 ± 4.24 (n = 9) ** | 16.09 ± 7.01 (n = 9) * | 33.02 ± 6.72 (n = 9) *** | 57.47 ± 21.14 (n = 9) | 6.16 ± 1.65 (n = 9) ** | 7.01 ± 1.96 (n = 9) ** |
| 2. huPBMCs-No antibody | 20.68 ± 10.72 (n = 10) | 25.83 ± 11.95 (n = 7) | 91.12 ± 48.9 (n = 10) | 50.42 ± 29.96 (n = 7) | 129.5 ± 51.28 (n = 10) | 76.51 ± 33.48 (n = 7) | 14.11 ± 5.75 (n = 10) | 18.3 ± 7.64 (n = 7) |
| 3. huPBMCs-Isotype control antibody | 20.7 ± 9.30 (n = 10) | 25.44 ± 11.31 (n = 7) | 77.91 ± 55.73 (n = 10) | 95.06 ± 35.59 (n = 7) | 106.8 ± 35.56 (n = 10) | 128.7 ± 93.29 (n = 7) | 15.47 ± 10.12 (n = 10) | 17.98 ± 4.05 (n = 7) |
| 4. huPBMCs-COMP1499 | 13.82 ± 6.96 (n = 10) | 20.96 ± 21 (n = 8) | 69.83 ± 49.04 (n = 10) | 32.67 ± 29.2 (n = 8) | 101 ± 60.19 (n = 10) | 88.56 ± 30.26 (n = 8) | 10.1 ± 4.67 (n = 10) | 12.21 ± 3.64 (n = 8) |
| 5. huPBMCs-H4H12889P | 4.43 ± 1.16 (n = 10) *** | 12.02 ± 13.94 (n = 10) | 12.4 ± 3.96 (n = 10) *** | 13.24 ± 7.64 (n = 10) ** | 40.22 ± 15.65 (n = 10) ** | 55.33 ± 34.05 (n = 10) * | 6.46 ± 1.21 (n = 10) ** | 7.22 ± 2.42 (n = 10) ** |
| 6. huPBMCs-H4H12922P2 | 6.45 ± 3.37 (n = 10) ** | 7.77 ± 5.28 (n = 10) * | 17.89 ± 8.94 (n = 10) | 14.78 ± 8.12 (n = 10) ** | 40.83 ± 8.6 (n = 10) * | 65.77 ± 74.79 (n = 10) * | 5.93 ± 0.90 (n = 10) *** | 8.69 ± 5.13 (n = 10) * |

Note:
Statistical significance determined by Kruskal-Wallis One-way ANOVA with Dunn's multiple comparison post-hoc test is indicated (* = p < 0.05,  = p < 0.01, * = p < 0.001, compared to groups 3: huPBMCs-Isotype control antibody).
n = number of mice analyzed.

Figure 7:
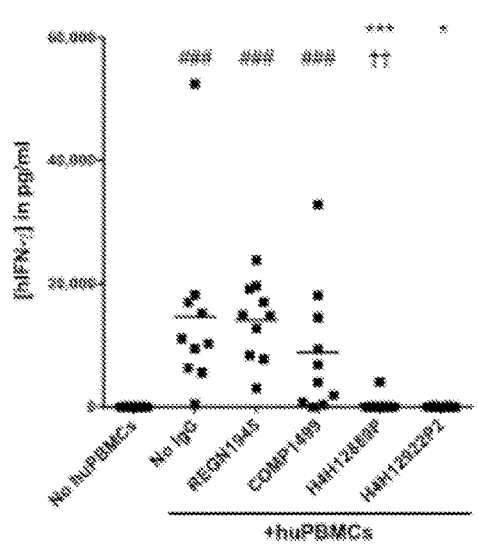
FIG. 7(A) is a graph showing serum levels of human interferon-gamma cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(B) is a graph showing serum levels of human TNF-alpha cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(C) is a graph showing serum levels of human IL-6 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(D) is a graph showing serum levels of human IL-8 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(E) is a graph showing serum levels of human IL-10 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(F) is a graph showing serum levels of mouse TNF-alpha cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(G) is a graph showing serum levels of mouse IL-6 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(H) is a graph showing serum levels of mouse KC/GRO cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
FIG. 7(I) is a graph showing serum levels of mouse IL-10 cytokine at day 42 post-huPBMC injection in mice administered no antibody (No IgG), REGN1945, COMP1499 or anti-IL2Rgamma antibody H4H12889P or H4H12922P2 or in mice with no human PBMCs. #, significantly different from group "No huPBMCs"; †, significantly different from group "huPBMCs—No IgG"; *, significantly different from group "huPBMCs—REGN1945". Each symbol represents a mouse.
Figure 7:
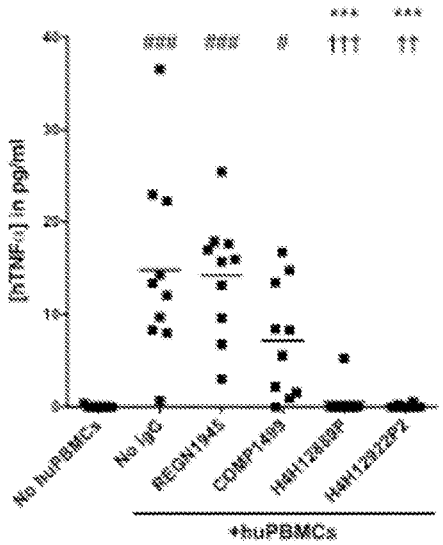
Figure 7:
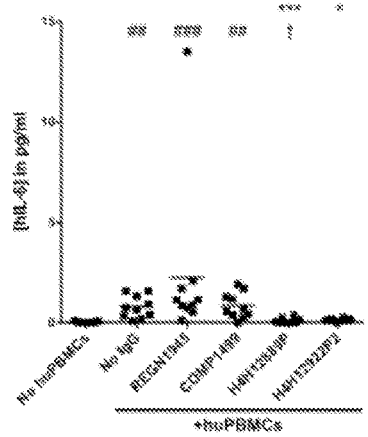
Figure 7:
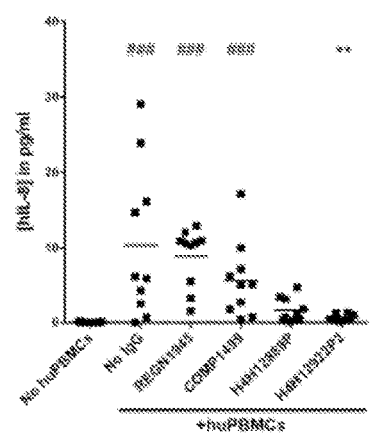
Figure 7:
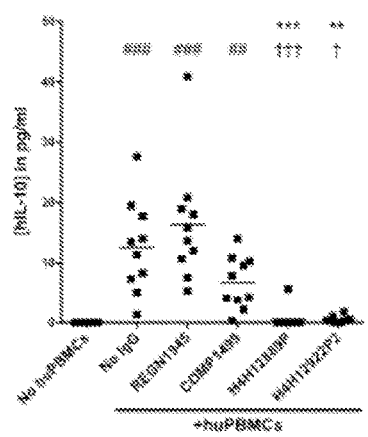
Figure 7:
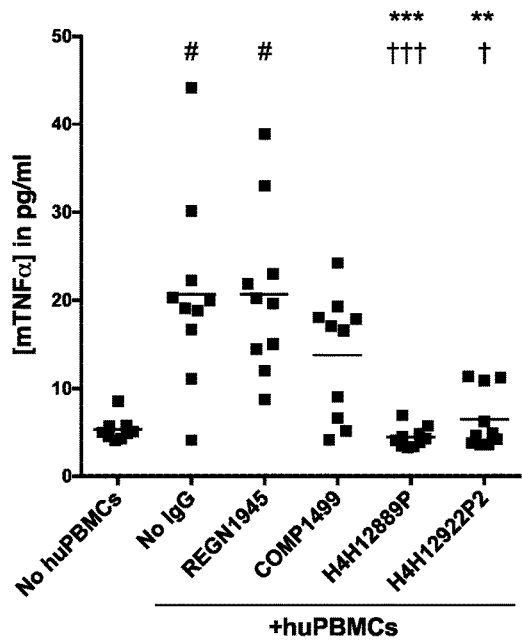
Figure 7:
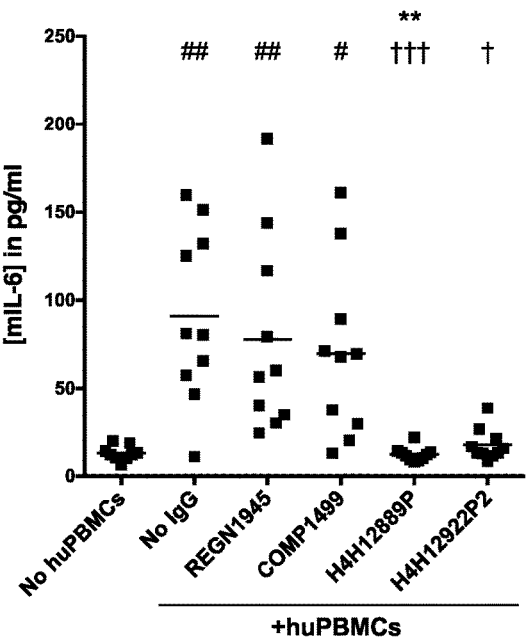
Figure 7:
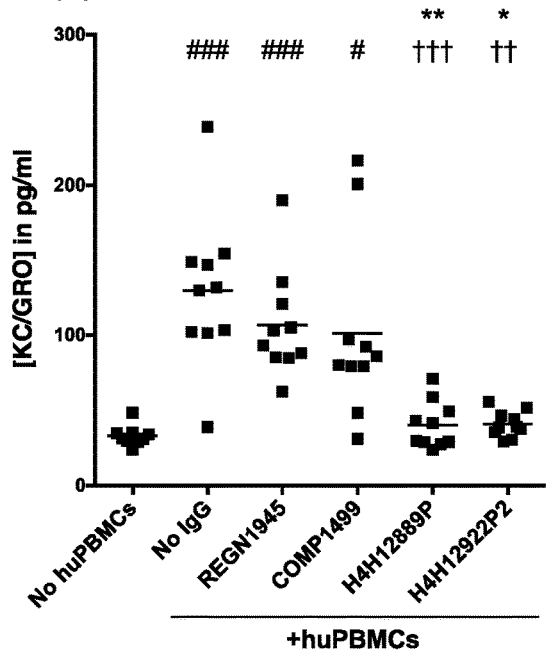
Figure 7:
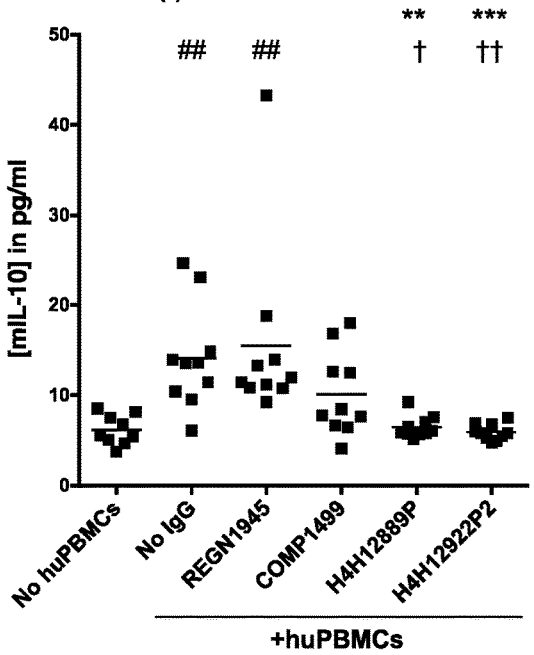
Figure 8:
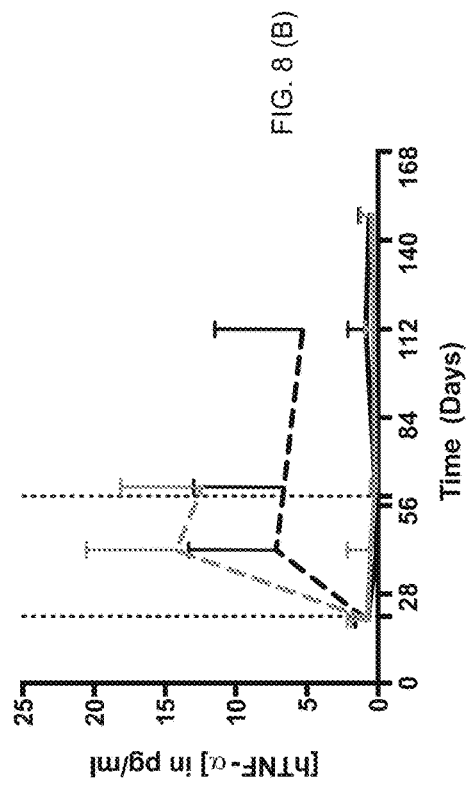
FIG. 8(A) is a graph showing serum levels of human IFN-γ over time in mice administered anti-IL2R gamma antibody H4H12889P or H4H12922P2; or COMP1499 or isotype control antibody.
FIG. 8(B) is a graph showing serum levels of human TNFα over time in mice administered anti-IL2R gamma antibody H4H12889P or H4H12922P2; or COMP1499 or isotype control antibody.
FIG. 8(C) is a graph showing serum levels of mouse TNFα over time in mice administered anti-IL2R gamma antibody H4H12889P or H4H12922P2; or COMP1499 or isotype control antibody.
FIG. 8(D) is a graph showing serum levels of mouse IL-6 over time in mice administered anti-IL2R gamma antibody H4H12889P or H4H12922P2; or COMP1499 or isotype control antibody.
Figure 8:
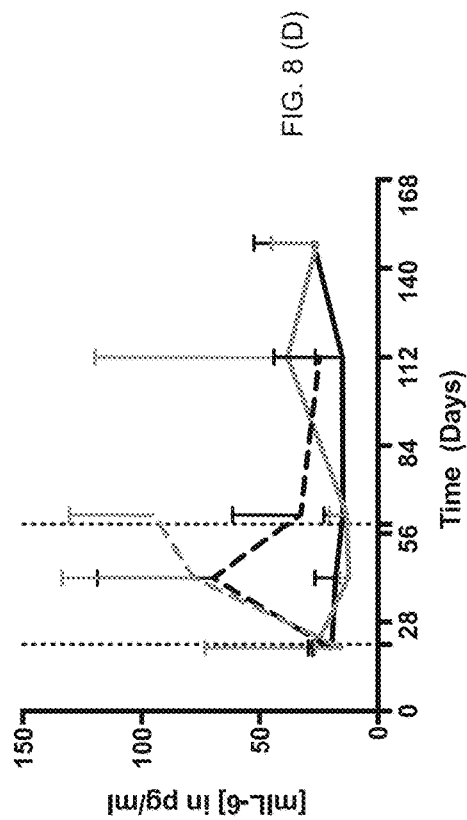
Figure 8:
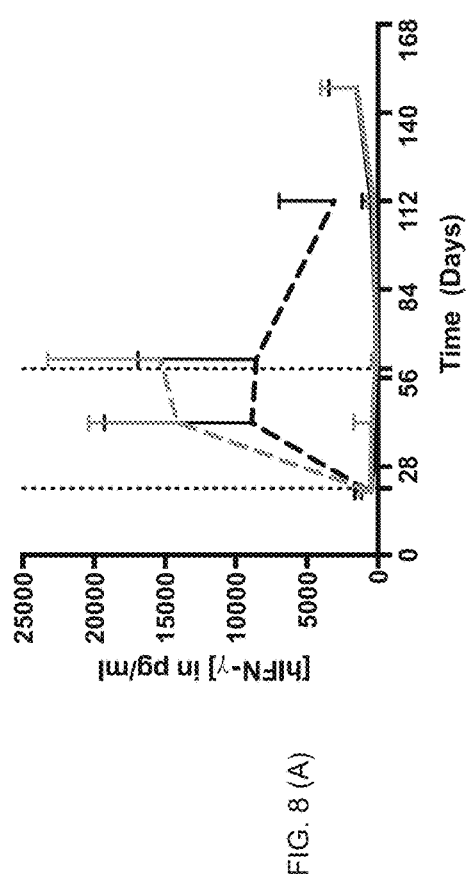
Figure 8:
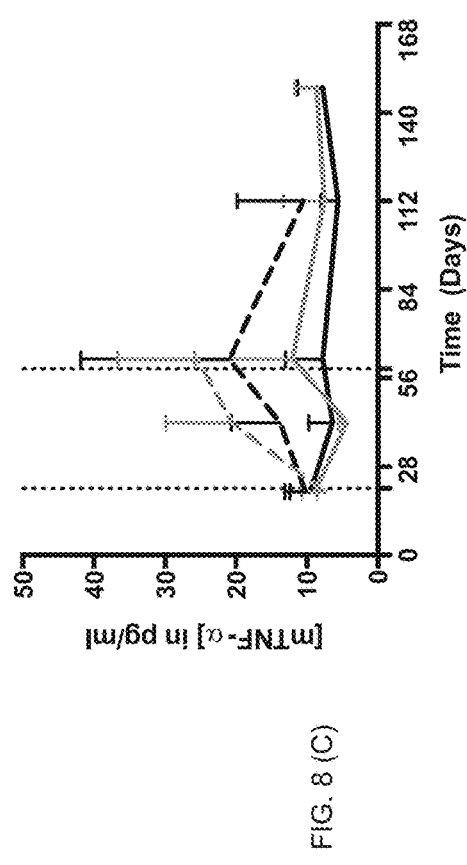

Also, as an example, serum human and mouse cytokine levels at day 42 post huPBMC injection are shown in FIG. 7 (A-I). Serum levels of human IFN-γ, human TNFα, mouse TNFα and mouse IL-6 during time are shown in FIG. 8 (A-D).

This in vivo study demonstrated the efficacy of anti-IL2Rγ antibodies, H4H12889P and H4H12922P2, when administered therapeutically in a model of Graft-versus-Host Disease. Both H4H12889P and H4H12922P2, but not COMP1499, efficiently blocked the development of GvHD in mice. Mice therapeutically treated with either of these two antibodies were protected from weight loss and death, and this was associated with drastic reductions in both mouse and human serum cytokine levels and human T cell numbers in the blood. See Tables 7-3, 7-4 and 7-5.

Example 8: Bioassay Using NK92/hIL7R/STAT3-Luc and Ramos.2G6.4C10/STAT3-Luc Cells The IL2Rγ family of cytokines, IL-2, IL-4, IL-7, IL-9, IL-15 and IL-21, signal through the JAK-STAT (Janus kinases—Signal Transducer and Activator of Transcription) pathway (Rochman et al., New insights into the regulation of T cells by gamma(c) family cytokines. Nat Rev Immunol. 2009 July; 9(7):480-90). In order to assess the inhibition of cytokine signaling by anti-IL2Rγ antibodies, a bioassay was developed using NK-92 cells (human natural killer cell line, ATCC) that stably expressed a luciferase reporter (STAT3-Luc; SABiosciences, #CLS-6028L). NK-92 endogenously expressed IL2Rγ and the ligand-selective receptors that mediated signaling of IL-2, IL-9, IL-15 and IL-21. In order to also assess the regulation of IL-7 signaling, NK-92 cells were transduced with lentivirus containing human IL-7R and stably expressing cells were selected and maintained in G418. The resulting cell line is referred to hereafter as NK-92/hIL7R/STAT3-Luc. To test the regulation of IL-4 mediated signaling, Ramos.2G6.4C10 (human B-lymphocytic cell line, ATCC) cells that endogenously expressed IL2Rγ and IL-4R receptor were transduced with STAT3-luc reporter and the resulting cell line is referred to as Ramos.2G6.4C10/STAT3-Luc.

Anti-IL2γ antibodies of the invention were tested for the inhibition of human IL-2 (hIL-2), human IL-7 (hIL-7), human IL-9 (hIL-9), human IL-15 (hIL-15), or human IL-21 (hIL-21) signaling by plating 20,000 NK-92/hIL7R/STAT3-Luc cells per well in growth media (prepared according to instructions by ATCC, but without IL-2) in a 96-well plate and incubated overnight at 37° C. in 5% $CO_2$. The following day, anti-IL2Rγ antibodies or an isotype control were serially diluted from 500-0.008 nM in assay buffer (plus a sample containing buffer alone without test molecule), added to the cells and incubated for 30 minutes. After the incubation, ligands were added to the cells at the following final concentrations: 30 pM hIL-2, 50 pM hIL-7, 20 pM hIL-9, 60 pM or 100 pM hIL-15, or 5 pM or 3 pM hIL-21. Dose-dependent activation was determined using serial dilution of the ligands, from 10 nM to 0.2 pM (plus a sample containing buffer alone without ligand), added to cells. After a 5 hour incubation at 37° C. in 5% $CO_2$, luciferase activity was measured with OneGlo™ reagent (Promega, #E6031) and Victor™ X multilabel plate reader (Perkin Elmer).

To test the anti-IL2γ antibodies of the invention in the inhibition of human IL-4 (hIL-4) signaling, Ramos.2G6.4C10/STAT3-Luc cells were plated in growth media (prepared according to instructions by ATCC) at a density of 100,000 cells per well in a 96-well plate. The anti-IL2Rγ antibodies or an isotype control were serially diluted from 500-0.008 nM in assay buffer (plus a sample containing buffer alone without test molecule), added to the cells and incubated for 20 minutes. After the incubation, hIL-4 was added to cells at a final concentration of 250 pM or 200 pM. Dose-dependent activation was determined using serial dilution of hIL-4, from 10 nM to 0.2 pM (plus a sample containing buffer alone without ligand), added to cells. After an overnight incubation at 37° C. in 5% $CO_2$, luciferase activity was measured with OneGlo™ reagent (Promega, #E6031) and Victor™ X multilabel plate reader (Perkin Elmer).

The results were analyzed using nonlinear regression (4-parameter logistics) with Prism 5 software (GraphPad) to obtain $EC_{50}$ and $IC_{50}$ values. The percentage of inhibition was calculated with the RLU values by using the following equation:

$$\% \text{ Inhibition} = 100 \times \frac{RLU_{Baseline} - RLU_{Inhibition}}{RLU_{Baseline} - RLU_{Background}}$$

In this equation, "$RLU_{Baseline}$" is the luminescence value from the cells treated with constant amount of ligand without antibodies, "$RLU_{Inhibition}$" is the minimum luminescence value from cells treated with a dose response of a particular antibody at a particular ligand concentration, and "$RLU_{Background}$" is the luminescence value from cells treated without any ligand or antibody.

TABLE 8-1

Inhibition of IL2Rγ signaling by nineteen anti-IL2γ antibodies in bioassay using NK-92/hIL7R/STAT3-Luc and Ramos.2G6.4C10/STAT3-Luc cells.

| Cells | NK92/hIL7R/STAT3-luc | | Ramos.2G6.4C10/STAT3-luc | | NK/hIL7R/STAT3-luc | | NK92/hIL7R/STAT3-luc | | NK92/hIL7R/STAT3-luc | | NK92/hIL7R/STAT3-luc | |
|---|---|---|---|---|---|---|---|---|---|---|---|---|
| Ligand | IL-2 | | IL-4 | | IL-7 | | IL-9 | | IL-15 | | IL-21 | |
| EC50 [M] | 3.3E−11 | | 1.6E−10 | | 3.9E−11 | | 2.0E−11 | | 1.5E−10 | | 3.1E−12 | |
| Constant Ligand | 30 pM | | 250 pM | | 50 pM | | 20 pM | | 60 pM | | 5 pM | |
| Ab PID # | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) |
| H4H12857P | >1.0E−07 | 44 | 3.8E−08 | 96 | 1.6E−08 | 94 | >1.0E−07 | 83 | >1.0E−07 | 78 | NB | NB |
| H4H12858P | NB | NB | NB | NB | NB | NB | NB | NB | NB | NB | NB | NB |
| H4H12859P | WB | 29 | NB | NB | NB | NB | NB | NB | NB | NB | NB | NB |
| H4H12863P | 4.3E−10 | 48 | 3.6E−10 | 70 | 1.5E−09 | 42 | 4.7E−10 | 38 | WB | 30 | >1.0E−07 | 28 |
| H4H12871P | NB | NB | WB | 31 | 8.2E−10 | 36 | NB | NB | NB | NB | NB | NB |
| H4H12874P | WB | 26 | >1.0E−07 | 70 | 4.1E−08 | 93 | >1.0E−07 | 50 | >1.0E−07 | 55 | NB | NB |
| H4H12884P | WB | 13 | WB | 19 | 2.3E−09 | 34 | NB | NB | NB | NB | NB | NB |
| H4H12886P | WB | 27 | >1.0E−07 | 92 | >1.0E−07 | 81 | >1.0E−07 | 84 | >1.0E−07 | 64 | WB | 18 |
| H4H12889P | 2.7E−08 | 81 | 1.9E−09 | 101 | 3.0E−09 | 100 | 7.1E−09 | 100 | 8.5E−09 | 92 | >1.0E−07 | 35 |
| H4H12890P | WB | 15 | >1.0E−07 | 54 | >1.0E−07 | 66 | WB | 36 | WB | 35 | NB | NB |
| H4H12899P | NB | NB | NB | NB | NB | NB | NB | NB | NB | NB | NB | NB |
| H4H12900P | NB | NB | NB | NB | NB | NB | NB | NB | NB | NB | NB | NB |
| H4H12908P | NB | NB | NB | NB | NB | NB | NB | NB | NB | NB | NB | NB |
| H4H12913P2 | WB | 24 | >1.0E−07 | 55 | >1.0E−07 | 77 | >1.0E−07 | 57 | >1.0E−07 | 58 | NB | NB |
| H4H12922P2 | 1.6E−08 | 85 | 1.3E−09 | 100 | 2.6E−09 | 98 | 3.1E−09 | 99 | 9.3E−09 | 91 | >1.0E−07 | 49 |
| H4H12924P2 | NB | NB | NB | NB | NB | NB | NB | NB | NB | NB | NB | NB |
| H4H12926P2 | NB | NB | NB | NB | NB | NB | NB | NB | NB | NB | NB | NB |
| H4H12927P2 | WB | 18 | WB | 33 | >1.0E−07 | 46 | NB | NB | WB | 34 | NB | NB |
| H4H12934P2 | NB | NB | WB | 22 | WB | 12 | NB | NB | NB | NB | NB | NB |
| Isotype Control mAb | NB | NB | NB | NB | NB | NB | NB | NB | NB | NB | NB | NB |

NB: No blocking

WB: Weak blocking

TABLE 8-2

Inhibition of IL2Rγ signaling by four anti-IL2γ antibodies in bioassay using NK-92/hIL7R/STAT3-Luc and Ramos.2G6.4C10/STAT3-Luc cells.

| Cells<br>Ligand<br>EC50 [M]<br>Constant Ligand | NK92/hIL7R/<br>STAT3-luc<br>IL-2<br>4.5E−11<br>30 pM | | Ramos.2G6.4C10/<br>STAT3-luc<br>IL-4<br>3.3E−10<br>200 pM | | NK92/hIL7R/<br>STAT3-luc<br>IL-7<br>3.9E−11<br>50 pM | | NK92/hIL7R/<br>STAT3-luc<br>IL-9<br>3.3E−11<br>20 pM | | NK92/hIL7R/<br>STAT3-luc<br>IL-15<br>2.3E−10<br>100 pM | | NK92/hIL7R/<br>STAT3-luc<br>IL-21<br>6.0E−12<br>3 pM | |
|---|---|---|---|---|---|---|---|---|---|---|---|---|
| Ab PID # | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) | IC50 [M] | Max Inhibition (%) |
| H4H13538P | NB | NB | NB | NB | NB | NB | NB | NB | NB | NB | NB | NB |
| H4H13841P | NB | NB | NB | NB | NB | NB | NB | NB | NB | NB | NB | NB |
| H4H13544P2 | NB | NB | NB | NB | NB | NB | NB | NB | NB | NB | NB | NB |
| H4H13545P2 | NB | NB | NB | NB | NB | NB | NB | NB | NB | NB | NB | NB |
| Isotype Control mAb | NB | NB | NB | NB | NB | NB | NB | NB | NB | NB | NB | NB |

Twenty-three anti-IL2γ antibodies of the invention were tested for their ability to inhibit signaling by the IL2Rγ family of cytokines using a bioassay. As shown in Table 8-1, nineteen out of twenty-three anti-IL2γ antibodies inhibited the activation of IL2Rγ to different extents, and as shown in Table 8-2, four out of twenty-three anti-IL2γ antibodies showed no inhibition of IL2Rγ activation by ligands.

Example 9: Cell Binding Analysis by Flow Cytometry with NK-92, Jurkat, NIH/3T3, MC/9 and HEK293 Cells In order to assess the binding of anti-IL2Rγ antibodies to human and mouse IL-2Rγ expressed on cells, flow cytometry analyses were performed with cell lines that endogenously express IL-2Rγ: NK-92 (human natural killer cell line), Jurkat (human T-lymphocytic cell line), and MC/9 (mouse mast cell line) cells. NIH/3T3 (mouse fibroblast) and HEK293 (human embryonic kidney) cell lines were included as negative controls.

For flow cytometry analyses, the cells were pre-incubated with mouse IgG at 100 μg/ml for 15 minutes at room temperature (RT) to block the binding of the antibodies to Fc receptors. The anti-IL2Rγ antibodies of the invention and an isotype control antibody were used at 10 μg/ml with 0.5-1× $10^6$ cells/well of each cell type in PBS (without calcium and magnesium) containing 1% FBS for Jurkat, NIH/3T3, and HEK293 cells or in growth media (prepared according to instruction by ATCC) for NK-92 and MC/9 for 30-45 minutes at RT. Cells were washed and incubated with an anti-human antibody conjugated to allophycocyanin (APC) (Jackson ImmunoResearch, #109-136-170) for 30 minutes on ice. Cells were washed, fixed using BD CytoFix™ (BD biosciences, #554655) and analyzed on an IQue® (IntelliCyt®) Flow Cytometer or Accuri Flow cytometer (BD). Unstained and secondary antibody alone controls were also included for all cell lines. The results were analyzed using ForeCyt® (IntelliCyt®) software to determine the geometric means of fluorescence (MFI) for viable cells. Binding ratios were calculated by normalizing the MFI of the test sample by the MFI of the unstained sample.

As shown in Table 9-1, nineteen out of twenty-three anti-IL2Rγ antibodies of the invention tested at 10 μg/ml demonstrated binding to Jurkat and NK-92 cells with binding ratios of 1-19 and 1-94, respectively. The anti-IL2Rγ antibodies demonstrated binding to NIH/3T3 and MC/9 cells with binding ratios of 1-13 and 1. The human isotype control antibody, REGN1945, and secondary only control condition exhibited binding ratios of 1-13 to all cell lines tested.

As shown in Table 9-2, four out of twenty-three anti-IL2Rγ antibodies of the invention tested at 10 μg/ml demonstrated binding to NK-92 cells with binding ratios of 1-37 and to HEK293 cells with binding ratios of 1-3. The human isotype control antibody, REGN1945, and secondary only control condition exhibited binding ratios of 1-2 to NK-92 and HEK293 cells.

TABLE 9-1

Flow cytometry analysis with nineteen of twenty-three anti-IL2Rγ antibodies binding to NIH/3T3, MC/9, Jurkat, and NK-92 cells.

| | Raw MFI | | | | Binding Ratio (Sample over unstained MFIs) | | | |
|---|---|---|---|---|---|---|---|---|
| Conditions | NIH/3T3 | MC/9 | Jurkat | NK92 | NIH/3T3 | MC/9 | Jurkat | NK92 |
| H4H12857P | 461 | 198 | 103 | 5494 | 2 | 1 | 1 | 37 |
| H4H12858P | 2951 | 199 | 99 | 228 | 13 | 1 | 1 | 2 |
| H4H12859P | 153 | 201 | 89 | 176 | 1 | 1 | 1 | 1 |
| H4H12863P | 452 | 185 | 1171 | 12991 | 2 | 1 | 13 | 87 |
| H4H12871P | 840 | 184 | 1619 | 13713 | 4 | 1 | 18 | 92 |
| H4H12874P | 366 | 202 | 507 | 6583 | 2 | 1 | 6 | 44 |
| H4H12884P | 744 | 172 | 1425 | 13517 | 3 | 1 | 16 | 90 |
| H4H12886P | 368 | 185 | 488 | 4720 | 2 | 1 | 6 | 32 |
| H4H12889P | 502 | 91 | 1661 | 14092 | 2 | 1 | 19 | 94 |
| H4H12890P | 486 | 170 | 500 | 4569 | 2 | 1 | 6 | 30 |

TABLE 9-1-continued

Flow cytometry analysis with nineteen of twenty-three anti-IL2Rγ antibodies binding to NIH/3T3, MC/9, Jurkat, and NK-92 cells.

| Conditions | Raw MFI | | | | Binding Ratio (Sample over unstained MFIs) | | | |
|---|---|---|---|---|---|---|---|---|
| | NIH/3T3 | MC/9 | Jurkat | NK92 | NIH/3T3 | MC/9 | Jurkat | NK92 |
| H4H12899P | 941 | 167 | 114 | 2670 | 4 | 1 | 1 | 18 |
| H4H12900P | 1602 | 128 | 110 | 4195 | 7 | 1 | 1 | 28 |
| H4H12908P | 831 | 154 | 86 | 2539 | 4 | 1 | 1 | 17 |
| H4H12913P2 | 436 | 178 | 472 | 4912 | 2 | 1 | 5 | 33 |
| H4H12922P2 | 587 | 187 | 1570 | 12518 | 3 | 1 | 18 | 84 |
| H4H12924P2 | 502 | 192 | 104 | 231 | 2 | 1 | 1 | 2 |
| H4H12926P2 | 526 | 175 | 179 | 1853 | 2 | 1 | 2 | 12 |
| H4H12927P2 | 436 | 191 | 315 | 3494 | 2 | 1 | 4 | 23 |
| H4H12934P2 | 1391 | 164 | 295 | 6441 | 6 | 1 | 3 | 43 |
| REGN1945 (hIgG$_4$ control) | 396 | 196 | 92 | 1890 | 2 | 1 | 1 | 13 |
| Anti-hIgG-APC | 205 | 173 | 80 | 210 | 1 | 1 | 1 | 1 |
| Unstained | 231 | 146 | 88 | 150 | 1 | 1 | 1 | 1 |

TABLE 9-2

Flow cytometry analysis with four of twenty-three anti-IL2Rγ antibodies binding to HEK293 and NK-92 cells.

| Conditions | Raw MFI | | Binding Ratio (Sample over unstained MFIs) | |
|---|---|---|---|---|
| | HEK293 | NK92 | HEK293 | NK92 |
| H4H13538P | 571 | 235 | 3 | 1 |
| H4H13841P | 274 | 7051 | 1 | 37 |
| H4H13544P2 | 334 | 4647 | 2 | 24 |
| H4H13545P2 | 295 | 592 | 1 | 3 |
| Isotype control (REGN1945) | 509 | 223 | 2 | 1 |
| anti-hIgG-APC | 260 | 234 | 1 | 1 |
| Unstained | 219 | 190 | 1 | 1 |

Example 10: In Vivo Immunosuppression Experiment to Assess the Effects of the Anti-IL2Rγ Antibody H4H12889P on Immune Cell Populations in the Blood Experimental Procedure.

Velocigene® (VG) background mice (C57BL/6NTac (75%)/129S6SvEvTac (25%)) from the Regeneron Velocigene® breeding colony that were genetically modified to replace the endogenous IL2RG ectodomain with the corresponding human sequences were administered or not an isotype control (REGN1945) or H4H12889P subcutaneously at doses 10 mg/kg or 25 mg/kg at a frequency of 2 times per week for 3 weeks (6 doses total).

TABLE 10-1

Experimental dosing and treatment protocol for groups of mice

| Group | Recipient Strain | n | mAb Treatment |
|---|---|---|---|
| A | Il2rg$^{hu/hu}$ | 8 | No mAb |
| B | Il2rg$^{hu/hu}$ | 8 | REGN1945 (Isotype), 10 mg/kg |
| C | Il2rg$^{hu/hu}$ | 8 | REGN1945 (Isotype), 25 mg/kg |
| D | Il2rg$^{hu/hu}$ | 8 | H4H12889P (anti-hIL2RG), 10 mg/kg |
| E | Il2rg$^{hu/hu}$ | 8 | H4H12889P (anti-hIL2RG), 25 mg/kg |

Analysis of Immune Cell Populations in Blood During Time by Flow Cytometry.

Total immune cell, B cell, T cell, NK cell, and neutrophil counts in the peripheral blood were analyzed at various timepoints (once a week) via flow cytometry to assess the effects of H4H12889P on the absolute numbers of these cell types. Briefly, at each timepoint, blood samples from mice were collected into Microtainer tubes with K2EDTA [BD #365974] and 30-75 uL of each blood sample were incubated in red blood cell lysis buffer [Sigma #R7757] for 5 min at room temperature to lyse red blood cells. A second round of lysis was performed if needed. Cells were then washed in DPBS [Gibco #14190-144], stained for 20 min with LIVE/DEAD™ Fixable Near-IR Dead Cell Stain [Invitrogen #L34962] diluted 1:500 in DPBS, washed again in DPBS, then blocked with purified anti-mouse CD16/CD32 (Fc Shield) [Tonbo Biosciences, #70-0161-M001] diluted 1:50 in MACS buffer [autoMACS Running Buffer; Miltenyi Biotec, #130-091-221]. Subsequently, cells were stained for cell surface markers to identify CD45$^+$ cells, T cells, B cells, NK cells, and neutrophils by the addition of mix of fluorescently labeled antibodies (described in Table 2) diluted in BD horizon brilliant stain buffer [BD #566349]. Finally, samples were washed in MACS buffer, fixed in BD CytoFix [BD #554655] diluted 1:4 in DPBS, then washed and resuspended in MACS buffer prior to acquisition. Sample data was acquired on a FACSymphony A5 analyzer using the HTS attachment [BD]. A fixed volume of each sample was run. Data analysis was performed using FlowJo v10 Software [Tree Star, OR]. CD45$^+$ immune cells were defined as singlets, live cells, CD45$^+$; within this population, T cells were further defined as CD3$^+$, B cells as CD3$^-$CD19$^+$, NK cells as CD3$^-$CD19$^-$NKp46$^+$, and neutrophils as F4/80$^-$Ly6G$^+$. Absolute numbers of each cell type run through the analyzer, sample volume run, and the volume of blood originally stained were used to calculate cells/μL blood counts for each sample.

TABLE 10-2

Antibodies Used for Flow Cytometry Analysis

| Antibody | Fluorochrome | Manufacturer | Final dilution |
|---|---|---|---|
| NKp46 | FITC | ebioscience | 1:200 |
| Ly6G | BB700 | BD | 1:100 |
| F4/80 | PE | BD | 1:500 |
| CD3 | PE-Cy7 | BD | 1:200 |
| CD4 | BV786 | BD | 1:200 |

TABLE 10-2-continued

Antibodies Used for Flow Cytometry Analysis

| Antibody | Fluorochrome | Manufacturer | Final dilution |
|---|---|---|---|
| CD8a | BUV395 | BD | 1:200 |
| CD19 | BUV737 | BD | 1:200 |
| CD45 | Alexa Fluor 700 | BioLegend | 1:200 |

Analysis of Serum Therapeutic Antibody Levels During Time by Antigen Capture ELISA.

Serum levels of IL2Rγ antibody or isotype control antibody were measured once a week by Human total IgG Platinum ELISA kit. Serial dilutions were made of each antibody in 0.5% solution of BSA in PBS to generate a standard curve from 1.56-100 ng/mL of H4H12889P and REGN1945. Absorbance at 450 nm measured on a SpectraMax M5 plate reader [Molecular Devices]. Data analysis was performed using Prism 8.1.2 [Graph Pad].

Results Summary and Conclusions.

Figure 9:
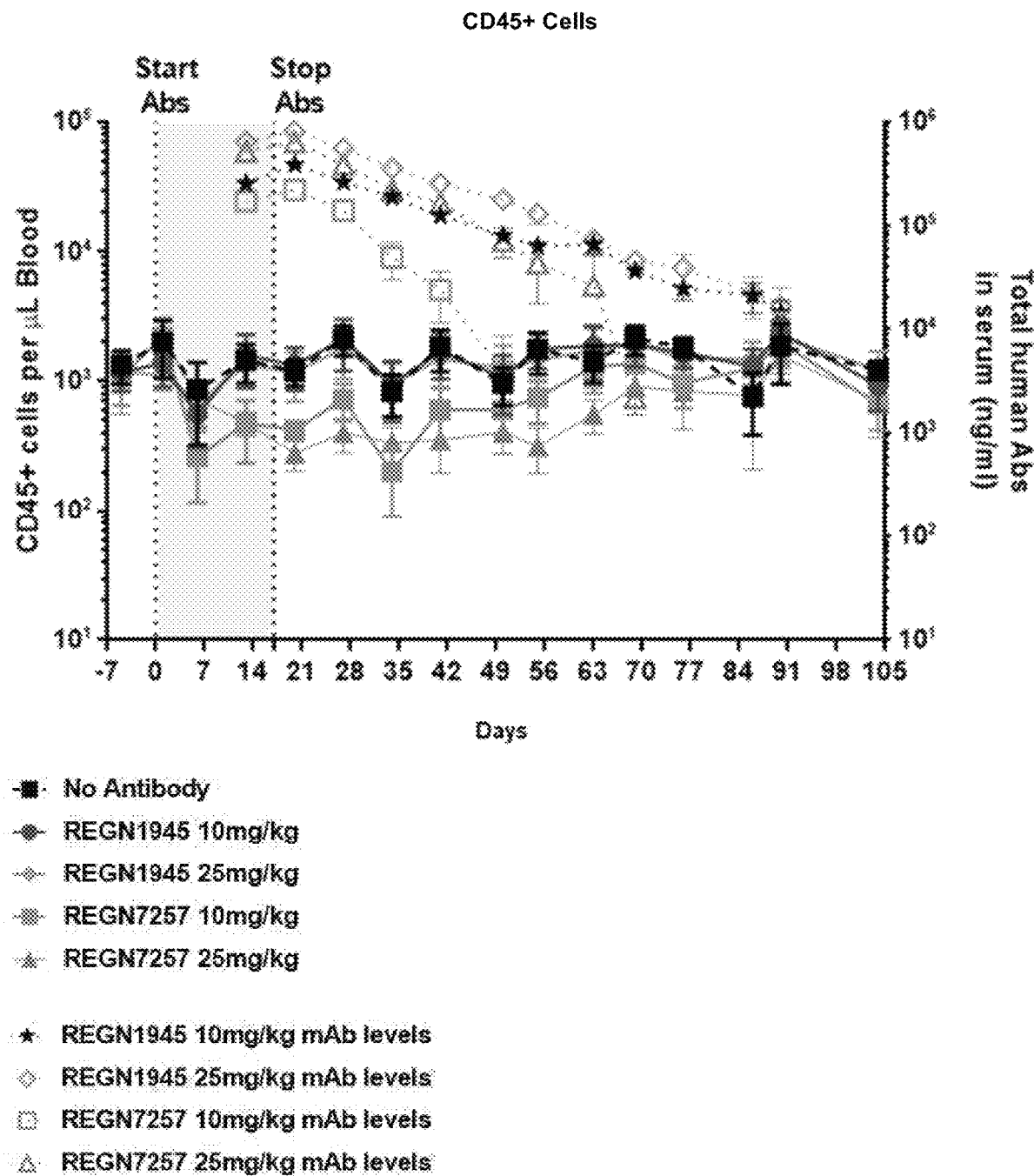
FIG. 9(A) is a graph showing levels of total human antibodies or CD45+ immune cells in blood of mice treated with various doses of antibody REGN1945 or H4H12889P.
FIG. 9(B) is a graph showing levels of total human antibodies or NK cells in blood of mice treated with various doses of antibody REGN1945 or H4H12889P.
FIG. 9(C) is a graph showing levels of total human antibodies or T cells in blood of mice treated with various doses of antibody REGN1945 or H4H12889P.
FIG. 9(D) is a graph showing levels of total human antibodies or B cells in blood of mice treated with various doses of antibody REGN1945 or H4H12889P.
FIG. 9(E) is a graph showing levels of total human antibodies or neutrophils in blood of mice treated with various doses of antibody REGN1945 or H4H12889P.
Figure 9:
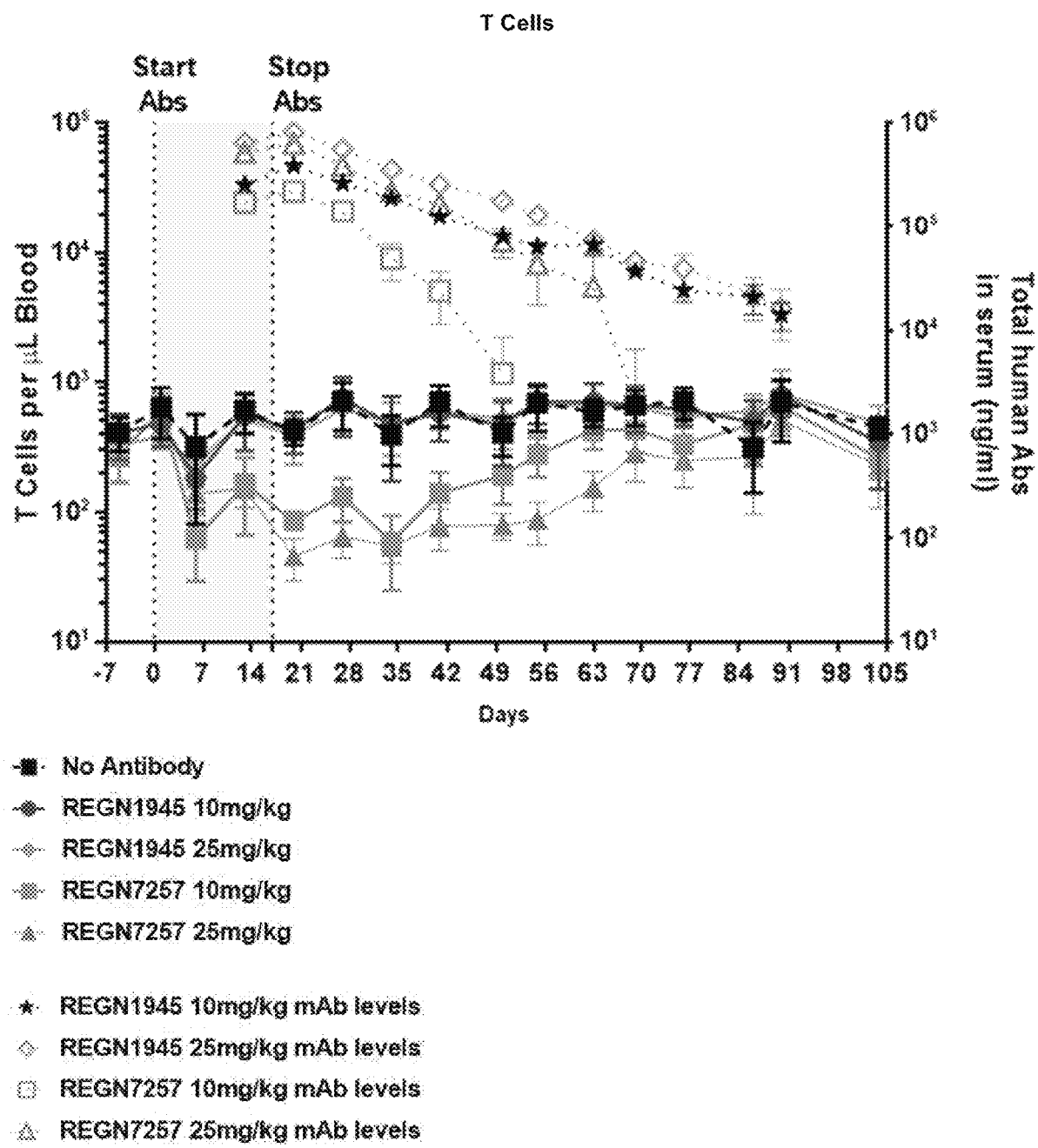
Figure 9:
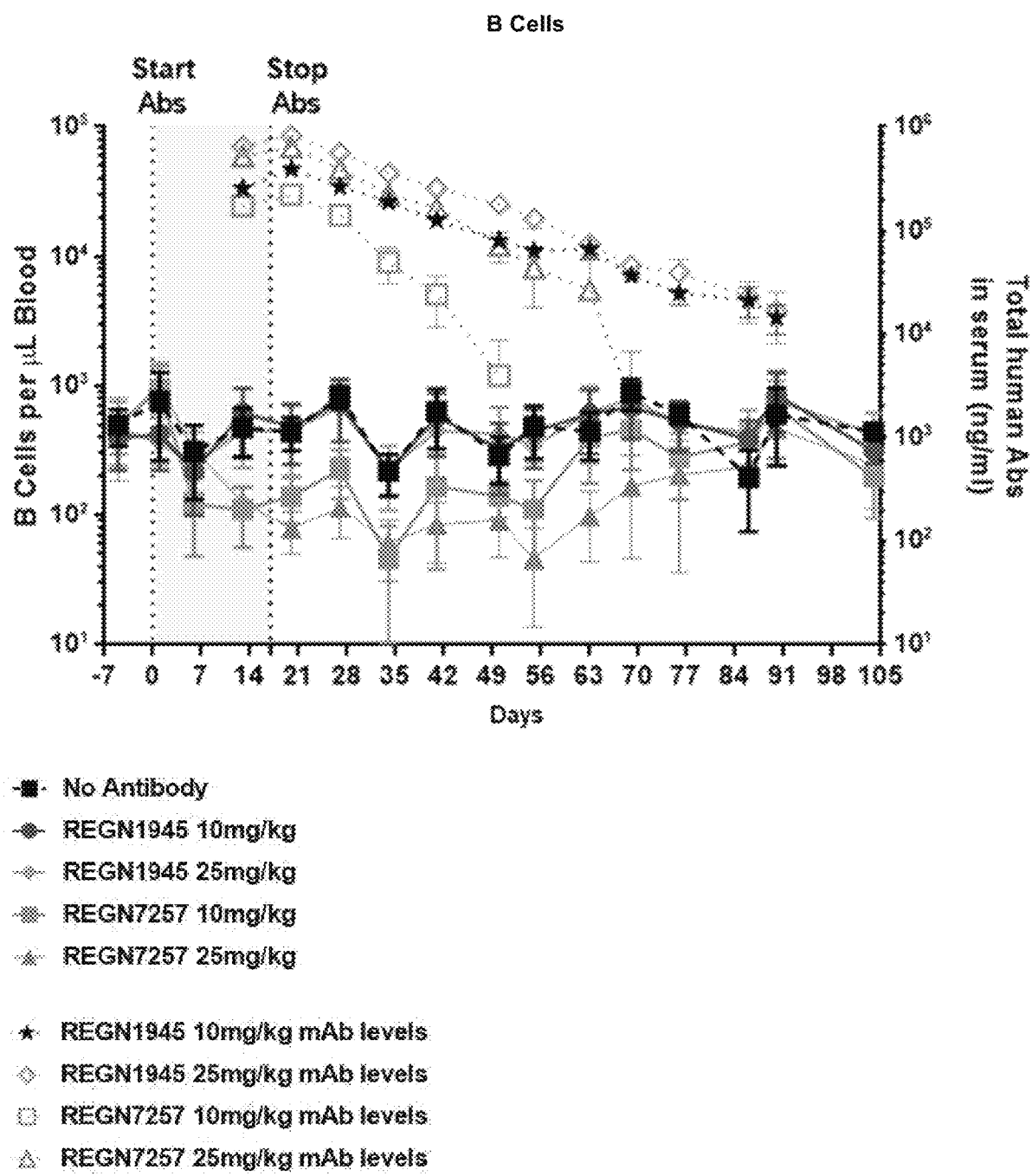
Figure 9:
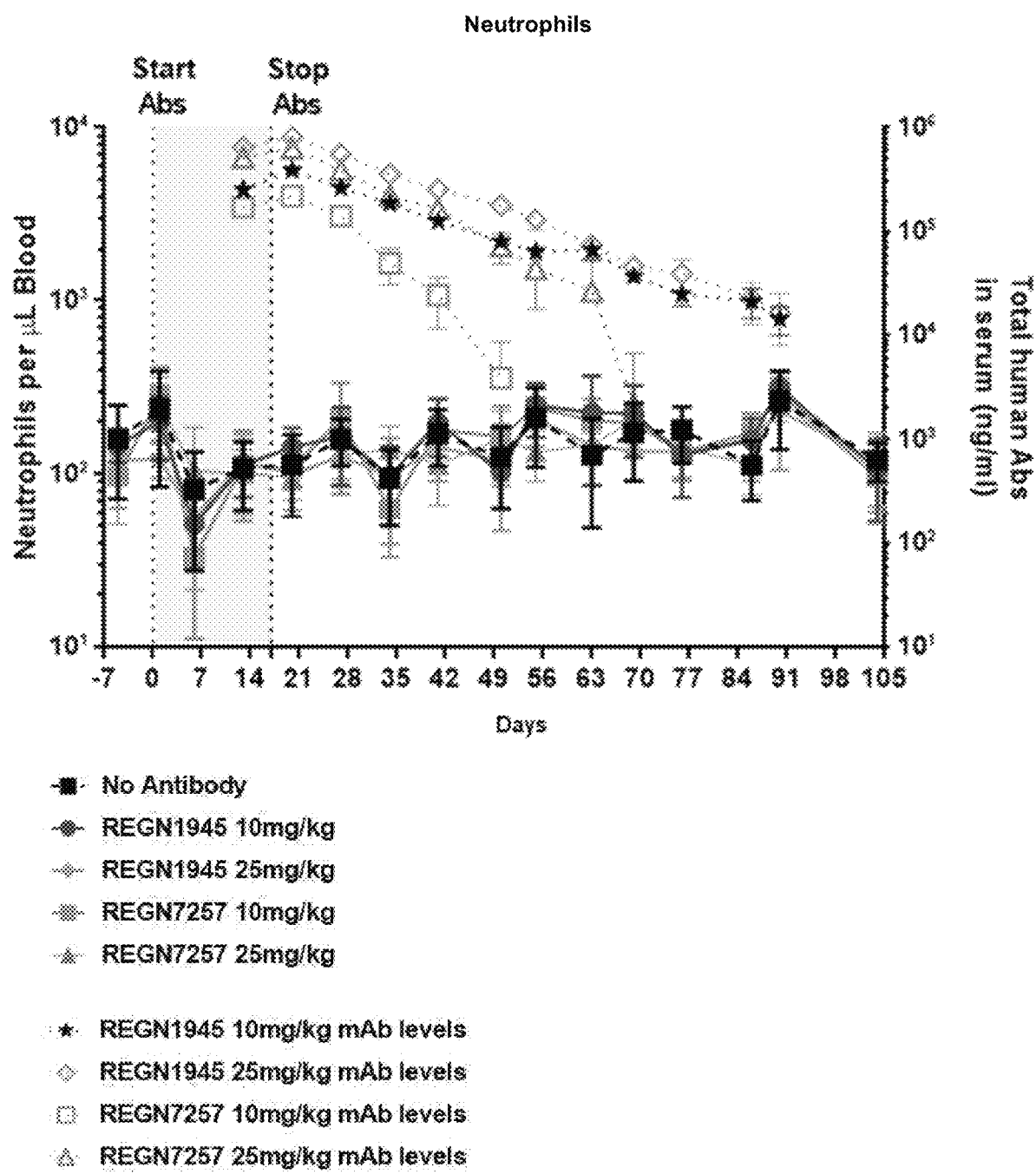

Treatment with H4H12889P (10 mg/kg and 25 mg/kg) resulted in a marked reduction in the numbers of total CD45$^+$ immune cells (FIG. 9 (A)), NK cells (FIG. 9 (B)), T cells ((FIG. 9 (C)) and B cells (FIG. 9 (D)) in blood while neutrophil counts (FIG. 9 (E)) were unaffected. After the 3-week dosing period ended, the serum concentration of H4H12889P decreased over time. This decrease in the concentration of H4H12889P was associated with a continuous increase in the numbers of total CD45$^+$ immune cells (FIG. 9 (A)), NK cells (FIG. 9 (B)), T cells (FIG. 9 (C)) and B cells (FIG. 9 (D)). By the end of the study, all these populations recovered to similar levels as observed pretreatment, and levels observed in untreated or mice treated with REGN1945 (isotype control).

Example 11: In Vivo Skin Graft Rejection Model to Assess the Blocking Activity of the IL2Rγ Antibody H4H12889P Experimental Procedure.

BALB/cJ mice obtained from The Jackson Laboratory (Bar Harbor, Me.) were used as skin graft donors, and MHC mismatched Velocigene® (VG) background mice (C57BL/6NTac (75%)/129S6SvEvTac (25%)) from the Regeneron Velocigene® breeding colony that were genetically modified to replace the endogenous IL2RG ectodomain with the corresponding human sequences were used as recipients. The skin graft was obtained from the tail of the donor mice. The skin was the peeled off using forceps and punched with a 10 mm diameter biopsy punch. VG mice (humanized for IL2Rγ), used as graft recipients, were administered or not an isotype control (REGN1945) or H4H12889P subcutaneously at doses 25 mg/kg at a frequency of 2 times per week starting 3 weeks prior to transplant, and continuing until rejection. Recipients with the surgical site shaved were anesthetized by isoflurane via a nose cone and administered an analgesic (buprenorphine-sustained release) (ZooPharm). The shaved dorsal area was swabbed with applications of povidone-iodine and alcohol. The graft bed was created midway laterally between the dorsal and ventral sides of the mouse by pinching skin with forceps followed by skin excision utilizing a sterile 10 mm diameter biopsy skin punch. The graft was then placed down on the graft bed and covered with an adhesive bandage that was secured with two sterile surgical staples to the skin. Aseptic technique was practiced during the entire procedure. After 5 days, the bandages and staples were removed and monitoring ensued.

TABLE 11-1

Experimental dosing and treatment protocol for groups of mice

| Group | Recipient Strain | n | Donor Strain | Donor Tissue | mAb Treatment |
|---|---|---|---|---|---|
| A | Il2rg$^{hu/hu}$ | 10 | BALB/cJ | Tail skin | No mAb |
| B | Il2rg$^{hu/hu}$ | 10 | BALB/cJ | Tail skin | REGN1945 (Isotype) |
| C | Il2rg$^{hu/hu}$ | 10 | BALB/cJ | Tail skin | H4H12889P (anti-hIL2Rγ) |

Figure 10:
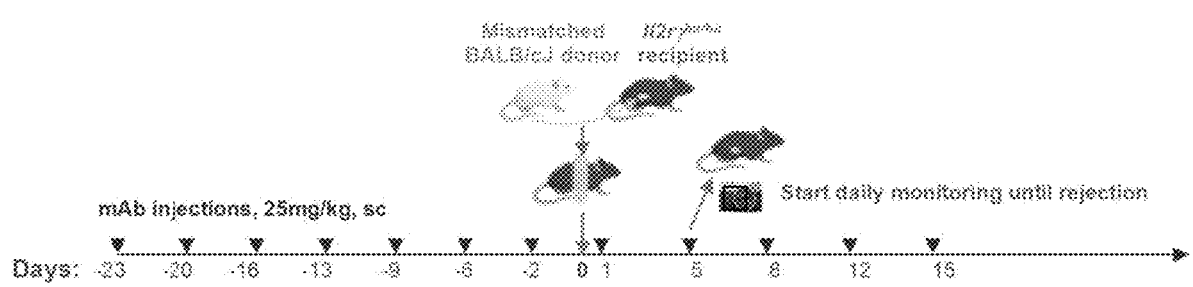
FIG. 10. Experimental layout for in vivo skin graft rejection experiments.

The experiment layout is set forth in FIG. 10.

Monitoring of Skin Graft Rejection.

Figure 11:
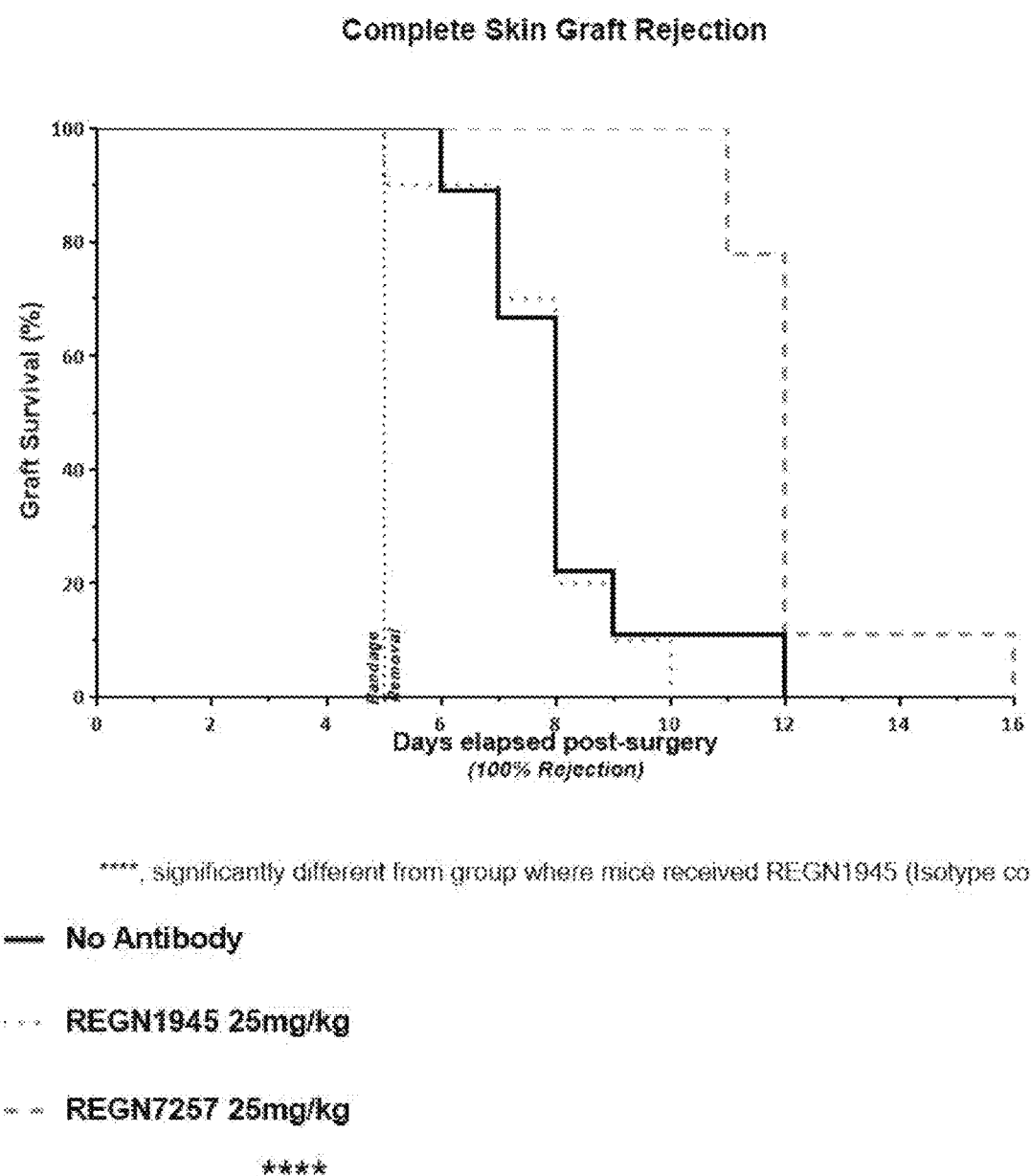
FIG. 11. Time of onset of skin graft rejection in mice administered no antibody, REGN1945 or H4H12889P.
Figure 12:
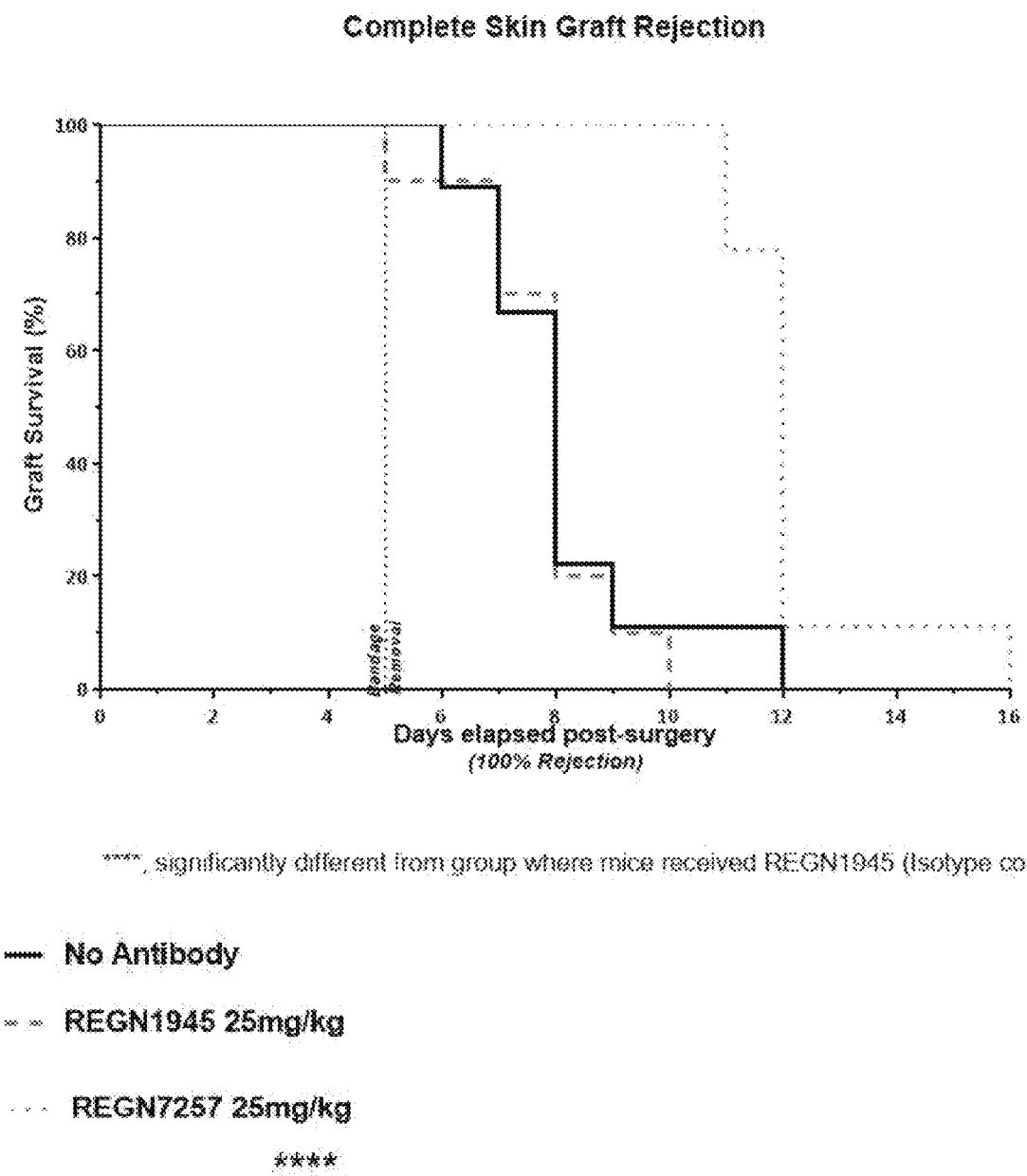
FIG. 12. Time of complete rejection of skin graft in mice administered no antibody, REGN1945 or H4H12889P.

Monitoring of the skin grafts included the following criteria: (1) Skin grafts that failed to vascularize properly were considered technical failures and excluded from analysis. These grafts will display scabbing and contraction several hours from bandage removal. (2) "Scabbing" and contraction of the graft at later times was used as indicators of graft rejection. The complete rejection timepoint is recorded as the first day where 100% of the graft tissue was necrotic (FIG. 12). Rejection onset was recorded as the first day where there were signs of rejection (i.e., redness) (FIG. 11). Significance was determined by Log-rank (Mantel-Cox) test with Bonferroni correction (adjusted p value 0.005, K=9).

Detection of Donor Specific Antibodies by Flow Cytometry.

Figure 13:
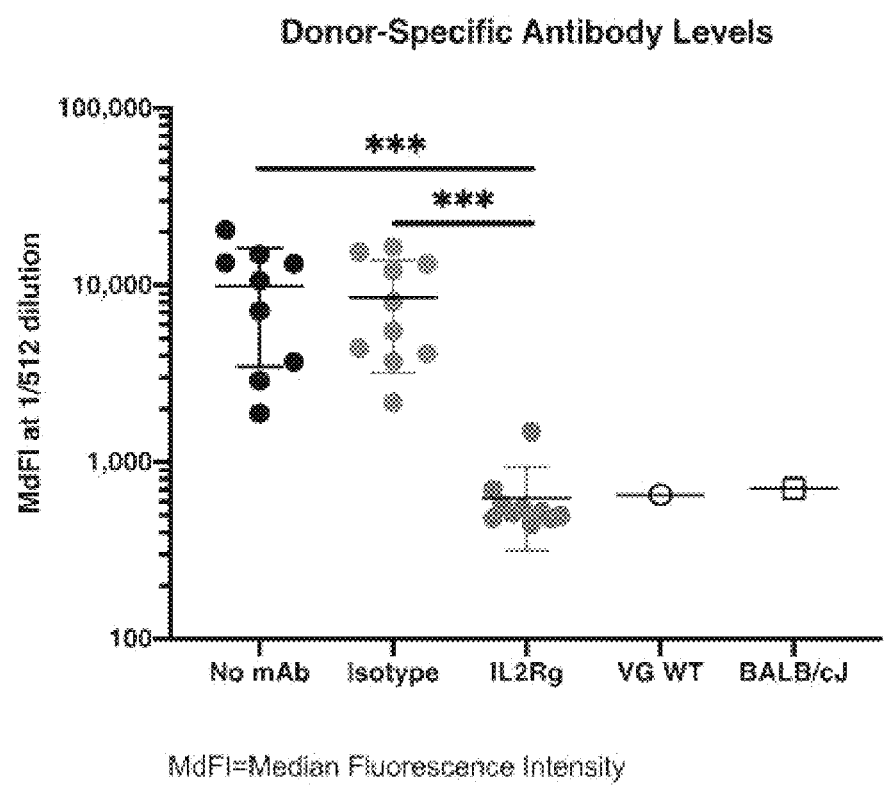
FIG. 13. Total donor specific IgG antibodies in non-engrafted mice or grafted mice administered no antibody, REGN1945 or H4H12889P.

Blood was sampled at the day 56 post-transplant timepoint to assess formation of donor-specific antibodies (FIG. 13).

CT26.WT (ATCC® CRL-2638™) cells were cultured in tissue culture flasks to 80% confluent. Cells were washed with 1×DPBS and dissociated with TrypLE Express reagent (Gibco) by incubating at room temperature for 5 minutes and washing flask with complete RPMI 1640 media. Cells were then centrifuged (500 g, 10 minutes), and resuspended at 5 million cells/ml with 1×DPBS with 1:50 dilution of 4 ug/ml of Fc block (Tonbo) for 15 minutes at room temperature. The suspension was plated at 250,000 cells/well (50 uL) in a 384 well V-bottom plate.

50 ul of serially diluted sample serum from transplanted mice and from non-engrafted wild type VG mouse (C57BL/6NTac (75%)/129S6SvEvTac (25%)) and wild type BALB/cJ mouse obtained from The Jackson Laboratory was added to its respective well and incubate at 37° C. for 45 minutes. Following 2 washes with MACS buffer (500 g, 4 minutes), the cells were resuspended in 50 ul of LIVE/DEAD™ Fixable Blue Dead Cell Stain Kit (Invitrogen) diluted 1:500 in 1×DPBS at 50 ul total volume per well and incubate at room temperature for 15 minutes. After centrifugation at 500 g for 4 minutes, the supernatant was discarded, and the cells were resuspended in 25 ul of Fc Block (Tonbo) and incubated at 4° C. for 15 minutes. 25 ul of 2× antibody cocktail (Table 11-2) was then added and incubated at 4° C. for 25 minutes. Cells were washed in MACS buffer following centrifugation (500 g, 4 minutes) by adding 100 ul of MACS™ buffer to each well. Cells were fixed by resuspending cells in 100 ul of Cytofix™ Fixation Buffer (BD) diluted 1:4 in 1×DPBS and incubated at 4° C. for 15 minutes. The samples were then resuspended in MACS buffer after centrifuging and discarding the fixative. Cells were acquired on a BD Fortessa X-20. Acquired events were analyzed with FlowJo (BD). MFIs were derived from cells that were doublet discriminated (FSC-H, FSC-A) and then Live/Dead dye negative. Results plotted were median fluorescent intensity values at the 1/512 dilution of sample serum.

TABLE 11-2

Antibodies used in flow cytometry staining cocktail

| Antigen | Conjugate | Clone | Supplier | Dilution (1/) |
|---|---|---|---|---|
| CD45 | BV421 | 30-F11 | BioLegend | 200 |
| IgG | APC | Poly4053 | BioLegend | 200 |
| B220 | BUV395 | RA3-6B2 | BD | 200 |
| IgG1 | PE-Cy7 | RMG1-1 | BioLegend | 200 |
| IgM | APC-Cy7 | RMM-1 | BioLegend | 200 |
| IgG2a | FITC | R19-15 | BD | 200 |
| IgG2c | FITC | Goat polyclonal IgG | Bio-Rad | 200 |

Results Summary and Conclusions.

In a skin transplant model (BALB/cJ to VG mice), H4H12889P (anti-IL2Rγ Ab) treatment delayed onset of skin graft rejection and improved overall skin graft survival. H4H12889P treatment also prevented generation of donor-specific antibodies in this transplant model.

We claim:

1. An isolated antibody or antigen-binding fragment thereof that specifically binds to interleukin-2 receptor gamma (IL2Rγ) or an antigenic fragment thereof, wherein the antibody or antigen-binding fragment thereof comprises: a heavy chain immunoglobulin or variable region thereof comprising a CDR-H1 comprising the amino acid sequence set forth in SEQ ID NO: 347, a CDR-H2 comprising the amino acid sequence set forth in SEQ ID NO: 349, and a CDR-H3 comprising the amino acid sequence set forth in SEQ ID NO: 351; and a light chain immunoglobulin or variable region thereof comprising a CDR-L1 comprising the amino acid sequence set forth in SEQ ID NO: 72, a CDR-L2 comprising the amino acid sequence set forth in SEQ ID NO: 54, and a CDR-L3 comprising the amino acid sequence set forth in SEQ ID NO: 355.

2. The antibody or antigen-binding fragment of claim 1 which is an antibody.

3. The antibody or antigen-binding fragment thereof of claim 2, wherein the antibody is a human antibody.

4. The antibody or antigen-binding fragment of claim 1 which is an antigen-binding fragment of an antibody.

5. The antibody or antigen-binding fragment of claim 1, wherein the heavy chain variable region comprises the amino acid sequence set forth in SEQ ID NO: 345; and/or the light chain variable region comprises the amino acid sequence set forth in SEQ ID NO: 353.

6. The antibody or antigen-binding fragment thereof of claim 1, wherein the heavy chain variable region comprises an amino acid sequence having at least 90% amino acid sequence identity to the amino acid sequence set forth in SEQ ID NO: 345; and/or the light chain variable region comprises an amino acid sequence having at least 90% amino acid sequence identity to the amino acid sequence set forth in SEQ ID NO: 353.

7. The antibody or antigen-binding fragment thereof of claim 1, wherein the heavy chain comprises the amino acid sequence set forth in SEQ ID NO: 357; and/or the light chain comprises the amino acid sequence set forth in SEQ ID NO: 359.

8. The antibody or antigen-binding fragment thereof of claim 1, which is multispecific.

9. A complex comprising the antibody or antigen-binding fragment thereof of claim 1 bound to an IL2Rγ polypeptide or an antigenic fragment thereof.

10. A method for making the antibody or antigen-binding fragment thereof of claim 1 or an immunoglobulin chain thereof, comprising:
 (a) introducing one or more polynucleotides encoding an immunoglobulin chain of said antibody or antigen-binding fragment into a host cell;
 (b) culturing the host cell under conditions favorable to expression of the polynucleotide; and
 (c) optionally, isolating the antibody or antigen-binding fragment or immunoglobulin chain from the host cell and/or medium in which the host cell is grown.

11. The method of claim 10 wherein the host cell is a Chinese hamster ovary cell.

12. An antibody or antigen-binding fragment or immunoglobulin chain produced by the method of claim 10.

13. A host cell comprising the antibody or antigen-binding fragment of claim 1.

14. A composition or kit comprising the antibody or antigen-binding fragment of claim 1, optionally in association with a further therapeutic agent.

15. The composition or kit of claim 14 in association with a further therapeutic agent which is one or more members selected from the group consisting of an anti-inflammatory agent, an anti-TNFα antibody or binding protein, infliximab, adalimumab, etanercept, golimumab, a corticoid, prednisolone, methylprednisolone, antithymocyte globulin, alemtuzumab, daclizumab, tacrolimus, cyclosporine, extracorporeal photophoresis, mycophenolate mofetil, sirolimus, pentostatin, mesenchymal stem cells, inolimomab, denileukin, and basiliximab.

16. A pharmaceutical formulation comprising the antibody or antigen-binding fragment of claim 1 and a pharmaceutically acceptable carrier or excipient and, optionally, a further therapeutic agent.

17. A vessel or injection device comprising the antibody or antigen-binding fragment of claim 1.

18. The antibody or antigen-binding fragment thereof of claim 1, wherein the heavy chain comprises an amino acid sequence having at least 90% amino acid sequence identity to the amino acid sequence set forth in SEQ ID NO: 357; and/or the light chain comprises an amino acid sequence having at least 90% amino acid sequence identity to the amino acid sequence set forth in SEQ ID NO: 359.

19. An isolated antibody or antigen-binding fragment thereof that specifically binds to interleukin-2 receptor gamma (IL2Rγ) or an antigenic fragment thereof, wherein the antibody or antigen-binding fragment comprises: a heavy chain variable region that comprises the amino acid sequence set forth in SEQ ID NO: 345; and a light chain variable region that comprises the amino acid sequence set forth in SEQ ID NO: 353.

20. The antibody or antigen-binding fragment thereof of claim 19, wherein the antibody or antigen-binding fragment thereof comprises a heavy chain comprising the amino acid sequence set forth in SEQ ID NO: 357, and a light chain comprising the amino acid sequence set forth in SEQ ID NO: 359.

21. A polypeptide comprising:
 (a) CDR-H1, CDR-H2, and CDR-H3 of a heavy chain variable region that comprises the amino acid sequence set forth in SEQ ID NO: 345; and
 (b) CDR-L1, CDR-L2, and CDR-L3 of a light chain variable region that comprises the amino acid sequence set forth in SEQ ID NO: 353.

22. A polynucleotide encoding the polypeptide of claim 21.

23. A vector comprising the polynucleotide of claim 22.

* * * * *

UNITED STATES PATENT AND TRADEMARK OFFICE
CERTIFICATE OF CORRECTION

| | | |
|---|---|---|
| PATENT NO. | : 11,629,195 B2 | Page 1 of 1 |
| APPLICATION NO. | : 16/776928 | |
| DATED | : April 18, 2023 | |
| INVENTOR(S) | : Orengo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this
First Day of October, 2024

Katherine Kelly Vidal
*Director of the United States Patent and Trademark Office*